United States Patent
Bridger et al.

(10) Patent No.: US 7,091,217 B2
(45) Date of Patent: Aug. 15, 2006

(54) CHEMOKINE RECEPTOR BINDING HETEROCYCLIC COMPOUNDS

(75) Inventors: Gary Bridger, Bellingham, WA (US); Renato Skerlj, Vancouver (CA); Al Kaller, Vancouver (CA); Curtis Harwig, White Rock (CA); David Bogucki, Surrey (CA); Trevor R. Wilson, Langley (CA); Jason Crawford, Vancouver (CA); Ernest J. McEachern, White Rock (CA); Bem Atsma, Abbotsford (CA); Siqiao Nan, Richmond (CA); Yuanxi Zhou, Surrey (CA); Dominique Schols, Herent (BE); Christopher Dennis Smith, Vancouver (CA); Maria Rosaria Di Fluri, Burnaby (CA)

(73) Assignee: AnorMED, Inc., Langley (CA)

( * ) Notice: Subject to any disclaimer, the term of this patent is extended or adjusted under 35 U.S.C. 154(b) by 0 days.

(21) Appl. No.: 10/799,386

(22) Filed: Mar. 11, 2004

(65) Prior Publication Data

US 2004/0171638 A1 Sep. 2, 2004

Related U.S. Application Data

(62) Division of application No. 10/031,812, filed on Mar. 28, 2002, now Pat. No. 6,734,191.

(60) Provisional application No. 60/234,816, filed on Sep. 22, 2000, provisional application No. 60/234,510, filed on Sep. 22, 2000, provisional application No. 60/232,891, filed on Sep. 15, 2000, provisional application No. 60/233,087, filed on Sep. 15, 2000.

(51) Int. Cl.
*A61K 31/47* (2006.01)
*C07D 221/02* (2006.01)

(52) U.S. Cl. ............ 514/311; 514/314; 546/134; 546/135

(58) Field of Classification Search ............ 546/134, 546/135; 514/311, 314
See application file for complete search history.

(56) References Cited

U.S. PATENT DOCUMENTS

| 5,021,409 | A | 6/1991 | Murrer et al. | 514/183 |
|---|---|---|---|---|
| 5,583,131 | A | 12/1996 | Bridger et al. | 514/183 |
| 5,698,546 | A | 12/1997 | Bridger et al. | 514/183 |
| 5,817,807 | A | 10/1998 | Bridger et al. | 540/474 |
| 6,001,826 | A | 12/1999 | Murrer et al. | 514/183 |
| 6,365,583 | B1 | 4/2002 | MacFarland et al. | 514/183 |

FOREIGN PATENT DOCUMENTS

| JP | 11-269146 | 10/1999 |
|---|---|---|
| WO | WO 99/38514 | 8/1999 |
| WO | WO 00/42852 | 7/2000 |
| WO | WO 00/51607 | 9/2000 |
| WO | WO 00/56729 | 9/2000 |
| WO | WO 02/22600 | 3/2002 |

OTHER PUBLICATIONS

U.S. Appl. No. 60/172,153, filed Dec. 17, 1999.
U.S. Appl. No. 09/111,895, filed Jul. 8, 1998.
U.S. Appl. No. 09/535,314, filed Mar. 24, 2000.
U.S. Appl. No. 60/172,153, filed Dec. 17, 1999.
U.S. App. No. 09/111,895, filed Jul. 8, 1998, Bridger et al.
U.S. Appl. No. 09/535,314, filed Mar. 24, 2000, Bridger et al.
Abi-Younes et al., *Clin. Res.* 86:131-138 (2000).
Alkhatib et al., *Science* 272:1955-1958 (1996).
Arai et al., *Eur. J. Haematol.* 64:323-332 (2000).
Arenburg et al., *J. Leukocyte Biol.* 62:554-562 (1997).
Aiuti et al., *J. Exp. Med.* 185:111-120 (1997).
Baggiolini, *Nature* 392:565-568 (1998).
Bajetto et al., *J. Neurochem.* 73:2348-2357 (1999).
Berger et al., *Annu. Rev. Immunol.* 17: 657-700 (1999).
Biard-Piechaczyk et al., *Virology* 268:329-344 (2000).
Blaak et al., *Proc. Natl. Acad. Sci.* 97:1269-1274 (2000).
Blanco et al., *Antimicrobial Agents and Chemother* 44:51-56 (2000).
Bleul et al., *Nature* 382:829-833 (1996).

(Continued)

*Primary Examiner*—Rita Desai
(74) *Attorney, Agent, or Firm*—Morrison & Foerster LLP

(57) ABSTRACT

Compounds which modulate chemokine receptor activities are disclosed. These compounds are preferably tertiary amines comprising tetrahydroquinoline and benzimidazole.

12 Claims, No Drawings

OTHER PUBLICATIONS

Bleul et al., *J. Exp. Med.* 187:753-762 (1998).
Bradstock et al., *Leukemia* 14:882-888 (2000).
Bridger et al., "Bicyclam Derivatives as HIV Inhibitors" in *Advances in Antiviral Drug Design* vol. 3, p. 161-229; Published by JAI press (1999); E. De Clercq (ed.).
Bridger et al., *J. Med. Chem.* 42:3971-3981 (1999).
Burger et al., *Blood* 94:3658-3667 (1999).
Buttini et al., *Nature Med.* 4:441-446 (1998).
Carroll et al., *Science* 276:273-276 (1997).
Cocchi et al., *Science* 270:1811-1815 (1995).
Connor and Ho, *J. Virol.* 68:4400-4408 (1994).
Deng et al., *Nature* 381:661-666 (1996).
Donzella et al., *Nature Medicine* 4:72-77 (1998).
Dragic et al., *Nature* 381:667-673 (1996).
Egberink et al., *J. Virol.* 73:6346-6352 (1999).
Eitner et al. *Transplantation* 66:1551-1557 (1998).
Fedyk et al., *J. Leukocyte Biol* . 66:667-673 (1999).
Feng et al., *Science* 272:872-877 (1996).
Gonzalo et al., *J. Immunol.* 165:499-508 (2000).
Herbein et al., *Nature* 395:189-194 (1998).
Hesselgesser et al., "Chemokines and Chemokine receptors in the Brain" in *Chemokines in Disease* published by Humana Press (1999) Herbert (ed.).
Hesselgesser et al. *Curr. Biol.* 7:112-121 (1997).
Hesselgesser et al., *Curr. Biol.* 8:595-598 (1998).
Ishii et al., *J. Immunol.* 163:3612-3620 (1999).
Lataillade et al., *Blood* 95:756-768 (1999).
Liu et al., *Cell* 86:367-377 (1996).
Locati et al., *Annu. Rev. Med.* 50:425-40 (1999).
Ma et al., *Immunity* 10:463-471 (1999).
Maekawa et al., *Internal Medicine* 39:90-100 (2000).
Michael et al., *Nature Med.* 3:338-340 (1997).
Michael et al., *J. Virol.* 72:6040-6047 (1998).
Miedema et al., *Immune. Rev.* 140:35 (1994).
Moore et al., *J. Invest. Med.* 46:113-120 (1998).
Moore et al., *Trends cardiovasc. Med.* 8:51-58 (1998).
Murdoch et al., *Blood* 95:3032-3043 (2000).
Nagasawa et al., *Nature* 382:635-638 (1996).
Nagase et al., *J. Immunol.* 164:5935-5943 (2000).
Nanki et al., *J. Immunol.* 164:5010-5014 (2000).
Oberlin et al., *Nature* 382:833-835 (1996).
Obrien et al., *Lancet* 349:1219 (1997).
Ohagen et al., *J. Virol.* 73:897-906 (1999).
Peled et al., *Science* 283:845-848 (1999).
Peled et al., *Blood* 95:3289-3296 (2000).
Rana et al., *J. Virol.* 71:3219-3227 (1997).
Rizzuto et al., *Science* 280:1949-1953 (1998).
Salcedo et al., *Am. J. Pathol.* 154:1125-1135 (1999).
Samson et al., *Nature* 382:722-725 (1996).
Sanders et al., *J. Neuroscience Res.* 59:671-679 (2000).
Schols et al., *Antiviral Research* 35:147-156 (1997).
Schols et al., *J. Exp. Med.* 186:1383-1388 (1997).
Schuitemaker et al., *J. Virol.* 66:1354-1360 (1992).
Sehgal et al., *J. Surg. Oncol.* 69:99-104 (1998).
Simmons et al., *J. Virol.* 72:8453-8457 (1998).
Simmons et al., *J. Virol.* 70:8355-8360 (1996).
Tachibana et al., *Nature* 393:591-594 (1998).
Tersmette et al., *J. Virol.* 62:2026-2032 (1988).
Theodorou et al., *Lancet* 349:1219-1220 (1997).
Viardot et al., *Ann. Hematol.* 77:195-197 (1998).
Volin et al., *Biochem. Biophys Res. Commun.* 242:46-53 (1998).
Wyatt et al., *Science* 280:1884-1888 (1998).
Xia et al., *J. Neurovirology* 5:32-41 (1999).
Yssel et al., *Clinical and Experimental Allergy* 28:104-109 (1998).
Zhang et al., *AIDS Res. Hum. Retroviruses* 13:1357-1366 (1997).
Zhang et al., *J. Virol.* 72:9307-9312 (1998).
Zhang et al., *J. Virol.* 73:3443-3448 (1999).
Zheng et al., *J. Virol.* 73:8256-8267 (1999).
Zou et al., *Nature*, 393:591-594 (1998).

CHEMOKINE RECEPTOR BINDING HETEROCYCLIC COMPOUNDS

This application is a divisional of U.S. patent application Ser. No. 10/031,812, now U.S. Pat. No. 6,734,191, which claims priority under 35 U.S.C. 119(e) from Provisional Applications 60/232,891 filed 15 Sep. 2000; 60/234,510 filed 22 Sep. 2000; Application 60/233,087 filed 15 Sep. 2000; and Application 60/234,816 filed 22 Sep. 2000. The contents of these applications are incorporated herein by reference.

TECHNICAL FIELD

This invention generally relates to novel compounds, pharmaceutical compositions and their use. This invention more specifically relates to novel heterocyclic compounds that bind to chemokine receptors, including CXCR4 and CCR5, and demonstrate protective effects against infection of target cells by a human immunodeficiency virus (HIV).

BACKGROUND OF THE INVENTION

Approximately 40 human chemokines have been described, that function, at least in part, by modulating a complex and overlapping set of biological activities important for the movement of lymphoid cells and extravasation and tissue infiltration of leukocytes in response to inciting agents (See, for example: P. Ponath, *Exp. Opin. Invest. Drugs*, 7:1–18, 1998; Baggiolini, M. *Nature* 392, 565–568 (1998); Locati et al. *Annu. Rev. Med.* 50, 425–40 (1999)). These chemotactic cytokines, or chemokines, constitute a family of proteins, approximately 8–10 kDa in size. Chemokines appear to share a common structural motif, that consists of 4 conserved cysteines involved in maintaining tertiary structure. There are two major subfamilies of chemokines: the "CC" or β-chemokines and the "CXC" or a-chemokines. The receptors of these chemokines are classified based upon the chemokine that constitutes the receptor's natural ligand. Receptors of the β-chemokines are designated "CCR" while those of the a-chemokines are designated "CXCR".

Chemokines are considered to be principal mediators in the initiation and maintenance of inflammation (see *Chemokines in Disease* published by Humana Press (1999), Edited by C. Herbert; Murdoch et al. *Blood* 95, 3032–3043 (2000)). More specifically, chemokines have been found to play an important role in the regulation of endothelial cell function, including proliferation, migration and differentiation during angiogenesis and re-endothelialization after injury (Gupta et al., *J. Biol. Chem.*, 7:4282–4287 (1998); Volin et al *Biochem. Biophys. Res. Commun.* 242, 46–53 (1998)). Two specific chemokines have been implicated in the etiology of infection by human immunodeficiency virus (HIV).

In most instances, HIV initially binds via its gp120 envelope protein to the CD4 receptor of the target cell. A conformational change appears to take place in gp120 which results in its subsequent binding to a chemokine receptor, such as CCR5 (Wyatt et al., *Science*, 280:1884–1888 (1998); Rizzuto et al. *Science*, 280:1949–1953 (1998); Berger et al. *Annu. Rev. Immunol.* 17: 657–700 (1999)). HIV-1 isolates arising subsequently in the infection bind to the CXCR4 chemokine receptor.

Following the initial binding by HIV to CD4, virus-cell fusion results, which is mediated by members of the chemokine receptor family, with different members serving as fusion cofactors for macrophage-tropic (M-tropic) and T cell line-tropic (T-tropic) isolates of HIV-1 (Carroll et al., *Science*, 276: 273–276 1997; Feng et al. *Science* 272, 872–877 (1996); Bleul et al. *Nature* 382, 829–833 (1996); Oberlin et al. *Nature* 382, 833–835 (1996); Cocchi et al. *Science* 270, 1811–1815 (1995); Dragic et al. *Nature* 381, 667–673 (1996); Deng et al. *Nature* 381, 661–666 (1996); Alkhatib et al. *Science* 272, 1955–1958, 1996). During the course of infection within a patient, it appears that a majority of HIV particles shift from the M-tropic to the more pathogenic T-tropic viral phenotype (Blaak et al. *Proc. Natl. Acad. Sci.* 97, 1269–1274 (2000); Miedema et al., *Immune. Rev.*, 140:35 (1994); Simmonds et al. *J. Virol.* 70, 8355–8360 (1996); Tersmette et al. *J. Virol.* 62, 2026–2032, 1988); Connor, R. I., Ho, D. D. *J. Virol.* 68, 4400–4408 (1994); Schuitemaker et al. *J. Virol.* 66, 1354–1360 (1992)). The M-tropic viral phenotype correlates with the virus's ability to enter the cell following binding of the CCR5 receptor, while the T-tropic viral phenotype correlates with viral entry into the cell following binding and membrane fusion with the CXCR4 receptor. Clinical observations suggest that patients who possess genetic mutations in CCR5 appear resistant, or less susceptible to HIV infection (Liu et al. *Cell* 86, 367–377 (1996); Samson et al. *Nature* 382, 722–725 (1996); Michael et al. *Nature Med.* 3, 338–340 (1997); Michael et al. *J. Virol.* 72, 6040–6047 (1998); Obrien et al. *Lancet* 349, 1219 (1997); Zhang et al. *AIDS Res. Hum. Retroviruses* 13, 1357–1366 (1997); Rana et al. *J. Virol.* 71, 3219–3227 (1997); Theodorou et al. *Lancet* 349, 1219–1220 (1997). Despite the number of chemokine receptors which have been reported to HIV mediate entry into cells, CCR5 and CXCR4 appear to be the only physiologically relevant coreceptors used by a wide variety of primary clinical HIV-1 strains (Zhang et al. *J. Virol.* 72, 9307–9312 (1998); Zhang et al. *J. Virol.* 73, 3443–3448 (1999); Simmonds et al. *J. Virol.* 72, 8453–8457 (1988)). Fusion and entry of T-tropic viruses that use CXCR4 are inhibited by the natural CXC-chemokine stromal cell-derived factor-1, whereas fusion and entry of M-tropic viruses that use CCR5 are inhibited by the natural CC-chemokines namely, Regulated on Activation Normal T-cell Expressed and Secreted (RANTES) and Macrophage Inflammatory proteins (MIP-1 alpha and beta).

In addition to serving as a co-factor for HIV entry, the direct interaction of virus-associated gp120 with CXCR4 has been recently suggested as a possible cause of CD8+T-cell apoptosis and AIDS-related dementia via induction of neuronal cell apoptosis (Hesselgesser et al. *Curr. Biol.* 8, 595–598 (1998); Hesselgesser et al. *Curr. Biol.* 7, 112–121 (1997); Hesselgesser et al. "Chemokines and Chemokine receptors in the Brain" in *Chemokines in Disease* published by Humana Press (1999), Edited by C. Herbert; Herbein et al. *Nature* 395, 189–194 (1998); Buttini et al. *Nature Med.* 4, 441–446 (1998); Ohagen et al. *J. Virol.* 73, 897–906 (1999); Biard-Piechaczyk et al. *Virology* 268, 329–344 (2000); Sanders et al. *J. Neuroscience Res.* 59, 671–679 (2000); Bajetto et al. *J. Neurochem.* 73, 2348–2357 (1999); Zheng et al. *J. Virol.* 73, 8256–8267 (1999)).

However, the binding of chemokine receptors to their natural ligands appears to serve a more evolutionary and central role than only as mediators of HIV infection. The binding of the natural ligand, pre-B-cell growth-stimulating factor/stromal cell derived factor (PBSF/SDF-1) to the CXCR4 chemokine receptor provides an important signaling mechanism: CXCR4 or SDF-1 knock-out mice exhibit cerebellar, cardiac and gastrointestinal tract abnormalities and die in utero (Zou et al., *Nature*, 393:591–594 (1998); Tachibana et al., *Nature*, 393:591–594 (1998); Nagasawa et al. *Nature* 382, 635–638 (1996)). CXCR4-deficient mice also display hematopoietic defects (Nagasawa et al. *Nature* 382, 635–638 (1996)); the migration of CXCR4 expressing leukocytes and hematopoietic progenitors to SDF-1 appears to be important for maintaining B-cell lineage and localization of CD34[+]progenitor cells in bone marrow (Bleul et al. *J. Exp. Med*. 187, 753–762 (1998); Viardot et al. *Ann. Hematol*. 77, 195–197 (1998); Auiti et al. *J. Exp. Med*. 185, 111–120 (1997); Peled et al. *Science* 283, 845–848 (1999); Qing et al. *Immunity* 10, 463–471 (1999); Lataillade et al. *Blood* 95, 756–768 (1999); Ishii et al. *J. Immunol*. 163, 3612–3620 (1999); Maekawa et al. *Internal Medicine* 39, 90–100 (2000); Fedyk et al. *J. Leukocyte Biol*. 66, 667–673 (1999); Peled et al. *Blood* 95, 3289–3296 (2000)).

The signal provided by SDF-1 on binding to CXCR4 may also play an important role in tumor cell proliferation and regulation of angiogenesis associated with tumor growth (See *"Chemokines and Cancer"* published by Humana Press (1999); Edited by B. J. Rollins; Arenburg et al. *J. Leukocyte Biol*. 62, 554–562 (1997); Moore et al. *J. Invest. Med*. 46, 113–120 (1998); Moore et al. *Trends cardiovasc. Med*. 8, 51–58 (1998); Seghal et al. *J. Surg. Oncol*. 69, 99–104 (1998)); the known angiogenic growth factors VEG-F and bFGF, up-regulate levels of CXCR4 in endothelial cells, and SDF-1 can induce neovascularization in vivo (Salcedo et al. *Am. J. Pathol*. 154, 1125–1135 (1999)); Leukemia cells that express CXCR4 migrate and adhere to lymph nodes and bone marrow stromal cells that express SDF-1 (Burger et al. *Blood* 94, 3658–3667 (1999); Arai et al. *Eur. J. Haematol*. 64, 323–332 (2000); Bradstock et al. *Leukemia* 14, 882–888 (2000)).

The binding of SDF-1 to CXCR4 has also been implicated in the pathogenesis of atherosclerosis (Abi-Younes et al. *Circ. Res*. 86, 131–138 (2000)), renal allograft rejection (Eitner et al. *Transplantation* 66, 1551–1557 (1998)), asthma and allergic airway inflammation (Yssel et al. *Clinical and Experimental Allergy* 28, 104–109 (1998); *J. Immunol*. 164, 5935–5943 (2000); Gonzalo et al. *J. Immunol*. 165, 499–508 (2000)), Alzheimers disease (Xia et al. *J. Neurovirology* 5, 32–41 (1999)) and Arthritis (Nanki et al. *J. Immunol*. 164, 5010–5014 (2000)).

In attempting to better understand the relationship between chemokines and their receptors, recent experiments to block the fusion, entry and replication of HIV via the CXCR4 chemokine receptor were carried out through the use of monoclonal antibodies or small molecules that appear to suggest a useful therapeutic strategy (Schols et al., *J. Exp. Med*. 186:1383–1388 (1997); Schols et al., *Antiviral Research* 35:147–156 (1997); Bridger et al. *J Med. Chem*. 42, 3971–3981 (1999); Bridger et al. "Bicyclam Derivatives as HIV Inhibitors" in *Advances in Antiviral Drug Design* Volume 3, p 161–229; Published by JAI press (1999); Edited by E. De Clercq). Small molecules, such as bicyclams, appear to specifically bind to CXCR4 and not CCR5 (Donzella et al., *Nature Medicine*, 4:72–77 (1998)). These experiments demonstrated interference with HIV entry and membrane fusion into the target cell in vitro. More recently, bicyclams were also shown to inhibit fusion and replication of Feline Immunodeficiency Virus (FIV) that uses CXCR4 for entry (Egberink et al. *J. Virol*. 73, 6346–6352 (1999)).

Additional experiments have shown that the bicyclam dose-dependently inhibits binding of 125I-labeled SDF-1 to CXCR4 and the signal transduction (indicated by an increase in intracellular calcium) in response to SDF-1. Thus, the bicyclam also functioned as an antagonist to the signal transduction resulting from the binding of stromal derived factor or SDF-1a, the natural chemokine to CXCR4.

Bicyclams also inhibited HIV gp120 (envelope)-induced apoptosis in non-HIV infected cells (Blanco et al. *Antimicrobial Agents and Chemother*. 44, 51–56 (2000)).

U.S. Pat. Nos. 5,583,131; 5,698,546; 5,817,807; 5,021,409; and 6,001,826 which are herein incorporated in their entirety by reference, disclose cyclic compounds that are active against HIV-1 and HIV-2 in in vitro tests. It was subsequently discovered and further disclosed in copending application U.S. Ser. No. 09/111,895 and U.S. Ser. No. 60/172,153 that these compounds exhibit anti-HIV activity by binding to the chemokine receptor CXCR4 expressed on the surface of certain cells of the immune system. This competitive binding thereby protects these target cells from infection by HIV which utilize the CXCR4 receptor for entry. In addition, these compounds antagonize the binding, signaling and chemotactic effects of the natural ligand for CXCR4, the chemokine stromal cell-derived factor 1α (SDF-1). We further disclosed that these novel compounds demonstrate protective effects against HIV infection of target cells by binding in vitro to the CCR5 receptor.

Additionally we have disclosed in U.S. Ser. No. 09/495,298 that these cyclic polyamine antiviral agents described in the above-mentioned patents have the effect of enhancing production of white blood cells as well as exhibiting antiviral properties. Thus, these agents are useful for controlling the side-effects of chemotherapy, enhancing the success of bone marrow transplantation, enhancing wound healing and burn treatment, as well as combating bacterial infections in leukemia.

More recently, we disclosed in U.S. Ser. No. 09/535,314, a series of heterocyclic compounds that exhibit anti-HIV activity by binding to the chemokine receptors CXCR4 and CCR5 expressed on the surface of certain cells of the immune system. This competitive binding thereby protects these target cells from infection by HIV which utilize the CXCR4 or CCR5 receptors for entry. In addition, these compounds antagonize the binding, signaling and chemotactic effects of the natural ligand for CXCR4, the chemokine stromal cell-derived factor 1α (SDF-1) and/or the natural ligand for CCR5, the chemokine RANTES.

Herein, we disclose novel compounds that exhibit protective effects against HIV infection of target cells by binding to chemokine receptor CXCR4 or CCR5 in a similar manner to the previously disclosed macrocyclic compounds. In addition, these compounds antagonize the binding, signaling and chemotactic effects of the natural ligand for CXCR4, the chemokine stromal cell-derived factor 1α (SDF-1) and/or the natural ligand for CCR5, the chemokine RANTES.

Citation of the above documents is not intended as an admission that any of the foregoing is pertinent prior art. All statements as to the date or representation as to the contents of these documents is based on the information available to the applicants and does not constitute any admission as to the correctness of the dates or contents of these documents. Further, all documents referred to throughout this application are hereby incorporated in their entirety by reference herein.

SUMMARY OF THE INVENTION

The present invention provides novel compounds that bind chemokine receptors and interfere with the binding of the natural ligand thereto. The compounds of the present invention are useful as agents demonstrating protective effects on target cells from HIV infection. Other embodiments of the present invention are compounds that act as antagonists or agonists of chemokine receptors, as well as other biological activities related to the ability of these compounds to inhibit the binding of chemokines to their receptors.

The compounds of the invention are of Formula (1), including the pharmaceutically acceptable salts and prodrug forms thereof. The compounds of Formula (1) are of the formula:

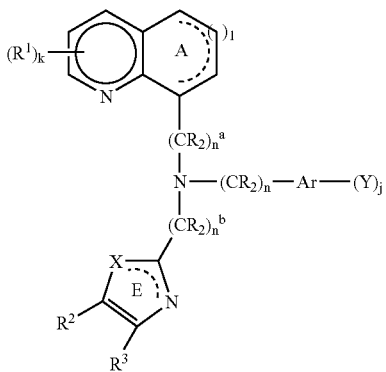

wherein:
Ring A optionally comprises a heteroatom selected from N, O and S;
the dotted lines represent optional unsaturation;
$R^1$, $R^2$ and $R^3$ are non-interfering substituents;
k is 0–4;
l is 0, 1, or 2;
X is unsubstituted or substituted C or N; or is O or S;
Ar is the residue of an aromatic or heteroarmatic moiety;
each n is independently 0–2;
each R is independently H or alkyl (1–6C);
j is 0–3; and
each Y is independently an optional substituent, as defined herein other than $CR_2NR(CR_2)_nB$ where B is aromatic or heteroaromatic or other heterocycle.
Preferably, each Y is independently halo, OH, SH, SO, $SO_2$, or an organic moiety of 1–20C atoms that does not contain N wherein two such Y may be connected to form a fused ring wth Ar, or is selected from the group consisting of
—$(CR_2)_mCN$,
—$(CR_2)_mNR^5_2$,
—$(CR_2)_mNR(CR_2)_mNRR^4$,
—$(CR_2)_mNR(CR_2)_mNR(CR_2)_mNR^5_2$,
—$(CR_2)_mCO(CR_2)_mNR^5_2$,
—$(CR_2)_mCO(CR_2)_mNR(CR_2)_mNRR^4$,
—$(CR_2)_mCO(CR_2)_mNR(CR_2)_mNR(CR_2)_mNR^5_2$,
—$(CR_2)_mNRCO(CR_2)_mNRR^4$,
—$(CR_2)_mNRCO(CR_2)_mNR(CR_2)_mNR^5_2$,
—$(CR_2)_mNRCO(CR_2)_mNR(CR_2)_mNR(CR_2)_mNR(CR_2)_mNR^5_2$,
—$CH=N-Z$,
—$(CR_2)_mZ$,
—$NR(CR_2)_mZ$,
—$(CR_2)_mNROH$,
$(CR_2)_mCONROH$, and
$(CR_2)_mCR=NOH$,
and those wherein Y comprises guanidino or NHNHR, or amidino;
wherein Z is an optionally substituted aromatic or heteroaromatic moiety containing 5–12 ring members; and wherein R is as defined above, each m is independently 0–4, and $R^4$ and each $R^5$ is independently H, alkyl (1–6C), alkenyl (1–6C), alkynyl (1–6C), or acyl (1–6C), each optional substituted by one or more nonaromatic, nonheterocyclic substituent(s), and wherein two $R^5$ may be connected to form a cyclic amine, optionally containing one or more additional heteroatoms selected from N, O, and S.

The compounds of the invention specifically exclude embodiments wherein Y is $CR_2NR(CR_2)_nB$ where B is aromatic or heteroaromatic or other heterocycle.

The optional substituents are defined infra.

The invention includes pharmaceutical compositions comprising a therapeutically effective amount of the compound of Formula (1); methods of treating a disease of the human body or the bodies of other mammals comprising the administration of such pharmaceutical compositions, and a method for blocking or interfering with the binding of a chemokine receptor with its natural ligand, comprising the contacting of said chemokine receptor with an effective amount of the compound of Formula (1).

This invention is also directed to use of a compound of Formula (1) in the manufacture of a medicament for the treatment of a disease in which blocking or interfering with binding of a chemokine receptor with its natural ligand is advantageous, which method may comprise formulating a composition comprising a therapeutically effective amount of the compound of Formula (1). The invention also provides a method of protecting target cells possessing chemokine receptors, the binding to which by a pathogenic agent results in disease or pathology, comprising administering to a mammalian subject a pharmaceutical composition comprising a therapeutically effective amount of the compound of Formula (1).

The compounds of the invention may be tin the form of "pro-drugs", that is, protected forms of the compounds, which release the compound after administration to a patient. For example, the compound may carry a protective groups which is split off by hydrolysis in body fluids e.g. in the bloodstream, thus releasing active compound or is oxidized or reduced in body fluids to release the compound. A discussion of pro-drugs may be found in "Smith and Williams' Introduction to the Principles of Drug Design", H. J. Smith, Wright, Second Edition, London 1988.

Acid addition salts, which are pharmaceutically acceptable, such as salt with inorganic base, a salt with organic base, a salt with inorganic acid, a salt with organic acid, a salt with basic or acidic amino acid, etc. are also encompassed in the present invention. Examples of a salt with an inorganic base include a salt with alkali metal (e.g. sodium, potassium, etc.), alkaline earth metal (e.g. calcium, magnesium, etc.), aluminum, ammonium, etc. Examples of the salt with an organic base include a salt with trimethylamine, triethylamine, pyridine, picoline, ethanolamine, diethanolamine, triethanolamine, dicyclohexylamine, N,N'-dibenzylethylenediamine etc. Examples of the salt with an inorganic acid include a salt with hydrochloric acid, hydrobromic acid, nitric acid, sulfuric acid, phosphoric acid, etc. Examples of the salt with an organic acid include a salt with formic acid, oxalic acid, acetic acid, tartaric acid, methanesulfonic acid, benzenesulfonic acid, malic acid, methanesulfonic acid, benzenesulfonic acid, p-toluenesulfonic acid, etc. Examples of salts with basic amino acids include a salt with arginine, lysine, ornithine, etc. Examples of salts with the acidic amino acid include a salt with aspartic acid, glutamic acid, etc. Non-toxic in the present context has to be considered with reference to the prognosis for the infected patient without treatment.

Modes of Carrying Out the Invention

The present invention is directed to compounds of Formula (1) which can act as agents that modulate chemokine receptor activity. Such chemokine receptors include but are not limited to CCR1, CCR2, CCR3, CCR4, CCR5, CCR6, CCR7, CCR8 and CXCR1, CXCR2, CXCR3, CXCR4 and CXCR5, preferably CXR4 and/or CCR5.

The compounds affect the binding of a natural ligand or chemokine to a receptor, such as CXCR4 and/or CCR5 of a target cell.

Thus the compounds affect chemokine receptors, such as CCR1, CCR2, CCR3, CCR4, CCR5, CCR6, CCR7, CCR8 and CXCR1, CXCR2, CXCR3, CXCR4 and CXCR5 where such chemokine receptors have been correlated as being important mediators of many human inflammatory as well as immunoregulatory diseases and cancer, and modulate the activity of such chemokine receptors so as to be useful for the treatment or prevention of such diseases.

In particular, the compounds of Formula 1 have protective effects on target cells from HIV infection in a manner as to bind specifically to the chemokine receptor.

The term "modulators" as used herein is intended to encompass antagonist, agonist, partial antagonist, and or partial agonist, inhibitors, and activators. In the preferred embodiment of the present invention, compounds of Formula 1 demonstrate protective effects against HIV infection by inhibiting the binding of HIV to a chemokine receptor such as CXCR4 and/or CCR5 of a target cell. The invention includes a method which comprises contacting the target cell with an amount of the compound which is effective at inhibiting binding to the chemokine receptor.

The term "therapeutically effective amount" means the amount of the subject compound that will elicit a biological or medical response in a cell, tissue, organ, system, animal or human that is being sought by the researcher, veterinarian, medical doctor or other clinician.

The term "administration" and or "administering" of the subject compound should be understood to mean as providing a compound of the invention including a pro-drug of a compound of the invention to the individual in need of treatment.

Compounds of the invention that inhibit chemokine receptors may be used for the treatment both prophylactic and therapeutic of diseases associated with hematopoiesis, including but not limited to, controlling the side-effects of chemotherapy, enhancing the success of bone marrow transplantation, enhancing wound healing and burn treatment, as well as combating bacterial infections in leukemia.

Compounds of the invention that inhibit chemokine receptor activity and function may be used for the treatment of diseases that are associated with inflammation, including but are not limited to, inflammatory or allergic diseases such as asthma, allergic rhinitis, hypersensitivity lung diseases, hypersensitivity pneumonitis, eosinophilic pneumonias, delayed-type hypersensitivity, interstitial lung disease (ILD) (e.g., idiopathic pulmonary fibrosis, or ILD associated with rheumatoid arthritis, systemic lupus erythematosus, ankylosing spondylitis, systemic sclerosis, Sjogren's syndrome, polymyositis or dermatomyositis); systemic anaphylaxis or hypersensitivity responses, drug allergies, insect sting allergies; autoimmune diseases, such as rheumatoid arthritis, psoriatic arthritis, systemic lupus erythematosus, myasthenia gravis, juvenile onset diabetes; glomerulonephritis, autoimmune throiditis, graft rejection, including allograft rejection or graft-versus-host disease; inflammatory bowel diseases, such as Crohn's disease and ulcerative colitis; spondyloarthropathies; scleroderma; psoriasis (including T-cell mediated psoriasis) and inflammatory dermatoses such as dermatitis, eczema, atopic dermatitis, allergic contact dermatitis, urticaria, vasculitis (e.g., necrotizing, cutaneous, and hypersensitivity vasculitis); eosinphilic myotis, eosiniphilic fasciitis; and cancers.

Compounds of the invention that activate or promote chemokine receptor function may be used for the treatment of diseases that are associated with immunosuppression such as individuals undergoing chemotherapy, radiation therapy, enhanced wound healing and burn treatment, therapy for autoimmune disease or other drug therapy (e.g., corticosteroid therapy) or combination of conventional drugs used in the treatment of autoimmune diseases and graft/transplantation rejection, which causes immunosuppression; immunosuppression due to congenital deficiency in receptor function or other causes; and infectious diseases, such as parasitic diseases, including but not limited to helminth infections, such as nematodes (round worms); Trichuriasis, Enterobiasis, Ascariasis, Hookworm, Strongyloidiasis, Trichinosis, filariasis; trematodes; visceral worms, visceral larva migtrans (e.g., Toxocara), eosinophilic gastroenteritis (e.g., *Anisaki* spp., *Phocanema* ssp.), cutaneous larva migrans (*Ancylostona braziliense, Ancylostoma caninum*); the malaria-causing protozoan *Plasmodium vivax*, Human cytomegalovirus, *Herpesvirus saimiri*, and Kaposi's sarcoma herpesvirus, also known as human herpesvirus 8, and poxvirus *Moluscum contagiosum*.

One or more compounds of Formula 1 may be used in combination with any other pharmaceutical composition where such combined therapy modulates chemokine receptor activity and thereby prevent and treat diseases associated with hematopoiesis, inflammation, autoimmune, inflammatory dermatoses, cancers, inflammatory bowel diseases, and immunoregulatory disorders.

It is also contemplated that the present invention may be used in combinations with one or more agents useful in the prevention or treatment of HIV. Examples of such agents include:

(1) nucleotide reverse transcriptase inhibitor such as zidovudine, didanosine, lamivudine, zalcitabine, abacavir, stavudine, adefovir, adefovir dipivoxil, fozivudine todoxil, etc.;

(2) non-nucleotide reverse transcriptase inhibitor (including an agent having anti-oxidation activity such as immunocal, oltipraz, etc.) such as nevirapine, delavirdine, efavirenz, loviride, immunocal, oltipraz, etc.; and (3) protease inhibitors such as saquinavir, ritonavir, indinavir, nelfinavir, amprenavir, palinavir, lasinavir, etc.

The scope of combinations of compounds of Formula (1) with HIV agents is not limited to (1), (2), and or (3), but includes in principle, any combination with any pharmaceutical composition useful for the treatment of HIV. Further, in such combinations the compounds of the present invention and other HIV agents may be administered separately or in conjunction. In addition, the administration of one element may be prior to, concurrent to, or subsequent to the administration of other agent(s).

The compounds of Formula (1) may be administered by oral, parenteral (e.g., intramuscular, intraperitoneal, intravenous, intracistemal injection or infusion, subcutaneous injection, or implant), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration.

The compounds of Formula 1 are all active and used to treat animals, including but not limited to, mice, rats, horses, cattle, sheep, dogs, cats, and monkeys. The compounds of the invention are also effective for use in humans.

The compounds of Formula 1 may form hydrates or solvates. Those compounds of Formula 1 which can exist as regioisomers, configurational isomers, conformers, or diasteroisomeric forms may occur as mixtures of such forms. Mixtures may be treated so as to isolate individual isomers using known separation and purification methods, if desired. For example when the compound of Formula (1) is a racemate, it can be separated into the (S)-compound and (R)-compound by optical resolution. Individual optical isomers and a mixtures thereof are included in the scope of the present invention.

This invention also relates to a pharmaceutical composition comprising a pharmaceutically acceptable carrier or diluent and an effective amount of compound of Formula 1. A compound of Formula 1 may be administered alone or as an admixture with a pharmaceutically acceptable carrier (e.g. solid formulations such as tablets, capsules, granules, powders, etc.; liquid formulations such as syrups, injections, etc.) may be orally or non-orally administered. Examples of non-oral formulations include injections, drops, suppositories, pessaryies.

In the treatment or prevention of conditions which require chemokine receptor modulation an appropriate dosage level will generally be about 0.01 to 500 mg per kg patient body weight per day which can be administered in singe or multiple doses. Preferably, the dosage level will be about 0.1 to about 250 mg/kg per day. It will be understood that the specific dose level and frequency of dosage for any particular patient may be varied and will depend upon a variety of factors including the activity of the specific compound used, the metabolic stability and length of action of that compound, the age, body weight, general health, sex, diet, mode and time of administration, rate of excretion, drug combination, the severity of the particular condition, and the patient undergoing therapy.

The present invention further provides novel compounds that bind chemokine receptors and interfere with the binding of the natural ligand thereto. The compounds of the present invention are useful as agents demonstrating protective effects on target cells from HIV infection. The compounds of the present invention are also useful as antagonists or agonists of chemokine receptors, as well as other biological activities related to the ability of these compounds to inhibit the binding of chemokines to their receptors.

Further Definition of Substituents

In the compounds of Formula 1, R may be straight or branched chain alkyl or may be cyclic, and may optionally be substituted by 1–2 substituents selected from halo, hydroxy and alkoxy. Preferably each R is H or lower straightchain alkyl (1–4C), preferably methyl.

Ar is the residue of an aromatic or heteroaromatic moiety which contains a single or fused ring system and containing 5–6 ring members in the monocyclic system and 9–12 members in the fused ring system. The residue may be optionally substituted. Examples of optionally substituted aromatic and heteroaromatic groups include benzene, naphthalene, dihydronaphthalene, tetrahydronaphthalene, pyridine, quinoline, isoquinoline, imidazole, benzimidazole, azabenzimidazole, benzotriazole, furan, benzofuran, thiazole, benzothiazole, oxazole, benzoxazole, pyrrole, indole, imidazole, tetrahydroquinoline, tetrahydroisoquinoline, pyrazole, thiophene, isoxazole, isothiazole, triazole, tetrazole, oxadiazole, thiadiazole, imidazoline, and benzopyran. Oxides of the nitrogen and sulfur containing heteroaromatic rings are also included in the present invention. Particularly preferred forms of Ar are phenylene, pyridylene or pyridinylene.

When compounds of Formula (1) contain elements that are "optionally substituted" these substituents are preferably halogen, nitro, cyano, carboxylic acid, optionally substituted alkyl, alkenyl or cycloalkyl groups, an optionally substituted hydroxyl group, an optionally substituted thiol group, an optionally substituted amino, an optionally substitute acyl group, an optionally substituted carboxylate, carbamate, carboxamide or sulfonamide group, or an optionally substituted aromatic or heterocyclic group.

Examples of halogen include fluorine, chlorine, bromine, iodine, etc., with fluorine and chlorine preferred.

Examples of optionally substituted alkyl include $C_{1-10}$ alkyl, including methyl, ethyl propyl etc.; examples of optionally substituted alkenyl groups include $C_{2-10}$ alkenyl such as allyl, crotyl, 2-pentenyl, 3-hexenyl, etc.; and examples of optionally substituted cycloalkyl groups include $C_{3-10}$ cycloalkyl such as cyclopropyl, cyclobutyl, cyclopentyl, cyclohexyl, cycloheptyl, etc. In these cases, $C_{1-6}$ alkyl, alkenyl and cycloalkyl are preferred. The optional substituent may also be an optionally substituted aralkyl (e.g. phenyl $C_{1-4}$ alkyl) or heteroalkyl for example, phenylmethyl (benzyl), phenylethyl, pyridinylmethy, pyridinylethyl, etc. The heterocyclic group may be a 5 or 6 membered ring containing 1–4 heteroatoms.

Examples of optionally substituted hydroxyl and thiol groups include those wherein the substituent is an optionally substituted alkyl (e.g. $C_{1-10}$ alkyl) such as methyl, ethyl, propyl, isopropyl, butyl, isobutyl, sec-butyl, tert-butyl, pentyl, etc., preferably ($C_{1-6}$) alkyl; an optionally substituted cycloalkyl (e.g. $C_{3-7}$ cycloalkyl, etc., such as cyclopropyl, cyclobutyl, cyclopentyl, cyclohexyl, cycloheptyl, etc.); an optionally substituted aralkyl (e.g. phenyl-$C_{1-4}$ alkyl, e.g. benzyl, phenethyl, etc.). Where there are two adjacent hydroxyl or thiol substituents, the heteroatoms may be connected via an alkylene group such as $O(CH_2)_nO$ and $S(CH_2)_nS$ (where n=1–5). Examples include methylenedioxy, ethylenedioxy, etc. Oxides of thio-ether groups such as sulfoxides and sulfones are also encompassed.

Further examples of the optionally substituted hydroxyl group include an optionally substituted $C_{2-4}$ alkanoyl (e.g. acetyl, propionyl, butyryl, isobutyryl, etc.), $C_{1-4}$ alkylsufonyl (e.g. methanesulfonyl, ethanesulfonyl, etc.) and an optionally substituted aromatic and heterocyclic carbonyl group including benzoyl, pyridinecarbonyl, etc.

The substituents on optionally substituted amino group may bind to each other to form a cyclic amino group (e.g. 5- to 6-membered cyclic amino, etc., such as tetrahydropyrrole, piperazine, piperidine, pyrrolidine, morpholine, thiomorpholine, pyrrole, imidazole, etc.). Said cyclic amino group may have a substituent, and examples of the substituents include halogen (e.g. fluorine, chlorine, bromine, iodine, etc.), nitro, cyano, hydroxy group, thiol group, amino group, carboxyl group, an optionally halogenated $C_{1-4}$ alkyl (e.g. trifluoromethyl, methyl, ethyl, etc.), an optionally halogenated $C_{1-4}$ alkoxy (e.g. methoxy, ethoxy, trifluoromethoxy, trifluoroethoxy, etc.), $C_{2-4}$ alkanoyl (e.g. acetyl, propionyl, etc.), $C_{1-4}$ alkylsulfonyl (e.g. methanesulfonyl, ethanesulfonyl, etc.) the number of preferred substituents are 1 to 3.

The amino group may also be substituted once or twice (to form a secondary or tertiary amine) with a group such as an optionally substituted alkyl group including $C_{1-10}$ alkyl (e.g. methyl, ethyl propyl etc.); an optionally substituted alkenyl group such as allyl, crotyl, 2-pentenyl, 3-hexenyl, etc., or an optionally substituted cycloalkyl group such as cyclopropyl, cyclobutyl, cyclopentyl, cyclohexyl, cycloheptyl, etc. In these cases, $C_{1-6}$ alkyl, alkenyl and cycloalkyl are preferred. The amine group may also be optionally substituted with an aromatic or heterocyclic group, aralkyl (e.g. phenyl $C_{1-4}$ alkyl) or heteroalkyl for example, phenyl, pyridine, phenylmethyl (benzyl), phenethyl, pyridinylmethyl, pyridinylethyl etc. The heterocyclic group may be a 5 or 6 membered ring containing 1–4 heteroatoms. The optional substituents of the "optionally substituted amino groups are the same as defined above for the "optionally substituted cyclic amino group."

The amino group may be substituted with an optionally substituted $C_{2-4}$ alkanoyl e.g. acetyl, propionyl, butyryl, isobutyryl etc., or a $C_{1-4}$ alkylsulfonyl (e.g. methanesulfonyl, ethanesulfonyl, etc.) or a carbonyl or sulfonyl substituted aromatic or heterocyclic ring, e.g. benzenesulfonyl, benzoyl, pyridinesulfonyl, pyridinecarbonyl etc. The heterocycles are as defined above.

Examples of the optionally substituted acyl groups include a carbonyl group or a sulfinyl or sulfonyl group binding to hydrogen; or to an optionally substituted alkyl (e.g. $C_{1-10}$ alkyl such as methyl, ethyl, propyl, isopropyl, butyl, isobutyl, sec-butyl, tert-butyl, pentyl, isopentyl, neopentyl, hexyl, heptyl, octyl, nonyl, decyl, etc., preferably lower $(C_{1-6})$ alkyl, etc.; an optionally substituted cycloalkyl (e.g. $C_{3-7}$ cycloalkyl, etc., such as cyclopropyl, cyclobutyl, cyclopentyl, cyclohexyl, cycloheptyl, etc.); an optionally substituted alkenyl (e.g. $C_{2-10}$ alkenyl such as allyl, crotyl, 2-pentenyl, etc., preferably lower $(C_{2-6})$ alkenyl, etc.); an optionally substituted cycloalkenyl (e.g. $C_{3-7}$ cycloalkenyl, etc., such as 2-cyclopentenyl, 2-cyclohexenyl, 2-cyclopentenylmethyl, 2-cyclohexenylmethyl, etc.) an optionally substituted 5- to 6-membered monocyclic aromatic group (e.g. phenyl, pyridyl, etc.).

Examples of the optionally substituted carboxylate group (ester groups) include an optionally substituted alkyl (e.g. $C_{1-10}$ alkyl such as methyl, ethyl, propyl, isopropyl, butyl, isobutyl, sec-butyl, tert-butyl, pentyl, isopentyl, neopentyl, hexyl, heptyl, octyl, nonyl, decyl, etc., preferably lower $(C_{1-6})$ alkyl, etc.); an optionally substituted cycloalkyl (e.g. $C_{3-7}$ cycloalkyl, etc. such as cyclopropyl, cyclobutyl, cyclopentyl, cyclohexyl, cycloheptyl, etc.); an optionally substituted alkenyl (e.g. $C_{2-10}$ alkenyl such as allyl, crotyl, 2-pentenyl, 3-hexenyl, etc., preferably lower $(C_{2-6})$ alkenyl, etc.); an optionally substituted cycloalkenyl (e.g. $C_{3-7}$ cycloalkenyl, etc., such as 2-cyclohexenylmethyl, etc.); an optionally substituted aryl (e.g. phenyl, naphthyl, etc.) and $C_{1-4}$ aryl for example, benzyl, phenethyl etc. Groups such as methoxymethyl, methoxyethyl, etc., are also encompassed.

Examples of the optionally substituted carboxamide and sulfonamide groups are identical in terms of the amine definition as the "optionally substituted amino group" defined above.

Examples of the optionally substituted aromatic or heterocyclic groups are phenyl, naphthyl, or a 5- or 6-membered heterocyclic ring containing 1–4 heteroatoms. The optional substituents are essentially identical to those listed above.

The noninterferring substituents $R^1$, $R^2$ and $R^3$ are similar to those set forth as "optional substituents". Preferably, $R^1$ is selected from the optional substituents set forth above, preferably halo, substituted or unsubstituted alkyl, substituted or unsubstituted hydroxyl, substituted or unsubstituted amino, substituted or unsubstituted thiol, and substituted or unsubstituted acyl. Preferably k is 0–2, preferably 0–1, and more preferably 0.

The substituents $R^2$ and $R^3$ are preferably selected from the preferred embodiments of $R^1$ listed immediately above, or, more preferably, may be joined to form a saturated or unsaturated ring system, preferably a benzo ring system.

In the above Formula 1, examples of the optionally substituted ring system containing ring A are dihydroquinoline, tetrahydroquinoline, pyranopyridine, dihydropyranopyridine, thiapyranopyridine, dihydrothiapyranopyridine, dihydronaphthyridine, tetrahydronaphthyridine. Oxides of sulfur-containing heterocycles are also encompassed in the present invention. In the above ring system containing Ring A, the optional nitrogen atom may be substituted with hydrogen, a substituted alkyl, alkenyl, cycloalkyl or aryl group, or may be the nitrogen atom of a carboxamide, carbamate or sulfonamide. Preferred for 1 is 1=1, it is preferred that ring A be saturated. The most preferred combination is tetrahydroquinoline.

In the above Formula 1, X may be CH (pyrrole), O (oxazole), S (thiazole), NH or NR (imidazole) where R is a $C_{1-6}$ alkyl group or acyl, sulfonyl group. In Formula 1, two adjacent $R^1$ and/or $R^2$ and $R^3$ may be joined to form an optionally substituted, fused 5–7 membered ring. Examples of fused ring systems include but are not limited to indole, tetrahydroindole, benzimidazole, tetrahydrobenzimidazole, azabenzimidazole, benzoxazole, tetrahydrobenzoxazole, benzothiazole, tetrahydrobenzothiazole. The preferred ring systems resulting from $R^2$ and $R^3$ include those which result in benzothiazole and benzoimidazole.

In the compounds of Formula 1, it is preferred that one of the $(CR_2)_n$ linkers between the ring system containing ring A and ring E is that wherein n is 0, i.e., the linkage is merely a covalent bond. Also preferred embodiments of $(CR_2)_n$ in this context are ethlylene or methylene, preferrably methylene. In the most preferred embodiments, the linkage between the nitrogen shown in Formula 1 and ring A is a bond and that between the nitrogen shown and ring E is $CH_2$. As shown, ring E may be coupled to the linker through any position, but preferably through position 2, 4 or 5, most preferably through position 2.

In the compounds of Formula 1, preferred values of j are 0–2, preferrably 1–2. The embodiments of Y may be varied widely provided Y does not contain nitrogen. Thus, Y may be halo, OH, SH, SO, $SO_2$ and the like, or a substituent of 1–20 carbons, optionally containing as a substitution, for one or more said carbons, a heteroatom such as O or S. Preferred embodiments wherein N is not present in Y include halo, optionally substituted alkyl, optionally substiued hydroxyl, optionally substituted thiol, and optionally substituted carboxylate, and a saturated or unsaturated ring. These substituents are described above. Where N is included in Y, Y is selected from the moieties set forth hereinabove. In these substituents, "Z" is an aromatic or heteroaromatic moiety containing 5–12 ring members. Thus, Y may include a single or fused ring. Examples of preferred forms of "Z" are identical to those set forth with regard to the aromatic residue "Ar" set forth above, but are monovalent.

As shown, in certain embodiments, R, defined as H or alkyl (1–6C), is replaced by $R^4$ or $R^5$ which have a broader definitions and can include the embodiments of R as well as embodying optionally substituted alkenyl, acyl, and the like as set forth above. Preferred forms of $R^4$ and $R^5$ include those typified by R and optionally substituted alkenyl. Also preferred are embodiments where two $R^5$ are connected to form a cyclic amine, including those which contain one or more additional heteroatoms such as N, O, and/or S.

Preferred forms of Y when Y contains N are those wherein R is in all cases H or methyl, preferably H and those where two $R^5$ are coupled. Especially preferred are those of the formula
—$(CR_2)_m CN$,
—$(CR_2)_m NR^5_2$,
—$(CR_2)_m NR(CR_2)_m NRR^4$,
—$(CR_2)_m CO(CR_2)_m NR^5_2$,
—$(CR_2)_m Z$, and
—$NR (CR_2)_m Z$,
and those wherein Y comprises guanidino or NHNHR, or amidino;

especially wherein $(CR_2)_m$ is $CH_2$, $CH_2CH_2$, or $CH_2CH_2CH_2$, or wherein m is 0, and those wherein $R^4$ or $R^5$ is H or is lower alkyl, alkenyl, or hydrogen, or wherein both $R^5$ are identical.

Particularly preferred are —$CH_2NH_2$, $CH_2CH_2NH_2$, —$CH_2NMe_2$, —$CH_2CH_2NMe_2$, —$CONH_2$, —$CONMe_2$, and the like.

Preferred Z are optionally substituted residues of benzene, oxazole, imidazole, thiazole, benzimidazole, benzthiazole, benzoxazole, indole, thiophene, tetrazine, pyrimidine, pyridine, and the like.

The novel compounds of Formula 1 of the present invention may be formulated as pharmaceutical compositions that may be administered topically; percutaneously, including intravenously; orally; and by other standard routes of pharmaceutical administration to mammalian subjects as determined according to routine clinical practice.

Having now generally described the invention, the same will be more readily understood through reference to the following examples which are provided by way of illustration, and are not intended to be limiting of the present invention, unless specified.

EXPERIMENTAL

The intermediates 8-hydroxy-5,6,7,8-tetrahydroquinoline and 8-amino-5,6,7,8-tetrahydroquinoline were prepared according to the procedures described in Bridger et al. U.S. patent application Ser. No. 09/535,314, incorporated herein by reference. The intermediate N'-(1H-benzimidazol-2-ylmethyl)-N'-(5,6,7,8-tetrahydro-8-quinolinyl)-1,4-benzenedimethanamine was prepared as described by Bridger et al, U.S. patent applications U.S. Ser. No. 60/232,891, and U.S. Ser. No. 60/234,510, incorporated herein by reference. The intermediate 1-N-tert-butoxycarbonyl-2-chloromethylbenzimidazole was prepared as described by An, H.; Wang, T.; Mohan, V.; Griffey, R. H.; Cook, P. D. *Tetrahedron* 1998, 54, 3999–4012.

General Procedures:

General Procedure for N-Alkylation of (1-tert-butoxycarbonyl-1H-Benzimidazol-2-ylmethyl)-(5,6,7, 8-tetrahydro-quinolin-8-yl)-amine with Mesylates or Alkyl Chlorides To a solution of (1-tert-butoxycarbonyl-1H-Benzimidazol-2-ylmethyl)-(5,6,7,8-tetrahydro-quinolin-8-yl)-amine (or amine) (1–1.4 equivalents), N,N,-diisopropylethylamine (or $K_2CO_3$) (1.5–2 equivalents) and KI (0.05–0.16 equivalent) in $CH_3CN$ (concentration ~0.1–0.2 M) was added the mesylate or alkyl chloride (such as 1-N-tert-butoxycarbonyl-2-chloromethylbenzimidazole) (1–1.4 equivalents) and the mixture stirred at 50–70° C. for 3–25 hours, as monitored by analytical thin layer chromatography. The reaction mixture was cooled, diluted with $CH_2Cl_2$ (10 mL/mmol amine) and poured into either saturated aqueous $NaHCO_3$ or brine (10 mL/mmol alcohol). The phases were separated and the aqueous phase extracted with $CH_2Cl_2$ (3×10 mL/mmol amine). The combined organic phases were dried ($Na_2SO_4$ or $MgSO_4$) and concentrated under reduced pressure. The crude material was purified by chromatography to afford the desired N-alkylated product.

General Procedure A

Direct Reductive Amination with $NaBH_3CN$

To a stirred solution of the amine (1 equivalent) in anhydrous methanol (concentration ~0.1 M), at room temperature, was added the carbonyl compound (~1–2 equivalents) in one portion. Once the carbonyl had dissolved (~5 minutes), $NaBH_3CN$ (~2–4 equiv.) was added in one portion and the resultant solution was stirred at room temperature. The solvent was removed under reduced pressure and $CH_2Cl_2$ (20 mL/mmol of amine) and brine or 1.0 M aqueous NaOH (10 mL/mmol amine) were added to the residue. The phases were separated and the aqueous phase was extracted with $CH_2Cl_2$ (3×10 mL/mmol amine). The combined organic phases were dried ($Na_2SO_4$) and concentrated under reduced pressure. The crude material was purified by chromatography.

General Procedure B

Direct Reductive Amination with $NaBH(OAc)_3$ or $NaBH_4$

To a stirred solution of the amine (1 equivalent) in $CH_2Cl_2$ (concentration ~0.2 M), at room temperature, was added the carbonyl compound (~1–2 equivalents), glacial acetic acid (0–2 equivalents) and $NaBH(OAc)_3$ (~1.5–3 equivalents) and the resultant solution stirred at room temperature. The reaction mixture was poured into either saturated aqueous $NaHCO_3$ or 1.0 M aqueous NaOH (10 mL/mmol amine). The phases separated and the aqueous phase extracted with $CH_2Cl_2$ (3×10 mL/mmol amine). The combined organic phases were dried ($Na_2SO_4$) and concentrated under reduced pressure. The crude material was purified by chromatography.

Similarly, to a stirred solution of the amine (1 equivalent) in anhydrous MeOH (concentration ~0.1 M), at room temperature, was added the carbonyl compound (1 equivalent). The resultant solution was stirred at room temperature or heated to reflux for 4–24 hours. $NaBH_4$ (1–2 equivalents) was added and the resultant mixture stirred at room temperature for ~20 minutes. The reaction mixture was concentrated, dissolved in $CH_2Cl_2$, washed consecutively with saturated aqueous $NaHCO_3$ and saturated aqueous NaCl. The aqueous layers were extracted with $CH_2Cl_2$ (2×) and the combined organic extracts were dried ($MgSO_4$) and concentrated.

General Procedure C

Reaction of Alcohols with Methanesulfonyl Chloride

To a stirred solution of the alcohol (1 equivalent) and $Et_3N$ (1.5–2 equivalents) in $CH_2Cl_2$ (or THF) (concentration ~0.1 M) at room temperature (or 0° C.) was added methanesulfonyl chloride (~1.5 equivalents) and the reaction stirred at room temperature for 0.5–1 h. The reaction mixture was poured into either saturated aqueous NaHCO₃ or saturated NH₄Cl (10 mL/mmol alcohol). The phases were separated and the aqueous phase extracted with CH₂Cl₂ (3×10 mL/mmol amine). The combined organic phases were dried (Na₂SO₄) and concentrated under reduced pressure. The crude material was either purified by chromatography or used without further purification in the N-alkylation step.

General Procedure D

Salt Formation Using Saturated HBr(g) in Acetic Acid

To a solution of the free base in glacial acetic acid (2 mL) was added, a saturated solution of HBr(g) in acetic acid (2 mL). A large volume of ether (25 mL) was then added to precipitate a solid, which was allowed to settle to the bottom of the flask and the supernatant solution was decanted. The solid was washed by decantation with ether (3×25 mL) and the remaining traces of solvent were removed under vacuum. For additional purification, the solid was dissolved in methanol and re-precipitated with a large volume of ether. Washing the solid with ether by decantation, followed by drying of the solid in vacuo (0.1 Torr) gave the desired compound.

Intermediates:

Preparation of 4-hydroxymethylbenzaldehyde

Terephthaldicarboxaldehyde (30.02 g, 224 mmol), methanol (200 mL), palladium on activated carbon, (10%, 3.02 g) and 2-(aminomethyl)pyridine (2.3 mL, 22 mol, 0.01 mol equiv) were combined in a hydrogenation vessel and the reaction mixture was shaken on a Parr hydrogenator for 2.5 hours at 40 psi of hydrogen. The mixture was filtered through celite, the cake washed with methanol and the solvent from the eluent removed in vacuo. Purification of the crude product by column chromatography on silica gel (EtOAc/Hexanes, 1:1) afforded the title compound (23.8 g, 78%) as a white solid. ¹H NMR (CDCl₃) δ 4.80 (s, 2H), 7.53 (d, 2H, J=9 Hz), 7.87 (d, 2H, J=9 Hz), 10.00 (s, 1H).

Preparation of 6,7-Dihydro-5H-quinolin-8-one

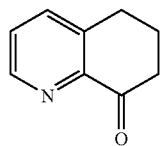

To a stirred solution of 8-hydroxy-5,6,7,8-tetrahydroquinoline (13.96 g, 93.6 mmol) in dry CH₂Cl₂ (400 mL) was added activated manganese dioxide (85% purity, 82.22 g, 804 mmol). The resulting heterogeneous mixture was stirred 18 h, at which point the black slurry was filtered through a cake of celite and washed with CH₂Cl₂ (3×50 mL). The combined washings were concentrated to afford 11.27 g (82%) of the title compound as a pale yellow solid, which was used in subsequent reactions without further purification. ¹H NMR (CDCl₃) δ 2.17–2.25 (m, 2H), 2.82 (t, 2H, J=7 Hz), 3.04 (t, 2H, J=6 Hz), 7.37 (dd, 1H, J=9, 6 Hz), 7.66 (dd, 1H, J=9, 1 Hz), 8.71 (dd, 1H, J=6, 1 Hz); ¹³C NMR (CDCl₃) δ 22.2, 28.6, 39.2, 126.6, 137.3, 140.5, 147.6, 148.6, 196.5. ES-MS m/z 148 (M+H).

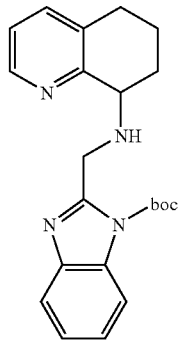

Preparation of (1-tert-butoxycarbonyl-1H-Benzimidazol-2-ylmethyl)-(5,6,7,8-tetrahydro-quinolin-8-yl)-amine Using General Procedure for N-Alkylation: To a stirred solution of 8-amino-5,6,7,8-tetrahydroquinoline (7.34 g, 49.6 mmol) in dry CH₃CN (250 mL) was added 1-N-tert-butoxycarbonyl-2-chloromethylbenzimidazole (13.22 g, 49.6 mmol), N,N-diisopropylethylamine (15.5 mL, 89.2 mmol) and potassium iodide (0.41 g, 8.2 mmol) and the mixture was stirred at 60° C. for 3.5 h. Purification by column chromatography on silica gel (CH₂Cl₂/MeOH, 99:1 followed by 97:3 and 96:4) gave the intermediate amine (6.38 g, 34%) as an orange, sticky oil. ¹H NMR (CDCl₃) δ 1.76 (s, 9H), 1.81–2.10 (m, 2H), 2.25–2.37 (m, 1H), 2.72–2.89 (m, 2H), 3.77–3.84 (m, 1H), 4.39 (d, 1H, J=15.0 Hz), 4.56 (d, 1H, J=15.0 Hz), 7.00–7.06 (m, 1H), 7.27–7.37 m, 1H), 7.64–7.74 (m, 1H), 7.90–7.96 (d, 2H, J=8.1 Hz), 8.34 (d, 1H, J=3.0 Hz); ¹³C NMR (CDCl₃) δ 20.13, 28.48, 29.00, 29.20, 47.15, 56.89, 86.20, 115.32, 120.28, 122.06, 124.43, 124.85, 132.77, 133.74, 137.01, 142.44, 147.10, 149.22, 154.90, 157.72; ES-MS m/z 279 (M+H-boc).

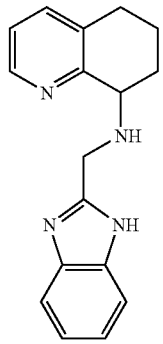

Preparation of (1H-Benzimidazol-2-ylmethyl)-(5,6,7,8-tetrahydro-quinolin-8-yl)-amine To a stirred solution of (2-aminomethyl)benzimidazole dihydrochloride hydrate (5.96 g, 27.1 mmol) in dry MeOH (225 mL) was added 6,7-dihydro-5H-quinolin-8-one (3.99 g, 27.1 mmol) and the mixture stirred at room temperature for 69 h. To the resultant solution was added sodium borohydride (2.06 g, 54.2 mmol) in two portions and the mixture stirred for 1.5 h. The reaction mixture was concentrated in vacuo and diluted with $CH_2Cl_2$ (150 mL). The organic layer was washed with saturated aqueous sodium bicarbonate (200 mL), the aqueous layer extracted with $CH_2Cl_2$ (2×50 mL) and the combined organic layers dried ($Na_2SO_4$), filtered, and concentrated in vacuo. Purification by column chromatography on silica gel ($CH_2Cl_2$/MeOH, 99:1 followed by 98:2 and 96:4) gave the intermediate amine (3.59 g, 50%) as a yellow foam. $^1$H NMR (CDCl$_3$) δ 1.66–1.90 (m, 3H), 1.91–2.00 (m, 1H), 2.00–2.17 (m, 1H), 2.33–2.69 (br m, 1H, 3.88–3.96 (m, 1H), 4.37 (d, 1H, J=3.0 Hz), 7.18–7.26 (m, 4H), 7.48 (d, 1H, J=6.0 Hz), 7.58–7.78 (br m, 1H), 8.55–8.58 (m, 1H); $^{13}$C NMR (CDCl$_3$) δ 19.66, 29.12, 30.24, 46.62, 57.28, 122.21, 122.83, 133.55, 138.07, 146.98, 156.17, 157.73.

EXAMPLE 1

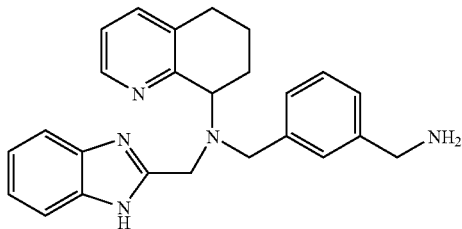

AMD9679: Preparation of N'-(1H-benzimidazol-2-ylmethyl)-N'-(5,6,7,8-tetrahydro-8-quinolinyl)-1,3-benzenedimethanamine To a stirred solution of 8-amino-5,6,7,8-tetrahydroquinoline (6.43 g, 43 mmol) in $CH_2Cl_2$ (450 mL) at room temperature was added 3-cyanobenzaldehyde (5.69 g, 43 mmol) and sodium triacetoxyborohydride (17.0 g, 80 mmol) and the mixture stirred 16 h. The reaction was quenched with 1N NaOH (200 mL) and the phases separated. The organic phase was dried ($Na_2SO_4$) and concentrated under reduced pressure to give a yellow oil (11.7 g) which was purified by flash chromatography on silica gel (97:3 $CH_2Cl_2$/$CH_3OH$) to provide N-(5,6,7,8-tetrahydro-8-quinolinyl)-3-cyanobenzylamine (9.10 g, 81%) as a pale yellow solid.

Using the General Procedure for N-Alkylation: A solution of the material from above (4.17 g, 15.8 mmol), potassium iodide (130 mg, 0.80 mmol) and N,N-diisopropylethylamine (5.2 mL, 30 mmol) in $CH_3CN$ (160 mL) was reacted with N-(tert-butoxycarbonyl)-2-chloromethylbenzimidazole (prepared as described by An, H.; Wang, T.; Mohan, V.; Griffey, R. H.; Cook, P. D *Tetrahedron* 1998, 54, 3999–4012) (4.22 g, 15.8 mmol). Purification of the crude material by flash chromatography on silica gel (1:1 EtOAc/hexanes) gave the alkylated product (6.86 g, 88%) as a yellow foam.

To a solution of the material from above (6.86 g, 13.9 mmol) in $NH_3$ saturated methanol (100 mL) in a Parr bottle was added Raney nicked (approx 1 g) and the mixture hydrogenated at 50 psi hydrogen in a Parr hydrogenator for 17 h. The product mixture was filtered through Celite 521 and the solvent from the eluent removed in vacuo. Purification of the crude material by flash chromatographed on silica gel (5% $CH_2Cl_2$/$CH_3OH$/$NH_4OH$, 19:1:0 followed by 18:1:1) gave AMD9679 (4.36 g, 79%) as a yellow foamy solid. $^1$H NMR (CDCl$_3$) δ 1.58–1.75 (m, 1H), 1.96–2.09 (m, 2H), 2.24–2.30 (m, 1H), 2.70–2.94 (m, 2H), 3.74 (s, 2H), 3.94–4.20 ((m, 3H), 7.07 (d, 1H, J=7.5 Hz), 7.15–7.21 (m, 4H), 7.30 (d, 1H, J=7.5 Hz), 7.36 (s, 1H, 7.43 (d, 1H, J=7.5 Hz), 7.47 (s br, 2H), 8.67 (d, 1H, J=4.2 Hz). $^{13}$C NMR (CDCl$_3$) δ 21.77, 23.70, 29.65, 46.47, 49.12, 54.51, 60.78, 121.93(2), 122.65, 126.45, 127.61, 127.98, 128.83, 135.23, 137.70, 140.08, 142.72, 147.27, 156.35, 157.72. ES-MS m/z 398 (M+H). Anal. Calcd. for $C_{25}H_{27}N_5 \cdot 1.0 H_2O \cdot 0.23 CH_2Cl_2$: C, 69.65; H, 6.82; N, 16.10. Found: C, 69.57; H, 69.91; N, 16.30.

EXAMPLE 2

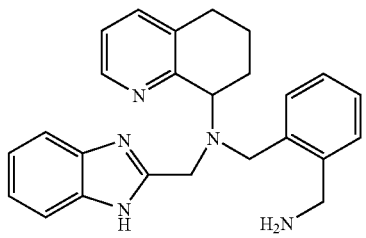

AMD9720: Preparation of (1H-Benzimidazol-2-ylmethyl)-(2-Aminomethyl-benzyl)-(5,6,7,8-tetrahydro-quinolin-8-yl)-amine (hydrobromide salt)

Preparation of [1-(tert-butoxycarbonyl)-(1H-Benzimidazol-2-ylmethyl)]-(2-cyano-benzyl)-(5,6,7,8-tetrahydro-quinolin-8-yl)-amine:

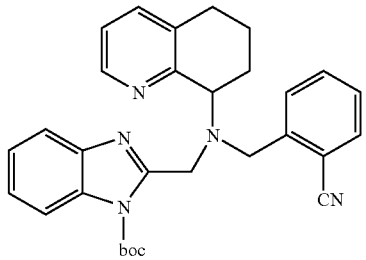

Following General Procedure B: To a solution of [1-(tert-butoxycarbonyl)-(1H-benzimidazol-2-ylmethyl)]-(5,6,7,8-tetrahydro-quinolin-8-yl)-amine (197 mg, 0.523 mmol) and 2-cyanobenzaldehyde (91.2 mg, 0.695 mmol) in $CH_2Cl_2$ (5 mL) was added NaBH(OAc)$_3$ (240 mg, 1.13 mmol) and the mixture stirred overnight. Purification of the resultant oil by flash chromatography (15 g silica, 50:1:1 $CH_2Cl_2$/$CH_3OH$/$NH_4OH$) gave the desired intermediate (167 mg, 65%). $^1$H NMR (CDCl$_3$) δ 1.72 (s, 9H), 1.91–2.15 (m, 2H), 2.31–2.42 (m, 1H), 2.62–2.86 (m, 2H), 4.12 (d, 1H, J=15.6 Hz), 4.29 (d, 1H, J=15.8 Hz), 4.38 (dd, 1H, J=9.6, 6.1 Hz), 4.64 (s, 2H), 6.93 (t, 1H, J=7.6 Hz), 7.00 (dd, 1H, J=7.5, 4.7 Hz), 7.14–7.32 (m, 5H), 7.58–7.69 (m, 3H), 8.44 (d, 1H, J=4.6 Hz).

To a solution of the material from above (101 mg, 0.204 mmol) in $NH_3$ saturated $CH_3OH$ (4 mL) in a Parr bottle was added Raney nickel (200 mg) and the mixture hydrogenated at 50 psi hydrogen in a Parr hydrogenator for 16 h. The product mixture was filtered through celite and the solvent from the eluent removed in vacuo. Purification of the crude material by flash chromatography (12 g silica, 50:1:1 $CH_2Cl_2/CH_3OH/NH_4OH$) afforded the deprotected freebase (30 mg, 37%).

Following General Procedure D: Conversion of the amine from above (30 mg) to the hydrobromide salt gave AMD9720 (39 mg, 77%). $^1$H NMR ($D_2O$) δ 1.80–1.97 (m, 1H), 2.17–2.37 (m, 2H), 2.42–2.54 (m, 1H), 2.99–3.08 (m, 2H), 3.91 (d, 1H, J=13.0 Hz), 4.16 (d, 2H, J=13.7 Hz), 4.32–4.41 (m, 2H), 4.54 (d, 1H, J=16.4 Hz), 6.89–7.00 (m, 2H, 7.15 (t, 1H, J=7.2 Hz), 7.41 (d, 1H, J=7.5 Hz), 7.48–7.61 (m, 4H), 7.88 (dd, 1H, J=7.7, 5.9 Hz), 8.36 (d, 1H. J=8.0 Hz), 8.71 (d, 1H, J=5.7 Hz). $^{13}$C NMR ($D_2O$) δ 20.46, 20.90, 27.92, 40.14, 48.91, 53.45, 62.31, 113.93 (2 carbons), 126.12, 126.79 (2 carbons), 129.35, 129.84, 129.98, 130.67, 131.52, 131.94, 135.10, 140.10, 141.02, 148.08 (2 carbons), 150.57, 150.88. ES-MS m/z 398 (M+H) Anal Calc. for $C_{25}H_{27}N_5 \cdot 3.0HBr \cdot 1.9H_2O$: C, 44.52; H, 5.05; N, 10.38; Br, 35.54. Found: C, 44.42; H, 4.97; N, 10.15; Br, 35.86.

EXAMPLE 3

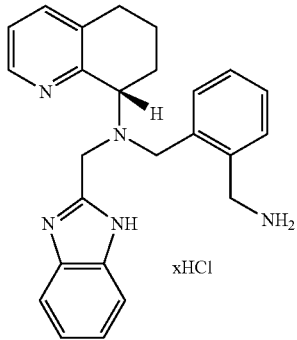

AMD11090: Preparation of (2-Aminomethyl-benzyl)-(1H-benzimidazol-2-ylmethyl)-(S)-5,6,7,8-tetrahydro-quinolin-8-yl-amine (hydrochloride salt)

Preparation of 2-(phthalamido-methyl)-benzaldehyde

To a stirred, cooled (0° C.) solution of 2-cyanobenzaldehyde (10.4 g, 79.0 mmol) in anhydrous THF (320 mL) was added LAH (14.3 g, 377 mmol) portionwise. The slurry was stirred under $N_2$ at room temperature for 15 h. The reaction was slowly quenched with distilled water (15 mL), then 15% (w/v) NaOH (15 mL) followed by more distilled water (45 mL). The mixture was stirred for 20 min, diluted with diethyl ether (200 mL) and the white fluffy precipitate was removed by filtration. The filtrate was dried ($MgSO_4$) and concentrated in vacuo. The resultant amino alcohol (12.6 g) was used without further purification in the next reaction.

A solution of the alcohol from above (assumed 79 mmol) and phthalic anhydride (12.3 g, 83 mmol) in 20% MeOH/$CHCl_3$ (200 mL) was stirred at reflux for 19 h. The mixture was cooled to room temperature and purified by flash chromatography (8 cm id, 300 g silica gel, eluted with 1% MeOH/$CH_2Cl_2$) followed by recrystallization from hot dichloromethane to give the desired alcohol as a pale pink solid (7.11 g, 34% over two steps).

To a stirred slurry of TPAP (465 mg, 1.3 mmol), NMO (4.7 g, 40 mmol) and 3 Å molecular seives (14 g) in $CH_2Cl_2$ (220 mL) was added dropwise a solution of the alcohol from above (7.11 g, 27 mmol) in $CH_2Cl_2$ (50 mL) over 30 min. The black slurry was stirred under $N_2$ for 40 min after the addition, concentrated in vacuo, and purified by flash chromatography (8 cm id., 300 g silica gel, eluted with EtOAc) to afford the pure title compound as a white solid (5.75 g, 82%). $^1$H NMR ($CDCl_3$) δ 5.38 (s, 2H), 7.24–7.28 (m, 1H), 7.44–7.54 (m, 2H), 7.74–7.78 (m, 2H), 7.85–7.92 (m, 3H), 10.35 (s, 1H).

Preparation of (2-Aminomethyl-benzyl)-(1H-benzimidazol-2-ylmethyl)-(S)-5,6,7,8-tetrahydro-quinolin-8-yl-amine (hydrochloride salt) (AMD11090)

Using General Procedure B: 2-(phthalamido-methyl)-benzaldehyde from above (5.44 g, 20.5 mmol) was reacted with S-(5,6,7,8-tetrahydro-quinolin-8-yl)-amine (3.34 g, 22.6 mmol) and $NaBH(OAc)_3$ (21.2 g, 100 mmol) in dichloromethane (2.0 L). Flash chromatography (8 cm id, 250 g silica gel, eluted with 5% MeOH/$CH_2Cl_2$) provided the pure 2° amine as a white foam (6.83 g, 84%).

To a solution of the amine from above (6.83 g, 17 mmol) in acetonitrile (170 mL) was added diisopropylethylamine (4.5 mL, 26 mmol), 1-boc-2-chloromethylbenzimidazole (5.0 g, 19 mmol), and potassium iodide (145 mg, 0.86 mmol). The mixture was stirred under an $N_2$ atmosphere at 60° C. for 15 h, cooled to room temperature and concentrated in vacuo. The residue was partitioned between dichloromethane (200 mL) and brine (100 mL). The separated organic layer was dried ($MgSO_4$), concentrated, and purified by flash chromatography (8 cm id, 300 g silica gel, eluted with $CH_2Cl_2$ to remove unreacted chloride then 2% MeOH/$CH_2Cl_2$ to remove desired product) to give the pure desired amine (7.6 g, 70%).

A solution of the amine from above (4.44 g, 7.1 mmol) in ethanol (35 mL) and dichloromethane (2 mL for solubility) was treated with hydrazine monohydrate (2.2 g, 44 mmol) and stirred for 16 h. The mixture was then concentrated in vacuo and purified by flash chromnatography (5 cm id., 80 g silica gel, eluted with 3% MeOH/$CH_2Cl_2$) to give the unprotected amine as a white foamy solid (2.05 g, 73%).

HCl gas was bubbled through a solution of the amine from above (2.05 g, 5.2 mmol) in glacial acetic acid (20 mL) for 10 min with stirring. The solution was allowed to stir at room temperature 5 min, then it was slowly dropped into diethyl ether (200 mL) with vigorous stirring. The resultant slurry was suction filtered through a glass fritted funnel and the filter cake was washed with diethyl ether (5×50 mL) and dried in a vacuum oven at 40° C. for 60 h to give AMD11090 as a white solid (2.71 g, 96%). $^1$H NMR ($D_2O$) δ 1.79–1.97 (m, 1H), 2.17–2.35 (m, 2H), 2.44–2.49 (m, 1H), 3.00–3.05 (m, 2H), 3.89 (d, 1H, J=13.5 Hz), 4.15 (d, 2H, J=14.1 Hz), 4.30–4.40 (m, 2H), 4.52 (d, 1H, J=16.4 Hz), 4.73–4.78 (m, 1H), 6.87–6.98 (m, 2H), 7.12 (td, 1H, J=1.2, 7.5 Hz), 7.38 (d, 1H, J=7.5Hz), 7.47–7.52 (m, 2H), 7.54–7.60 (m, 2H), 7.85–7.90 (m, 1H), 8.36 (d, 1H, J=8.1 Hz), 8.71 (d, 1H, J=5.1 Hz); $^{13}$C NMR ($D_2O$) δ 20.44, 20.86, 27.91, 40.16, 48.88, 53.52, 62.31, 113.91 (2 carbons), 126.15, 126.80 (2 carbons), 129.33, 129.78, 129.89, 130.58, 131.54, 131.96, 135.01, 140.03, 141.08, 148.19, 150.45, 150.82. ES-MS m/z 398 (M+H). Anal. Calcd. for $C_{25}H_{27}N_5 \cdot 3HCl \cdot 2H_2O \cdot 0.1CH_3COOH$: C, 55.14; H, 6.32; N, 12.76; Cl, 19.38. Found: C, 55.47; H, 6.50; N, 12.38; Cl, 19.26.

The enantiomeric purity of AMD11090 was determined to be 100% by chiral HPLC using the following conditions: Instrument: Hewlett Packard 1100 HPLC (VWD4); Column: ChiralCel OD, 0.46 cm×25 cm; Mobile Phases: A: 95:5 hexanes/methanol with 0.1% DEA, B: hexanes; Isocratic: 80% A, 20% B; Total Run Time: 45 min; Flow Rate: 0.5 mL/min; Temperature: 40° C.; Detector: UV @ 270 nm; Injection volume: 10 µL.

Retention time of the S enantiomer=28.7 min.
Retention time of the R enantiomer=32.6 min.

EXAMPLE 4

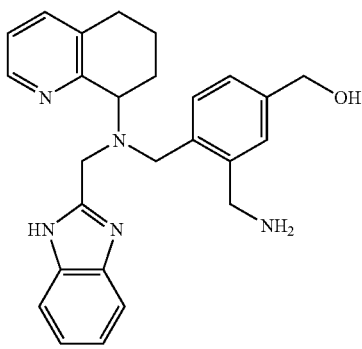

AMD11083: Preparation of (3-aminomethyl-4-{[(1H-benzoimidazol-2-ylmethyl)-(5,6,7,8-tetrahydro-quinolin-8-yl)-amino]-methyl}-phenyl)-methanol Preparation of 4-bromomethyl-3-cyano-benzoic acid methyl ester

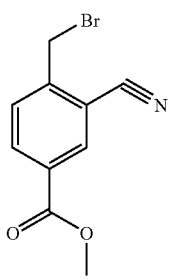

1,2-Dibromoethane (0.016 mL, 0.19 mmol) was added to a suspension of zinc dust (288 mg, 4.41 mmol) in THF (1 mL), and the mixture was heated to 70° C. for 10 minutes. The mixture was allowed to cool to room temperature, TMSCl (0.016 mL, 0.13 mmol) was added, and stirring was continued at room temperature for 30 minutes. The mixture was cooled to 0° C., a solution of methyl 4-(bromomethyl) benzoate (842 mg, 3.68 mmol) in THF (4 mL) was added over 2 h, and stirring was continued at 0° C. for 2 h. The mixture was cooled to −78° C., a solution of tosyl cyanide (571 mg, 3.15 mmol) in THF (4 mL) was added, and the mixture was stirred at room temperature for 18 h. The mixture was concentrated in vacuo, and the residue was partitioned between $CH_2Cl_2$ (20 mL) and saturated $NaHCO_3$ (aq) (20 mL). The aqueous phase was extracted with $CH_2Cl_2$ (3×10 mL), and the combined organic extracts were dried ($MgSO_4$) and concentrated in vacuo. Purification of the crude material by column chromatography on silica gel (10% EtOAc/hexanes) afforded colourless crystals (379 mg). This material was determined by $^1H$ NMR to be a mixture of 3-cyano-4-methyl-benzoic acid methyl ester and an unidentified by-product and was used in the next step without further purification.

A mixture of the nitrile from above (379 mg), NBS (400 mg, 2.25 mmol), and AIBN (53 mg, 0.32 mmol) in $CCl_4$ (11 mL) was heated at reflux for 4 days then allowed to cool to room temperature. The mixture was filtered, and the filtrate was concentrated in vacuo. Purification of the crude material by column chromatography on silica gel (5% EtOAc/hexanes) afforded colourless crystals (100 mg, 12%). $^1H$ NMR ($CDCl_3$) δ 3.96 (s, 3H), 4.66 (s, 2H), 7.65 (d, 1H, J=8.1 Hz), 8.23 (dd, 1H, J=8.1, 1.5 Hz), 8.33 (d, 1H, J=1.5 Hz).

A mixture of 2-[(5,6,7,8-tetrahydro-quinolin-8-ylamino)-methyl]-benzoimidazole-1-carboxylic acid tert-butyl ester (175 mg, 0.462 mmol), 4-bromomethyl-3-cyano-benzoic acid methyl ester (98 mg, 0.39 mmol), potassium iodide (4 mg, 0.02 mmol), and N,N-diisopropylethylamine (0.10 mL, 0.57 mmol) in acetonitrile (4.0 mL) was heated at 60° C. for 16 h. Saturated $NaHCO_3$(aq) (15 mL) was added, and the mixture was extracted with $CH_2Cl_2$ (3×10 mL). The organic extracts were dried ($MgSO_4$) and concentrated in vacuo. Purification of the crude material on silica gel (500:5:1 $CH_2Cl_2$/MeOH/$NH_4OH$) gave a yellow oil (213 mg, 100%). $^1H$ NMR ($CDCl_3$) δ 1.73 (m, 10H), 2.01 (m, 2H), 2.38 (m, 1H), 2.76 (m, 2H), 3.86 (s, 3H), 4.17 (d, 1H, J=17 Hz), 4.29 (d, 1H, J=17 Hz), 4.37 (m, 1H), 4.58 (d, 1H, J=14Hz), 4.69 (d, 1H, J=14 Hz), 7.01 (dd, 1H, J=7.5, 4.5 Hz), 7.18 (m, 2H), 7.31 (d, 1H, J=7.5 Hz), 7.58 (m, 2H), 7.76 (d, 2H, J=1.2 Hz), 7.87 (s, 1H), 8.44 (m, 1H).

A solution of 2-{[(2-cyano-4-methoxycarbonyl-benzyl)-(5,6,7,8-tetrahydro-quinolin-8-yl)-amino]-methyl}-benzoimidazole-1-carboxylic acid tert-butyl ester (213 mg, 0.386 mmol) in saturated $NH_3$(g)/MeOH (10 mL) was shaken at room temperature with a suspension of Raney® nickel (1.5 g) under hydrogen atmosphere (45 psi) for 17 h. The catalyst was removed by filtration, and the filtrate was concentrated in vacuo to give a green foam (195 mg).

To a solution of the crude amine from above (195 mg) in THF (4 mL) was added di-t-butyl dicarbonate (220 mg, 1.01 mmol), and the solution was stirred at room temperature for 3 days. The solution was concentrated in vacuo, and the residue was filtered through silica gel (600:5:1 $CH_2Cl_2$/MeOH/$NH_4OH$) to give a yellow foam (130 mg).

To a solution of the crude ester from above (130 mg) in THF (2 mL) was added $LiAlH_4$ (1.0 M/THF, 0.20 mL, 0.20 mmol) at 0° C., and the mixture was stirred at 0° C. for 15 minutes. Methanol (1 mL) was added followed by 10% HCl(aq) (1 mL). The mixture was made basic with saturated $NaHCO_3$(aq) (30 mL) then extracted with $CH_2Cl_2$ (4×12 mL). The combined organic extracts were dried ($MgSO_4$) and concentrated in vacuo to give a yellow foam (116 mg).

A solution of the crude alcohol from above (116 mg) in 3:1 TFA/$CH_2Cl_2$ (4 mL) was stirred at room temperature for 50 minutes then concentrated in vacuo. The residue was partitioned between $CH_2Cl_2$ (10 mL) and 1 N NaOH(aq) (15 mL), and the aqueous phase was extracted with $CH_2Cl_2$ (2×10 mL). The combined organic extracts were dried ($MgSO_4$) and concentrated in vacuo. Purification of the crude material by column chromatography on silica gel (200:5:1–50:5:1 $CH_2Cl_2$/MeOH/$NH_4OH$) afforded AMD11083 as a yellow foam (25 mg, 12%). $^1H$ NMR ($CDC_3$) δ 1.54 (m, 1H), 1.93 (m, 2H), 2.19 (m, 1H), 2.57–2.80 (m, 2H), 3.52–3.88 (m, 7H), 4.54 (s, 2H), 6.93 (m, 1H), 7.04 (d, 1H, J=7.5 Hz), 7.15 (m, 4H), 7.25 (m, 1H), 7.54 (m, 2H), 2H), 8.39 (d, 1H, J=3.6 Hz); $^{13}$C NMR (CDCl$_3$) δ 21.77, 21.94, 29.47, 43.14, 49.34, 53.99, 59.72, 64.62, 115.42, 122.27, 122.36, 126.33, 129.10, 131.52, 135.04, 135.66, 137.51, 141.25, 142.14, 147.24, 154.27, 156.94. 923 ES-MS m/z 428 (M+H). Anal. Calcd. for C$_{26}$H$_{29}$N$_5$O.0.2H$_2$O.1.2CH$_2$Cl$_2$: C, 61.29; H, 6.01; N, 13.14. Found: C, 61.36; H, 6.02; N, 12.84.

EXAMPLE 5

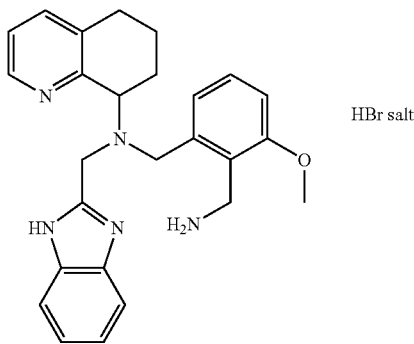

AMD11120: Preparation of (2-Aminomethyl-3-methoxy-benzyl)-(1H-benzimidazol-2-ylmethyl)-(5,6,7,8-tetrahydro-quinolin-8-yl)-amine(hydrobromide salt)

To a solution of ethyl 2-methoxy-6-methylbenzoate (1.23 g, 6.33 mmol) in dry diethyl ether (58 mL) was added LiAlH$_4$ (0.467 g, 12.31 mmol) and the resultant mixture was heated to reflux for 2 hours then cooled to room temperature. The mixture was treated sequentially with water (0.45 mL), 15% aqueous NaOH (0.45 mL) and water (1.35 mL). The mixture was filtered through Celite® and the cake was washed with ether (200 mL). The filtrate was concentrated under reduced pressure and provided 0.96 g (99%) of 2-methoxy-6-methylbenzyl alcohol as a yellow solid. $^1$H NMR (CDCl$_3$) δ 2.27 (t, 1H, J=6.3 Hz), 2.39 (s, 3H), 3.86 (s, 3H), 4.75 (d, 2H, J=6.3 Hz), 6.76 (d, 1H, J=8.4 Hz), 6.81 (d, 1H, J=7.8 Hz), 7.17 (dd, 1H, J=7.8, 8.4 Hz).

To a solution of 2-methoxy-6-methylbenzyl alcohol (0.96 g, 6.32 mmol) in CH$_2$Cl$_2$ (35 mL) was added triethylamine (2.00 mL, 14.35 mmol) followed by methanesulfonyl chloride (0.90 mL, 11.63 mmol) and the resultant solution was heated at 40° C. for 45 minutes then cooled to room temperature. The mixture was diluted with CH$_2$Cl$_2$ (35 mL), washed with brine (3×15 mL), dried (Na$_2$SO$_4$), and concentrated to provide a pale yellow solid. The solid (1.12 g) was dissolved in DMF (35 mL), treated with potassium phthalimide (2.62 g, 14.15 mmol), and heated at 80° C. overnight. The mixture was cooled to room temperature and diluted with EtOAc (70 mL), brine (35 mL), and water (20 mL). The phases were separated and the organic phase was washed with 1.0 N NaOH (6×10 mL) and brine (2×20 mL). The organic phase was dried (MgSO$_4$) and concentrated to provide an pale yellow solid. The solid was rinsed with hexanes (3×10 mL) and provided 1.18 g (66%) of (2-methoxy-6-methylbenzyl)phthalimide as a white solid. $^1$H NMR (CDCl$_3$) δ 2.53 (s, 3H), 3.75 (s, 3H), 4.89 (s, 2H), 6.70 (d, 1H, J=8.4 Hz), 6.80 (d, 1H, J=7.5 Hz), 7.15 (dd, 1H, J=7.5, 8.4 Hz), 7.66–7.68 (m, 2H), 7.76–7.80 (m, 2H); $^{13}$C NMR (CDCl$_3$) δ 20.27, 34.95, 55.90, 108.61, 122.38, 123.17, 123.41, 128.97, 132.60, 134.07, 139.55, 158.70, 168.36.

To a solution of (2-methoxy-6-methylbenzyl)phthalimide (0.286 g, 1.02 mmol) in CC$_4$ (25 mL) was added recrystallized N-bromosuccinimide (0.177 g, 0.99 mmol) followed by benzoyl peroxide (28 mg, 0.11 mmol). The resultant mixture was heated to reflux for 90 minutes then cooled to room temperature. The mixture was diluted with diethyl ether (25 mL), filtered through filter paper, and the filtrate was concentrated. Purification of the crude material by column chromatography (3:1 hexanes-EtOAc) provided 0.31 g (86%) of (6-(bromomethyl)-2-methoxybenzyl)phthalimide as a white solid. $^1$H NMR (CDCl$_3$) δ 3.78 (s, 3H), 4.90 (s, 2H), 5.00 (s, 2H), 6.83 (d, 1H, J=8.4 Hz), 6.98 (d, 1H, J=7.2 Hz), 7.25 (dd, 1H, J=7.2, 8.4 Hz), 7.67–7.69 (m, 2H), 7.78–7.81 (m, 2H). ES-MS m/z 382 (M+Na), 384 (M+Na).

To a solution of (1-tert-butoxycarbonyl-1H-Benzimidazol-2-ylmethyl)-(5,6,7,8-tetrahydro-quinolin-8-yl)-amine (0.202 g, 0.53 mmol) in CH$_3$CN (5 mL) was added N,N-diisopropylethylamine (0.20 mL, 1.15 mmol) followed by a suspension of (6-(bromomethyl)-2-methoxybenzyl)phthalimide (0.30 g, 0.83 mmol) in CH$_3$CN (5 mL). The resultant mixture was heated to 60° C. for 18 hours then cooled to room temperature. The mixture was concentrated and the residue was partitioned between CH$_2$Cl$_2$ (40 mL) and brine (10 mL). The phases were separated and the aqueous phase was extracted with CH$_2$Cl$_2$ (3×10 mL). The combined organic extracts were dried (Na$_2$SO$_4$) and concentrated. Purification of the crude material by column chromatography on silica gel (50:1 CH$_2$Cl$_2$—CH$_3$OH) provided 0.212 g (60%) of a white solid.

The solid (0.21 g) from above was dissolved in ethanol (6 mL), treated with hydrazine monohydrate (0.31 mL, 6.4 mmol), and stirred at room temperature overnight. The mixture was concentrated and CH$_2$Cl$_2$ (50 mL) was added to the residue. The resultant suspension was filtered through Celite® and the cake was washed with CH$_2$Cl$_2$ (50 mL). The filtrate was concentrated under reduced pressure and the residue was partitioned between CH$_2$Cl$_2$ (40 mL) and 1.0 N NaOH (10 mL). The phases were separated and the aqueous phase was extracted with CH$_2$Cl$_2$ (3×10 mL). The combined organic extracts were dried (Na$_2$SO$_4$) and concentrated. Purification of the crude material by radial chromatography on silica gel (1 mm plate, 50:1:1 CH$_2$Cl$_2$—CH$_3$OH—NH$_4$OH) provided 30 mg (22%) of the free base of the title compound as a white solid.

Using General Procedure D: Conversion of the solid from above (30 mg, 0.071 mmol) to the hydrobromide salt followed by re-precipitation of the intermediate solid from methanol/ether gave AMD11120 (34 mg, 67%) as a white solid. $^1$H NMR (D$_2$O) δ 1.91–1.99 (m, 1H), 2.20–2.38 (m, 2H), 2.46–2.50 (m, 1H), 3.05–3.13 (m, 2H), 3.38 (s, 3H), 3.90 (d, 1H, J=12.9 Hz), 4.11 (d, 1H, J=12.9 Hz), 4.16 (d, 1H, J=12.9 Hz), 4.29 (d, 1H, J=12.9 Hz), 4.34 (d, 1H, J=16.5 Hz), 4.54 (d, 1H, J=16.5 Hz), 4.74–4.79 (m, 1H, overlaps with HOD), 6.50 (d, 1H, J=8.4 Hz), 7.01 (d, 1H, J=7.8 Hz), 7.21 (dd, 1H, J=7.8, 8.4 Hz), 7.52–7.61 (m, 4H), 7.94 (dd, 1H, J=6.0, 7.8 Hz), 8.42 (d, 1H, J=7.8 Hz), 8.77 (d, 1H, J=6.0 Hz); $^{13}$C NMR (D$_2$O) δ 20.44, 20.98, 27.93, 35.25, 48.97, 53.77, 55.72, 62.69, 111.43, 113.85, 119.53, 124.35, 126.25, 126.89, 130.42, 131.20, 136.39, 139.95, 141.28, 148.39, 150.35, 151.05, 157.88. ES-MS m/z 428 (M+H). Anal. Calcd. for C$_{26}$H$_{22}$N$_5$O.3.0HBr.2.8H$_2$O: C, 43.33; H, 5.26; N, 9.72; Br, 33.26. Found: C 43.47; H, 5.14; N, 9.61; Br, 33.00.

EXAMPLE 6

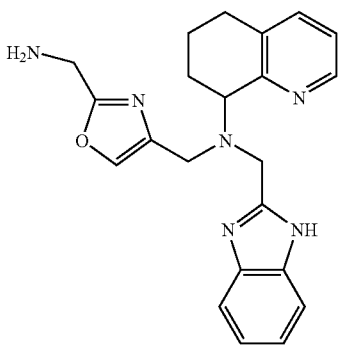

AMD9903: Preparation of (2-Aminomethyl-oxazol-4-ylmethyl)-(1H-benzoimidazol-2-ylmethyl)-(5,6,7,8-tetrahydro-quinolin-8-yl)-amine (hydrobromide salt)

Preparation of (4-hydroxymethyl-oxazol-2-ylmethyl)-carbamic acid tert-butyl ester

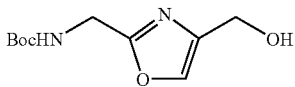

Using the procedure of P. Wipf et al. (A. J. Phillips, Y. Uto, P. Wipf, M. J. Reno and D. R. Williams *Org. Lett.* 2000, 2(8), 1165–1168), a −20° C. solution of N-(t-butoxycarbonyl)-Gly-Ser-OMe (170 mg, 0.615 mmol) in dichloromethane (5 mL) was treated with bis(2-methoxyethyl) aminosulfur trifluoride (0.125 mL, 0.677 mmol). The resulting solution was then stirred at −20° C. for 30 minutes, and bromotrichloromethane (0.212 mL, 2.21 mmol) was added, followed by DBU (0.330 mL, 2.21 mmol). The reaction was allowed to warm to 0° C., and was stirred at that temperature for 5 hours, then aqueous ammonium chloride (5 mL) was added. After separation of the aqueous and organic layers, the aqueous layer was extracted twice with dichloromethane. The combined organic fractions were then dried over anhydrous sodium sulfate and concentrated. Purification by chromatography on silica gel (2% methanol in dichloromethane), gave 2-(tert-butoxycarbonylamino-methyl)-oxazole-4-carboxylic acid methyl ester as an oil (123 mg, 78%). $^1$H NMR (CDCl$_3$) δ 1.25 (s, 9H), 3.88 (s, 3H), 4.51 (d, 2H, J=5.8 Hz), 5.22 (br s, 1H), 8.19 (s, 1H)

The ester (178 mg, 0.695 mmol) in 0° C. dichloromethane (8 mL) was treated with DIBAL-H (1 M in dichloromethane, 2.08 mL, 2.08 mmol). The mixture was then stirred at 0° C. for 2 hours before being treated with aqueous 5% sodium potassium tartrate (8 mL). The mixture was stirred rapidly for 30 minutes (until the aqueous and organic layers clarified), and the layers were then separated. The aqueous layer was extracted twice with dichloromethane. The combined organic fractions were then dried over anhydrous sodium sulfate and concentrated. Purification by chromatography on silica gel (5% methanol in dichloromethane) gave (4-hydroxymethyl-oxazol-2-ylmethyl)-carbamic acid tert-butyl ester as an oil (45 mg, 28%). $^1$H NMR (CDCl$_3$) δ 1.40 (s, 9H), 4.43 (d, 2H, J=5.6 Hz), 4.56 (s, 2H), 5.37 (s, 1H), 7.54 (s, 1H).

To a stirred solution of (4-hydroxymethyl-oxazol-2-ylmethyl)-carbamic acid tert-butyl ester (45 mg, 0.197 mmol) in dichloromethane (5 mL) was added triethylamine (0.055 mL, 0.4 mmol) followed by methanesulfonyl chloride (0.023 mL, 0.3 mmol). The resultant solution was stirred at room temperature for 20 minutes, before being treated with an aqueous saturated ammonium chloride solution (5 mL). The aqueous layer was extracted twice with dichloromethane. The combined organic fractions were then dried over anhydrous sodium sulfate and concentrated to afford the desired mesylate, which was used directly and immediately in the next reaction without further purification. $^1$H NMR (CDCl$_3$) δ 1.45 (s, 9H), 3.07 (s, 3H), 4.43 (d, 2H, J=5.6 Hz), 5.15 (s, 2H), 7.73 (s, 1H).

Using General Procedure for N-Alkylation, methanesutfonic acid 2-(tert-butoxycarbonylamino-methyl)-oxazol-4-ylmethyl ester (0.197 mmol) was stirred in 60° C. acetonitrile (5 mL) for 4 hours with diisopropylethylamine (0.05 mL, 0.295 mmol) and (1H-N-t-butoxycarbonyl-benzimidazol-2-ylmethyl)-(5,6,7,8-tetrahydroquinolin-8-yl)-amine (95 mg, 0.25 mmol). The reaction was then cooled and concentrated. The residue was taken up in dichloromethane and extracted with aqueous ammonium chloride, dried, concentrated and purified by chromatography on silica gel (20:1 dichloromethane:methanol) to afford 2-{[[2-(tert-Butoxycarbonylamino-methyl)-oxazol-4-ylmethyl]-(5,6,7,8-tetrahydro-quinolin-8-yl)-amino]-methyl}-benzoimidazole-1-carboxylic acid tert-butyl ester (23 mg, 19%). $^1$H NMR (CDCl$_3$) δ 1.46 (s, 9H), 1.63 (s, 9H), 1.91 (m, 1H), 2.02 (m, 1H), 2.24 (dq, 1H, J=6.8, 2.1 Hz), 2.51 (m, 1H), 2.61–2.78 (m, 2H), 4.27 (m, 1H), 4.43 (d, 2H, J=5.8 Hz), 4.49 (s, 2H), 4.73 (d, 1H, J=16.1 Hz), 5.09 (d, 1H, J=16.1 Hz, 5.15 (m, 1H), 6.88 (dd, 1H, J=7.1, 5.4 Hz), 7.13 (d, 1H, J=7.1 Hz), 7.24 (m, 2H), 7.61 (s, 1H), 7.61 (m, 1H), 7.74 (m, 1H), 8.23 (d, 1H, J=5.4 Hz).

2-{[[2-(tert-Butoxycarbonylamino-methyl)-oxazol-4-ylmethyl]-(5,6,7,8-tetrahydro-quinolin-8-yl)-amino]-methyl}-benzoimidazole-1-carboxylic acid tert-butyl ester (23 mg 0.039 mmol), was taken up in acetic acid (1 mL), to which a saturated solution of HBr in acetic acid (1 mL) was added. The mixture was then stirred, precipitated and isolated as per procedure D to yield AMD9903 as a white crystalline solid (14 mg). $^1$H NMR (D$_2$O). δ 1.84 (m, 1H), 2.05 (m, 2H), 2.21 (m, 1H), 3.00 (m, 2H), 3.72 (d, 1H, J=14.1 Hz), 3.92 (d, 1H, J=14.1 Hz), 3.99 (d, 2H, J=6.0 Hz), 4.39 (d, 1H, J=16.5 Hz), 4.58 (d, 1H, J=16.5 Hz), 4.72 (m, 1H), 7.59 (m, 2H), 7.75 (m, 2H), 7.84 (s, 1H), 7.86 (m, 1H), 8.33 (d, 1H, J=8.1 Hz), 8.67 (d, 1H, J=5.8 Hz). $^{13}$C NMR (D$_2$O) δ 20.35, 20.57, 27.62, 35.70, 46.40, 48.16, 60.94, 114.15 (2C), 125.95, 127.06 (2C), 139.57, 140.46, 148.03, 151.23, 154.96. ES-MS m/z 389 (M+H); Anal. Calcd. for (C$_{22}$H$_{24}$N$_6$O×4 HBr× 2.6 H$_2$O): C, 34.82; H, 4.41; N, 11.07; Br, 42.11. Found: C, 35.10; H, 4.44; N, 10.73; Br, 41.80.

EXAMPLE 7

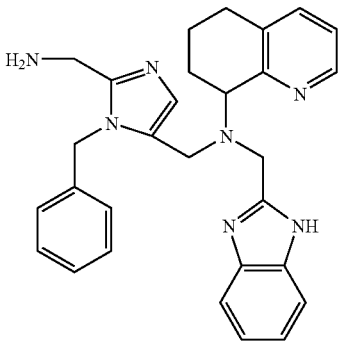

AMD9986: Preparation of (1H-Benzimidazol-2-ylmethyl)-(5,6,7,8-tetrahydroquinolin-8-yl)-[(1-benzyl-2-aminomethyl)-imidazol-5-ylmethyl)]-amine Preparation of 2,5-bis-(hydroxymethyl)-N-benzylimidazole

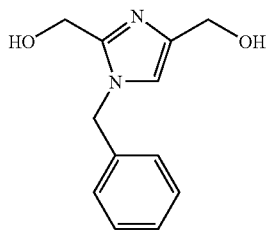

Using the procedure of S. Zimmerman et al. (S. C. Zimmerman, K. D. Cramer and A. A. Galan *J. Org. Chem.* 1989, 54, 1256–1264) N-Benzylimidazole (15 g, 95 mmol) was treated with formaldehyde (60 mL of a 37% aqueous solution), to which glacial acetic acid (8 mL) and sodium acetate (10.5 g) were added. The resulting mixture was stirred until homogeneous, then was transferred to a thick-walled glass tube, which was sealed and placed in a 140° C. oil bath for 12 hours. The tube was then cooled, concentrated, made basic with 10N NaOH, and extracted twice with a 10:1 isopropanol:chloroform mixture. The combined organic fractions were then dried over anhydrous sodium sulfate and concentrated. Purification by chromatography on silica gel (7% methanol in dichloromethane) gave 2,5-bis-(hydroxymethyl)-N-benzylimidazole as a white crystalline solid (4.9 g, 24%). $^1$H NMR (CDCl$_3$) δ 4.41 (s, 2H), 4.48 (s, 2H), 5.36 (s, 2H), 6.77 (s, 1H), 7.00 (m, 2H), 7.28 (m, 3H).

To a solution of 2,5-bis-(hydroxymethyl)-N-benzylimidazole (436 mg, 2.0 mmol) in dichloromethane (10 mL) was added triethylamine (0.35 mL, 2.0 mmol) and acetic anhydride (0.19 mL, 2.0 mmol). The mixture was then stirred overnight (16 h) at room temperature. The reaction was then washed with aqueous ammonium chloride and the layers separated. The aqueous layer was extracted twice with dichloromethane. The combined organic fractions were then dried over anhydrous sodium sulfate and concentrated. Purification by chromatography on silica gel (5% methanol in dichloromethane) gave the monoacetate, 2-acetoxymethyl-5-hydroxymethyl-N-benzylimidazole, as a white powder (300 mg, 58%). $^1$H NMR (CDCl$_3$) δ 1.83 (s, 3H), 4.49 (s, 2H), 5.06 (s, 2H), 5.33 (s, 2H), 6.97 (m, 2H), 7.28 (m, 3H).

To a stirred solution of 2-acetoxymethyl-5-hydroxymethyl-N-benzylimidazole (130 mg, 0.5 mmol) in dichloromethane (5 mL) was added triethylamine (0.104 mL, 0.75 mmol) followed by methanesulfonyl chloride (0.046 mL, 0.6 mmol). The resultant solution was stirred at room temperature for 20 minutes, before being treated with an aqueous saturated ammonium chloride solution (5 mL). The aqueous layer was extracted twice with dichloromethane. The combined organic fractions were then dried over anhydrous sodium sulfate and concentrated to afford the desired mesylate, which was used directly and immediately in the next reaction without further purification. $^1$H NMR (CDCl$_3$) δ 1.86 (s, 3H), 4.44 (s, 2H), 5.18 (s, 2H), 5.29 (s, 2H), 6.97 (m, 2H), 7.33 (m, 3H).

Using General Procedure for N-Alkylation, O-methanesulfonyl-2-acetoxymethyl-5-hydroxymethyl-N-benzylimidazole (0.5 mmol) was stirred in 60° C. acetonitrile (5 mL) for 4 hours with diisopropylethylamine (0.130 mL, 0.75 mmol) and (1H-N-t-butoxycarbonyl-benzimidazol-2-ylmethyl)-(5,6,7,8-tetrahydroquinolin-8-yl)-amine (226 mg, 0.6 mmol). The reaction was cooled and concentrated. The residue was taken up in dichloromethane and extracted with aqueous ammonium chloride, dried, concentrated and purified by chromatography on silica gel (20:1 dichloromethane:methanol) to afford [N-(t-butoxycarbonyl)-benzimidazol-2-ylmethyl]-(5,6,7,8-tetrahydroquinolin-8-yl)-[(2-acetoxymethyl-N-benzylimidazol-5-yl)-methyl]-amine along with the product resulting from cleavage of the acetate group (mixture, 138 mg).

The mixture of products from above (138 mg) was treated with potassium carbonate (100 mg) in methanol (5 mL) and the suspension was stirred for 8 hours at room temperature. The mixture was then filtered and concentrated, and the residue purified by silica gel flash chromatography using a 20:1 dichloromethane:methanol mixture as an eluent to afford [1H-benzimidazol-2-ylmethyl]-(5,6,7,8-tetrahydroquinolin-8-yl)-[(2-hydroxymethyl-N-benzylimidazol-5-yl)-methyl]-amine as a pale yellow foam (100 mg, 43% for 2 steps). $^1$H NMR (CDCl$_3$) δ 1.61 (m, 1H), 1.89 (m, 2H), 2.15 (m, 1H), 2.70 (m, 2H), 3.56 (d, 1H, J=15.1 Hz), 3.68 (d, 1H, J=15.1 Hz), 4.00 (s, 2H), 4.01 (m, 1H), 4.35 (s, 2H), 5.28 (s, 2H), 6.64 (m, 2H), 6.88 (s, 1H), 7.07 (m, 4H), 7.17 (m, 2H), 7.34 (d, 1H, J=7.8 Hz), 7.54 (br s, 1H), 8.45 (d, 1H, J=4.8 Hz).

To a solution of [1H-benzimidazol-2-ylmethyl]-(5,6,7,8-tetrahydroquinolin-8-yl)-[(2-hydroxymethyl-N-benzylimidazol-5-yl)-methyl]-amine (81 mg, 0.17 mmol) in dichloromethane (5 mL) was added triethylamine (0.095 mL, 0.68 mmol) followed by methanesulfonyl chloride (0.040 mL, 0.5 mmol). The resultant solution was stirred at room temperature for 20 minutes, before being treated with an aqueous saturated ammonium chloride solution (5 mL). The aqueous layer was extracted twice with dichloromethane. The combined organic fractions were then dried over anhydrous sodium sulfate and concentrated to afford the desired mesylate, which was used directly and immediately in the next reaction without further purification.

To a solution of the mesylate (0.17 mmol) in DMF (2 mL) and dichloromethane (2 mL) was added sodium azide (33 mg, 0.51 mmol). The mixture was then heated to 50° C. for 2 hours. After cooling, the solution was washed with 1N NaOH (5 mL), and extracted repeatedly with dichloromethane. The combined organic fractions were then dried over anhydrous sodium sulfate, concentrated, and purified by silica gel flash chromatography using a 20:1 dichlororomethane:methanol mixture as an eluent to afford [1H-benzimidazol-2-ylmethyl]-(5,6,7,8-tetrahydroquinolin-8-yl)-[(2-azamethyl-N-benzylimidazol-5-yl)-methyl]-amine as a white foam (34 mg, 40% over 2 steps). ¹H NMR (CDCl₃) δ 1.68 (m, 1H), 1.95 (m, 2H), 2.44 (m, 1H), 2.88 (m, 2H), 2.64 (d, 1H, J=16.1 Hz), 3.79 (s, 2H), 4.09 (m, 1H), 4.11 (d, 1H, J=13.8 Hz), 4.18 (d, 1H, J=13.8 Hz), 4.49 (d, 1H, J=12.8 Hz), 5.71 (d, 1H, J=16.1 Hz), 6.70 (m, 2H), 6.90 (m, 1H), 6.91 (s, 1H), 7.18 (m, 2H), 7.20 (m, 1H), 7.32 (m, 3H), 7.58 (d, 1H, J=8.1 Hz), 7.81 (m, 1H), 8.09 (d, 1H, J=4.9 Hz).

To a solution of [1H-benzimidazol-2-ylmethyl]-(5,6,7,8-tetrahydroquinolin-8-yl)-[(2-azamethyl-N-benzylimidazol-5-yl)-methyl]-amine (34 mg, 0.068 mmol) in methanol (10 mL) was added 5% palladium on calcium carbonate (Lindlar's catalyst, 30 mg). The suspension was then placed under 1 atm hydrogen gas pressure, and was stirred for 12 hours at room temperature. The mixture was then filtered, and the filtrate concentrated to afford [1H-benzimidazol-2-ylmethyl]-(5,6,7,8-tetrahydroquinolin-8-yl)-[(2-aminomethyl-N-benzylimidazol-5-yl)-methyl]-amine (23 mg, 71%) as a white foam. ¹H NMR (CDCl₃) δ 1.68 (m, 1H), 2.02 (m, 2H), 2.35 (m, 1H), 2.64 (m, 2H), 3.48 (br s, 2H, NH₂), 3.80 (m, 2H), 3.87 (s, 2H), 4.01 (m, 1H), 4.16 (d, 1H, J=15.3 Hz), 4.51 (d, 1H, J=15.3 Hz), 5.26 (d, 1H, J=16.1 Hz), 5.73 (d, 1H, J=16.1 Hz), 6.71 (m, 2H), 6.94 (m, 2H, 7.16 (m, 2H), 7.22 (m, 2H), 7.24 (s, 1H), 7.32 (m, 2H), 7.66 (m, 1H), 7.85 (m, 1H), 8.08 (d, 1H, J=4.8 Hz).

[1H-benzimidazol-2-ylmethyl]-(5,6,7,8-tetrahydroquinolin-8-yl)-[(2-aminomethyl-N-benzylimidazol-5-yl)-methyl]-amine (23 mg, 0.048 mmol) was taken up in acetic acid (1 mL), to which a saturated solution of HBr in acetic acid (1 mL) was added. The mixture was then stirred, precipitated and isolated as per procedure D to yield AMD9986 as a white crystalline solid (19 mg). ¹H NMR (D₂O). δ 1.77 (m, 1H), 2.01 (m, 2H), 2.20 (m, 1H), 2.78 (m, 2H), 3.53 (d, 1H, J=1.48 Hz), 4.00 (d, 1H, J=14.8 Hz), 4.29 (m, 2H), 4.41 (d, 1H, J=15.3 Hz), 4.53 (d, 1H, J=15.3 Hz), 4.58 (m, 1H), 5.30 (m, 2H), 6.76 (m, 2H), 7.19 (m, 4H), 7.51 (s, 1H), 7.64 (m, 2H), 7.82 (m, 2H), 8.28 (d, 1H, J=7.8 Hz), 8.63 (d, 1H, J=4.9 Hz). ¹³C NMR (D₂O) δ 20.01, 20.19, 27.69, 33.06, 33.81, 45.27, 48.21, 48.74, 59.46, 114.36, 125.27, 125.72, 125.89, 126.09, 127.24, 129.02, 129.71, 130.91, 130.99, 133.72, 138.88, 140.95, 141.29, 148.26, 149.94. ES-MS m/z 478 (M+H); Anal. Calcd. for (C₂₂H₂₄N₆O×4 HBr×2.5 H₂O×0.7 HOAc): C, 41.10; H, 4.86; N, 11.04; Br, 35.98. Found: C, 41.16; H, 4.82; N, 11.04; Br, 36.06.

EXAMPLE 8

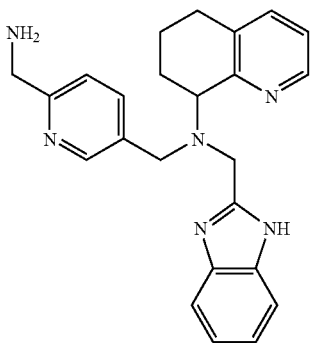

AMD9813: Preparation of 6-aminomethylpyridin-3-ylmethyl-(1H-benzimidazol-2-ylmethyl)-(5,6,7,8-tetrahydroquinolin-8-yl)-amine Preparation of 3-hydroxymethyl-6-cyanopyridine

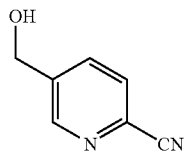

To a solution of ethyl-6-cyanonicotinate (prepared as per T. Sakamoto, S. Kaneda, S. Nishimura and H. Yamanaka Chem. Pharm. Bull. 1985, 33, 565) (1.58 g, 8.97 mmol) in MeOH (40 mL) was added NaBH₄ (1.00 g, 26.4 mmol) and the reaction stirred at room temperature for 8 h. After removal of the solvent, the residue was taken up in 15% NaOH (5 mL) and stirred for 20 min. The mixture was then extracted repeatedly with CH₂Cl₂, and the combined organic fractions were dried (Na₂SO₄), filtered and concentrated under reduced pressure. Purification of the residue by chromatography on silica gel (EtOAc/hexanes, 1:1) afforded 3-hydroxymethyl-6-cyanopyridine (414 mg, 34%). ¹H NMR (CDCl₃) δ 5.16 (s, 2H), 7.69 (d, 1H, J=6.8 Hz), 7.84 (d, 1H, J=6.8 Hz), 8.71 (s, 1H).

Using General Procedure C: To a solution of 3-hydroxymethyl-6-cyanopyridine (30 mg, 0.222 mmol) in CH₂Cl₂ (2 mL) was added methanesulfonyl chloride (0.022 mL, 0.289 mmol) and triethylamine (0.046 mL, 0.333 mmol) and the mixture stirred for 60 min at room temperature. Purification of the crude product by chromatography on silica gel (10:1 CH₂Cl₂/MeOH) gave the desired mesylate as a pale yellow solid (22 mg, 47%). ¹H NMR (CDCl₃) δ 3.14 (s, 3H), 5.32 (s, 2H), 7.75 (d, 1H, J=6.8 Hz), 7.91 (d, 1H, J=6.8 Hz), 8.75 (s, 1H).

Using the General N-Alkylation Procedure: To a solution of the mesylate from above (22 mg, 0.104 mmol), potassium iodide (3 mg, 0.015 mmol) and potassium carbonate (22 mg, 0.156 mmol) in CH₃CN (3 mL) was added (1-t-butoxycarbonyl-benzimidazol-2-ylmethyl)-(5,6,7,8-tetrahydroquinolin-8-yl)-amine (60 mg, 0.156 mmol) and the mixture heated to 70° C. for 4 h. Purification of the crude material by chromatography on silica gel (10:1 CH₂Cl₂/MeOH) afforded 6-cyanopyridin-3-yl-(1H-N-t-butoxycarbonyl-benzimidazol-2-ylmethyl)-(5,6,7,8-tetrahydroquinolin-8-yl)-amine (32 mg, 63%). ¹H NMR (CDCl₃) δ 1.68 (s, 9H), 1.91–2.04 (m, 2H), 2.22 (m, 1H), 2.72–2.79 (m, 2H), 3.80 (d, 1H, J=16.1 Hz), 3.98 (d, 1H, J=16.1 Hz), 4.31 (dd, 1H, J=12.1, 6.2 Hz), 4.58 (d, 1H, J=16.8 Hz), 4.76 (d, 1H, J=16.8 Hz), 7.02 (m, 2H), 27.24–7.31 (m, 3H), 7.61–7.63 (m, 3H), 8.44 (d, 1H, J=5.1 Hz), 8.53 (d, 1H, J=4.1 Hz).

Raney Nickel (65 mg of a 65% slurry in water) was added to a solution of 6-cyanopyridin-3-yl-(1H-N-t-butoxycarbonyl-benzimidazol-2-ylmethyl)-(5,6,7,8-tetrahydroquinolin-8-yl)-amine (32 mg, 0.065 mmol) in MeOH (2 mL) and the solution was saturated with anhydrous ammonia. The mixture was hydrogenated in a Parr bottle at 50 psi for 6 h and the mixture filtered through celite, washing the cake with MeOH. The solvent from the eluent was removed under reduced pressure and the resultant crude material was purified by chromatography on silica gel (85% CH₂Cl₂, 12% MeOH, 3% NH₄OH) to afford 6-aminomethylpyridin-3-yl-(1H-benzimidazol-2-ylmethyl)-(5,6,7,8-tetrahydroquinolin- 8-yl)-amine as a white foam (18 mg, 70%). $^1$H NMR (CDCl$_3$) δ 1.62 (m, 1H), 1.94–2.08 (m, 2H), 2.25–2.31 (m, 1H), 2.70–2.92 (m, 2H), 3.49 (s, 2H), 3.72 (s, 2H), 3.85 (br s, 2H (NH)), 4.00 (d, 2H, J=16.5 Hz), 4.08 (dd, 1H, J=12.1, 8.3 Hz), 4.13 (d, 1H, J=16.5 Hz), 7.10–7.22 (m, 4H), 7.43 (d, 1H, J=7.2 Hz), 7.53 (m, 2H), 7.69 (d, 1H, J=7.8 Hz), 8.58 (s, 1H), 8.66 (d, 1H, J=4.8 Hz).

Following General Procedure D: Conversion of the amine from above (18 mg, 0.045 mmol) to the hydrobromide salt gave AMD9813 as a white solid (28 mg). $^1$H NMR (D$_2$O). δ 1.86 (m, 1H), 2.23 (m, 2H), 2.46 (m, 1H), 3.04 (m, 2H), 3.69 (d, 1H, J=14.9 Hz), 3.76 (d, 1H, J=14.9 Hz), 3.93 (q, 2H, J=13.4 Hz), 4.46 (d, 1H, J=16.8 Hz), 4.67 (d, 1H, J=16.8 Hz), 4.78 (m, 1H), 7.06 (d, 1H, J=7.8 Hz), 7.55 (m, 2H), 7.62 (m, 2H), 7.69 (dd, 1H, J=8.1, 6.0 Hz), 8.35 (d, 1H, J=1.8 Hz), 8.44 (d, 1H, J=8.1 Hz), 8.77 (d, 1H, J=4.5 Hz). $^{13}$C NMR (D$_2$O) δ 20.38, 20.83, 27.84, 42.67, 49.63, 53.93, 62.71, 114.05 (2C), 122.99, 126.22, 127.03 (2C), 130.50, 132.87, 133.10, 139.87 (2C), 141.14, 148.41, 149.98, 150.49, 151.44, 154.29. ES-MS m/z 399 (M+H); Anal. Calcd. for (C$_{24}$H$_{26}$N$_6$×3.8 HBr×2.2 H$_2$O): C, 38.66; H, 4.62; N, 11.27; Br, 40.72. Found: C, 39.98; H, 4.68; N, 10.97; Br, 40.63.

EXAMPLE 9

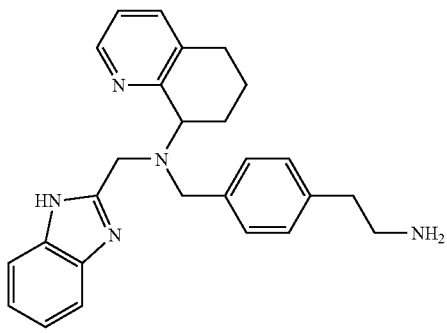

AMD9739: Preparation of [4-(2-amino-ethyl)-benzyl]-(1H-benzoimidazol-2-ylmethyl)-(5,6,7,8-tetrahydro-quinolin-8-yl)-amine (hydrobromide salt)

Preparation of
[2-(4-Formyl-phenyl)-ethyl]-carbamic acid tert-butyl ester

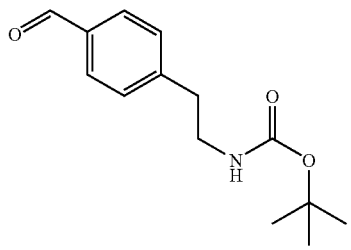

A mixture of methyl 4-(bromomethyl)benzoate (10.09 g, 44.05 mmol), sodium cyanide (6.42 g, 131 mmol) and cetyltrimethylammonium bromide (1.59 g, 4.36 mmol) in benzene/water (2:1, 187.5 mL) was heated at reflux for 5 h then extracted with CH$_2$Cl$_2$ 3×50 mL). The organic extracts were dried (MgSO$_4$), filtered and concentrated under reduced pressure. Purification of the crude material by chromatography on silica gel (35% EtOAc/hexanes) gave 4-cyanomethyl-benzoic acid methyl ester as a colourless solid (4.64 g, 60%). $^1$H NMR (CDCl$_3$) δ 3.82 (s, 2H), 3.93 (s, 3H), 7.42 (d, 2H, J=9 Hz), 8.06 (d, 2H, J=9 Hz).

To a solution of the nitrile from above (1.57 g, 8.96 mmol) in NH$_3$ saturated CH$_3$OH (30 mL) in a Parr bottle was added Raney nickel (5 g) and the mixture hydrogenated at 45 psi hydrogen in a Parr hydrogenator for 67 h. The product mixture was filtered through celite and the solvent from the eluent removed in vacuo to give a green liquid (1.30 g). A solution of the green liquid (1.29 g) and di-t-butyl dicarbonate (1.90 g, 8.71 mmol) in THF (24 mL) was stirred at room temperature for 2 hours then concentrated. Purification of the crude material on silica gel (20% EtOAc/hexanes) gave 4-(2-tert-Butoxycarbonylamino-ethyl)-benzoic acid methyl ester (1.37 g, 55%) as colourless crystals. $^1$H NMR (CDCl$_3$) δ 1.43 (s, 9H), 2.86 (m, 2H), 3.39 (m, 2H), 3.91 (s, 3H), 4.53 (br s, 1H), 7.26 (d, 2H, J=8.1 Hz), 7.98 (d, 2H, J=8.1 Hz).

To a solution of the ester from above (606 mg, 2.17 mmol) in THF (4 mL) at 0° C. was added diisobutylaluminum hydride (1.0 M/THF, 13 mL, 13 mmol). The mixture was stirred at room temperature for 1 hour then water was added followed by 10% aqueous HCl until acidic (pH 1–2). The mixture was made basic with 1N NaOH(aq) and extracted with CH$_2$Cl$_2$. The organic extracts were dried (MgSO$_4$), filtered and concentrated. Purification of the crude material by chromatography on silica gel (30% EtOAc/hexanes) gave [2-(4-Hydroxymethyl-phenyl)-ethyl]-carbamic acid tert-butyl ester (370 mg, 68%) as colourless crystals. $^1$H NMR (CDCl$_3$) δ 1.44 (s, 9H), 2.80 (m, 2H), 3.37 (m, 2H), 4.53 (br s, 1H), 4.68 (d, 2H, J=5.7 Hz), 7.19 (d, 2H, J=7.8 Hz), 7.32 (d, 2H, J=7.8 Hz).

To a solution of the alcohol from above (200 mg, 0.796 mmol) in CH$_2$Cl$_2$ (8 mL) was added activated MnO$_2$ (814 mg, 7.96 mmol) and the mixture stirred at room temperature for 69 h. The reaction mixture was filtered through Celite and the cake was washed with CH$_2$Cl$_2$. The solvent was removed from the filtrate under reduced pressure to give the desired aldehyde as colourless crystals (175 mg, 88%). $^1$H NMR (CDCl$_3$) δ 1.43 (s, 9H), 2.89 (m, 2H), 3.41 (m, 2H), 4.55 (br s, 1H), 7.37 (d, 2H, J=8.1 Hz), 7.83 (d, 2H, J=7.8 Hz), 9.99 (s, 1H).

Using General Procedure B: To a solutio of [1-(tert-butoxycarbonyl)-(1H-benzimidazol-2-ylmethyl)]-(5,6,7,8-tetrahydro-quinolin-8-yl)-amine (102 mg, 0.27 mmol) and [2-(4-formyl-phenyl)-ethyl]-carbamic acid tert-butyl ester (81 mg, 0.32 mmol) in THF (3 mL) was added acetic acid (0.017 mL, 0.30 mmol) and NaBH(OAc)$_3$ (187 mg, 0.882 mmol) and the mixture stirred for 46 h. Purificatio of the crude yellow oil by chromatography on silica gel (300:5:1 CH$_2$Cl$_2$/MeOH/NH$_4$OH) gave a colourless foam (153 mg).

A solution of the colourless foam in 1:1 trifluoroacetic acid/CH$_2$Cl$_2$ (4 mL) was stirred at room temperature for 45 min then concentrated. The residue was partitioned between CH$_2$Cl$_2$ (10 mL) and saturated aqueous NaHCO$_3$ (10 mL), and the aqueous phase was extracted with CH$_2$Cl$_2$ (3×10 mL). The combined organic phases were dried (MgSO$_4$) and concentrated. Purification of the crude material by column chromatography on silica gel (100:5:1 EtOAc/MeOH/NH$_4$OH) gave a colourless oil (38 mg, 35%).

Using General Procedure D: Conversion of the colourless oil from above (38 mg, 0.092 mmol) to the hydrobromide salt gave AMD9739 (50 mg, 79%) as a colourless solid. $^1$H NMR (D$_2$O) δ 1.94 (m, 1H), 2.26 (m, 2H), 2.43–2.60 (m, 5H), 3.03 (m, 2H), 3.74 (d, 1H, J=13 Hz), 3.82 (d, 1H, J=13 Hz), 4.42 (d, 1H, J=16 Hz), 4.60 (d, 1H, J=16 Hz), 4.79 (m, 1H), 6.85 (d, 2H, J=7.8 Hz), 7.14 (d, 2H, J=7.8 Hz), 7.47–7.59 (m, 4H), 7.91 (m, 1H), 8.37 (d, 1H, J=7.87 Hz), 8.75 (d, 1H, J=5.7 Hz); $^{13}$C NMR (D$_2$O) δ 18.88, 19.33, 26.26, 30.88, 38.90, 48.70, 55.03, 61.59, 112.33, 124.34, 124.75, 127.27, 128.98, 129.38, 133.59, 135.32, 138.18, 139.18, 146.31, 149.49, 150.55. ES-MS m/z 412 (M+H). Anal Calcd for (C$_{26}$H$_{29}$N$_5$) 3.0(HBr) 1.8(H$_2$O): C, 45.48; H, 5.23; N, 10.20; Br, 34.91. Found: C, 45.45; H, 5.13; N, 9.95; Br, 34.94.

EXAMPLE 10

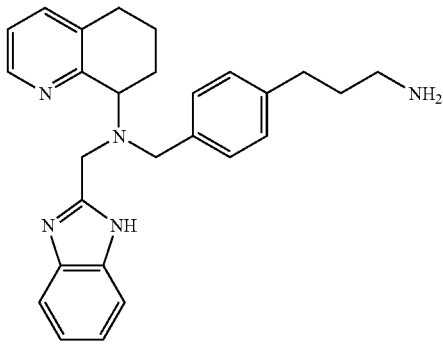

AMD9756: Preparation of [4-(3-amino-propyl)-benzyl]-(1H-benzoimidazol-2-ylmethyl)-(5,6,7,8-tetrahydro-quinolin-8-yl)-amine (hydrobromide salt)

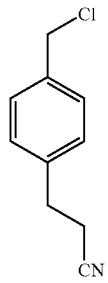

Preparation of 3-(4-chloromethyl-phenyl)-propionitrile

Acetonitrile (0.30 mL, 5.7 mmol) was added to a solution of n-butyllithium (2.4 m in hexanes, 1.96 mL, 4.7 mmol) in dry THF (5 mL) at −78° C. and stirred for 45 min. solution of α,α'-dichloro-p-xylene (2.485 g, 14.2 mmol) in dry THF at −78° C. was added to give a yellow, cloudy solution. The mixture was stirred at −78° C. for an additional hour and quenched with saturated aqueous NaCl (30 mL) before warming to room temperature. The mixture was extracted with CH$_2$Cl$_2$ (3×200 mL). The combined organic extracts were dried over MgSO$_4$ and concentrated to a white solid (2.45 g). The product was purified by column chromatography on silica gel (10:1—EtOAc:Hex) to give the desired nitrile (1.49 g, 60%) as a light yellow syrup. $^1$H NMR (300 MHz, CDCl$_3$) δ 7.37 (d, 2H, J=8.1 Hz), 7.24 (d, 2H, J=8.1 Hz), 4.58 (s, 2H), 2.96 (t, 2H, J=7.4 Hz), 2.62 (t, 2H, J=7.4 Hz).

Using the general alkylation procedure C: To a stirred solution of 3-(4-chloromethyl-phenyl)-propionitrile (63 mg, 0.35 mmol) and (1-tert-butoxycarbonyl-1H-Benzimidazol-2-ylmethyl)-(5,6,7,8-tetrahydro-quinolin-8-yl)-amine (121 mg, 0.32 mmol) in dry CH$_3$CN (3 mL) was added KI (2.6 mg, 0.016 mmol) and N,N-diisopropylethylamine (0.08 mL, 0.48 mmol) and the mixture was heated to 60° C. for 24 h. The product was purified by column chromatography on silica gel (200:1:1—CH$_2$Cl$_2$:MeOH:NH$_4$OH) to give the desired coupled product (128 mg, 77%) as a yellow syrup. $^1$H NMR (300 MHz, CDCl$_3$) δ 8.46 (d, 1H, J=3.6 Hz), 7.65–7.61 (m, 1H), 7.55–7.51 (m, 1H), 7.28 (d, 1H, J=9.6 Hz), 7.20–7.15 (m, 4H), 7.04–7.00 (m, 1H), 6.77 (d, 2H, J=8.1 Hz), 4.74 (d, 1H, J=14.4 Hz), 4.66 (d, 1H, J=14.4 Hz), 4.36–4.30 (m, 1H), 3.87 (d, 1H, J=14.7 Hz), 3.73 (d, 1H, J=14.7 Hz), 2.77–2.63 (m, 4H), 2.30–2.25 (m, 3H), 2.02–1.94 (m, 2H), 1.74–1.71 (m, 10H).

A solution of 2-{[[4-(2-cyano-ethyl)-benzyl]-(5,6,7,8-tetrahydro-quinolin-8-yl)-amino]-methyl}-benzoimidazole-1-carboxylic acid tert-butyl ester (128 mg, 0.24 mmol) in MeOH (10 mL) was saturated with NH$_3$(g). Raney nickel (~2 g, excess) was rinsed with MeOH (3×), transferred into the hydrogenation flask containing the nitrile and the mixture was hydrogenated at 45 psi for 16 h. The product mixture was diluted with MeOH (100 mL) and filtered through celite and the solvent from the eluent removed in vacuo. The product was purified by column chromatography on silica gel (100:1:1—CH$_2$Cl$_2$:MeOH:NH$_4$OH) to give the desired amine (51 mg, 50%) as a white foam. $^1$H NMR (300 MHz, CDCl$_3$) δ 8.70 (d, 1H, J=3.6 Hz), 7.59 (br s, 2H), 7.42 (d, 1H, J=8.1 Hz), 7.30 (d, 2H, J=8.1 Hz), 7.20–7.15 (m, 3H), 7.04 (d, 2H, J=7.8 Hz), 4.17(d, 1H, J=16.8 Hz), 4.12–4.06 (m, 1H), 3.97 (d, 1H, J=16.8 Hz), 3.71 (s, 2H), 2.86–2.74 (m, 2H), 2.66 (t, 2H, J=6.9 Hz), 2.56 (t, 2H, J=7.8 Hz), 2.33–2.24 (m, 1H), 2.09–1.98 (m, 2H), 1.73–1.64 (m, 3H).

Following General Procedure D: Conversion of the foam from above (51 mg) to the hydrobromide salt gave AMD9756. $^1$H NMR (300 MHz, D$_2$O) δ 8.75 (d, 1H, J=5.7 Hz), 8.40 (d, 1H, J=7.8 Hz), 7.93 (dd, 1H, J=7.8, 5.7 Hz), 7.60–7.56 (m, 2H), 7.53–7.47 (m, 2H), 7.11 (d, 2H, J=7.8 Hz), 6.83 (d, 2H, J=8.1 Hz), 4.78–4.73 (m, 1H), 4.62 (d, 1H, J=16.5 Hz), 4.44 (d, 1H, J=16.5 Hz), 3.82 (d, 1H, J=12.3 Hz), 3.75 (d, 1H, J=12.3 Hz), 3.06–3.03 (m, 2H), 2.76 (t, 2H, J=7.8 Hz), 2.46–2.43 (m, 1H), 2.34–2.17 (m, 4H), 2.97–1.91 (m, 1H), 1.46–1.35 (m, 2H), $^{13}$C NMR (75.5 MHz, D$_2$O) δ 153.8, 152.7, 150.0, 143.1, 142.7, 141.4, 135.8, 132.3, 132.2, 130.3, 128.4, 127.9, 115.7, 65.0, 58.4, 52.1, 41.2, 33.3, 30.4, 29.7, 22.7, 22.3. ES-MS m/z 426.3 (M+H). Anal Calcd for (C$_{27}$H$_{31}$N$_5$).2.9(HBr).1.9(H$_2$O): C, 46.70; H, 5.47; N, 10.08; Br, 33.37. Found: C, 46.69; H, 5.14; N, 10.03; Br, 33.43.

EXAMPLE 11

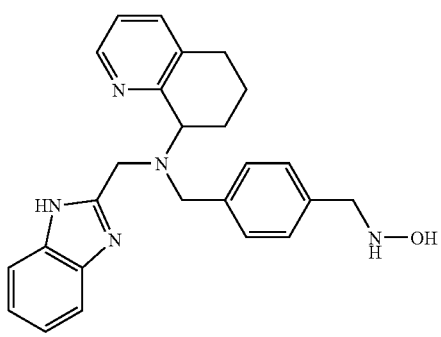

AMD9768: Preparation of N-(4-{[(1H-benzimidazol-2-ylmethyl)-(5,6,7,8-tetrahydro-quinolin-8-yl)-amino]-methyl}-benzyl)-hydroxylamine A solution of 4-{[(1H-benzimidazol-2-ylmethyl)-(5,6,7,8-tetrahydro-quinolin-8-yl)-amino]-methyl}-benzaldehyde (350 mg, 0.883 mmol) and hydroxylamine hydrochloride (100 mg, 1.44 mmol) in MeOH (3 mL) was stirred at room temperature for 45 minutes then concentrated in vacuo. The residue was partitioned between saturated NaHCO$_3$(aq) (15 mL) and CH$_2$Cl$_2$ (20 mL), and the aqueous phase was extracted with CH$_2$Cl$_2$ (10 mL). The combined organic phases were dried (MgSO$_4$), filtered and concentrated in vacuo to give a yellow solid (363 mg).

To a solution of the crude oxime from above (90 mg, 0.22 mmol) in 6:1 MeOH/THF (2.2 mL) was added NaBH$_4$ (19 mg, 0.50 mmol) and the solution was adjusted to pH 4 using saturated HCl/1,4-dioxane. The mixture was stirred at room temperature for 15 minutes, then additional NaBH$_4$ (19 mg, 0.50 mmol) was added and the solution was adjusted to pH 4. The mixture was stirred for 15 minutes then made basic using 1 N NaOH(aq) and extracted with CH$_2$Cl$_2$ (3×15 mL). The combined extracts were dried (MgSO$_4$), filtered and concentrated in vacuo. Purification of the crude material by column chromatography on silica gel (100:5:1 CH$_2$Cl$_2$/MeOH/NH$_4$OH) afforded AMD9768 (67 mg, 68%) as a colourless foam. $^1$H NMR (CDCl$_3$) δ 1.66 (m, 1H), 1.99 (m, 2H), 2.24 (m, 1H), 2.67–2.90 (m, 2H), 3.71 (s, 2H), 3.94 (d, 1H, J=17 Hz), 3.94 (s, 2H), 4.07 (m, 1H), 4.14 (d, 1H, J=17 Hz), 7.17 (m, 5H), 7.38 (m, 3H), 7.55 (m, 2H), 8.66 (d, 1H, J=3.9 Hz); $^{13}$C NMR (CDCl$_3$) δ 21.34, 23.30, 29.18, 48.50, 53.81, 57.91, 60.37, 121.87, 122.36, 128.80, 129.06, 134.94, 136.13, 137.55, 138.46, 146.72, 155.89, 157.15. ES-MS m/z 414 (M+H). Anal. Calcd. for C$_{25}$H$_{27}$N$_5$O.0.3H$_2$O.0.36CH$_2$Cl$_2$: C, 67.76; H, 6.35; N, 15.58. Found: C, 67.85; H, 6.39; N, 15.51.

EXAMPLE 12

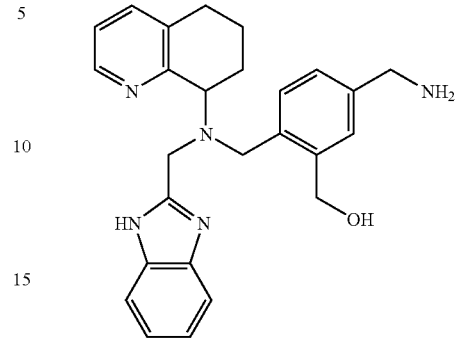

AMD11088: Preparation of (5-aminomethyl-2-{[(1H-benzoimidazol-2-ylmethyl)-(5,6,7,8-tetrahydro-quinolin-8-yl)-amino]-methyl}-phenyl)-methanol Preparation of 2-methyl-5-nitro-benzoic acid methyl ester

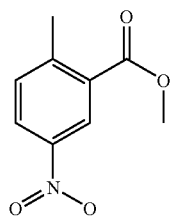

A solution of 2-methyl-5-nitrobenzoic acid (1.51 g, 8.34 mmol) and H$_2$SO$_4$ (catalytic) in MeOH (20 mL) was heated at reflux for 17 h, then concentrated in vacuo. The residue was dissolved in CH$_2$Cl$_2$ (40 mL), washed with saturated NaHCO$_3$(aq) (30 mL), then dried (MgSO$_4$) and concentrated in vacuo to give yellow crystals (1.62 g, 99%). $^1$H NMR (CDCl$_3$) δ 2.72 (s, 3H), 3.96 (s, 3H), 7.44 (d, 1H, J=8.7 Hz), 8.24 (dd, 1H, J=8.7, 2.7 Hz), 8.78 (d, 1H, J=2.7 Hz).

Preparation of 5-Amino-2-methyl-benzoic acid methyl ester

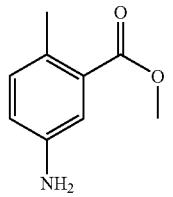

A solution of 2-methyl-5-nitro-benzoic acid methyl ester (1.96 g, 10.0 mmol) in 4:1 MeOH/EtOAc (25 mL) was shaken at room temperature with a suspension of 10% Pd/C (200 mg, 0.19 mmol) under hydrogen atmosphere (35 psi) for 2 h. The catalyst was removed by filtration, and the filtrate was concentrated in vacuo to give an orange oil (1.64 g, 99%). $^1$H NMR (CDCl$_3$) δ 2.47 (s, 3H), 3.62 (br s, 2H), 3.87 (s, 3H), 6.75 (dd, 1H, J=8.1, 2.7 Hz), 7.02 (d, 1H, J=8.1 Hz), 7.25 (d, 1H, J=2.7 Hz).

Preparation of 5-Cyano-2-methyl-benzoic acid methyl ester

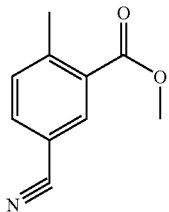

To a stirred suspension of 5-amino-2-methyl-benzoic acid methyl ester (1.00 g, 6.05 mmol) in H$_2$O (1.5 mL) was slowly added conc. HCl (1.5 mL) at room temperature. More H$_2$O (7 mL) was added, and the mixture was stirred at 0° C. while a solution of NaNO$_2$ (459 mg, 6.65 mmol) in H$_2$O (1 mL) was added dropwise. After the amine had completely dissolved, K$_2$CO$_3$(s) was added slowly at 0° C. until the solution was neutralized.

Copper(I) cyanide (651 mg, 7.27 mmol) was dissolved in a solution of NaCN (712 mg, 14.5 mmol) in H$_2$O (2.2 mL), and the solution was heated to 60° C. The cold neutralized diazonium salt solution was added dropwise to the vigorously stirred cyanide solution at 60° C. The mixture was heated to 110° C. for 30 minutes then allowed to cool to room temperature. The mixture was diluted with saturated NaHCO$_3$(aq) (10 mL) and extracted with CH$_2$Cl$_2$ (4×12 mL). The combined organic extracts were dried (MgSO$_4$) and concentrated in vacuo. The crude material was filtered through silica gel (10% EtOAc/hexanes) to give yellow crystals (896 mg, 85%). $^1$H NMR (CDCl$_3$) δ 2.68 (s, 3H), 3.93 (s, 3H), 7.37 (d, 1H, J=8.1 Hz), 7.66 (dd, 1H, J=7.8, 1.8 Hz), 8.22 (d, 1H, J=1.8 Hz).

Preparation of 2-Bromomethyl-5-cyano-benzoic acid methyl ester

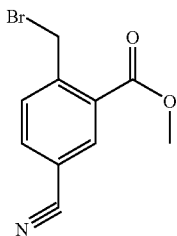

A mixture of 5-cyano-2-methyl-benzoic acid methyl ester (894 mg, 5.10 mmol), NBS (1.00 g, 5.62 mmol), and AIBN (125 mg, 0.761 mmol) in CCl$_4$ (20 mL) was heated at reflux for 3 days then allowed to cool to room temperature. The mixture was filtered, and the filtrate was concentrated in vacuo. Purification of the crude material by column chromatography on silica gel (5% EtOAc/hexanes) afforded yellow crystals (800 mg, 62%). $^1$H NMR (CDCl$_3$) δ 3.99 (s, 3H), 4.96 (s, 2H), 7.61 (d, 1H, J=8.1 Hz), 7.77 (dd, 1H, J=8.1, 1.8 Hz), 8.27 (d, 1H, J=1.8 Hz).

A mixture of 2-[(5,6,7,8-tetrahydro-quinolin-8-ylamino)-methyl]-benzoimidazole-1-carboxylic acid tert-butyl ester (253 mg, 0.668 mmol), 2-bromomethyl-5-cyano-benzoic acid methyl ester (170 mg, 0.669 mmol), potassium iodide (6 mg, 0.04 mmol), and N,N-diisopropylethylamine (0.17 mL, 0.98 mmol) in acetonitrile (6.7 mL) was heated at 60° C. for 18 h. Saturated NaHCO$_3$(aq) (15 mL) was added, and the mixture was extracted with CH$_2$Cl$_2$ (3×15 mL). The organic extracts were dried (MgSO$_4$) and concentrated in vacuo. Purification of the crude material on silica gel (500:5:1 CH$_2$Cl$_2$/MeOH/NH$_4$OH) gave a yellow foam (360 mg, 98%). $^1$H NMR (CDCl$_3$) δ 1.74 (m, 10H), 1.99 (m, 2H), 2.29 (m, 1H), 2.74 (m, 2H), 3.86 (s, 3H), 4.22 (d, 1H, J=17 Hz), 4.33 (m, 1H), 4.36 (d, 1H, J=17 Hz), 4.59 (d, 1H, J=14 Hz), 4.65 (d, 1H, J=14 Hz), 6.98 (dd, 1H, J=8.0, 4.7 Hz), 7.25 (m, 3H), 7.33 (dd, 1H, J=8.1, 1.8 Hz), 7.50 (m, 1H), 7.68 (m, 2H), 8.11 (d, 1H, J=8.1 Hz), 8.41 (m, 1H).

A solution of 2-{[(4-cyano-2-methoxycarbonyl-benzyl)-(5,6,7,8-tetrahydro-quinolin-8-yl)-amino]-methyl}-benzoimidazole-1-carboxylic acid tert-butyl ester (356 mg, 0.645 mmol) in saturated NH$_3$(g)/MeOH (20 mL) was shaken at room temperature with a suspension of Raney® nickel (1.5 g) under hydrogen atmosphere (45 psi) for 20 h. The catalyst was removed by filtration, and the filtrate was concentrated in vacuo. The crude material was filtered through silica gel (100:5:1 CH$_2$Cl$_2$/MeOH/NH$_4$OH) to give a yellow oil (203 mg, 69%). $^1$H NMR (CDCl$_3$) δ 1.69 (m, 1H), 2.01 (m, 2H), 2.27 (m, 1H), 2.80 (m, 2H), 3.69 (br s, 2H), 3.90 (m, 5H), 4.10 (d, 1H, J=17 Hz), 4.15 (m, 1H), 4.53 (d, 1H, J=14 Hz), 7.19 (m, 4H), 7.41 (m, 1H), 7.47 (m, 1H), 7.58 (m, 2H), 7.68 (d, 1H, J=7.8 Hz), 8.62 (m, 1H).

To a solution of 5-aminomethyl-2-{[(1H-benzoimidazol-2-ylmethyl)-(5,6,7,8-tetrahydro-quinolin-8-yl)-amino]-methyl}-benzoic acid methyl ester (192 mg, 0.421 mmol) in THF (4.2 mL) was added LiAlH$_4$ (1.0 M/THF, 0.42 mL, 0.42 mmol) at 0° C., and the mixture was stirred at 0° C. for 15 minutes. To the mixture was added H$_2$O (0.016 mL) followed by 15% NaOH(aq) (0.016 mL) and H$_2$O (0.048 mL). The mixture was allowed to warm to room temperature then filtered and concentrated in vacuo. Purification of the crude material by column chromatography on silica gel (100:5:1 CH$_2$Cl$_2$/MeOH/NH$_4$OH) afforded AMD11088 as a colourless foam (29 mg, 15%). $^1$H NMR (CDCl$_3$) δ 1.69 (m, 1H), 2.04 (m, 2H), 2.36 (m, 1H), 2.80 (m, 2H), 3.69 (s, 2H), 3.78–4.07 (m, 5H), 4.52 (d, 1H, J=12 Hz), 4.62 (d, 1H, J=12 Hz), 6.97 (dd, 1H, J=7.5, 1.5 Hz), 7.13 (m, 4H), 7.29 (d, 1H, J=1.5 Hz), 7.44 (m, 3H), 8.46 (m, 1H); $^{13}$C NMR (CDCl$_3$) δ 21.09, 21.41, 29.05, 45.95, 49.53, 55.39, 61.07, 62.90, 121.81, 122.28, 126.35, 130.44, 131.20, 134.88, 135.67, 137.72, 140.42, 143.53, 146.80, 153.73, 156.25. ES-MS m/z 428 (M+H). Anal. Calcd. for C$_{26}$H$_{29}$N$_5$O.0.4H$_2$O.0.3CH$_2$Cl$_2$: C, 68.64; H, 6.66; N, 15.22. Found: C, 68.67; H, 6.67; N, 15.25.

EXAMPLE 13

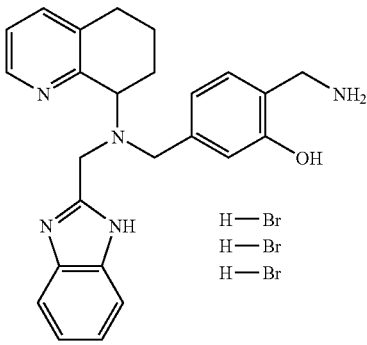

AMD11071: Preparation of 2-Aminomethyl-5-{[(1H-benzimidazol-2-ylmethyl)-(5,6,7,8-tetrahydro-quinolin-8-yl)-amino]-methyl}-phenol (hydrobromide salt)

2-Hydroxy-4-methylbenzonitrile was prepared following a modification of the procedure reported by Makoto Adachi and Tsutomu Sugasawa (*Synthetic Communications* 1990, 20, 71–84.). To a cold (0° C.) solution of $BCl_3$ (1.0 M in heptane, 12.0 mL, 12.0 mmol) in 1,2-dichloroethane was added neat m-cresol (1.00 mL, 9.56 mmol) followed by $CH_3SCN$ (0.83 mL, 12.1 mmol) and $AlCl_3$ (1.38 g, 10.4 mmol). The cooling bath was removed and the resultant mixture was heated to 80° C. for 3 hours then cooled to room temperature. The mixture was poured into 4 N NaOH (35 mL) and the mixture was heated at 80° C. for 45 minutes then cooled to room temperature. The phases were separated and the aqueous phase was extracted with $CH_2Cl_2$ (3×50 mL). The aqueous phase was acidified with 6 N HCl (30 mL) and extracted with diethyl ether (3×50 mL). The combined ether extracts were dried ($MgSO_4$) and concentrated. Purification of the crude material by column chromatography on silica gel (20:1 $CH_2Cl_2$—EtOAc) provided 1.16 g (91%) of 2-Hydroxy-4-methylbenzonitrile as a white solid. $^1$H NMR ($CDCl_3$) δ 2.36 (s, 3H), 6.20 (br s, 1H), 6.79–6.81 (m, 2H), 7.38 (d, 1H, J=9 Hz).

To a solution of 2-Hydroxy-4-methylbenzonitrile (0.563 g, 4.23 mmol) in $CH_2Cl_2$ (21 mL) was added acetic anhydride (0.60 mL, 6.36 mmol) followed by triethylamine (1.20 mL, 8.61 mmol) and the resultant solution was stirred at room temperature for 30 minutes. The mixture was diluted with $CH_2Cl_2$ (60 mL), washed with saturated aqueous $NaHCO_3$ (20 mL) and brine (2×20 mL). The organic phase was dried ($Na_2SO_4$) and concentrated and provided 0.72 g (97%) of (2-cyano-5-methyl-phenyl) acetate as a white solid. $^1$H NMR ($CDCl_3$) δ 2.38 (s, 3H), 2.43 (s, 3H), 7.08 (s, 1H), 7.13 (d, 1H, J=9 Hz), 7.54 (d, 1H, J=9 Hz).

To a solution of (2-cyano-5-methyl-phenyl) acetate (0.72 g, 4.11 mmol) in $CCl_4$ (10 mL) was added recrystallized N-bromosuccinimide (0.767 g, 4.31 mmol) followed by benzoyl peroxide (56 mg, 0.23 mmol). The resultant mixture was heated to reflux for 2.5 hours then cooled to room temperature. The mixture was diluted with diethyl ether (50 mL), filtered through filter paper, and the filtrate was concentrated. Purification of the crude material by column chromatography (6:1 hexanes-EtOAc) provided 0.31 g (30%) of (5-bromomethyl-2-cyano-phenyl) acetate as a colorless oil. $^1$H NMR ($CDCl_3$) δ 2.40 (s, 3H), 4.45 (s, 2H), 7.33 (s, 1H), 7.35 (d, 1H, J=9 Hz), 7.65 (d, 1H, J=9 Hz).

To a solution of (1-tert-butoxycarbonyl-1H-Benzimidazol-2-ylmethyl)-(5,6,7,8-tetrahydro-quinolin-8-yl)-amine (0.375 g, 0.99 mmol) in $CH_3CN$ (5 mL) was added N,N-diisopropylethylamine (0.35 mL, 2.00 mmol) followed by a solution of (5-bromomethyl-2-cyano-phenyl) acetate (0.318 g, 1.25 mmol) in $CH_3CN$ (5 mL). The resultant mixture was heated to 60° C. for 15 hours then cooled to room temperature. The mixture was concentrated and the residue was partitioned between $CH_2Cl_2$ (40 mL) and brine (10 mL). The phases were separated and the aqueous phase was extracted with $CH_2Cl_2$ (3×10 mL). The combined organic extracts were dried ($Na_2SO_4$) and concentrated. Purification of the crude material by column chromatography on silica gel (20:1 $CH_2Cl_2$—$CH_3OH$) followed by radial chromatography on silica gel (2 mm plate, 2:1 hexanes-EtOAc) provided 0.28 g (51%) of a tan foam.

The foam from above (0.28 g, 0.51 mmol) was dissolved in $NH_3$ saturated methanol (10 mL), treated with Raney nickel (140 mg), and placed under 50 psi $H_2$ on a Parr shaker for 17 hours. The mixture was filtered through Celite® and the cake was washed with methanol. The eluant was concentrated under reduced pressure. Purification of the crude material by column chromatography on silica gel (20:1:1 $CH_2Cl_2$—$CH_3OH$—$NH_4OH$) followed by radial chromatography on silica gel (1 mm plate, 100:1:1 $CH_2Cl_2$—$CH_3OH$—$NH_4OH$) provided 76 mg (33%) of the free base of the title compound as a yellow foam.

Using General Procedure D: Conversion of the foam from above (72 mg, 0.16 mmol) to the hydrobromide salt followed by re-precipitation of the intermediate solid from methanol/ether gave AMD11071 (73 mg, 65%) as a white solid. $^1$H NMR ($D_2O$) δ 1.83–1.95 (m, 1H), 2.19–2.30 (m, 2H), 2.40–2.45 (m, 1H), 3.02–3.04 (m, 2H), 3.55 (s, 2H), 3.72 (d, 1H, J=12.9 Hz), 3.77 (d, 1H, J=12.9 Hz), 4.44 (d, 1H, J=16.2 Hz), 4.62 (d, 1H, J=16.2 Hz), 4.72–4.79 (m, 1H, overlaps with HOD), 6.61 (s, 1H), 6.72 (d, 1H, J=7.8 Hz), 6.90 (d, 1H, J=7.8 Hz), 7.50–7.55 (m, 2H), 7.58–7.62 (m, 2H), 7.92 (dd, 1H, J=6.0, 7.8 Hz), 8.40 (d, 1H, J=7.8 Hz), 8.74 (d, 1H, J=5.1 Hz); $^{13}$C NMR ($D_2O$) δ 20.44, 20.88, 27.83, 38.85, 50.22, 56.74, 63.17, 113.86, 116.57, 118.99, 122.04, 126.07, 126.69, 130.58, 131.10, 139.63, 139.66, 140.96, 148.21, 150.83, 151.77, 154.96. ES-MS m/z 414 (M+H). Anal. Calcd. for $C_{25}H_{27}N_5O·3.1HBr·2.5H_2O$: C, 42.33; H, 4.99; N, 9.87; Br, 34.92. Found: C, 42.26; H, 4.94; N, 9.87; Br, 35.06.

EXAMPLE 14

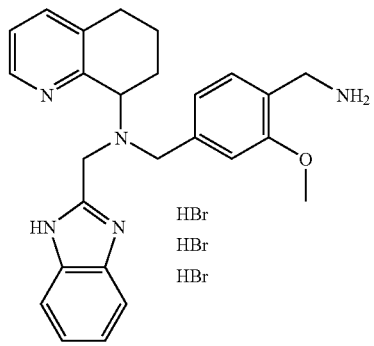

AMD11077: Preparation of (4-Aminomethyl-3-methoxy-benzyl)-(1H-benzimidazol-2-ylmethyl)-(5,6,7,8-tetrahydro-quinolin-8-yl)-amine (hydrobromide salt)

To a solution of 2-Hydroxy-4-methylbenzonitrile (0.46 g, 3.46 mmol) in THF (17 mL) was added lithium hydroxide monohydrate (0.292 g, 6.95 mmol) followed by dimethyl sulfate (0.50 mL, 5.28 mmol). The resultant mixture was heated to reflux for 2 hours then cooled to room temperature. The mixture was diluted with diethyl ether (50 mL), washed with saturated aqueous NaHCO$_3$ (3×15 mL), dried (MgSO$_4$) and concentrated. Purification of the crude material by column chromatography on silica gel (4:1 hexanes-EtOAc) provided 0.456 g (90%) of 2-methoxy-4-methylbenzonitrile as a white solid. $^1$H NMR (CDCl$_3$) δ 2.41 (s, 3H), 3.91 (s, 3H), 6.77 (s, 1H), 6.81 (d, 1H, J=6Hz), 7.43 (d, 1H, J=6 Hz). ES-MS m/z 148 (M+H).

To a solution of 2-methoxy-4-methylbenzonitrile (0.438 g, 2.98 mmol) in CCl$_4$ (6 mL) was added recrystallized N-bromosuccinimide (0.544 g, 3.05 mmol) followed by benzoyl peroxide (47 mg, 0.19 mmol). The resultant mixture was heated to reflux for 45 minutes then cooled to room temperature. The mixture was diluted with diethyl ether (30 mL), filtered through filter paper, and the filtrate was concentrated. Purification of the crude material by column chromatography (6:1 hexanes-EtOAc) provided 0.46 g (68%) of 4-(bromomethyl)-2-methoxybenzonitrile as a white solid. $^1$H NMR (CDCl$_3$) δ 3.96 (s, 3H), 4.45 (s, 2H), 6.99 (s, 1H), 7.03 (d, 1H, J=9 Hz), 7.53 (d, 1H, J=9 Hz).

To a solution of (1-tert-butoxycarbonyl-1H-Benzimidazol-2-ylmethyl)-(5,6,7,8-tetrahydro-quinolin-8-yl)-amine (0.386 g, 1.02 mmol) in CH$_3$CN (10 mL) was added N,N-diisopropylethylamine (0.35 mL, 2.00 mmol) followed by of 4-(bromomethyl)-2-methoxybenzonitrile (0.363 g, 1.60 mmol). The resultant mixture was heated to 60° C. for 15 hours then cooled to room temperature. The mixture was concentrated and the residue was partitioned between CH$_2$Cl$_2$ (40 mL) and brine (10 mL). The phases were separated and the aqueous phase was extracted with CH$_2$Cl$_2$ (3×10 mL). The combined organic extracts were dried (Na$_2$SO$_4$) and concentrated. Purification of the crude material by column chromatography on silica gel (20:1 CH$_2$Cl$_2$—CH$_3$OH) followed by radial chromatography on silica gel (2 mm plate, 2:1 hexanes-EtOAc) provided 0.30 g (56%) of a white foam.

The foam from above (0.29 g, 0.55 mmol) was dissolved in NH$_3$ saturated methanol (15 mL), treated with Raney nickel (300 mg), and placed under 50 psi H$_2$ on a Parr shaker for 7 hours. The mixture was filtered through Celite® and the cake was washed with methanol. The eluant was concentrated under reduced pressure. Purification of the crude material by column chromatography on silica gel (10:1:1 CH$_2$Cl$_2$—CH$_3$OH—NH$_4$OH) provided 0.197 g (83%) of the free base of the title compound as a white solid.

Using General Procedure D: Conversion of the solid from above (183 mg, 0.43 mmol) to the hydrobromide salt followed by re-precipitation of the intermediate solid from methanol/ether gave AMD11077 (268 mg, 88%) as a white solid. $^1$H NMR (D$_2$O) δ 1.84–1.97 (m, 1H), 2.20–2.31 (m, 2H), 2.43–2.50 (m, 1H), 3.03–3.06 (m, 2H), 3.55 (s, 2H), 3.73 (s, 3H), 3.82 (d, 1H, J=12.6 Hz), 3.88 (d, 1H, J=12.6 Hz), 4.45 (d, 1H, J=16.5 Hz), 4.63 (d, 1H, J=16.5 Hz), 4.72–4.79 (m, 1H, overlaps with HOD), 6.75 (s, 1H), 6.83 (d, 1H, J=7.5 Hz), 6.99 (d, 1H, J=7.5 Hz), 7.50–7.54 (m, 2H), 7.57–7.61 (m, 2H), 7.93 (dd, 1H, J=6.0, 7.5 Hz), 8.40 (d, 1H, J=8.1 Hz, 8.74 (d, 1H, J=6.0 Hz); $^{13}$C NMR (D$_2$O) δ 20.46, 20.94, 27.86, 39.08, 50.07, 55.62, 57.24, 63.25, 112.27, 113.78, 120.28, 122.61, 126.16, 126.82, 130.47, 131.11, 139.65, 140.03, 141.06, 148.30, 150.77, 151.78, 157.51. ES-MS m/z 428 (M+H). Anal. Calcd. for C$_{26}$H$_{22}$N$_5$O.3.0HBr.2.4H$_2$O: C, 43.77; H, 5.20; N, 9.82; Br, 33.60. Found: C, 43.61; H, 5.18; N, 9.45; Br, 33.88.

EXAMPLE 15

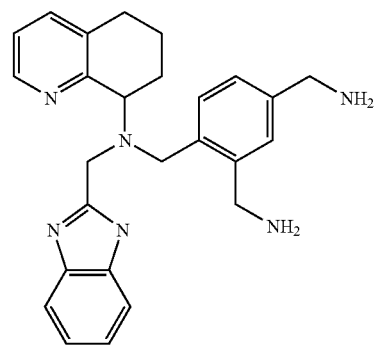

AMD9923: Preparation of (1H-benzoimidazol-2-ylmethyl)-(2,4-bis-aminomethyl-benzyl)-(5,6,7,8-tetrahydro-quinolin-8-yl)-amine (hydrobromide salt)

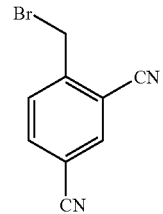

Preparation of 4-bromomethyl-isophthalonitrile

To a stirred solution of 4-methyl-isophthalonitrile (prepared as described by Klement, I.; Lennick, K.; Tucker, C. E.; Knochel, P. *Tetrahedron Lett.* 1993, 34, 4623–4626) (500 mg, 3.52 mmol) in CCl$_4$ (4 mL) was added solid N-bromosuccinimide (1.25 g, 7.0 mmol) followed by benzoyl peroxide (8 mg, 0.04 mmol). The resulting mixture was heated to reflux for 8 h, at which time it was cooled to room temperature and concentrated in vacuo. The crude material was purified by flash chromatography (silica gel, 4:1 hexanes-EtOAc) to give 457 mg of a mixture 4-methyl-isophthalonitrile and 4-bromomethyl-isophthalonitrile in a 3:1 molar ratio, respectively. 4-Bromomethyl-isophthalonitrile displayed $^1$H NMR (CDCl$_3$) δ 2.04 (s, 2H), 7.70–7.74 (m, 1H), 7.86–7.74 (m, 1H), 7.96 (s, 1H).

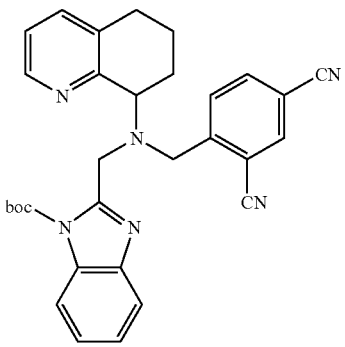

Preparation of 2-{[(2,4-dicyano-benzyl)-(5,6,7,8-tetrahydro-quinolin-8-yl)-amino]-methyl}-benzoimidazole-1-carboxylic acid tert-butyl ester:

Following the General Procedure for N-alkylation, the 3:1 mixture of mixture 4-methyl-isophthalonitrile and 4-bromomethyl-isophthalonitrile obtained from the previous step (457 mg) and (1H-N-tert-butoxycarbonyl-benzimidazol-2-ylmethyl)-(5,6,7,8-tetrahydroquinolin-8-yl)-amine (257 mg, 0.68 mmol) were converted into the corresponding alkylation product using the following quantities of reagents and solvents: diisopropylethylamine (237 μL, 1.36 mmol), $CH_3CN$ (5 mL). The reaction time in this case was 3 days, while the reaction temperature was 40° C. The resulting crude material was purified by flash chromatography (silica gel, 20:1:1 $CH_2Cl_2$—MeOH—$NH_4OH$) to provide 326 mg (93%) of 2-{[(2,4-dicyano-benzyl)-(5,6,7,8-tetrahydro-quinolin-8-yl)-amino]-methyl}-benzoimidazole-1-carboxylic acid tert-butyl ester. $^1$H NMR (CDCl$_3$) δ 1.73 (s, 9H), 1.75–2.20 (m, 3H), 2.38–2.50 (m, 1H), 2.65–2.90 (m, 2H), 4.18 (d, 2H, J=6 Hz), 4.30–4.40 (m, 1H), 4.53 (d, 1H, J=15 Hz), 4.70 (d, 1H, J=15 Hz), 7.02–7.04 (m, 1H), 7.23–7.26 (m, 2H), 7.3–7.32 (m, 2H), 7.38 (s, 1H), 7.52–7.70 (m, 2H), 7.85 (d, 1H, J=9 Hz), 8.45–8.50 (m, 1H).

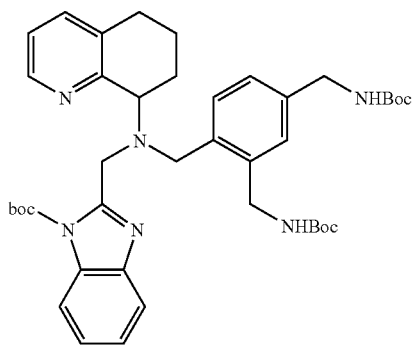

Preparation of 2-{[[2,4-Bis-(tert-butoxycarbonylamino-methyl)-benzyl]-(5,6,7,8-tetrahydro-quinolin-8-yl)-amino]-methyl}-benzoimidazole-1-carboxylic acid tert-butyl ester:

A hydrogenation flask was charged with a 50% slurry of Raney nickel in water (300 mg), which was then washed with methanol (3×10 mL). A solution of 2-{[(2,4-dicyano-benzyl)-(5,6,7,8-tetrahydro-quinolin-8-yl)-amino]-methyl}-benzoimidazole-1-carboxylic acid tert-butyl ester (326 mg, 0.63 mmol) in MeOH (10 mL) was then added, and $NH_3$ gas was bubbled through the solution for 5 min. The resulting heterogeneous mixture was hydrogenated (50 psi) on a Parr Shaker for 18 h; at this time, the crude mixture was filtered through celite, washed with MeOH (3×20 mL), and concentrated in vacuo. Flash chromatography (silica gel, 20:2:1 $CH_2Cl_2$—MeOH—$NH_4OH$, then 10:1 MeOH—$NH_4OH$) of the resulting material afforded 124 mg (46%) of the free base of AMD9923 as a white solid; however, combustion analysis revealed that this material was contaminated with silica gel, and repeated filtration and chromatography (celite, florisil, silica gel, basic alumina) failed to remove the contaminant. Thus, this compound (60 mg, 0.14 mmol) was taken up in a mixture of THF (5 mL), MeOH (1 mL) and water (3 drops) then di-tert-butyl dicarbonate (92 mg, 0.42 mmol) was added. The resulting solution was stirred 2 h, at which point saturated aqueous sodium bicarbonate (5 mL) was added, and the resulting mixture was extracted with $CH_2Cl_2$ (3×10 mL) then the combined organic extracts were dried (MgSO$_4$), and concentrated in vacuo. Purification of the crude material thus obtained by radial chromatography (silica gel, 1 mm plate, 50:1:1 $CH_2Cl_2$—MeOH—$NH_4OH$) afforded 71 mg (69%) of 2-{[[2,4-bis-(tert-butoxycarbonylamino-methyl)-benzyl]-(5,6,7,8-tetrahydro-quinolin-8-yl)-amino]-methyl}-benzoimidazole-1-carboxylic acid tert-butyl ester as a colourless oil. $^1$H NMR (CDCl$_3$) δ 1.44 (s, 18H), 1.53–1.54 (m, 1H), 1.69 (s, 9H), 1.99–2.04 (m, 1H), 2.17–2.29 (m, 2H), 2.49–2.54 (m, 1H), 2.72–2.83 (m, 1H), 3.84–3.94 (m, 2H), 4.19 (d, 2H, J=5 Hz), 4.28–4.54 (m, 6H), 4.86 (br s, 1H), 6.63 (dd, 1H, J=8, 5 Hz), 6.70 (dd, 1H, J=18, 8 Hz), 7.17–7.24 (m, 3H), 7.36 (s, 1H), 7.52–7.55 (m, 1H), 7.67–7.70 (m, 1H), 8.24 (d, 1H, J=4 Hz), 8.80 (br s, 1H).

Following the general procedure D for concomitant BOC deprotection and HBr salt formation, treatment of the oil from the previous step (71 mg, 0.10 mmol) with HBr-saturated acetic acid (1 mL) afforded 48 mg (60%) of the HBr salt of AMD9923 as a white solid. $^1$H NMR (CD$_3$OD) δ 1.48–1.59 (m, 1H), 2.07–2.14 (m, 2H), 2.29–2.30 (m, 1H), 2.63 (br d, 1H, J=17 Hz), 2.78–2.89 (m, 1H), 3.76 (d, 1H, J=14 Hz), 3.74–4.08 (m, 7H), 4.16 (d, 1H, J=13 Hz, 6.99 (dd, 1H, J=8, 5 Hz), 7.16–7.20 (m, 2H), 7.34–7.39 (m, 3H), 7.54–7.57 (m, 2H), 7.65 (s, 1H), 8.31 (d, 1H, J=5 Hz); $^{13}$C NMR (CD$_3$OD) δ 21.3, 22.6, 22.8, 41.8, 43.6, 48.6, 55.7, 60.9, 115.9, 123.4, 123.8, 130.9, 133.2, 134.2, 135.0, 135.8, 136.4, 138.9, 140.2, 147.5, 152.8, 156.6. ES-MS m/z 427 (M+H). Anal. Calcd. for $C_{26}H_{30}N_6 \cdot 4HBr \cdot 1.5H_2O \cdot 0.7C_2H_4O_2$: C, 40.17; H, 4.90; N, 10.26; Br, 39.01. Found: C, 40.13; H, 5.15; N, 10.20; Br, 39.08.

EXAMPLE 16

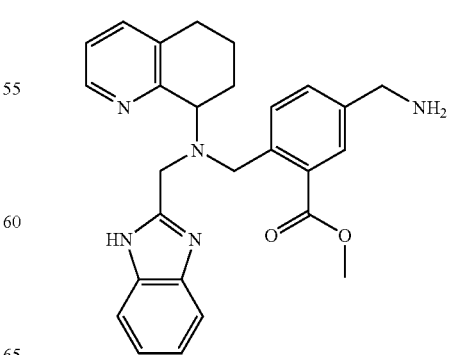

AMD11038: Preparation of 5-Aminomethyl-2-{[(1H-benzoimidazol-2-ylmethyl)-(5,6,7,8-tetrahydro-quinolin-8-yl)-amino]-methyl}-benzoic acid methyl ester (hydrobromide salt)

A solution of 2-{[(4-cyano-2-methoxycarbonyl-benzyl)-(5,6,7,8-tetrahydro-quinolin-8-yl)-amino]-methyl}-benzoimidazole-1-carboxylic acid tert-butyl ester (710 mg, 1.29 mmol) in saturated $NH_3(g)$/MeOH (25 mL) was shaken at room temperature with a suspension of Raney® nickel (1.2 g) under hydrogen atmosphere (50 psi) for 17 h. The catalyst was removed by filtration over celite, and the filtrate was concentrated in vacuo. The crude material was filtered through silica gel (20:1:1 $CH_2Cl_2$/MeOH/$NH_4OH$) to give a white foam (416 mg, 71%).

Using General Procedure D: Conversion of the white foam from above (46 mg, 0.10 mmol) to the hydrobromide salt followed by re-precipitation of the intermediate solid from methanol/ether gave AMD11138 (51 mg, 69%) as a colourless solid. $^1$H NMR ($D_2O$) δ 1.85–1.99 (m, 1H), 2.17–2.37 (m, 2H), 2.40–2.49 (m, 1H), 3.04 (m, 2H), 3.63 (d, 1H, J=13.5 Hz), 3.75 (d, 1H, J=13.8 Hz); 3.94 (s, 3H), 4.10 (d, 1H, J=12.6 Hz), 4.35 (d, 1H, J=12.6 Hz), 4.44 (d, 1H, J=16.2 Hz), 4.55 (d, 1H, J=16.2 Hz), 7.26 (dd, 1H, J=8.1, 1.8 Hz), 7.42 (d, 1H, J=8.1 Hz, 7.50–7.61 (m, 5H), 7.92 (dd, 1H, J=7.8, 6.0 Hz), 8.40 (d, 1H, J=7.8 Hz), 8.77 (d, 1H, J=5.1 Hz); $^{13}$C NMR ($D_2O$) δ 20.52, 20.95, 27.80, 42.02, 49.21, 53.44, 54.23, 63.26, 113.88, 126.10, 126.89, 130.46, 130.70, 131.45, 132.75, 133.22, 133.67, 138.50, 139.66, 140.83, 148.14, 150.33, 151.34, 168.79. ES-MS m/z 456 (M+H). Anal. Calcd. for $C_{27}H_{29}N_5O_2 \cdot 3.0HBr \cdot 2.2H_2O$: C, 43.95; H, 4.97; N, 9.49; Br, 32.48. Found: C, 43.86; H, 4.97; N, 9.35; Br, 32.77.

EXAMPLE 17

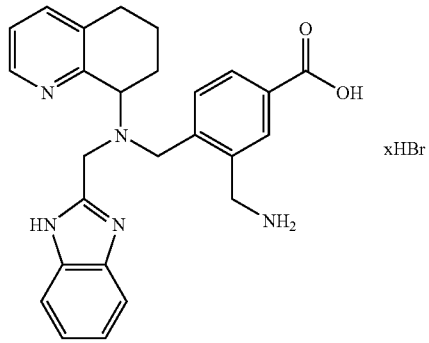

AMD11163: Preparation of 3-aminomethyl-4-{[(1H-benzimidazole-2-ylmethyl)-(5,6,7,8-tetrahydro-quinolin-8-yl)-amino]-methyl}-benzoic acid hydrobromide salt To a stirred solution of LiOH (41 mg, 1.7 mmol) in deionized water (2 mL) was added a solution of AMD11140 (77 mg, 0.17 mmol) in THF (2 mL). The mixture was heated to 50° C., stirred for 15 h, and concentrated to remove THF. 1 N HCl (1.7 mL) was slowly added and the aqueous solution was extracted with $CHCl_3$ (3×10 mL). The combined organic extracts were dried over $MgSO_4$ and concentrated in vacuo. The pale yellow solid (75 mg) was purified by flash column chromatography (1.5 cm i.d., 7 g silica gel, eluted with 10% $NH_4OH$/10% MeOH/$CHCl_3$) to afford the desired amino-acid as a white solid (32 mg).

A saturated solution of HBr in acetic acid (0.5 mL) was added dropwise to a stirred solution of the amino-acid from above (30 mg, 0.068 mmol) in acetic acid (0.5 mL) and stirring was continued for 1 h. Diethy ether (25 mL) was added quickly and the resultant white precipitate was allowed to settle. The ether was decanted, the white solid was washed repeatedly with diethyl ether (5×25 mL), and the residual ether was removed in vacuo. The residue was dried in a vacuum oven at 50° C. for 85 h to give AMD11163 as a white solid (35 mg, 28% over 2 steps). $^1$H NMR($D_2O$) δ 1.81–2.01 (m, 1H), 2.20–2.35 (m, 2H), 2.43–2.54 (m, 1H), 3.00–3.08 (m, 2H), 3.96 (d, 1H, J=15 Hz), 4.19–4.56 (m, 5H), 4.76–4.92 (m, 1H, overlaps with HOD), 7.42–7.55 (m, 6H), 7.62 (d, 1H, J=8.0 Hz), 7.91 (t, 1H, J=6.8 Hz), 8.38 (d, 1H, J=8.0 Hz), 8.75 (d, 1H, 5.7 Hz); $^{13}$C NMR ($D_2O$) δ 20.44, 21.15, 27.94, 40.03, 49.09, 53.60, 63.12, 113.83 (2 carbons), 126.23, 127.06 (2 carbons), 130.39, 130.53, 130.93, 131.85, 132.33, 140.23, 140.38, 141.18, 148.22, 150.33, 150.58, 169.92. ES-MS m/z 442 (M+H). Anal. Calcd. for $C_{26}H_{27}N_5O_2 \cdot 3.0HBr \cdot 2.5H_2O$: C, 42.82; H, 4.84; N, 9.60; Br, 32.87. Found: C, 42.74; H, 4.55; N, 9.51; Br, 32.53.

EXAMPLE 18

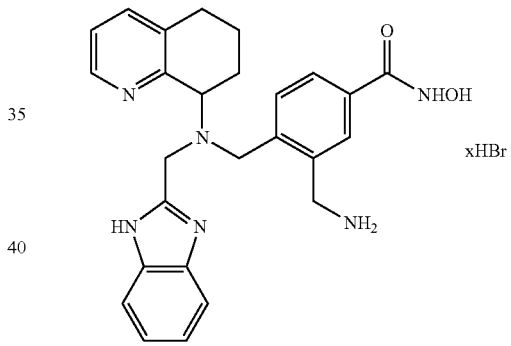

AMD11177: Preparation of 3-aminomethyl-4-{[(1H-benzimidazole-2-ylmethyl)-(5,6,7,8-tetrahydro-quinolin-8-yl)-amino]-methyl}-N-hydroxy-benzamide hydrobromide salt To a stirred solution of sodium metal (42 mg, 1.8 mmol) in anhydrous methanol (6 mL) was slowly added a solution of AMD11140 (159 mg, 0.36 mmol) and hydroxylamine hydrochloride (75 mg, 1.1 mmol) in anhydrous methanol (6 mL). The mixture was heated to reflux, with stirring under a nitrogen atmosphere. After 16 h the solution was concentrated and the resultant residue was partitioned between $CHCl_3$ (15 mL) and deionized $H_2O$ (10 mL). The aqueous layer was extracted with $CHCl_3$ (10 mL) and the combined organic extracts were dried over $MgSO_4$ and concentrated in vacuo. The pale yellow solid (185 mg) was purified by flash column chromatography (3 cm i.d., 15 g silica gel, eluted with 10% $NH_4OH$/10% MeOH/$CHCl_3$) followed by radial chromatography (1 mm plate, eluted with 50:1:1 $CH_2Cl_2$/MeOH/$NH_4OH$) to afford the desired hydroxy-amide as a white solid (63 mg).

A saturated solution of HBr in acetic acid (3 mL) was added dropwise to a stirred solution of the hydroxy-amide from above (63 mg, 0.11 mmol) in acetic acid (3 mL) and stirring was continued for 10 min. Diethy ether (50 mL) was added quickly and the resultant white precipitate was allowed to settle. The ether was decanted, the white solid was washed repeatedly with diethyl ether (5×50 mL), and the residual ether was removed in vacuo. The residue was dried in a vacuum oven at 50° C. for 42 h to give AMD11177 as a white solid (80 mg, 28% over 2 steps). $^1$H NMR(D$_2$O) δ 1.74–1.86 (m, 1H), 2.11–2.30 (m, 2H), 2.35–2.44 (m, 1H), 2.85–2.93 (m, 2H), 3.96 (d, 1H, J=15 Hz), 4.12–4.39 (m, 5H), 4.57–4.62 (m, 1H), 7.31 (s, 1H), 7.38–7.43 (m, 3H), 7.48–7.52 (m, 3H), 7.59–7.64 (m, 1H), 8.03 (d, 1H, J=8.0 Hz), 8.56 (d, 1H, 5.7 Hz); $^{13}$C NMR (D$_2$O) δ 20.73, 21.28, 28.23, 40.14, 48.90, 54.08, 62.97, 114.15 (2 carbons), 124.98, 125.90 (2 carbons), 127.60, 128.81, 132.42, 132.82, 139.26, 140.89, 142.38, 144.62. ES-MS m/z 457 (M+H). Anal. Calcd. for C$_{26}$H$_{28}$N$_6$O$_2$.3.2HBr.3.0H$_2$O.0.17NH$_4$Br: C, 39.72; H, 4.86; N, 10.99; Br, 34.25. Found: C, 39.34; H, 4.78; N, 11.36; Br, 34.51.

EXAMPLE 19

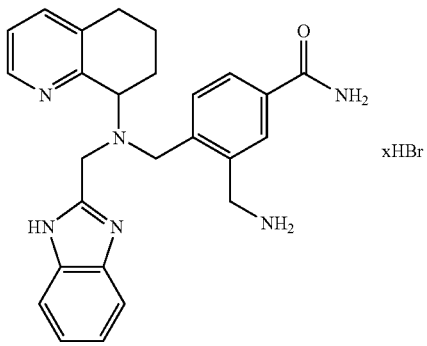

AMD11180: Preparation of 3-aminomethyl-4-{[(1H-benzimidazole-2-ylmethyl)-(5,6,7,8-tetrahydro-quinolin-8-yl)-amino]-methyl}-benzamide hydrobromide salt Preparation of 3-cyano-4-{[(1H-benzimidazole-2-ylmethyl)-(5,6,7,8-tetrahydro-quinolin-8-yl)-amino]-methyl}-benzamide To a stirred solution of LiOH (120 mg, 5.0 mmol) in deionized water (5 mL) was added a solution of 2-{[(2-cyano-4-methoxycarbonyl-benzyl)-(5,6,7,8-tetrahydro-quinolin-8-yl)-amino]-methyl}-benzimidazole-1-carboxylic acid tert-butyl ester (273 mg, 0.49 mmol) in THF (5 mL). The mixture was heated to 50° C. and stirred for 17 h. The solution was cooled to room temperature, concentrated to remove THF, and neutralized with 1 N HCl. The aqueous solution was extracted with CHCl$_3$ (3×25 mL) and the combined organic extracts were dried over MgSO$_4$ and concentrated in vacuo to give the desired acid as a yellow solid (224 mg).

A stirred solution of the acid from above (220 mg, 0.41 mmol) in CH$_2$Cl$_2$ (1.6 mL) was treated with oxalyl chloride (0.41 mL, 0.82 mmol) and heated to reflux for 1 h. The red solution was cooled to room temperature, then ammonia gas was bubbled through the stirred solution for 10 min. The crude mixture was poured into a saturated NaHCO$_3$ solution, extracted with CHCl$_3$ (5×10 mL), and the combined organic extracts were dried over MgSO$_4$ and concentrated in vacuo. The orange foam (200 mg) was purified by flash column chromatography (2 cm i.d., 10 g silica, eluted with 5% NH$_4$OH/5% MeOH/CH$_2$Cl$_2$) to afford the title compound as an orange foam (106 mg, 50% over 2 steps). $^1$H NMR (CDCl$_3$) δ 1.70–1.93 (m br, 1H), 1.99–2.11 (m, 2H), 2.34–2.38 (m, 1H), 2.74–2.88 (m, 2H), 3.88–3.99 (m, 2H), 4.13–4.28 (m, 3H), 5.70 (s br, 1H), 6.05 (s br, 1H), 7.17–7.22 (m, 3H), 7.46 (d, 1H, J=7.5 Hz), 7.50–7.68 (m br, 2H), 7.79–7.95 (m, 3H), 8.64 (d, 1H, J=3.0 Hz).

Preparation of 3-aminomethyl-4-{[(1H-benzimidazole-2-ylmethyl)-(5,6,7,8-tetrahydro-quinolin-8-yl)-aminol-methyl}-benzamide hydrobromide salt (AMD11180)

A solution of 3-cyano-4-{[(1H-benzimidazole-2-ylmethyl)-(5,6,7,8-tetrahydro-quinolin-8-yl)-amino]-methyl}-benzamide (105 mg, 0.24 mmol) in MeOH (10 mL) was treated with Raney nickel (50 mg, cat.) and placed under 50 psi H$_2$ on a shaker for 3.5 h. The slurry was filtered through diatomaceous earth, concentrated in vacuo, and purified by flash column chromatography (3 cm i.d., 20 g silica, eluted with 5% NH$_4$OH/5% MeOH/CH$_2$Cl$_2$) to afford the desired amide (35 mg).

A saturated solution of HBr in acetic acid (2 mL) was added dropwise to a stirred solution of the amide from above (35 mg, 0.079 mmol) in acetic acid (2 mL) and stirring was continued for 10 min. Diethy ether (50 mL) was added quickly and the resultant white precipitate was allowed to settle. The ether was decanted, the white solid was washed repeatedly with diethyl ether (5×50 mL), and the residual ether was removed in vacuo. The residue was dried in a vacuum oven at 50° C. for 17 h to give AMD11180 as a white solid (49 mg, 25% over 2 steps). $^1$H NMR(D$_2$O) δ 1.84–2.00 (m, 1H), 2.19–2.35 (m, 2H), 2.46–2.54 (m, 1H), 3.00–3.08 (m, 2H), 3.97 (d, 1H, J=15 Hz), 4.21–4.58 (m, 5H), 4.75–4.92 (m, 1H, overlaps with HOD), 7.40 (s, 1H), 7.40 (s, 1H), 7.44–7.55 (m, 6H), 7.93 (t, 1H, J=6.8 Hz), 8.40 (d, 1H, J=8.0 Hz), 8.77 (d, 1H, 5.5 Hz); $^{13}$C NMR (D$_2$O) δ 20.43, 21.17, 27.94, 40.12, 49.11, 53.67, 63.17, 113.83 (2 carbons), 126.33, 127.19 (2 carbons), 128.29, 129.24, 130.38, 132.10, 132.51, 132.66, 139.96, 140.12, 141.33, 148.49, 150.15, 150.57, 170.44. ES-MS m/z 441 (M+H). Anal. Calcd. for C$_{26}$H$_{28}$N$_6$O.3.3HBr.2.4H$_2$O.0.7NH$_4$Br: C, 38.11; H, 4.79; N, 11.45; Br, 39.01. Found: C, 37.73; H, 4.64; N, 11.56; Br, 39.27.

EXAMPLE 20

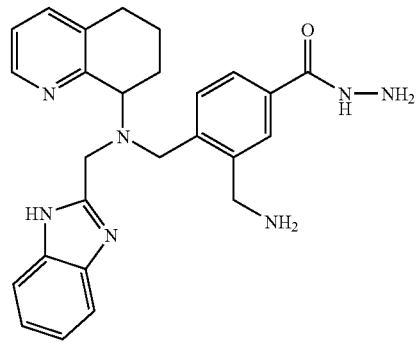

AMD11190: 3-Aminomethyl-4-{[(1H-benzimidazole-2-ylmethyl)-(5,6,7,8-tetrahydro-quinolin-8-yl)-amino]-methyl}-benzoic acid hydrazide (hydrobromide salt)

Preparation of (2-{[(1H-Benzimidazol-2-ylmethyl)-(5,6,7,8-tetrahydro-quinolin-8-yl)-amino]-methyl}-5-hydrzinocarbonyl-benzyl)-carbamic acid tert-butyl ester To a solution of 4-{[(1H-benzimidazol-2-ylmethyl)-(5,6,7,8-tetrahydro-quinolin-8-yl)-amino]-methyl}-3-(tert-butoxycarbonylamino-methyl)-benzoic acid methyl ester (100 mg, 0.18 mmol) in ethanol (2 mL) was added hydrazine hydrate (0.5 mL, 10.31 mmol). The reaction mixture was heated to 80° C. overnight. Then it was cooled, quenched with saturated sodium bicarbonate (2 mL), and washed with $CH_2Cl_2$ (4×5 mL). The combined organic layers were dried ($Na_2SO_4$), filtered, concentrated, and dried in vacuo to afford a yellow oil. Purification by radial chromatography on silica gel (1 mm plate, using $CH_3OH/NH_4OH/CH_2Cl_2$; 1:1:98 then 2:1:97) to afford the product as a crude white solid (60 mg), which was used without further purification. $^1$H NMR ($CDCl_3$) δ 1.55 (s, 9H), 1.61–1.71 (m, 1H), 189–1.96 (m, 1H), 2.27 (br s, 3H), 2.35 (br m, 1H), 2.69–2.90 (m, 2H), 3.80 (q, 2H, J=15 Hz), 3.92–4.04 (m, 4H), 4.41 (br m, 1H), 7.11–7.18 (m, 3H), 7.18 (s, 1H), 7.28–7.42 (m, 3H), 7.60–7.61 (m, 1H), 7.72 (s, 1H), 7.72 (br m, 1H), 8.66 (d, 1H, J=3.7 Hz). ES-MS m/z 557 [M+H]$^+$.

Preparation of 3-Aminomethyl-4-{[(1H-benzimidazol-2-ylmethyl)-(5,6,7,8-tetrahydro-quinolin-8-yl)amino]-methyl}-benzoic acid hydrazide (hydrobromide salt)

To a solution of the above solid (30 mg, 0.054 mmol) in acetic acid (1 mL) was added a solution of hydrobromic acid in acetic acid (0.5 mL) and the reaction mixture was stirred for 30 minutes. Then diethyl ether was added until a precipitation of AMD11190 was afforded as a white solid (35 mg, 77%). $^1$H NMR ($D_2O$) δ 1.90–2.00 (m, 1H), 2.23–2.34 (m, 2H), 2.48–2.52 (m, 1H), 3.04 (br s, 2H), 3.98 (d, 1H, J=13.8 Hz), 4.23 (d, 1H, J=7.5 Hz), 4.29 (t, 1H, J=8.7 Hz), 4.38 (s, 1H), 4.45 (s, 1H), 4.51 (d, 1H, J=6.0 Hz), 4.57 (s, 1H), 7.43–7.54 (m, 7H), 7.92 (t, 1H, J=7.5 Hz), 8.40 (d, 1H, J=7.8 Hz), 8.75 (d, 1H, J=5.1 Hz). $^{13}$C NMR ($D_2O$) δ 20.40, 21.09, 27.91, 39.99, 48.94, 53.55, 62.94, 113.90, 126.31, 127.04, 128.04, 129.15, 130.45, 132.47, 140.11, 140.65, 141.31, 148.47, 150.13, 150.53. ES-MS m/z 456 {M+H]$^+$. Anal. Calcd. for $C_{26}H_{29}N_7$—O.4.0HBr.3.6H$_2$O: C, 37.00; H, 4.80; N, 11.62; Br, 37.87. Found: C, 37.18; H, 4.64; N, 11.31; Br, 37.91.

EXAMPLE 21

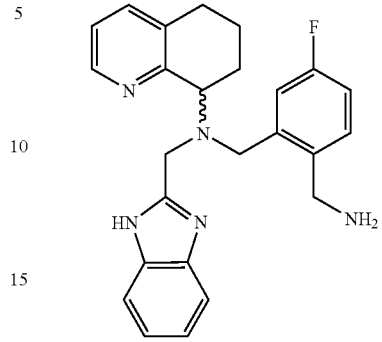

AMD11175: Preparation of (2-aminomethyl-5-fluorobenzyl)-(1H-benzimidazol-2-ylmethyl)-(5,6,7,8-tetrahydro-quinolin-8-yl)-amine (hydrobromide salt)

Preparation of 4-fluoro-2-methylbenzonitrile

A solution of CuCN (4.45 g, 50.0 mmol) and NaCN (3.91 g, 80.0 mmol) in $H_2O$ (15 mL) was heated to 60° C. A suspension of 4-fluoro-2-methylaniline (5.16 g, 41.2 mmol) in $H_2O$ (20 mL) was acidified with concentrated HCl (10 mL). Additional $H_2O$ (approx. 50 mL) was added until the resulting suspension stirred freely and the mixture was cooled to below 0° C. with an ice/salt water bath. A solution of $NaNO_2$ (3.19 g, 46.2 mmol) in $H_2O$ (8 mL) was added dropwise along with crushed ice, ensuring that ice was always present in the diazonium salt solution. The mixture was stirred at 0° C. for 15 minutes, then powdered $K_2CO_3$ (6.62 g, 47.9 mmol) was added portionwise to neutralize the solution. The resulting bright orange solution was then added portionwise to the 60° C. cyanide solution over approx. 40 minutes. The resulting green suspension was heated to 110° C. for 45 minutes and, once cooled to room temperature, saturated aqueous $NaHCO_3$ (80 mL) was added. Extraction of this thick, black solution with $CH_2Cl_2$ (150 mL×3) did not yield any desired material.

An orange solid that was found to have sublimed in the condenser during the reflux portion of the reaction was rinsed out with $CH_2Cl_2$ (100 mL) and washed with $H_2O$ (50 mL). The aqueous solution was extracted with $CH_2Cl_2$ (25 mL×2) and the combined organic solution was dried ($MgSO_4$), filtered and concentrated under reduced pressure, affording the nitrile as a yellow solid (3.00 g, 22.2 mmol, 54%). $^1$H NMR ($CDCl_3$) δ 2.55 (s, 3H), 6.94–7.04 (m, 2H), 7.60 (dd, 1H, J=8.6, 5.6 Hz). IR (thin film, KBr) ν 2223 cm$^{-1}$.

Preparation of 2-bromomethyl-4-fluorobenzonitrile

To a solution of the o-tolunitrile (1.62 g, 12.0 mmol) in benzene (80 mL) was added NBS (1.33 g, 7.47 mmol) and AIBN (153 mg, 0.93 mmol). The solution was heated at reflux under nitrogen for 3 hours and a second portion of each of NBS (1.25 g, 7.02 mmol) and AIBN (150 mg, 0.91 mmol) were added. The reaction was heated at reflux for a further 2 hours and, once cooled, the solution was washed with $H_2O$ (80 mL×2) and brine (80 mL). The organic solution was dried ($MgSO_4$), filtered and concentrated under reduced pressure. Purification by flash column chromatography on silica (EtOAc/hexane, 1:9) gave the bromide as an orange solid (721 mg, 3.37 mmol, 28%). $^1$H NMR ($CDCl_3$) δ 4.60 (s, 2H), 7.13 (td, 1H, J=8.2, 2.5 Hz), 7.28 (dd, 1H, J=8.9, 2.6 Hz), 7.69 (dd, 1H, J=8.6, 5.3 Hz).

Preparation of 2-{[(2-cyano-5-fluorobenzyl)-(5,6,7,8-tetrahydroquinolin-8-yl)-amino]-methyl}-benzimidazole-1-carboxylic acid tert-butyl ester A solution of the benzyl bromide (263 mg, 1.23 mmol), (1-tert-butoxycarbonyl-1H-benzimidazol-2-ylmethyl)-(5,6,7,8-tetrahydro-quinolin-8-yl)-amine (381 mg, 1.01 mmol), DIPEA (0.26 mL, 1.5 mmol), and KI (10 mg, 0.06 mmol) in $CH_3CN$ (7 mL) was stirred at 60° C. under nitrogen for 17 hours. Once cooled to room temperature, saturated aqueous $NaHCO_3$ (10 mL) was added and the mixture was extracted with $CH_2Cl_2$ (25 mL×3). The combined organic solution was dried ($MgSO_4$), filtered and concentrated under reduced pressure. Purification by flash column chromatography on silica (EtOAc/hexane, 1:1) gave the tertiary amine as a pale yellow foam (411 mg, 0.80 mmol, 80%). $^1$H NMR ($CDCl_3$) δ 1.75 (s, 9H), 1.85–2.11 (m, 3H), 2.31–2.41 (m, 1H), 2.64–2.92 (m, 2H), 4.03 (d, 1H, J=16.2 Hz), 4.18 (d, 1H, J=16.2 Hz), 4.34 (dd, 1H, J=10.2, 5.7 Hz), 4.62 (d, 1H, J=14.1 Hz), 4.74 (d, 1H, J=14.1 Hz), 6.55 (td, 1H, J=8.1, 2.7 Hz), 7.0 (dd, 1H, J=7.7, 4.7 Hz), 7.14 (dd, 1H, J=8.4, 5.4 Hz), 7.20 (dd, 2H, J=6.2, 3.2 Hz), 7.23–7.31 (m, 1H), 7.56–7.66 (m, 3H), 8.44 (dd, 1H, J=4.5, 1.2 Hz).

Preparation of 2-{[(1H-benzimidazol-2-ylmethyl)-(5,6,7,8-tetrahydroquinolin-8-yl)-amino]-methyl}-4-fluorobenzonitrile To LiOH $H_2O$ (51 mg, 1.2 mmol) and 10% Pd/C (39 mg, 0.04 mmol) in a 50 mL round bottom flask flushed with nitrogen was added $H_2O$ (2 mL). A solution of the nitrile (201 mg, 0.39 mmol) in dioxane (6 mL) was added followed by Raney-Ni (0.07 mL, 0.6 mmol) as a 50% suspension in $H_2O$ (as described by Klenke, B.; Gilbert, I. H. *J. Org. Chem.* 2001, 66, 2480–2483). The flask was flushed with $H_2$ and heated to 45° C. for 15 hours. Once cooled to room temperature and flushed with nitrogen, the mixture was filtered through Celite, washing with EtOAc. The filtrate was concentrated under reduced pressure, the residue was taken up into saturated aqueous $NaHCO_3$ (15 mL) and extracted with $CH_2Cl_2$ (25 mL×3). The organic solution was dried ($MgSO_4$), filtered and evaporated under reduced pressure, giving the free benzimidazole as a pale yellow solid (153 mg, 0.37 mmol, 95%). $^1$H NMR ($CDCl_3$) δ 1.63–1.78 (m, 1H), 1.93–2.13 (m, 3H), 2.30–2.42 (m, 1H), 2.69–2.90 (m, 2H), 3.88 (d, 1H, J=14.9 Hz), 3.93 (d, 1H, J=14.9 Hz), 4.09–4.13 (m, 1H), 4.21 (d, 1H, J=16.1 Hz), 4.28 (d, 1H, J=16.1 Hz), 6.95 (td, 1H, J=8.3, 2.6 Hz), 7.18–7.22 (m, 3H), 7.45–7.57 (m, 3H), 7.63–7.67 (m, 2H), 8.67 (dd, 1H, J=4.8, 1.5 Hz).

Preparation of AMD11175

The nitrile (153 mg, 0.37 mmol) in a solution of MeOH saturated with $NH_3$ (10 mL) was hydrogenated over Raney-Ni at 50 psi for 4 hours. The mixture was filtered through Celite, washed with MeOH, and the filtrate was concentrated under reduced pressure. Purification by flash column chromatography on silica ($CH_2Cl_2$/MeOH/$NH_4OH$, 19:1:0.1 then 9:1:0.05) gave the primary amine as a white solid (44 mg, 0.11 mmol, 29%), along with recovered nitrile (24 mg, 0.06 mmol, 16%).

To the amine (42 mg, 0.10 mmol) in glacial HOAc (1 mL) was added a saturated solution of HBr in HOAc (0.5 mL) and the solution was stirred at room temperature for 30 minutes. $Et_2O$ (5 mL) was added, the precipitate was allowed to settle and the solvent was decanted. The precipitate was washed with $Et_2O$ (1 mL×5) and dried at 90° C. under reduced pressure giving AMD11175 as a beige solid (66 mg, 0.095 mmol, 95%). $^1$H NMR ($D_2O$) δ 1.82–1.97 (m, 1H), 2.17–2.36 (m, 2H), 2.41–2.53 (m, 1H), 2.98–3.08 (m, 2H), 3.91 (d, 1H, J=13.8 Hz), 4.16 (d, 2H, J=13.8 Hz), 4.32–4.38 (2×d, 2H, J=16.2 and 13.8 Hz), 4.54 (d, 1H, J=16.2 Hz), 6.68 (td, 1H, J=8.6, 2.7 Hz), 7.04 (dd, 1H, J=8.4, 6.0 Hz), 7.19 (dd, 1H, J=9.9, 2.4 Hz), 7.51–7.55 (m, 2H), 7.60–7.63 (m, 2H), 7.89 (t, 1H, J=6.8 Hz), 8.37 (d, 1H, J=7.8 Hz), 8.72 (d, 1H, J=5.4 Hz). $^{13}$C NMR ($D_2O$) δ 20.4, 20.9, 27.9, 39.5, 48.7, 53.3, 62.2, 113.9, 116.1 (d, J=21.7 Hz), 118.1 (d, J=22.0 Hz), 126.2, 127.0, 127.6, 130.7, 132.5 (d, J=8.7 Hz), 138.1, 140.2, 141.1, 148.2, 150.5 (d, J=20.9 Hz). $^{19}$F NMR ($D_2O$) δ −35.9. ES-MS m/z 416 (M+H). Anal. Calcd. for $C_{25}H_{26}FN_5$·3.0HBr·2.3$H_2O$: C, 42.92; H, 4.84; N, 10.01; Br, 343.26. Found: C, 43.00; H, 4.85; N, 9.71; Br, 34.37.

EXAMPLE 22

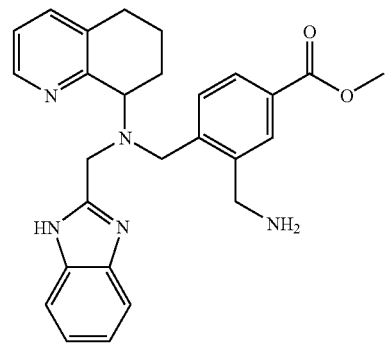

AMD11140: Preparation of 3-aminomethyl-4-{[(1H-benzimidazol-2-ylmethyl)-(5,6,7,8-tetrahydro-quinolin-8-yl)-amino]-methyl}-benzoic acid methyl ester Preparation of 4-bromomethyl-3-cyano-benzoic acid methyl ester A suspension of zinc dust (792 mg, 12.12 mmol) and 1,2-dibromoethane (44 μL, 0.51 mmol) in THF (3 mL) was stirred at 70° C. for 10 minutes. The mixture was cooled to room temperature and chlorotrimethylsilane (45 μL, 0.36 mmol) was added. The mixture was cooled to 0° C. and a solution of methyl-4(bromomethyl)benzoate (2.314 g, 10.10 mmol) in THF (11 mL) was added at 0° C. over 2 hours and then stirred for an additional 2 hours at 0° C. The reaction mixture was cooled to −78° C. and a solution of tosyl cyanide (1.556 g, 8.59 mmol) in THF (11 mL) was added and the resultant mixture stirred at room temperature for 16 hours. The mixture was concentrated under reduced pressure, diluted with $CH_2Cl_2$ (100 mL) and saturated aqueous $NaHCO_3$ (15 mL) and filtered. The phases were separated and the aqueous layer was extracted with $CH_2Cl_2$ (3×50 mL). The combined organic extracts were dried ($MgSO_4$), filtered and concentrated under reduced pressure. Purification by column chromatography on silica gel (Hexanes/EtOAc, 10:1) afforded the desired nitrile (973 mg) as a 16:1 mixture (desired product/side product).

A solution of the nitrile from above (973 mg), N-bromosuccinimide (1.087 g, 6.11 mmol) and AIBN (137 mg, 0.83 mmol) in $CCl_4$ (18.5 mL) was heated to reflux for 4 days. The reaction mixture was cooled to room temperature, filtered and concentrated under reduced pressure. Purification of the yellow syrup by column chromatography on silica gel (Hexanes/EtOAc, 20:1 then 40:3) afforded the desired bromide (800 mg, 37% over 2 steps) as a white solid. $^1$H NMR ($CDCl_3$) δ 3.96 (s, 3H), 4.66 (s, 2H), 7.65 (d, 1H, J=8.1 Hz), 8.23 (dd, 1H, J=8.1, 1.8 Hz), 8.33 (d, 1H, J=1.5Hz).

Preparation of 2-{[(2-cyano-4-methoxycarbonyl-benzyl)-(5,6,7,8-tetrahydro-quinolin-8-yl)-amino]-methyl}-benzimidazole-1-carboxylic acid tert-butyl ester A solution of 4-bromomethyl-3-cyano-benzoic acid methyl ester (800 mg, 3.15 mmol), 2-[(5,6,7,8-tetrahydro-quinolin-8-ylamino)-methyl]-benzimidazole-1-carboxylic acid tert-butyl ester (1.253 g, 3.15 mmol), KI (26 mg, 0.16 mmol) and DIPEA (0.82 mL, 4.72 mmol) in $CH_3CN$ (31.5 mL) was heated at 60° C. overnight. The reaction mixture was cooled to room temperature and concentrated under reduced pressure. The resultant brown syrup was diluted with $CH_2Cl_2$ (100 mL) and washed with saturated aqueous NaCl (30 mL). The aqueous phase was extracted with $CH_2Cl_2$ (2×50 mL) and the combined organic extracts were dried ($MgSO_4$), filtered and concentrated under reduced pressure. Purification of the brown foam by column chromatography on silica gel ($CH_2Cl_2$/MeOH, 20:1) afforded the desired methyl ester (1.74 g, 100%) as a beige foam. $^1$H NMR ($CDCl_3$) δ 1.69–1.78 (m, 10H), 1.95–2.09 (m, 2H), 2.36–2.41 (m, 1H), 2.63–2.85 (m, 2H), 3.86 (s, 3H), 4.17 (d, 1H, J=16.2 Hz), 4.20 (d, 1H, J=15.9 Hz), 4.35–4.40 (m, 1H), 4.58 (d, 1H, J=14.4 Hz), 4.69 (d, 1H, J=14.4 Hz), 7.01 (dd, 1H, J=7.8, 4.8 Hz), 7.13–7.23 (m, 2H), 7.31 (d, 1H, J=7.5 Hz), 7.55–7.61 (m, 2H), 7.76 (d, 2H, J=1.2 Hz), 7.87 (s, 1H), 8.44 (d, 1H, J=4.5 Hz).

2-{[(2-Cyano-4-methoxycarbonyl-benzyl)-(5,6,7,8-tetrahydro-quinolin-8-yl)-amino]-methyl)}-benzimidazole-1-carboxylic acid tert-butyl ester (1.23 g, 2.23 mmol) was dissolved in $NH_3$ saturated MeOH (~15 mL), treated with Raney nickel (excess), and placed under 45 psi $H_2$ on a Parr shaker for 16 hours. The mixture was diluted with MeOH and filtered through Celite. The cake was washed with MeOH and the combined filtrate was concentrated under reduced pressure. The resultant syrup was filtered through a silica gel plug ($CH_2Cl_2$/MeOH/$NH_4OH$, 100:2:1) to afford the desired amine (720 mg) that was used without further purification in the next reaction.

To a solution of the amine from above (64 mg) in $CH_2Cl_2$ (1 mL) was added TFA (1 mL) and the resultant mixture was stirred at room temperature overnight. The mixture was concentrated under reduced pressure and the resultant syrup was dissolved in $H_2O$ and basified with 1N NaOH (pH 8). $CHCl_3$ (75 mL) was added, the phases were separated and the aqueous layer was extracted with $CHCl_3$ (2×75 mL). The combined organic extracts were dried ($MgSO_4$), filtered and concentrated under reduced pressure. Purification of the yellow foam by radial chromatography on silica gel ($CH_2Cl_2$/MeOH/$NH_4OH$, 100:1:1 then 200:3:1) afforded AMD11140 (39 mg, 43% over 2 steps) as a white foam. $^1$H NMR ($CDCl_3$) δ 1.55–1.73 (m, 1H), 1.92–2.07 (m, 2H), 2.23–2.35 (m, 1H), 2.63–2.89 (m, 2H), 3.74–4.02 (m, 10H), 7.06 (dd, 1H, J=7.5, 4.8 Hz), 7.16–7.19 (m, 2H), 7.35 (d, 1H, J=7.5 Hz), 7.47 (d, 1H, J=7.8 Hz), 7.57 (br s, 2H), 7.79–7.82 (m, 1H), 7.93 (br s, 1H), 8.49 (d, 1H, J=3.9 Hz); $^{13}$C NMR ($CDCl_3$) δ 21.75, 22.72, 29.47, 43.47, 49.67, 52.47, 53.72, 60.08, 122.16, 122.49, 128.59, 130.22, 131.01, 131.25, 135.03, 137.53, 142.15, 142.66, 147.34, 154.59, 156.99, 167.19. ES-MS m/z 456.4 (M+H). Anal. Calcd. for $C_{27}H_{29}N_5O_2 \cdot 1.0H_2O$: C, 68.48; H, 6.60; N, 14.79. Found: C, 68.54; H, 6.52; N, 14.51.

EXAMPLE 23

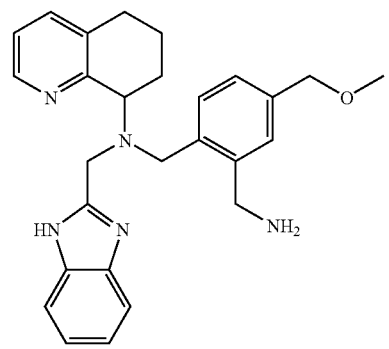

AMD11158: Preparation of (2-aminomethyl-4-methoxymethyl-benzyl)-(1H-benzimidazol-2-ylm-ethyl)-(5,6,7,8-tetrahydro-quinolin-8-yl)-amine Preparation of 2-{[[2-(tert-butoxycarbonylamino-methyl)-4-hydroxymethyl-benzyl]-(5,6,7,8-tetrahy-dro-quinolin-8-yl)-amino]-methyl}-benzimidazole-1-carboxylic acid tert-butyl ester 2-{[(2-Aminomethyl-4-methoxycarbonyl-benzyl)-(5,6,7,8-tetrahydro-quinolin-8-yl)-amino]-methyl}-benzimidazole-1-carboxylic acid tert-butyl ester (1.23 g, 2.23 mmol) was dissolved in $NH_3$ saturated MeOH (~15 mL), treated with Raney nickel (excess), and placed under 45 psi $H_2$ on a Parr shaker for 16 hours. The mixture was diluted with MeOH and filtered through Celite. The cake was washed with MeOH and the combined filtrate was concentrated under reduced pressure. The resultant syrup was filtered through a silica gel plug ($CH_2Cl_2$/MeOH/$NH_4OH$, 100:2:1) to afford the desired amine (720 mg) that was used without further purification in the next reaction.

To a solution of the amine from above (500 mg) in THF (7.2 mL) cooled to 0° C. was added $LiAlH_4$ (1.0M in THF, 1.80 mL, 1.80 mmol) dropwise. The mixture was stirred at room temperature for 15 minutes. MeOH (2 mL) was added and the mixture concentrated and this was repeated twice more. The light yellow foam (410 mg) was used in the next reaction without further purification.

To a solution of the alcohol from above (330 mg) in THF (2 mL) was added a solution of $BOC_2O$ (205 mg, 0.94 mmol) in THF (4 mL) and the resultant mixture was stirred at room temperature for 3 days. The reaction mixture was concentrated under reduced pressure. Purification of the yellow foam by column chromatography on silica gel ($CH_2Cl_2$/MeOH/$NH_4OH$, 100:2:1) afforded the desired amine (230 mg, 30% over 3 steps) as a light yellow foam. $^1$H NMR ($CDCl_3$) δ 1.44 (s, 9H), 1.65–1.70 (m, 10H), 1.96–2.08 (m, 1H), 2.16–2.27 (m, 2H), 2.46–2.57 (m, 1H), 2.71–2.85 (m, 1H), 3.86–3.97 (m, 2H), 4.31 (d, 1H, J=15.0 Hz), 4.38–4.48 (m, 2H), 4.54–4.59 (m, 4H), 6.63 (dd, 1H, J=7.2, 4.5 Hz), 6.98 (d, 1H, J=7.8 Hz), 7.13–7.24 (m, 4H), 7.45 (s, 1H), 7.53–7.56 (m, 1H), 7.68–7.71 (m, 1H), 8.24 (d, 1H, J=3.9 Hz), 8.82–8.87 (m, 1H).

A solution of 2-{[[2-(tert-butoxycarbonylamino-methyl)-4-hydroxymethyl-benzyl]-(5,6,7,8-tetrahydro-quinolin-8-yl)-amino]-methyl}-benzimidazole-1-carboxylic acid tert-butyl ester (230 mg, 0.37 mmol) and NaH (60% dispersion in mineral oil, 13.3 mg, 0.56 mmol) in DMF (2.0 mL) was stirred at room temperature for 30 minutes. Iodomethane (0.12 mL, 1.85 mmol) was added and the resultant mixture was stirred at room temperature for 1 hour. The mixture was concentrated in vacuo, diluted with EtOAc and washed consecutively with saturated aqueous NaHCO$_3$ (2×5 mL) and saturated aqueous NaCl (10 mL). The organic layer was dried (MgSO$_4$) and concentrated under reduced pressure. Purification of the yellow foam by column chromatography on silica gel (CH$_2$Cl$_2$/MeOH/NH$_4$OH, 200:1:1 then 200:2:1) afforded the desired product (97 mg) which was used in the next reaction without further purification.

To a solution of the amine from above (96 mg) in CH$_2$Cl$_2$ (1 mL) was added TFA (1 mL) and the resultant mixture was stirred at room temperature overnight. The mixture was concentrated under reduced pressure and the syrup was dissolved in H$_2$O and basified with 1N NaOH (pH 8). CHCl$_3$ (75 mL) was added, the phases were separated and the aqueous layer was extracted with CHCl$_3$ (2×75 mL). The combined organic extracts were dried (MgSO$_4$), filtered and concentrated under reduced pressure. Purification of the yellow foam by radial chromatography on silica gel (CH$_2$Cl$_2$/MeOH/NH$_4$OH, 100:1:1 then 200:3:1) afforded AMD11158 (20.2 mg, 13% over 2 steps) as a white solid. $^1$H NMR (CD$_3$OD) δ 1.52–1.66 (m, 1H), 2.04–2.25 (m, 3H), 2.61–2.71 (m, 1H), 2.82–2.93 (m, 1H), 3.60–3.65 (m, 1H), 3.72–3.75 (m, 4H), 3.81 (d, 1H, J=12.9 Hz), 3.91–3.98 (m, 3H), 4.13 (d, 1H, J=13.2 Hz), 4.53 (s, 2H), 7.02 (dd, 1H, J=7.5, 4.5 Hz), 7.14–7.27 (m, 4H), 7.33–7.40 (m, 3H), 7.54–7.56 (m, 1H), 8.32–8.36 (m, 1H); $^{13}$C NMR (CD$_3$OD) δ 23.27, 23.34, 30.59, 31.18, 44.23, 48.33, 55.77, 60.96, 65.21, 111.37, 119.67, 123.44, 123.69, 124.30, 127.17, 130.03, 132.72, 136.74, 136.87, 138.48, 142.81, 143.24, 148.08, 153.81, 158.22. ES-MS m/z 442.4 (M+H). Anal. Calcd. for C$_{27}$H$_{31}$N$_5$O.1.2CH$_4$O.0.2CH$_2$Cl$_2$: C, 68.63; H, 7.34; N, 14.09. Found: C, 69.03; H, 7.09; N, 13.79.

EXAMPLE 24

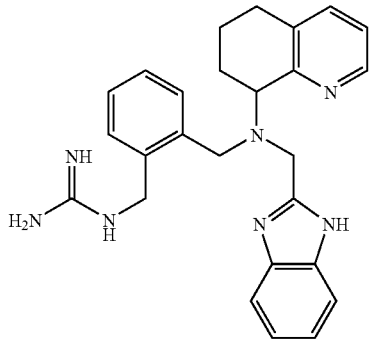

AMD9852: Preparation of N-(2-{[(1H-benzimidazol-2-ylmethyl)-(5,6,7,8-tetrahydroquinolin-8-yl)-amino]-methyl}-benzyl)-guanidine To a solution of (1H-Benzimidazol-2-ylmethyl)-(2-Aminomethyl-benzyl)-(5,6,7,8-tetrahydro-quinolin-8-yl)-amine (see AMD9720) (50 mg, 0.125 mmol) in THF (5 mL) was added added N,N'-di-t-butoxycarbonyl-pyrazole-1-carboxamidine (60 mg, 0.187 mmol) and potassium carbonate (35 mg, 0.25 mmol) and the mixture stirred overnight. The reaction was diluted with aqueous NH$_4$Cl (5 mL) and extracted with ethyl acetate (3×10 mL). The combined organic fractions were dried (Na$_2$SO$_4$), concentrated and purified by chromatography on silica gel (5% MeOH/CH$_2$Cl$_2$) to give the desired product as a pale foam (51 mg, 64%). $^1$H NMR (CDCl$_3$) δ 1.47 (s, 9H), 1.48 (s, 9H), 1.81 (m, 1H), 2.00 (m, 2H), 2.26 (m, 2H), 2.71–2.88 (m, 2H), 3.89–4.05 (m, 5H), 4.73 (dd, 1H, J=15.5, 5.1 Hz), 4.96 (dd, 1H, J=15.5, 5.7 Hz), 7.12 (m, 7H), 7.36–7.44 (m, 3H), 7.55 (br s, 1H (NH)), 8.55 (m, 1H (NH)), 8.66 (d, 1H, J=5.1 Hz).

Using General Procedure D: Conversion of the foam from above (51 mg, 0.08 mmol) to the hydrobromide salt gave AMD9852 as a white solid (108 mg). $^1$H NMR (D$_2$O). δ 1.88 (m, 1H), 2.21 (m, 2H), 2.43 (m, 1H), 3.01 (m, 2H), 3.81 (d, 1H, J=13.5 Hz), 4.01 (d, 1H, J=13.5 Hz), 4.34 (d, 1H, J=16.2 Hz), 4.38 (d, 1H, J=14.4 Hz), 4.44 (d, 1H, J=14.4 Hz), 4.55 (d, 1H, J=16.2 Hz), 4.78 (m, 1H), 6.99 (m, 2H), 7.10 (dt, 1H, J=7.2, 1.2 Hz), 7.40 (d, 1H, J=6.9 Hz), 7.55 (m, 2H), 7.62 (m, 2H), 7.87 (dd, 1H, J=7.8, 5.7 Hz), 8.35 (d, 1H, J=7.8 Hz), 8.68 (d, 1H, J=5.1 Hz.) $^{13}$C NMR (D$_2$O) δ 18.03, 18.26, 25.51, 40.78, 46.69, 50.49, 59.14, 111.69 (2C), 123.74, 124.50 (2C), 126.48, 126.65, 126.74, 128.35, 128.98, 132.04, 137.48, 138.22, 145.85, 150.02. ES-MS w/z 440 (M+H); Anal. Calcd. for (C$_{26}$H$_{29}$N$_7$×3.0 HBr×3.0 H$_2$O): C, 42.41; H, 5.07; N, 13.32; Br, 32.55 Found: C, 42.67; H, 5.07; N, 13.24; Br, 32.77.

EXAMPLE 25

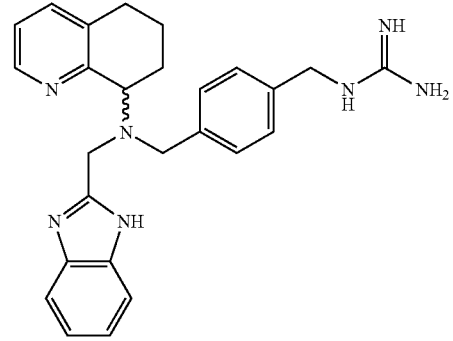

AMD9596: Preparation of N-(4-{[(1H-benzimidazol-2-ylmethyl)-(5,6,7,8-tetrahydroquinolin-8-yl)-amino]-methyl}-benzyl)-guanidine (hydrobromide salt)

To a solution of N'-(1H-benzimidazol-2-ylmethyl)-N'-(5,6,7,8-tetrahydro-8-quinolinyl)-1,4-benzenedimethanamine (397 mg, 1.0 mmol) in THF (10 mL) was added N,N'-di-t-butoxycarbonyl-pyrazole-1-carboxamidine (370 mg, 1.2 mmol) and potassium carbonate (207 mg, 1.5 mmol) and the mixture stirred at room temperature for 16 h. The reaction was diluted with aqueous NH$_4$Cl (15 mL) and the mixture extracted with ethyl acetate (3×10 mL). The combined organic fractions were dried (Na$_2$SO$_4$), filtered, concentrated and purified by chromatography on silica gel (19:1 CH$_2$Cl$_2$/MeOH) to afford N',N"-di-t-butoxycarbonyl-N-(4-{[(1H-benzimidazol-2-ylmethyl)-(5,6,7,8-tetrahydroquinolin-8- yl)-amino]-methyl}-benzyl)-guanidine as a pale foam (426 mg, 67%). $^1$H NMR (CDCl$_3$) δ 1.25 (s, 9H), 1.44 (s, 9H), 1.65 (m, 1H), 1.99 (m, 2H), 2.04 (m, 1H), 2.72–2.79 (m, 2H), 3.73 (s, 2H), 3.94 (d, 1H, J=16.1 Hz), 4.07 (m, 1H), 4.11 (d, 1H, J=12.1 Hz), 4.51 (d, 2H, J=6.2 Hz), 7.14 (m, 4H), 7.39 (m, 3H), 7.55 (m, 1H), 7.63 (m, 1H), 8.47 (m, 1H (NH)), 8.66 (d, 1H, J=4.8 Hz).

Using General Procedure D: Conversion of the material from above (106 mg, 0.1 mmol) to the hydrobromide salt with simultaneous removal of the Boc groups gave AMD 9596 (108 mg) as a white crystalline solid. $^1$H NMR (D$_2$O). δ 1.88 (m, 1H), 2.21 (m, 2H), 2.43 (m, 1H), 3.01 (m, 2H), 3.78 (d, 1H, J=12.6 Hz), 3.83 (d, 1H, J=12.6 Hz), 3.89 (s, 2H), 4.45 (d, 1H, J=16.5 Hz), 4.60 (d, 1H, J=16.5 Hz), 4.79 (m, 1H), 6.89 (d, 2H, J=7.8 Hz), 7.15 (d, 2H, J=7.8 Hz), 750 (m, 2H), 7.57 (m, 2H), 7.91 (dd, 1H, J=8.1, 6.0 Hz), 8.39 (d, 1H, J=8.1 Hz), 8.73 (d, 1H, J=6 Hz). $^{13}$C NMR (D$_2$O) δ 20.46, 20.87, 27.83, 43.90, 50.31, 56.69, 63.17, 113.76 (2C), 126.04, 126.62 (2C), 127.03 (2C), 130.52 (2C), 135.98, 136.24, 139.58, 140.92, 148.20, 150.93, 151.86. ES-MS m/z 440 (M+H); Anal. Calcd. for (C$_{26}$H$_{29}$N$_{7\times3.2}$ HBr$\times$2.2 H$_2$O): C, 42.31; H, 5.00; N, 13.28; Br, 33.64. Found: C, 42.48; H, 5.05; N, 13.15; Br, 32.64.

EXAMPLE 26

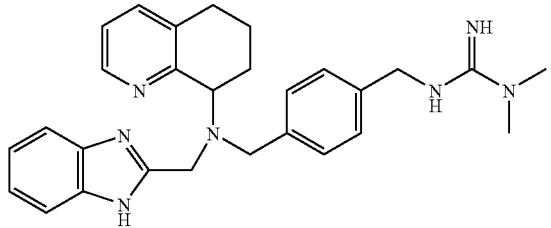

AMD9735: Preparation of N'-(4-{[(1H-Benzimidazol-2-ylmethyl)-(5,6,7,8-tetrahydro-quinolin-8-yl)-amino]-methyl}-benzyl)-N,N-dimethyl-guanidine (hydrobromide salt)

Preparation of N,N-dimethyl-1H-pyrazole-1-carboxamidine hydrochloride

To a solution of pyrazole (1.01 g, 14.8 mmol) and dimethylcyanamide (1.20 mL, 14.8 mmol) in 1,4-dioxane (15 mL) was added HCl (4.0 N in 1,4-dioxane, 3.8 mL, 15.2 mmol) and the resultant mixture was heated to reflux for 3 hours. The reaction mixture was cooled to room temperature and diluted with dry ether (15 mL) to precipitate a yellow solid. The resultant precipitate was allowed to settle to the bottom of the flask (overnight) and the supernatant solution was decanted. The solid was dried under vacuum and provided the title compound (2.01 g, 78%). ES-MS m/z 139 (M+H).

To a solution of N'-(1H-benzimidazol-2-ylmethyl)-N'-(5,6,7,8-tetrahydro-8-quinolinyl)-1,4-benzenedimethanamine (0.221 g, 0.56 mmol) in DMF (1 mL) was added N,N-dimethyl-1H-pyrazole-1-carboxamidine hydrochloride (0.250 g, 1.18 mmol) and N,N-diisopropylethylamine (0.70 mL, 4.02 mmol) and the resultant mixture was stirred at room temperature for 19 h. The reaction mixture was diluted with water (5 mL) and CH$_2$Cl$_2$ (25 mL) and the pH of the aqueous phase was adjust to 4 using dilute aqueous HCl (1 N, 3 mL). The phases were separated and the aqueous phase was extracted with CH$_2$Cl$_2$ (3×10 mL). The aqueous phase was concentrated under reduced pressure and the resultant colorless oil was dissolved in 10 N NaOH (4 mL). The basic aqueous solution was extracted with CH$_2$Cl$_2$ (4×10 mL) and the combined organic extracts were dried (Na$_2$SO$_4$) and concentrated. The crude material was purified by radial chromatography on silica gel (1 mm plate, 1:1:1 CH$_3$CN—CH$_3$OH—NH$_4$OH) and provided a white solid (147 mg).

Using General Procedure D: Conversion of the free base (124 mg) to the hydrobromide salt, followed by re-precipitation of the intermediate solid from methanol/ether, gave AMD9735 (121 mg) as a white solid. $^1$H NMR (D$_2$O) δ 1.84–1.98 (m, 1H), 2.20–2.34 (m, 2H), 2.40–2.47 (m, 1H), 2.99–3.06 (m, 8H), 3.77 (d, 1H, J=12.6 Hz), 3.84 (d, 1H, J=12.6 Hz), 3.96 (s, 2H) 4.47 (d, 1H, J=16.5 Hz), 4.65 (d, 1H, J=16.5 Hz), 4.72–4.79 (m, 1H, overlaps with HOD), 6.93 (d, 2H, J=7.8 Hz), 7.18 (d, 2H, J=7.8 Hz), 7.50–7.53 (m, 2H), 7.58–7.63 (m, 2H), 7.93 (dd, 1H J=6.6, 7.2 Hz), 8.39 (d, 1H, J=7.8 Hz), 8.77 (d, 1H, J=5.7 Hz); $^{13}$C NMR (D$_2$O) δ 20.29, 20.70, 27.67, 37.99, 44.43, 50.09, 56.39, 62.91, 113.65, 125.86, 126.39, 126.86, 130.33, 130.36, 135.80, 136.43, 139.47, 140.75, 148.01, 150.75, 151.75, 155.99; ES-MS m/z 468 (M+H). Anal. Calcd. for C$_{28}$H$_{33}$N$_7$.3.2 HBr.2.6 H$_2$O.1.4 NH$_4$Br: C, 36.94; H, 5.20; N, 12.92; Br, 40.37. Found: C, 36.94; H, 5.06; N, 12.88; Br, 40.45.

EXAMPLE 27

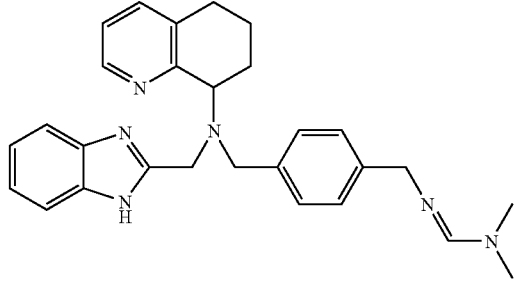

AMD9777: Preparation of [4-(1H-benzimidazol-2-ylmethyl)-(5,6,7,8-tetrahydroquinolin-8-yl)-aminomethylbenzyl]-N,N-dimethylformamidine (hydrobromide salt)

A solution of 2-pyridine sulfonyl chloride (41 mg, 0.23 mmol) in DMF (0.75 mL) was stirred for 10 min after which time a solution of N'-(1H-benzimidazol-2-ylmethyl)-N'-(5,6,7,8-tetrahydro-8-quinolinyl)-1,4-benzenedimethanamine (62 mg, 0.16 mmol) in DMF (0.8 mL) was added and the reaction stirred at room temperature for 3 h. The reaction was concentrated under reduced pressure and diluted with CH$_2$Cl$_2$ (5 mL) and saturated aqueous K$_2$CO$_3$ (5 mL). The layers were separated and the organic phase dried (MgSO$_4$), filtered, concentrated and purified by column chromatography on silica gel (5% MeOH/CH$_2$Cl$_2$) to give the desired N,N-dimethylformamidine (23 mg, 322%). $^1$H NMR (CDCl$_3$) δ 1.67 (m, 1H), 2.03 (m, 2H), 2.24 (m, 1H), 2.70 (m, 1H), 2.84 (m, 1H), 2.84 (s, 6H), 3.71 (s, 2H), 3.96 (d, 1H, J=15.0 Hz), 4.07 (m, 1H), 4.15 (d, 1H, J=18.0 Hz), 4.36

(s, 2H), 7.16 (m, 5H), 7.31 (s, 1H), 7.35 (d, 2H, J=7.8 Hz), 7.42 (d, 1H, J=7.8 Hz), (br, 1H), 7.64 (br, 1H), 8.68 (d, 1H, J=3.5 Hz).

Using General Procedure D: Conversion of the material from above (23 mg) to the hydrobromide salt provided AMD9777 (38 mg) as a white solid. $^1$H NMR (D$_2$O) δ 1.91 (br m, 1H), 2.26 (m, 2H), 2.45 (br m, 1H), 2.97 (s, 3H), 3.03 (br m, 2H), 3.24 (s, 3H), 3.78 (d, 1H, J=12.9 Hz), 3.85 (d, 1H, J=12.9 Hz), 4.04 (s, 2H), 4.45 (d, 1H, J=16.5 Hz), 4.63 (d, 1H, J=16.5 Hz), 4.80 (m, 1H), 6.90 (d, 2H, J=8.1 Hz), 7.18 (d, 2H, J=7.8 Hz), 7.52 (dd, 2H, J=3.0, 6.3 Hz), 7.59 (dd, 2H, J=3.0, 6.3 Hz), 7.64 (s, 1H (NCHN)), 7.94 (t, 1H, J=6.9 Hz), 8.41 (d, 1H, J=7.8 Hz), 8.76 (d, 1H, J=5.7 Hz); $^{13}$C NMR (D$_2$O) δ 20.47, 20.92, 27.85, 36.27, 43.38, 49.66, 50.21, 56.67, 63.21, 113.87 (2C), 126.09, 126.50 (2C), 127.63 (2C), 130.61 (2C), 136.44 (2C), 139.65, 141.01, 148.27 (2C), 150.90, 151.94, 156.35 (2C). ES-MS m/z 453 (M+H). Anal. Calcd. for $C_{28}H_{32}N_6$·3.3HBr·2.3H$_2$O: C, 44.29; H, 5.30; N, 11.07; Br, 34.46. Found: C, 44.36; H, 5.14; N, 10.74; Br, 34.44.

EXAMPLE 28

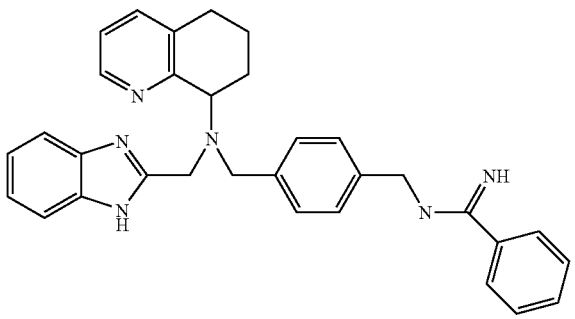

AMD9783: Preparation of N-(4-{[(1H-Benzimidazol-2-ylmethyl)-(5,6,7,8-tetrahydro-quinolin-8-yl)-amino]-methyl}-benzyl)-benzamidine (hydrobromide salt)

Preparation of S-benzylthiobenzimidate hydrobromide

To a solution of thiobenzamide (0.307 g, 2.24 mmol) in CH$_2$Cl$_2$ (11 mL) was added benzyl bromide (0.26 mL, 2.19 mmol) and the resultant solution was heated to reflux for 2 h. The mixture was cooled to room temperature and concentrated under reduced pressure. The resultant yellow solid was dried under vacuum to provide S-benzylthiobenzimidate hydrobromide (0.573 g, 85%). $^1$H NMR (DMSO-d$_6$) δ 4.76 (s, 2H), 7.34–7.44 (m, 3H), 7.51–7.54 (m, 2H), 7.61–7.66 (m, 2H), 7.78–7.83 (m, 1H), 7.88–7.91 (m, 2H), 11.92 (br s, 1H).

To a solution of N'-(1H-benzimidazol-2-ylmethyl)-N'-(5,6,7,8-tetrahydro-8-quinolinyl)-1,4-benzenedimethanamine (0.130 g, 0.33 mmol) in ethanol (2 mL) was added S-benzylthio-benzimidate hydrobromide (0.100 g, 0.33 mmol) and the resultant mixture was stirred at room temperature for 45 min. The mixture was treated with HBr saturated acetic acid (3 mL). Ether (50 mL) was added to precipitate a white solid that was allowed to settle to the bottom of the flask and the supernatant solution was decanted. The solid was washed with ether (3×50 mL) and the remaining traces of ether were removed under reduced pressure. The solid was partitioned between NaOH solution (10 N, 5 mL) and CH$_2$Cl$_2$ (20 mL). The phases were separated and the aqueous phase was extracted with CH$_2$Cl$_2$ (4×10 mL). The combined organic extracts were dried (Na$_2$SO$_4$) and concentrated. Purification of the crude material by radial chromatography on silica gel (1 mm plate, 20:1:1 CH$_2$Cl$_2$—CH$_3$OH—NH$_4$OH) provided 50 mg (32%) of the free base of the title compound as a white solid.

Using General Procedure D: Conversion of the free base (50 mg) to the hydrobromide salt, followed by re-precipitation of the intermediate solid from methanol/ether, gave AMD9783 (56 mg) as a white solid. $^1$H NMR (D$_2$O) δ 1.83–1.97 (m, 1H), 2.20–2.35 (m, 2H), 2.42–2.48 (m, 1H), 3.04 (br s, 2H), 3.79 (d, 1H, J=12.3 Hz), 3.87 (d, 1H, J=12.3 Hz), 4.21 (s, 2H), 4.47 (d, 1H, J=16.5 Hz), 4.65 (d, 1H, J=16.5 Hz), 4.74–4.79 (m, 1H, overlaps with HOD), 7.02 (d, 2H, J=7.8 Hz), 7.22 (d, 2H, J=7.8 Hz), 7.29 (dd, 2H, J=3.0, 6.0 Hz), 7.54 (dd, 2H, J=3.0, 6.0 Hz), 7.62–7.64 (m, 4H), 7.74–7.78 (m, 1H), 7.91 (dd, 1H, J=6.3, 7.2 Hz), 8.39 (d, 1H, J=8.1 Hz), 8.76 (d, 1H, J=5.7 Hz); $^{13}$C NMR (D$_2$O) δ 20.47, 20.93, 27.86, 45.43, 50.31, 56.67, 63.26, 113.73, 126.07, 126.55, 127.64, 128.09, 128.89, 129.83, 130.50, 130.67, 134.41, 136.54, 139.65, 140.99, 148.23, 150.92, 151.93, 164.65; ES-MS m/z 501 (M+H). Anal. Calcd. for $C_{32}H_{32}N_6$·3.0 HBr·2.4 H$_2$O: C, 48.86; H, 5.10; N, 10.68; Br, 30.47. Found: C, 48.97; H, 4.89; N, 10.62; Br, 30.30.

EXAMPLE 29

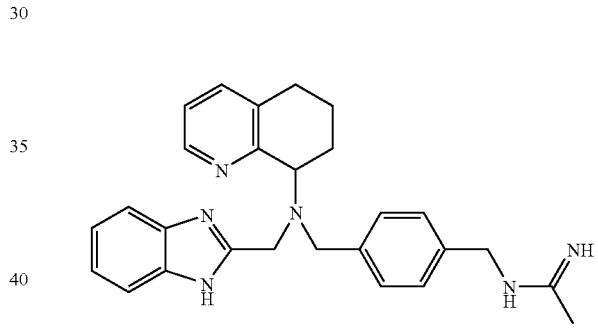

AMD9784: Preparation of N-(4-{[(1H-Benzimidazol-2-ylmethyl)-(5,6,7,8-tetrahydro-quinolin-8-yl)-amino]-methyl}-benzyl)-acetamidine (hydrobromide salt)

Preparation of S-benzylthioacetimidate hydrobromide

To a solution of thioacetamide (0.478 g, 6.36 mmol) in CHCl$_3$ (16 mL) was added benzyl bromide (0.76 mL, 6.39 mmol) and the resultant solution was heated to reflux for 2 hours. The mixture was cooled to room temperature. Ether (50 mL) was added and the mixture was cooled in an ice-water bath to precipitate a white solid. The supernatant solution was decanted and the solid was washed with ether (2×50 mL). The solid was dried under vacuum to provide 1.44 g (92%) of S-benzylthioacetimidate hydrobromide as a white solid. $^1$H NMR (DMSO-d$_6$) δ 2.63 (s, 3H), 4.61 (s, 2H), 7.34–7.46 (m, 5H), 11.89 (br s, 1H).

To a solution of N'-(1H-benzimidazol-2-ylmethyl)-N'-(5,6,7,8-tetrahydro-8-quinolinyl)-1,4-benzenedimethanamine (0.154 g, 0.39 mmol) in ethanol (2 mL) was added S-benzylthio-acetimidate hydrobromide (0.099 g, 0.40 mmol) and the resultant mixture was stirred at room temperature overnight. The mixture was treated with HBr saturated acetic acid (3 mL). The mixture was concentrated under reduced pressure and the residue was partitioned between NaOH solution (10 N, 5 mL) and CH$_2$Cl$_2$ (10 mL). The phases were separated and the aqueous phase was extracted with CH$_2$Cl$_2$ (3×10 mL). The combined organic extracts were dried (Na$_2$SO$_4$) and concentrated. Purification of the crude material by radial chromatography on silica gel (1 mm plate, 1:1:1 CH$_3$CN—CH$_3$OH—NH$_4$OH) provided 97 mg (57%) of the free base of the title compound as a white solid.

Using General Procedure D: Conversion of the free base (97 mg) to the hydrobromide salt, followed by re-precipitation of the intermediate solid from methanol/ether, gave AMD9784 (113 mg) as a white solid. $^1$H NMR (D$_2$O) δ 1.83–1.98 (m, 1H), 2.17–2.33 (m, 5H), 2.41–2.47 (m, 1H), 3.03–3.05 (m, 2H), 3.78 (d, 1H, J=12.3 Hz), 3.85 (d, 1H, J=12.3 Hz), 3.96 (s, 2H), 4.46 (d, 1H, J=16.5 Hz), 4.64 (d, 1H, J=16.5 Hz), 4.74–4.79 (m, 1H, overlaps with HOD), 6.91 (d, 2H, J=7.8 Hz), 7.18 (d, 2H, J=7.8 Hz), 7.49–7.60 (m, 4H), 7.92 (dd, 1H, J=6.0, 7.8 Hz), 8.39 (1H, J=7.5 Hz), 8.75 (d, 1H, J=5.7 Hz); $^{13}$C NMR (D$_2$O) δ 18.91, 20.47, 20.91, 27.86, 44.99, 50.26, 56.65, 63.18, 113.84, 126.08, 126.63, 127.58, 130.52, 130.60, 134.29, 136.43, 139.64, 140.99, 148.25, 150.91, 151.90, 164.99; ES-MS m/z 439 (M+H). Anal. Calcd. for C$_{27}$H$_{30}$N$_6$.3.1 HBr.2.2 H$_2$O: C, 44.48; H, 5.18; N, 11.53; Br, 33.98. Found: C, 44.49; H, 5.19; N, 11.25; Br, 34.13.

EXAMPLE 30

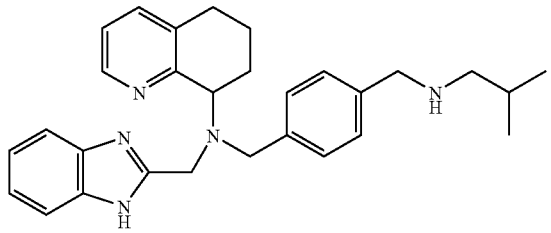

AMD9689: Preparation of N-isobutyl-N'-(1H-benzimidazol-2-ylmethyl)-N'-(5,6,7,8-tetrahydro-8-quinolinyl)-1 4-benzenedimethanamine (hydrobromide salt)

Isobutyraldehyde (0.1 mL, 1.1 mmol) was condensed with N'-(1H-benzimidazol-2-ylmethyl)-N'-(5,6,7,8-tetrahydro-8-quinolinyl)-1,4-benzenedimethanamine (152 mg, 0.382 mmol) in dry CH$_3$OH (5 mL) for 17 h and the resultant imine was reduced with NaBH$_4$ (81 mg, 2.14 mmol) for 1 h (see General Procedures A and B). Purification of the crude product by radial chromatography (2 mm TLC plate, 50:1:1 CH$_2$Cl$_2$/CH$_3$OH/NH$_4$OH) gave the free amine (43 mg, 25%).

Following General Procedure D: Conversion of the material from above (43 mg) to the hydrobromide salt gave AMD9689 (52 mg, 75%) as a white solid. $^1$H NMR (D$_2$O) δ 0.88 (d, 6H, J=6.1 Hz), 1.82–1.96 (m, 2H), 2.17–2.34 (m, 2H), 2.40–2.50 (m, 1H), 2.63 (d, 2H, J=7.6 Hz), 3.01–3.08 (m, 2H), 3.65 (s, 2H), 3.81 (d, 1H, J=12.7 Hz), 3.88 (d, 1H, J=12.7 Hz), 4.46 (d, 1H, J=16.6 Hz), 4.64 (d, 1H, J=16.1 Hz), 7.02 (d, 2H, J=7.9 Hz), 7.23 (d, 2H, J=8.0 Hz), 7.51 (dd, 2H, J=6.2, 3.1 Hz), 7.59 (dd, 2H, J=6.0, 3.6 Hz), 7.94 (dd, 1H, J=8.1, 6.0 Hz), 8.41 (d, 1H, J=7.9 Hz), 8.76 (d, 1H, J=5.7 Hz). $^{13}$C (D$_2$O) δ 19.67 (2 carbons), 20.64, 21.12, 25.95, 28.04, 50.35, 50.67, 54.46, 56.86, 63.38, 114.11 (2 carbons), 126.30, 126.90 (2 carbons), 130.35 (2 carbons), 130.75, 130.93 (2 carbons), 138.13, 139.87, 141.21, 148.46 (2 carbons), 151.03, 151.95. ES-MS m/z 454 (M+H) Anal Calc. for C$_{29}$H$_{35}$N$_5$.3.0HBr.1.9H$_2$O: C, 47.68; H, 5.77; N, 9.59; Br, 32.81. Found: C, 47.53; H, 5.68; N, 9.46; Br, 32.94.

EXAMPLE 31

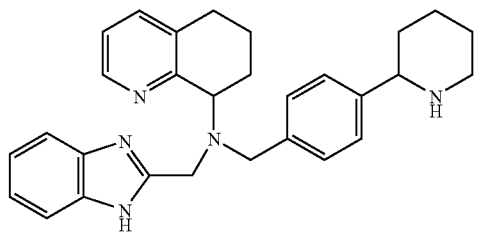

AMD9776: Preparation of (1H-Benzimidazol-2-ylmethyl)-(4-piperidin-2-yl-benzyl)-(5,6,7,8-tetrahydro-quinolin-8-yl -amine (hydrobromide salt)

Preparation of 4-[(1-butyoxycarbonyl)-piperidin-2-yl]-benzaldehyde

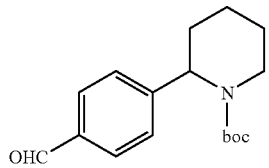

To a solution of 4-pyridin-2-yl-benzaldehyde (1.036 g, 5.65 mmol) in EtOH (95%, 3.1 mL) and conc. HCl (0.48 mL) in a Parr hydrogenation flask was added PtO$_2$ (57 mg, 0.251 mmol) and the mixture hydrogenated at 50 psi H$_2$ for 40 h. The mixture was filtered through celite, the cake washed with MeOH and the solvent was removed from the eluent under reduced pressure. The resultant yellow solid was dissolved in 1 N NaOH (30 mL) and extracted with ether (4×50 mL). The combined organic phases were dried (Na$_2$SO$_4$), filtered and concentrated under reduced pressure to give crude 1-(hydroxymethyl)-4-(piperidin-2-yl)-benzene (0.98 g) as white solid. To a solution of the solid in THF (25 mL), triethylamine (10 drops) and water (10 drops) was added di-tert-butyl dicarbonate (1.51 g, 6.92 mmol) and the reaction stirred at room temperature for 20 h. The mixture was concentrated under reduced pressure and the residue taken up in CH$_2$Cl$_2$ (100 mL) and washed with brine (3×75 mL). The organic phase was dried (Na2SO$_4$), filtered and concentrated under reduced pressure to give crude 1-(hydroxymethyl)-4-[(1-butoxycarbonyl)-piperidin-2-yl]-benzene (1.87 g) as an oil.

To a solution of the oil from above (1.87 g) in CH$_2$Cl$_2$ (100 mL) was added MnO$_2$ (85%, 5.90 g, 57.7 mmol) and the reaction stirred at room temperature for 18 h. The mixture was filtered through celite and the solvent from the eluent was removed under reduced pressure. Purification of the crude product (1.50 g) by flash chromatography (38 g silica, 99:1 $CH_2Cl_2:CH_3OH$) gave the title compound (0.98 g, 60%). $^1H$ NMR ($CDCl_3$) δ 1.25–1.69 (m, 13H), 1.95 (tt, 1H, J=13.4, 4.6 Hz), 2.31 (d, 1H, J=12.9 Hz), 2.77 (td, 1H, J=12.4, 4.3 Hz), 4.09 (d, 1H, J=13.7 Hz), 5.44 (s, 1H), 7.39 (d, 2H, J=7.7 Hz), 7.87 (d, 2H, J=8.2 Hz), 10.00 (s, 1H).

Following General Procedure B: To a solution of 4-[(1-butyoxycarbonyl)-piperidin-2-yl]-benzaldehyde (189 mg, 0.651 mmol) and [1-(tert-butoxycarbonyl)-(1H-benzimidazol-2-ylmethyl)]-(5,6,7,8-tetrahydro-quinolin-8-yl)-amine (138 mg, 0.366 mmol) in $CH_2Cl_2$ (8 mL) was added $NaBH(OAc)_3$ (219 mg, 1.03 mmol) and the reaction stirred overnight. Purification of the crude oil by column chromatography (12 g silica, 40:1:1 $CH_2Cl_2:CH_3OH:NH_4OH$) followed by radial chromatography (1 mm TLC plate, 100:1:1 $CH_2Cl_2:CH_3OH:NH_4OH$) gave the desired free base (59 mg, 29%).

Following General Procedure D: Conversion of the oil from above (59 mg) to the hydrobromide salt gave AMD9776 (59 mg, 75%). $^1H$ NMR ($D_2O$) δ 1.07–1.22 (m, 1H), 1.24–1.40 (m, 1H), 1.43–1.68 (m, 2H), 1.81–1.98 (m, 3H), 2.18–2.36 (m, 2H), 2.40–2.51 (m, 1H), 2.95–3.10 (m, 3H), 3.35 (d, 1H, J=13.3 Hz), 3.75–3.92 (m, 3H), 4.48 (dd, 1H, J=16.7, 8.7 Hz), 4.66 (dd, 1H, J=16.7, 5.7 Hz), 7.01 (d, 2H, J=7.5 Hz), 7.26 (dd, 2H, J=7.8, 4.9 Hz), 7.48–7.54 (m, 2H), 7.55–7.61 (m, 2H), 7.91–7.97 (m, 1H), 8.41 (d, 1H, J=8.3 Hz), 8.75–8.80 (m, 1H). $^{13}C$ NMR ($D_2O$) δ 20.48, 20.97, 21.84, 22.29, 27.88, 29.86, 45.87, 50.32, 50.49, 56.61, 60.24, 63.27, 63.37, 113.94 (2 carbons), 126.14, 126.71 (2 carbons), 127.06 (2 carbons), 130.46, 131.03 (2 carbons), 136.85, 137.49, 139.71, 141.02, 148.30 (2 carbons), 150.83, 151.88. ES-MS m/z 452 (M+H) Anal Calc. for $C_{29}H_{33}N_5.3.0HBr.2.0H_2O$: C, 47.69; H, 5.52; N, 9.59; Br, 32.82. Found: C, 47.54; H, 5.42; N, 9.48; Br, 33.09.

EXAMPLE 32

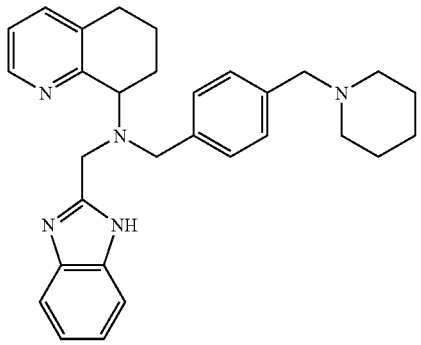

AMD9713: Preparation of (1H-Benzimidazol-2-ylmethyl)-(4-piperidin-1-ylmethyl-benzyl)-(5,6,7,8-tetrahydro-quinolin-8-yl)-amine (hydrobromide salt)

Using General Procedure A: To a stirred solution of 4-{[(1H-Benzimidazol-2-ylmethyl)-(5,6,7,8-tetrahydroquinolin-8-yl)-amino]-methyl}-benzaldehyde (AMD9882) (144 mg, 0.36 mmol) in dry MeOH (5 mL) was added piperidine (0.040 mL, 0.40 mmol) and sodium cyanoborohydride (44 mg, 0.70 mmol) and the mixture stirred for 5 h. Purification of the crude product by radial chromatography on silica gel (1 mm plate, $CH_2Cl_2/MeOH/NH_4OH$, 50:1:1) afforded the desired adduct (50 mg, 30%) as a white foam.

Using General Procedure D: Conversion of the foam from above (25 mg, 0.053 mmol) to the hydrobromide salt followed by re-precipitation of the intermediate solid from methanol/ether gave AMD9713 (40 mg, 98%) as a yellow solid. $^1H$ NMR ($D_2O$) δ 1.32–1.57 (m, 3H), 1.70–1.93 (m, 4H), 2.22–2.31 (m, 2H), 2.44–2.48 (m, 1H), 2.65 (br t, 2H, J=11.4 Hz), 3.01–3.03 (br m, 4H), 3.75 (s, 2H), 3.81 (d, 1H, J=12.6 Hz), 3.89 (d, 1H, J=12.6 Hz), 4.48 (d, 1H, J=16.5 Hz), 4.67 (d, 1H, J=16.5 Hz), 4.77–4.79 (m, 1H, overlap with HOD), 7.04 (d, 2H, J=7.8 Hz), 7.25 (d, 2H, J=7.8 Hz), 7.51 (dd, 2H, J=6.3, 3 Hz), 7.59 (dd, 2H, J=6.3, 3 Hz), 7.94 (dd, 1H, J=7.5, 6.3 Hz), 8.41 (d, 1H, J=8.1 Hz), 8.78 (d, 1H, J=5.4 Hz); $^{13}C$ NMR ($D_2O$) δ 20.30, 20.82, 21.25, 22.91, 27.71, 50.19, 52.80, 56.58, 59.44, 63.22, 113.70, 125.98, 126.62, 128.69, 130.29, 130.58, 131.14, 138.14, 139.55, 140.92, 148.17, 150.66, 151.68. ES-MS m/z 466 (M+H). Anal. Calcd. for $C_{30}H_{35}N_5.3.2HBr.1.5H_2O$: C, 47.94; H, 5.53; N, 9.32; Br, 34.02. Found: C, 47.72; H, 5.54; N, 9.22; Br, 34.32.

EXAMPLE 33

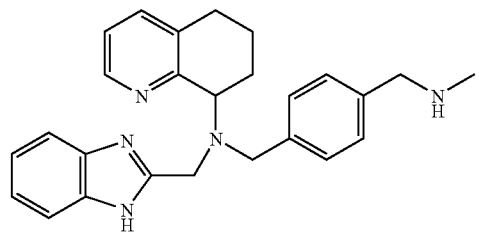

AMD9722: Preparation of (1H-Benzimidazol-2-ylmethyl)-(4-methylaminomethyl-benzyl)-(5,6,7,8-tetrahydro-quinolin-8-yl)-amine (hydrobromide salt)

Using General Procedure B: To a solution of 4-{[(1H-Benzimidazol-2-ylmethyl)-(5,6,7,8-tetrahydro-quinolin-8-yl)-amino]-methyl}-benzaldehyde (AMD9882) (120 mg, 0.30 mmol) in MeOH (2 mL) was added methylamine (2.0 M solution in methanol, 1 mL, 2.00 mmol) and the resultant solution was stirred at room temperature for 5 hours. Solid $NaBH_4$ (18 mg, 0.48 mmol) was added to the solution and the mixture was stirred at room temperature for an additional 30 minutes. Purification of the crude material by radial chromatography on silica gel (1 mm plate, 50:1:1 $CH_2Cl_2/CH_3OH/NH_4OH$) provided the free base of the title compound (74 mg, 59%) as a white solid.

Using General Procedure D: Conversion of the free base (74 mg) to the hydrobromide salt, followed by re-precipitation of the intermediate solid from methanol/ether, gave AMD9722 (111 mg) as a white solid. $^1H$ NMR ($D_2O$) δ 1.84–1.97 (m, 1H), 2.21–2.47 (m, 6H), 3.04 (br s, 2H), 3.66 (s, 2H), 3.81 (d, 1H, J=12.6 Hz), 3.88 (d, 1H, J=12.6 Hz), 4.46 (d, 1H, J=16.5 Hz), 4.64 (d, 1H, J=16.5 Hz), 4.77–4.79 (m, 1H, overlaps with HOD), 7.01 (d, 2H, J=8.1 Hz), 7.24 (d, 2H, J=8.1 Hz), 7.49–7.53 (m, 2H), 7.56–7.60 (m, 2H), 7.93 (dd, 1H, J=6.0, 7.5 Hz), 8.40 (d, 1H, J=8.1 Hz), 8.76 (d, 1H, J=5.7 Hz); 13C NMR ($D_2O$) δ 18.71, 19.20, 26.11, 30.37, 48.50, 49.69, 54.93, 61.49, 112.19, 124.37, 124.95, 128.27, 128.77, 128.84, 129.07, 136.21, 137.94, 139.28, 146.54, 149.08, 150.08; ES-MS m/z 412 (M+H). Anal. Calcd. for $C_{26}H_{29}N_5.3.0 HBr.2.0 H_2O$: C, 45.24; H, 5.26; N, 10.15; Br, 34.73. Found: C, 45.13; H, 5.20; N, 10.02; Br, 34.81.

EXAMPLE 34

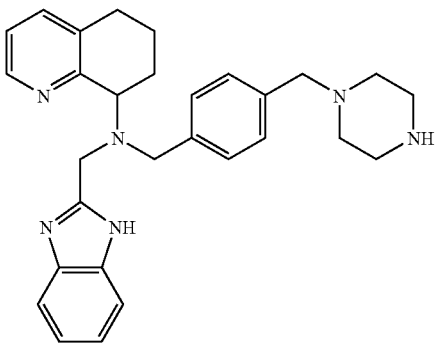

AMD9724: Preparation of (1H-Benzimidazol-2-ylmethyl)-(4-piperazin-1-ylmethyl-benzyl)-(5,6,7,8-tetrahydro-quinolin-8-yl)-amine (hydrobromide salt)

Preparation of 2.2,2-trifluoro-1-piperazin-1-yl-ethanone (Xu. D.; Repic, O.; Blacklock. J. *Tetrahedron Lett.* 1995, 41. 7357–7360)

To a solution of piperazine (1.444 g, 16.8 mmol) in MeOH (10 mL) was added trifluroacetic acid ethyl ester (2.0 mL, 16.8 mmol) and the mixture stirred at room temperature overnight. The reaction was concentrated and purified by column chromatography on silica gel ($CH_2Cl_2$/MeOH, 9:1) to afford the desired mono-protected piperazine adduct (1.77 g, 58%) as a pale yellow oil. $^1$H NMR ($CDCl_3$) δ 1.70 (br s, 1H), 2.90–2.94 (m, 4H), 3.56–3.59 (m, 2H), 3.64–3.67 (m, 2H).

Using General Procedure A: To a stirred solution of 4-{[(1H-Benzimidazol-2-ylmethyl)-(5,6,7,8-tetrahydro-quinolin-8-yl)-amino]-methyl}-benzaldehyde (AMD9882) (262 mg, 0.66 mmol) in dry MeOH (10 mL) was added 2,2,2-trifluoro-1-piperazin-1-yl-ethanone (172 mg, 0.95 mmol) and sodium cyanoborohydride (54 mg, 0.86 mmol) and the mixture stirred overnight. Purification of the crude product by column chromatography on silica gel ($CH_2Cl_2$/MeOH/$NH_4OH$, 100:1:1) followed by radial chromatography on silica gel (2 mm plate, $CH_2Cl_2$/MeOH/$NH_4OH$, 50:1:1) afforded the desired adduct (68 mg, 18%) as a white foam.

To a solution of the TFA-protected adduct from above (68 mg, 0.12 mmol) in MeOH (3 mL) was added powdered $K_2CO_3$ (55 mg, 0.40 mmol) and the mixture stirred at reflux for 1.5 h and at room temperature overnight. The reaction was diluted with $CH_2Cl_2$ (30 mL) and water (20 mL), the phases separated and the aqueous layer extracted with $CH_2Cl_2$ (2×15 mL). The combined organic extracts were dried ($Na_2SO_4$), filtered and concentrated in vacuo. Purification of the crude product by radial chromatography on silica gel (1 mm plate, $CH_2Cl_2$MeOH/$NH_4OH$, 100:1:1 then 50:1:1) afforded the desired adduct (54 mg, 97%) as a clear oil.

Using General Procedure D: Conversion of the foam from above (23 mg, 0.049 mmol) to the hydrobromide salt followed by re-precipitation of the intermediate solid from methanol/ether gave AMD9724 (35 mg, 85%) as a white solid. $^1$H NMR ($D_2O$) δ 1.89–1.93 (m, 1H), 2.21–2.33 (m, 2H), 2.42–2.48 (m, 1H), 3.03–3.05 (m, 2H), 3.24–3.28 (m, 4H), 3.42–3.44 (m, 4H), 3.82 (d, 1H, J=12.9 Hz), 3.87 (s , 2H), 3.90 (d, 1H, J=12.6 Hz), 4.46 (d, 1H, J=16.5 Hz), 4.65 (d, 1H, J=16.5 Hz), 4.77–4.79 (m, 1H, overlap with HOD), 7.07 (d, 2H, J=7.8 Hz), 7.27 (d, 2H, J=7.8 Hz), 7.51 (dd, 2H, J=6, 3 Hz), 7.59 (dd, 2H, J=6, 3 Hz), 7.94 (dd, 1H, J=7.2, 6.6 Hz), 8.41 (d, 1H, J=8.1 Hz), 8.78 (d, 1H, J=6.2 Hz); $^{13}$C NMR ($D_2O$) δ 20.45, 20.97, 27.87, 41.14, 48.19, 50.17, 56.75, 59.92, 63.27, 113.97, 126.15, 126.68, 128.00, 130.53, 130.94, 131.34, 138.82, 139.74, 141.09, 148.33, 150.78, 151.81. ES-MS m/z 467 (M+H). Anal. Calcd. for $C_{29}H_{34}N_6$·4HBr·2.5$H_2O$: C, 41.70; H, 5.19; N, 10.06; Br, 38.26. Found: C, 41.72; H, 5.16; N, 9.82; Br, 38.41.

EXAMPLE 35

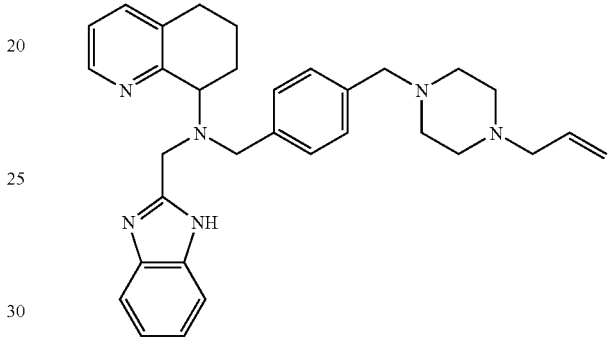

AMD9733: Preparation of [4-(4-Allyl-piperazin-1-ylmethyl)-benzyl]-(1H-benzimidazol-2-ylmethyl)-(5,6,7,8-tetrahydro-quinolin-8-yl)-amine (hydrobromide salt)

Preparation of 1-allyl-piperazine

To a stirred solution of 2,2,2-trifluoro-1-piperazin-1-yl-ethanone (515 mg, 2.83 mmol) in dry $CH_3CN$ (6 mL) was added allyl bromide (0.32 mL, 3.7 mmol) and powdered potassium carbonate (0.78 g, 5.65 mmol) and the mixture stirred overnight. The reaction was concentrated under reduced pressure, diluted with $CH_2Cl_2$ (30 mL) and water (30 mL) and the aqueous layer extracted with $CH_2Cl_2$ (2×20 mL). The combined organic extracts were dried ($Na_2SO_4$), filtered and concentrated in vacuo to afford the crude di-protected piperazine (0.554 g) which was used without further purification in the next reaction.

To a solution of the TFA-protected piperazine from above (0.554 g) in MeOH (10 mL) was added powdered $K_2CO_3$ (0.689 g, 5.0 mmol) and the mixture stirred at reflux for 1.5 h and at room temperature overnight. The reaction was diluted with $CH_2Cl_2$ (30 mL) and water (20 mL), the phases separated and the aqueous layer extracted with $CH_2Cl_2$ (2×15 mL). The combined organic extracts were dried ($Na_2SO_4$), filtered and concentrated in vacuo to afford the title compound (0.132 g, 42%) as a pale yellow oil. $^1$H NMR ($CDCl_3$) δ 1.96 (br s, 1H), 2.39–2.44 (br m, 4H), 2.89–2.92 (m, 4H), 2.98 (d, 2H, J=6Hz), 5.13–5.21 (m, 2H), 5.79–5.93 (m, 1H).

Using General Procedure B: To a stirred solution of 4-{[(1H-Benzimidazol-2-ylmethyl)-(5,6,7,8-tetrahydro-quinolin-8-yl)-amino]-methyl}-benzaldehyde (AMD9882) (262 mg, 0.66 mmol) and 1-allyl-piperazine (132 mg, 1.05 mmol) in CH$_2$Cl$_2$ (6 mL) was added NaBH(OAc)$_3$ (184 mg, 0.87 mmol) and the resultant mixture was stirred at room temperature for 2 h. Purification of the crude material by column chromatography on silica gel gel (CH$_2$Cl$_2$/MeOH/NH$_4$OH, 95:4:1) afforded the desired adduct (267 mg) as a clear oil.

Using General Procedure D: Conversion of the oil from above (233 mg) to the hydrobromide salt followed by re-precipitation of the intermediate solid from methanol/ether gave AMD9733 (335 mg, 56% over 2 steps) as a yellow solid. $^1$H NMR (D$_2$O) δ 1.89–1.94 (m, 1H), 2.21–2.33 (m, 2H), 2.42–2.46 (m, 1H), 3.03–3.05 (m, 2H), 3.30–3.34 (m, 4H), 3.44–3.51 (m, 4H), 3.80–3.90 (m, 6H), 4.47 (d, 1H, J=16.5 Hz), 4.65 (d, 1H, J=16.5 Hz), 4.77–4.79 (m, 1H, overlap with HOD), 5.62 (d, 1H, J=17.1 Hz), 5.64 (d, 1H, J=9.6 Hz), 5.81–5.91 (m, 1H), 7.07 (d, 2H, J=7.8 Hz), 7.28 (d, 2H, J=7.8 Hz), 7.50 (dd, 2H, J=6, 3 Hz), 7.59 (dd, 2H, J=6, 3 Hz), 7.95 (dd, 1H, J=7.8, 6 Hz), 8.42 (d, 1H, J=7.8 Hz), 8.78 (d, 1H, J=5.5 Hz); $^{13}$C NMR (D$_2$O) δ 20.72, 21.26, 28.15, 48.52, 48.64, 50.48, 56.99, 59.47, 59.73, 63.48, 114.29, 125.18, 126.44, 126.97, 127.79, 128.76, 130.70, 131.28, 131.71, 139.20, 140.03, 141.33, 148.62, 150.97, 152.01. ES-MS m/z 507 (M+H). Anal. Calcd. for C$_{32}$H$_{38}$N$_6$·3.9HBr·2.7H$_2$O·0.4C$_4$H$_{10}$O: C, 44.81; H, 5.74; N, 9.33; Br, 34.60. Found: C, 44.62; H, 5.49; N, 9.26; Br, 34.84.

EXAMPLE 36

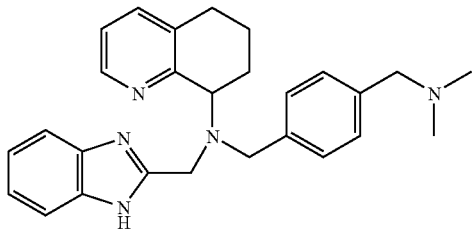

AMD9734: Preparation of (1H-Benzimidazol-2-ylmethyl)-(4-dimethylaminomethyl-benzyl)-(5,6,7,8-tetrahydro-quinolin-8-yl)-amine (hydrobromide salt)

Using General Procedure B: Reaction of 4-{[(1H-Benzimidazol-2-ylmethyl)-(5,6,7,8-tetrahydro-quinolin-8-yl)-amino]-methyl}-benzaldehyde (AMD9882) (157 mg, 0.40 mmol) and dimethylamine (2.0 M in THF, 0.4 mL, 0.80 mmol) with NaBH(OAc)$_3$ (0.179 g, 0.84 mmol) in CH$_2$Cl$_2$ (4 mL) overnight followed by purification of the crude material by radial chromatography on silica gel (2 mm plate, 50:1:1 CH$_2$Cl$_2$—CH$_3$OH—NH$_4$OH) provided the free base of the title compound (72 mg, 43%) as a colorless oil.

Using General Procedure D: Conversion of the free base (72 mg) to the hydrobromide salt, followed by re-precipitation of the intermediate solid from methanol/ether, gave AMD9734 (77 mg) as a white solid. $^1$H NMR (D$_2$O) δ 1.86–1.98 (m, 1H), 2.20–2.48 (m, 9H), 3.05 (br s, 2H), 3.80 (s, 2H), 3.81 (d, 1H, J=12.6 Hz), 3.90 (d, 1H, J=12.6 Hz), 4.50 (d, 1H, J=16.5 Hz), 4.68 (d, 1H, J=16.5 Hz), 4.78–4.83 (m, 1H, overlaps with HOD), 7.06 (d, 2H, J=7.8 Hz), 7.28 (d, 2H, J=7.8 Hz), 7.48–7.52 (m, 2H), 7.57–7.61 (m, 2H), 7.95 (dd, 1H, J=6.0, 7.5 Hz), 8.42 (d, 1H, J=7.8 Hz), 8.79 (d, 1H, J=5.7 Hz); $^{13}$C NMR (D$_2$O) δ 20.47, 21.03, 27.90, 42.16, 50.41, 56.77, 60.12, 63.45, 113.98, 126.18, 126.85, 129.16, 130.43, 130.91, 131.12, 138.45, 139.74, 141.11, 148.37, 150.77, 151.99; ES-MS m/z 426 (M+H). Anal. Calcd. for C$_{27}$H$_3$N$_5$·3.2 HBr·2.2 H$_2$O: C, 44.78; H, 5.37; N, 9.67; Br, 35.31. Found: C, 44.76; H, 5.27; N, 9.52; Br, 35.29.

EXAMPLE 37

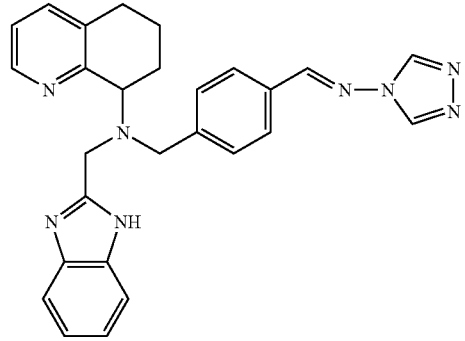

AMD 9775: Preparation of (1H-Benzimidazol-2-ylmethyl)-(5,6,7,8-tetrahydro-quinolin-8-yl)-[4-(1,2,4-triazol-4-yliminomethyl)-benzyl]-amine hydrobromide salt)

Using General Procedure B: Reaction of 4-{[(1H-Benzimidazol-2-ylmethyl)-(5,6,7,8-tetrahydro-quinolin-8-yl)-amino]-methyl}-benzaldehyde (AMD9882) (206 mg, 0.52 mmol) and 4-amino-1,2,4-triazole (70 mg, 0.82 mmol) with NaBH(OAc)$_3$ (0.223 g, 1.05 mmol) in CH$_2$Cl$_2$ (4 mL) and acetic acid (0.12 mL) overnight followed by purification of the crude material by radial chromatography on silica gel (2 mm plate, 100:1:1 CH$_2$Cl$_2$—CH$_3$OH—NH$_4$OH) provided 87 mg (36%) of the free base of the title compound as a colorless oil.

Using General Procedure D: Conversion of the free base (87 mg) to the hydrobromide salt, followed by re-precipitation of the intermediate solid from methanol/ether, gave AMD9775 (83 mg) as a white solid. $^1$H NMR (D$_2$O) δ 1.85–1.99 (m, 1H), 2.20–2.34 (m, 2H), 2.45–2.49 (m, 1H), 3.06 (s, 2H), 3.82 (d, 1H, J=12.6 Hz), 3.91 (d, 1H, J=12.6 Hz), 4.46 (d, 1H, J=16.5 Hz), 4.65 (d, 1H, J=16.5 Hz), 4.79–4.83 (m, 1H, overlaps with HOD), 7.27–7.32 (m, 2H), 7.36–7.44 (m, 4H), 7.50–7.56 (m, 2H), 7.95 (dd, 1H, J=6.3, 7.5 Hz), 8.41–8.43 (m, 2H), 8.79 (d, 1H, J=5.4 Hz), 9.07 (br s, 2H); $^{13}$C NMR (D$_2$O) δ 20.44, 21.04, 27.86, 50.24, 56.96, 63.44, 113.90, 113.97, 126.21, 126.53, 126.82, 129.02, 129.99, 130.44, 130.69, 130.84, 135.15, 139.77, 141.11, 141.88, 144.07, 148.36, 150.67, 151.27, 151.54, 160.78, 195.56; ES-MS m/z 463 (M+H). Anal. Calcd. for C$_{27}$H$_{26}$N$_8$·3.0 HBr·1.8 H$_2$O: C, 43.96; H, 4.45; N, 15.19; Br, 32.49. Found: C, 43.99; H, 4.40; N, 14.83; Br, 32.61.

EXAMPLE 38

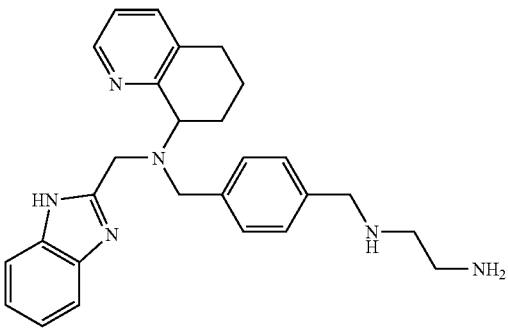

AMD9671: Preparation of N'-(4-{[(1H-Benzimidazol-2-ylmethyl)-(5,6,7,8-tetrahydro-quinolin-8-yl)-amino]-methyl}-benzyl)-ethane-1,2-diamine (hydrobromide salt)

Using General Procedure B: To a stirred solution of N'-(1H-benzimidazol-2-ylmethyl)-N'-(5,6,7,8-tetrahydro-8-quinolinyl)-1,4-benzenedimethanamine (250 mg, 0.629 mmol) and (2-oxo-ethyl)-carbamic acid tert-butyl ester (100 mg, 0.628 mmol) in THF (6.3 mL) was added NaBH(OAc)$_3$ (173 mg, 0.816 mmol) and the mixture was stirred at room temperature for 22 h. Purification of the crude material by column chromatography on silica gel (200:5:1 CH$_2$Cl$_2$/MeOH/NH$_4$OH) afforded a colourless oil (47 mg).

Using General Procedure D: Conversion of the oil from above (47 mg, 0.11 mmol) to the hydrobromide salt followed by re-precipitation of the intermediate solid from methanol/ether gave AMD9671 (72 mg, 14%) as a colourless solid. $^1$H NMR (D$_2$O) δ 1.88 (m, 1H), 2.24 (m, 2H), 2.42 (m, 1H), 3.01 (m, 2H), 3.25 (m, 4H), 3.73 (m, 2H), 3.82 (dd, 2H, J=19, 12 Hz), 4.40 (d, 1H, J=16 Hz), 4.59 (d, 1H, J=16 Hz), 4.75 (m, 1H), 7.03 (d, 2H, J=7.8 Hz), 7.23 (d, 2H, J=7.8 Hz), 7.48 (m, 2H), 7.55 (m, 2H), 7.88 (dd, 1H, J=7.8, 6.0 Hz), 8.35 (d, 1H, J=7.8 Hz), 8.73 (d, 1H, J=5.7 Hz); 13C NMR (D$_2$O) δ 20.46, 20.91, 27.85, 35.73, 43.93, 50.12, 50.82, 56.63, 63.00, 114.01, 126.02, 126.50, 130.05, 130.86, 138.23, 139.77, 140.88, 148.06, 150.92, 151.74. ES-MS m/z 441 (M+H). Anal. Calcd. for C$_{27}$H$_{32}$N$_6$.3.9HBr.2.5H$_2$O: C, 40.48; H, 5.15; N, 10.49; Br, 38.90. Found: C, 40.35; H, 4.96; N, 10.25; Br, 39.04.

EXAMPLE 39

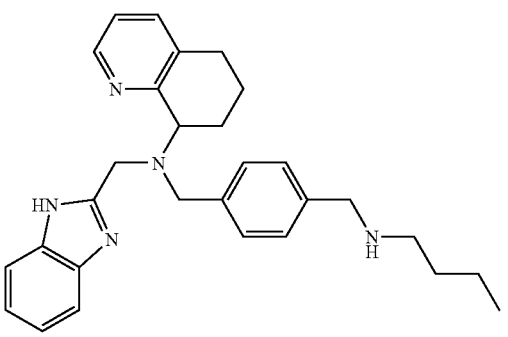

AMD9701: Preparation of (1H-benzimidazol-2-ylmethyl)-(4-butylaminomethyl-benzyl)-(5,6,7,8-tetrahydro-quinolin-8-yl)-amine A solution of N'-(1H-benzimidazol-2-ylmethyl)-N'-(5,6,7,8-tetrahydro-8-quinolinyl)-1,4-benzenedimethanamine (165 mg, 0.415 mmol) and butyraldehyde (50 mg, 0.69 mmol) in MeOH (4 mL) was heated at reflux for 30 minutes. The solution was allowed to cool to room temperature, 1.0% Pd/C (20 mg, 0.019 mmol) was added, and the mixture was stirred under hydrogen atmosphere (1 atm) at room temperature for 20 h. The mixture was filtered through Celite and the solvent from the filtrate was removed under reduced pressure. Purification of the crude material by column chromatography on silica gel (200:5:1 CH$_2$Cl$_2$/MeOH/NH$_4$OH) afforded AMD9701 (16 mg, 8%) as a colourless foam. $^1$H NMR (CDCl$_3$) δ 0.87 (m, 3H), 1.24–1.49 (m, 4H), 1.68 (m, 1H), 2.02 (m, 2H), 2.26 (m, 1H), 2.56 (m, 2H), 2.79 (m, 2H), 3.68 (s, 2H), 3.73 (s, 2H), 3.97 (d, 1H, J=17 Hz), 4.08 (m, 1H), 4.17 (d, 1H, J=17 Hz), 7.18 (m, 5H), 7.35 (m, 2H), 7.42 (m, 1H), 7.58 (m, 2H), 8.69 (d, 1H, J=3.9 Hz); $^{13}$C NMR (CDCl$_3$) δ 14.39, 20.84, 21.79, 23.77, 29.63, 32.57, 48.88, 49.53, 54.11, 60.58, 111.30, 119.11, 121.68, 122.04, 122.60, 128.47, 128.99, 135.09, 137.55, 138.30, 139.82, 147.33, 156.73, 157.89. ES-MS m/z 454 (M+H). Anal. Calcd. for C$_{29}$H$_{35}$N$_5$.1.3H$_2$O: C, 73.02; H, 7.94; N, 14.68. Found: C, 73.06; H, 7.70; N, 14.32.

EXAMPLE 40

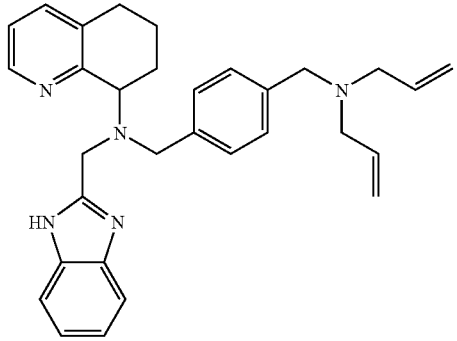

AMD9725: Preparation of (1H-benzimidazol-2-ylmethyl -(4-diallylaminomethyl-benzyl)-(5,6,7,8-tetrahydro-quinolin-8-yl)-amine To a solution of N'-(1H-benzimidazol-2-ylmethyl)-N'-(5,6,7,8-tetrahydro-8-quinolinyl)-1,4-benzenedimethanamine (156 mg, 0.39 mmol) in CH$_2$Cl$_2$ (4 mL) was added N,N-diisopropylethylamine (65 μL, 0.37 mmol). Allyl bromide (35 μL, 0.40 mmol) was added dropwise and the resultant mixture stirred at room temperature for 3 days. The reaction mixture was diluted with CH$_2$Cl$_2$ (50 mL) and washed consecutively with H$_2$O (2×5 mL), saturated aqueous NaHCO$_3$ (5 mL) and saturated aqueous NaCl (5 mL). The aqueous layer was extracted with CH$_2$Cl$_2$ (20 mL) and the combined organic extracts were dried (MgSO$_4$) and concentrated under reduced pressure to afford a light yellow foam (100 mg). Purification by column chromatography on silica gel (200:1:1 followed by 100:1:1—CH$_2$Cl$_2$:MeOH:NH$_4$OH) followed by radial chromatography on silica gel (1000:1:1—EtOAc:MeOH:NH$_4$OH) afforded AMD9725 (24.5 mg, 14%) as a light yellow foam. $^1$H NMR (CDCl$_3$)

δ 1.62–1.75 (m, 1H), 1.97–2.08 (m, 2H), 2.22–2.30 (m, 1H), 2.66–2.77 (m, 1H), 2.77–2.92 (m, 1H), 3.01 (d, 4H, J=6.3 Hz), 3.48 (s, 2H), 3.74 (s, 2H), 3.99 (d, 1H, J=16.8 Hz), 4.07–4.12 (m, 1H), 4.18 (d, 1H, J=16.8 Hz), 5.09–5.17 (m, 4H), 5.83 (ddt, 2H, J=16.8, 10.2, 6.3 Hz), 7.15–7.20 (m, 5H), 7.34 (d, 2H, J=7.8 Hz), 7.41 (d, 1H, J=7.8 Hz), 7.48–7.56 (m, 1H), 7.60–7.69 (m, 1H), 8.69 (d, 1H, J=4.2 Hz); $^{13}$C NMR (CDCl$_3$) δ 19.69, 21.65, 27.53, 46.90, 52.08, 54.63, 55.44, 58.47, 109.24, 115.61, 117.04, 119.79, 120.49, 126.67, 127.13, 132.99, 134.17, 135.45, 136.13, 136.56, 145.22, 154.64, 155.80. ES-MS m/z 478.4 (M+H). Anal. Calcd. for C$_{31}$H$_{35}$N$_5$·0.5H$_2$O: C, 76.51; H, 7.46; N, 14.39. Found: C, 76.67; H, 7.45; N, 14.18.

EXAMPLE 41

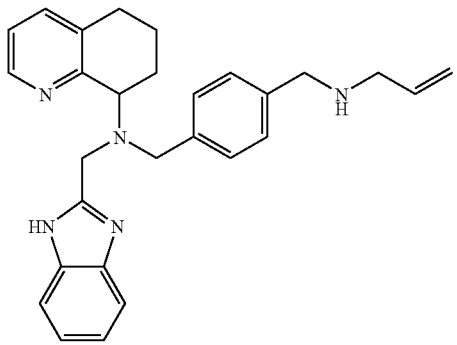

AMD9726: Preparation of (4-allylaminomethyl-benzyl)-(1H-benzimidazol-2-ylmethyl)-(5,6,7,8-tetrahydro-quinolin-8-yl)-amine To a solution of N'-(1H-benzimidazol-2-ylmethyl)-N'-(5,6,7,8-tetrahydro-8-quinolinyl)-1,4-benzenedimethanamine (200 mg, 0.39 mmol) in CH$_2$Cl$_2$ (~0.4 mL) was added N,N-diisopropylethylamine (90 μL, 0.52 mmol). Allyl bromide (35 μL, 0.40 mmol) was dissolved in CH$_2$Cl$_2$ (~9.6 mL) and added to the amine mixture at a rate of 5.5 mL/hour. The resultant mixture was stirred at room temperature for 24 hours. The reaction mixture was diluted with CH$_2$Cl$_2$ (50 mL) and washed consecutively with H$_2$O (5 mL), saturated aqueous NaHCO$_3$ (5 mL) and saturated aqueous NaCl (5 mL). The aqueous layer was extracted with CH$_2$Cl$_2$ (20 mL) and the combined organic extracts were dried (MgSO$_4$) and concentrated under reduced pressure. Purification by column chromatography on silica gel (200:1:1 followed by 100:1:1—EtOAc:MeOH:NH$_4$OH) followed by radial chromatography on silica gel (250:1:1—EtOAc:MeOH:NH$_4$OH) afforded AMD9725 (36 mg, 21%) as a light yellow foam. $^1$H NMR (CDCl$_3$) δ 1.56–1.75 (m, 1H), 1.97–2.08 (m, 2H), 2.24–2.31 (m, 1H), 2.65–2.77 (m, 1H), 2.77–2.91 (m, 1H), 3.21 (d, 2H, J=5.7 Hz), 3.69 (s, 2H), 3.73 (s, 2H), 3.97 (d, 1H, J=16.8 Hz), 4.04–4.16 (m, 1H), 4.17 (d, 1H, J=16.8 Hz), 5.07 (d, 1H, J=9.9 Hz), 5.15 (dd, 1H, J=17.1, 1.2 Hz), 5.88 (ddt, 1H, J=17.1, 10.5, 6.0 Hz), 7.10–7.19 (m, 5H), 7.35 (d, 2H, J=7.8 Hz), 7.42 (d, 1H, J=7.5 Hz), 7.45–7.57 (m, 1H), 7.58–7.68 (m, 1H), 8.69 (d, 1H, J=4.2 Hz); $^{13}$C NMR (CDCl$_3$) δ 20.83, 22.89, 28.67, 47.95, 51.11, 52.33, 53.17, 59.68, 110.37, 115.39, 118.11, 120.91, 121.66, 127.59, 128.07, 134.13, 136.17, 136.60, 137.48, 138.56, 146.38, 155.80, 156.94. ES-MS m/z 438.3 (M+H). Anal. Calcd. for C$_{28}$H$_{31}$N$_5$·0.8H$_2$O: C, 74.40; H, 7.27; N, 15.49. Found: C, 74.36; H, 7.25; N, 15.31.

EXAMPLE 42

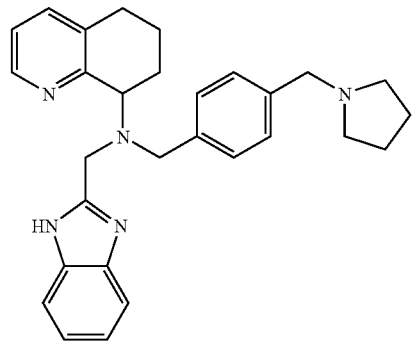

AMD9754: Preparation of (1H-benzimidazol-2-ylmethyl)-(4-pyrrolidin-1-ylmethyl-benzyl)-(5,6,7,8-tetrahydro-quinolin-8-yl)-amine Using General Procedure B: To a stirred solution of 4-{[(1H-benzimidazol-2-ylmethyl)-(5,6,7,8-tetrahydro-quinolin-8-yl)-amino]-methyl}-benzaldehyde (150 mg, 0.37 mmol), pyrrolidine (30 μL, 0.36 mmol) and AcOH (20 μL, 0.37 mmol) in THF (4 mL) was added NaBH(OAc)$_3$ (235 mg, 1.11 mmol) and the mixture was stirred at room temperature for 1.5 hours. Purification of the crude white foam (205 mg) by column chromatography on silica gel (100:1:1—CH$_2$Cl$_2$:MeOH:NH$_4$OH) afforded the desired product (160 mg, 96%) as a white foam.

Using General Procedure D: Conversion of the foam from above to the hydrobromide salt afforded AMD9754 as a white solid. $^1$H NMR (CD$_3$OD) δ 1.82–1.98 (m, 3H), 1.98–2.15 (m, 2H), 2.18–2.36 (m, 2H), 2.42–2.53 (m, 1H), 2.85–2.97 (m, 2H), 3.03–3.14 (m, 4H), 3.85 (d, 1H, J=12.9 Hz), 3.94 (d, 1H, J=12.9 Hz), 4.07 (s, 2H), 4.45 (d, 1H, J=16.5 Hz), 4.66 (d, 1H, J=16.2 Hz), 4.74–4.79 (m, 1H), 7.27 (d, 2H, J=7.8 Hz), 7.55 (dd, 2H, J=6.3, 3.3 Hz), 7.63 (d, 2H, J=7.8 Hz), 7.77 (dd, 2H, J=6.3, 3.3 Hz), 7.97 (dd, 1H, J=7.8, 6.0 Hz), 8.42 (d, 1H, J=8.1 Hz), 9.01 (d, 1H, J=5.4 Hz); $^{13}$C NMR (D$_2$O) δ 20.47, 21.05, 22.81, 27.90, 50.46, 53.75, 56.76, 57.26, 63.49, 113.98, 126.18, 126.74, 130.31, 130.42, 130.62, 130.94, 138.04, 139.76, 141.10, 148.36, 150.77, 152.06. ES-MS m/z 452.3 (M+H). Anal. Calcd. for C$_{29}$H$_{33}$N$_5$·3.0HBr·2.1H$_2$O: C, 47.57; H, 5.53; N, 9.57; Br, 32.74. Found: C, 47.69; H, 5.53; N, 9.48; Br, 32.48.

EXAMPLE 43

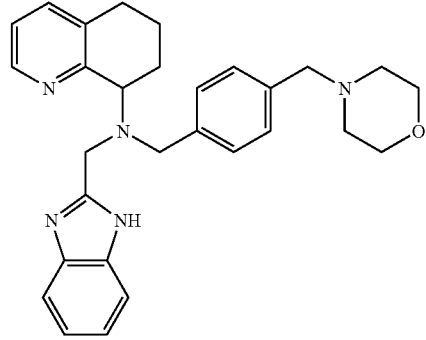

AMD9723: Preparation of (1H-Benzimidazol-2-ylmethyl)-(4-morpholin-4-ylmethyl-benzyl)-(5,6,7,8-tetrahydro-quinolin-8-yl)-amine (hydrobromide salt)

Using General Procedure A: To a stirred solution of 4-{[(1H-Benzimidazol-2-ylmethyl)-(5,6,7,8-tetrahydro-quinolin-8-yl)-amino]-methyl}-benzaldehyde (0.285 g, 0.72 mmol) in dry MeOH (5 mL) was added morpholine (0.068 mL, 0.78 mmol) and sodium cyanoborohydride (0.107 g, 1.7 mmol) and the mixture stirred at room temperature for 24 h. Purification of the crude product by radial chromatography on a 2 mm TLC grade silica gel plate (CH$_2$Cl$_2$/MeOH/NH$_4$OH, 100:1:1) afforded the desired product (23 mg, 7%) as a colourless oil.

Using General Procedure D: Conversion of the oil from above (23 mg, 0.049 mmol) to the hydrobromide salt gave AMD9723 as a white solid (36 mg). $^1$H NMR (D$_2$O) δ 1.79–2.03 (br m, 1H), 2.14–2.38 (br m, 2H), 2.38–2.54 (br m, 1H), 2.83–3.15 (m, 6H), 3.51–3.71 (m, 2H), 3.76–4.10 (m, 6H), 4.48 (d, 1H, J=16.5 Hz), 4.66 (d, 1H, J=16.8 Hz), 7.07 (d, 2H, J=7.8 Hz), 7.27 (d, 2H, J=7.5 Hz), 7.12–7.68 (m, 4H), 7.94 (t, 1H, J=6.3 Hz), 8.41 (d, 1H, J=7.8 Hz), 8.78 (d, 1H, J=5.7 Hz); $^{13}$C NMR (D$_2$O) δ 20.45, 20.99, 27.87, 50.33, 51.31 (2 carbons), 56.75, 59.89, 63.39, 63.98 (2 carbons), 113.92 (2 carbons), 126.13, 126.66 (2 carbons), 127.83, 130.56, 130.84 (2 carbons), 131.47 (2 carbons), 138.67, 139.75, 141.07, 148.27, 150.81, 151.94; ES-MS m/z 468 (M+H); Anal. Calcd. for C$_{29}$H$_{33}$N$_5$O.3.0HBr.2.0H$_2$O: C, 46.67; H, 5.40; N, 9.38; Br, 32.12. Found: C, 46.71; H, 5.34; N, 9.22; Br, 32.17.

EXAMPLE 44

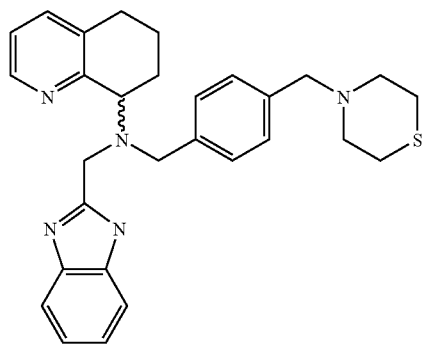

AMD9698: Preparation of (1H-benzoimidazol-2-ylmethyl)-(5,6,7,8-tetrahydro-quinolin-8-yl)-(4-thiomorpholin-4-ylmethyl-benzyl)-amine Following the General Procedure A: 4-{[(1H-benzoimidazol-2-ylmethyl)-(5,6,7,8-tetrahydro-quinolin-8-yl)-amino]-methyl}-benzaldehyde (200 mg, 0.50 mmol) and thiomorpholine (51 µL, 0.50 mmol) were converted into the corresponding reductive amination product using the following quantities of reagents and solvents: sodium cyanoborohydride (63 mg, 1.0 mmol), MeOH (3 mL). The reaction time in this case was 5 h. Purification of the crude material thus obtained by radial chromatography (silica gel, 1 mm plate, 50:2:1 CH$_2$Cl$_2$—MeOH—NH$_4$OH) afforded 63 mg (26%) of AMD9698 as a white foam. $^1$H NMR (CDCl$_3$) δ 1.67–1.72 (m, 1H), 2.02–2.09 (m, 2H), 2.25–2.27 (m, 1H), 2.62 (s, 8H), 2.68–2.73 (m, 1H), 2.80–2.85 (m, 1H), 3.40 (s, 2H), 3.74 (s, 2H), 3.98 (d, 1H, J=16 Hz), 4.10 (dd, 1H, J=9, 6 Hz), 4.19 (d, 1H, J=16 Hz), 7.14–7.20 (m, 5H), 7.35 (d, 2H, J=8 Hz), 7.42 (dd, 1H, J=8, 1 Hz), 7.53–7.63 (m, 2H), 8.70 (dd, 1H, J=5, 1 Hz), $^{13}$C NMR (CDCl$_3$) δ 21.3, 23.4, 27.9, 29.1, 48.5, 53.6, 54.8, 60.2, 63.3, 110.8, 118.6, 121.3, 122.2, 128.3, 128.9, 134.6, 136.9, 137.1, 138.1, 146.9, 156.3, 157.4. ES-MS m/z484 (M+H). Anal. Calcd. for C$_{29}$H$_{33}$N$_5$S.0.1CH$_2$Cl$_2$.0.3H$_2$O: C, 70.25; H, 6.85; N, 14.08; S, 6.44. Found: C, 70.42: H, 6.90; N, 13.70; S, 6.29.

EXAMPLE 45

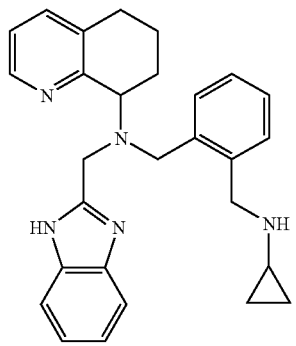

AMD11173: Preparation of (1H-Benzimidazol-2-ylmethyl)-(5,6,7,8-tetrahydro-quinolin-8-yl)-(2-cyclopropylaminomethyl-benzyl)-amine (HBr salt)

Using general procedure B {direct reductive amination using NaBH(OAc)$_3$}: Reaction of phthalic dicarboxaldehyde (0.960 g, 7.16 mmol) and (1H-benzimidazol-2-ylmethyl)-(5,6,7,8-tetrahydro-quinolin-8-yl)-amine (0.991 g, 3.58 mmol) with NaBH(OAc)$_3$ (3.24 g, 15.3 mmol) in CH$_2$Cl$_2$ (20 mL) for 65 hours, followed by stirring in THF (10 mL) and 4 N HCl (20 mL) provided a crude product. Purification of the crude material by column chromatography on silica gel (37 g silica, 30:1 CH$_2$Cl$_2$:CH$_3$OH) provided 1.21 g (45%) of mixture of benzylic aldehyde and benzylic alcohol products.

This mixture of aldehyde and alcohol (1.21 g, 3.04 mmol) was dissolved in CH$_2$Cl$_2$ (20 mL), treated with MnO$_2$ (1.990 g, 19.5 mmol) and stirred for 48 hours. The suspension was filtered through celite and concentrated to give the crude product. Purification by column chromatography on silica gel (51 g silica, 60:1 CH$_2$Cl$_2$:CH$_3$OH) provided 942 mg (66% over threee steps) of o-benzylic aldehyde intermediate as a yellow foam.

The aldehyde from above (0.119 g, 0.300 mmol) was stirred with cyclopropyl amine (32 µL, 0.461 mmol) in CH$_3$OH (2.5 mL) for 1 hour, then treated with NaBH$_4$ (18 mg, 0.475 mmol). The mixture was concentrated after 1 hour. The residue was diluted with CH$_2$Cl$_2$ (20 mL) and washed with brine (3×10 mL). The combined aqueous phase was extracted with CH$_2$Cl$_2$ (1×15 mL). The combined organic phases were dried (Na$_2$SO$_4$), filtered and concentrated to give the crude product. Purification by radial chromatography on silica gel (1 mm plate, 100:1:1 CH$_2$Cl$_2$:CH$_3$OH:NH$_4$OH) provided 0.066 g (50%) of a white foam.

Using General Procedure D: Conversion of the foam from above (66 mg, 0.151 mmol) to the hydrobromide salt followed by re-precipitation of the intermediate solid from methanol/ether gave AMD11173 (100 mg, 92%) as a white solid. $^1$H NMR (D$_2$O) δ 0.63–0.79 (m, 4H), 1.83–1.98 (m, 1H), 2.18–2.30 (m, 1H), 2.31–2.41 (m, 1H), 2.43–2.58 (m, 2H), 2.98–3.13 (m, 2H), 3.92 (d, 1H, J=13.7 Hz), 4.14 (d, 1H, J=13.2 Hz), 4.24 (d, 1H, J=13.6 Hz), 4.41 (d, 1H, J=16.6 Hz), 4.48 (d, 1H, J=13.1 Hz), 4.59 (d, 1H, J=16.4 Hz), 6.92 (t, 1H, J=7.5 Hz), 7.00 (d, 1H, J=J=7.4 Hz), 7.19 (t, 1H, 1H, J=7.0 Hz), 7.41 (d, 1H, J=7.4 Hz), 7.51–7.56 (m, 2H), 7.58–7.63 (m, 2H), 7.91 (dd, 1H, J=7.7, 6.1 Hz), 8.40 (d, 1H, J=7.9 Hz), 8.74 (d, 1H, J=5.22); $^{13}$C NMR (D$_2$O) δ 3.53, 20.43, 20.93, 27.92, 30.04, 48.44, 49.35, 53.22, 62.29, 113.95, 126.24, 126.91, 129.42, 129.54, 130.32, 130.60, 131.16, 132.17, 135.58, 139.96, 141.16, 148.33, 150.52, 150.89. ES-MS m/z 438 (M+H). Anal. Calcd. for C$_{28}$H$_{31}$N$_5$.3.0HBr.2.2H$_2$O: C, 46.71; H, 5.38; N, 9.73; Br, 33.30. Found: C, 46.72; H, 5.36; N, 9.59; Br, 33.21.

EXAMPLE 46

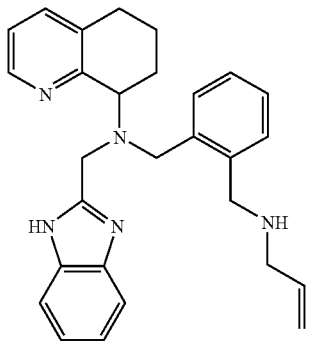

AMD 11173: Preparation of (1H-Benzimidazol-2-ylmethyl)-(5,6,7,8-tetrahydro-quinolin-8-yl)-(2-allylaminomethyl-benzyl)-amine (HBr salt)

Using general procedure B {direct reductive amination using NaBH(OAc)$_3$}: Reaction of phthalic dicarboxaldehyde (0.960 g, 7.16 mmol) and (1H-benzimidazol-2-ylmethyl)-(5,6,7,8-tetrahydro-quinolin-8-yl)-amine (0.991 g, 3.58 mmol) with NaBH(OAc)$_3$ (3.24 g, 15.3 mmol) in CH$_2$Cl$_2$ (20 mL) for 65 hours, followed by stirring in THF (10 mL) and 4 N HCl (20 mL) provided a crude product. Purification of the crude material by column chromatography on silica gel (37 g silica, 30:1 CH$_2$Cl$_2$:CH$_3$OH) provided 1.21 g (45%) of mixture of benzylic aldehyde and benzylic alcohol products.

This mixture of aldehyde and alcohol (1.21 g, 3.04 mmol) was dissolved in CH$_2$Cl$_2$ (20 mL), treated with MnO$_2$ (1.990 g, 19.5 mmol) and stirred for 48 hours. The suspension was filtered through celite and concentrated to give the crude product. Purification by column chromatography on silica gel (51 g silica, 60:1 CH$_2$Cl$_2$:CH$_3$OH) provided 942 mg (66% over threee steps) of o-benzylic aldehyde intermediate as a yellow foam.

The aldehyde from above (0.150 g, 0.378 mmol) was stirred with allyl amine (42 μL, 0.968 mmol) in CH$_3$OH (2.5 mL) for 18 hours, then treated with NaBH$_4$ (24 mg, 0.634 mmol). The mixture was concentrated after 90 minutes. The residue was diluted with CH$_2$Cl$_2$ (30 mL) and washed with brine (3×15 mL). The combined aqueous phase was extracted with CH$_2$Cl$_2$ (1×15 mL). The combined organic phases were dried (Na$_2$SO$_4$), filtered and concentrated to give the crude product. Purification by radial chromatography on silica gel (2 mm plate, 100:1:1 CH$_2$Cl$_2$:CH$_3$OH:NH$_4$OH) provided 53 mg (32%) of a white foam.

Using General Procedure D: Conversion of the foam from above (53 mg, 0.121 mmol) to the hydrobromide salt followed by re-precipitation of the intermediate solid from methanol/ether gave AMD11174 (77 mg, 88%) as a white solid.

$^1$H NMR (D$_2$O) δ 1.83–1.99 (m, 1H), 2.19–2.40 (m, 2H), 2.45–2.55 (m, 1H), 2.99–3.12 (m, 2H), 3.61 (d, 2H, J=6.5 Hz), 3.92 (d, 1H, J=13.5 Hz), 4.12–4.20 (m, 2H), 4.58 (d, 1H, J=16.3 Hz), 5.44 (s, 1H), 5.89 (d, 1H, J=5.2 Hz), 5.77–5.91 (m, 1H), 6.93 (t, 1H, J=7.5 Hz), 7.02 (d, 1H, J=7.9 Hz), 7.18 (t, 1H, J=7.7 Hz), 7.43 (d, 1H, J=7.9 Hz), 7.51–7.56 (m, 2H), 7.58–7.64 (m, 2H), 7.92 (t, 1H, J=6.8 Hz), 8.41 (d, 1H, J=8.4 Hz), 8.75 (d, 1H, J=5.8 Hz); $^{13}$C NMR (D$_2$O) δ 20.43, 20.96, 27.90, 47.07, 49.16, 49.69, 53.30, 62.33, 113.95, 124.80, 126.25, 126.93, 127.51, 129.38, 129.67, 130.31, 130.53, 130.96, 132.10, 135.49, 139.88, 141.18, 148.44, 150.41, 150.73. ES-MS m/z 438 (M+H). Anal. Calcd. for C$_{28}$H$_{31}$N$_5$.3.0HBr.2.2H$_2$O: C, 46.71; H, 5.38; N, 9.73; Br, 33.30. Found: C, 46.79; H, 5.27; N, 9.62; Br, 33.17.

EXAMPLE 47

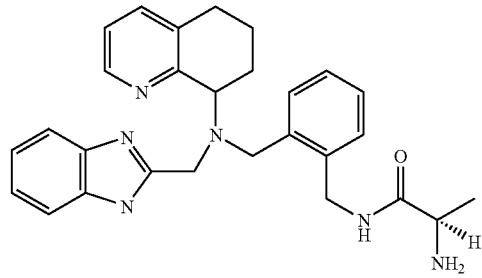

AMD11133: Preparation of (1H-Benzimidazol-2-ylmethyl)-[2-(R)-(2-aminopropionamidylmethyl)-benzyl]-(5,6,7,8-tetrahydro-quinolin-8-yl)-amine (hydrobromide salt)

To a solution of N-t-butoxycarbonyl-1-alanine (37 mg, 0.195 mmol) in dichloromethane (5 mL) was added, in the following order: diisopropyleth-ylamine (0.08 mL, 0.468 mmol), 1-hydroxybenzotriazole ((HOBT) 32 mg, 0.234 mmol), (1H-Benzimidazol-2-ylmethyl)-(2-Aminomethyl-benzyl)-(5,6,7,8-tetrahydro-quinolin-8-yl)-amine (62 mg, 0.156 mmol) and 1-(3-dimethylaminopropyl)-3-ethylcarbodiimide hydrochloride ((EDAC) 45 mg, 0.234 mmol). The resulting solution was then stirred overnight at room temperature under nitrogen. The solution was then extracted with aqueous ammonium chloride, dried, concentrated and purified by silica gel flash chromatography using a 20:1 dichloromethane:methanol solution as an eluent to afford (1H-Benzimidazol-2-ylmethyl)-{2-(R)-[2-(N-t-butoxycarbonyl)-aminopropionamidylmethyl]-benzyl}-(5,6,7,8-tetrahydro-quinolin-8-yl)-amine as a mixture of two diastereomers in a yield of 61 mg (69%). $^1$H NMR (CDCl$_3$) δ 1.14 and 1.56 (d, total of 3H, J=6.9Hz), 1.370 and 1.483 (s, total of 9H), 1.88 (m, 1H), 1.93 (m, 1H), 2.03 (m, 1H), 2.36 (m, 1H), 2.75–2.86 (m, 2H), 3.74 (m, 3H), 3.91 (m, 2H), 4.05 and 4.41 (m, total of 1H), 4.66 (m, 1H), 5.34 (m, 1H), 7.13 (m, 5H), 4H), 7.68 (br s, 1H (NH)), 8.38 and 8.56 (m, total of 1H), 8.59 and 8.76 (d, total of 1H, J=4.9 Hz).

(1H-Benzimidazol-2-ylmethyl)-{2-(R)-[2-(N-t-butoxycarbonyl)-aminopropionamidylmethyl]-benzyl}-(5,6,7,8-tetrahydro-quinolin-8-yl)-amine (61 mg 0.107 mmol), was taken up in acetic acid (1 mL), to which a saturated solution of HBr in acetic acid (1 mL) was added. The mixture was then stirred, precipitated and isolated as per procedure D to yield AMD11133 as a white crystalline solid in a yield of 64 mg. $^1$H NMR (D$_2$O). δ 1.43 and 1.46 (d, total of 3H, J=6.9 Hz), 1.88 (m, 1H), 2.28 (m, 2H), 2.46 (m, 1H), 3.00 (m, 2H), 3.81 (d, 1H, J=12.8 Hz), 4.03 (m, 2H), 4.21 (d, 1H, J=12.8 Hz), 4.43–4.77 (m, 4H), 6.68 (m, 2H), 6.91 (m, 1H), 7.25 (t, 1H, J=6.1 Hz), 7.51 (m, 4H), 7.88 (m, 1H), 8.28 (m, 1H), 8.68 (d, 1H, J=4.8 Hz). $^{13}$C NMR (D$_2$O) 17.01, 20.43 and 20.67 (1C total), 27.89, 40.78, 48.93 and 49.22 (1C total), 49.43, 53.87 and 54,46 (1C total), 62.01 and 62.15 (1C total), 113.92 and 113.97 (2C total), 126.08, 126.74 (2C), 128.03, 129.13, 131.45, 131.55, 133.92, 136.00, 139.91, 140.78, 148.19 and 148.27 (1C total), 150.25 and 150.43 (1C total), 170.69 and 170.91 (1total). ES-MS m/z 469 (M+H); Anal. Calcd. for (C$_{28}$H$_{32}$N$_6$O×3.1 HBr×1.1 H$_2$O× 1.0HOAc): C, 45.04; H, 5.21; N, 10.53; Br, 31.04. Found: C, 45.04; H, 5.19; N, 10.53; Br, 31.04.

EXAMPLE 48

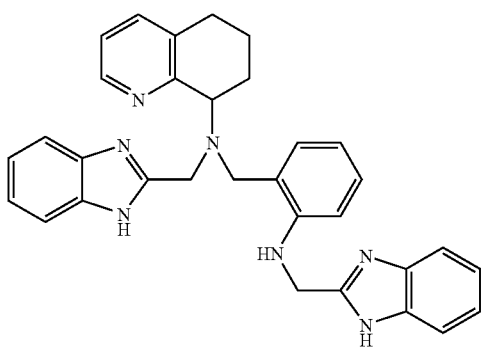

AMD9872: Preparation of (1H-benzimidazol-2-ylmethyl)-[2-(1H-benzimidazol-2-ylmethyl)-aminobenzyl]-(5 6.7,8-tetrahydroquinolin-8-yl)-amine Preparation of (5,6,7,8-tetrahydroquinolin-8-yl)-(2-aminobenzyl)-amine Using General Procedure B: To a solution of 2-aminobenzylamine (0.36 g, 2.9 mmol) and 6,7-dihydro-5H-quinolin-8-one (0.43 g, 2.9 mmol) in CH$_2$Cl$_2$ (15 mL) was added NaBH(OAc)$_3$ (0.92 g, 4.4 mmol) and the mixture stirred at room temperature for 64 h. Purification of the crude material by column chromatography on silica gel (2% MeOH/CH$_2$Cl$_2$) gave (5,6,7,8-tetrahydroquinolin-8-yl)-(2-aminobenzyl)-amine (0.39 g, 52%) as a yellow oil. $^1$H NMR (CDCl$_3$) δ 1.80 (m, 1H), 1.94 (m, 2H), 2.17 (m, 1H), 2.79 (m, 2H), 3.84 (m, 1H), 3.87 (d, 1H, J=11.7 Hz), 4.02 (d, 1H, J=12.0 Hz), 6.64 (d, 1H, J=7.8 Hz), 6.67 (t, 1H, J=7.8 Hz), 7.09 (m, 3H), 7.38 (d, 1H, J=3.0 Hz), 8.38 (d, 1H, J=3.9 Hz).

Using the general N-alkylation procedure: A solution of (5,6,7,8-tetrahydroquinolin-8-yl)-(2-aminobenzyl)-amine (0.16 g, 0.6 mmol), N,N-diisopropylethylamine (0.32 mL, 1.8 mmol) and potassium iodide (10 mg, 40 μmol) in CH$_3$CN (6 mL) was reacted with 1-(N-tert-butoxycarbonyl)-2-chloromethylbenzimidazole (0.32 g, 1.2 mmol) at 70° C. for 16 h to yield after purification by column chromatography on silica gel (CH$_2$Cl$_2$/MeOH, 250:1) the N-alkylated product (0.16 g, 37%) as a pale yellow solid. $^1$H NMR (CDCl$_3$) δ 1.56 (s, 9H), 1.70 (s, 10H), 1.95 (m, 2H), 2.48 (m, 1H), 2.65 (m, 2H), 4.23 (d, 1H, J=3.0 Hz), 4.27 (d, 1H, J=8.1 Hz), 4.29 (m, 1H), 4.48 (d, 1H, J=3.0 Hz), 4.53 (d, 1H, J=8.4 Hz), 4.93 (m, 2H), 6.55 (m, 2H), 6.98 (m, 2H), 7.10 (d, 1H, J=7.8 Hz), 7.20–7.32 (m, 4H), 7.55 (m, 1H), 7.68 (m, 1H), 7.82 (m, 2H), 7.90 (m, 1H), 8.44 (d, 1H, J=3.2 Hz).

A solution of the material from above (0.17 g, 0.24 mmol) in CH$_2$Cl$_2$/TFA (1:1, 2 mL) was stirred for 0.5 h and the solution concentrated under redcued pressure. The reaction was partitioned between 15% aqueous NaOH (5 mL) and CH$_2$Cl$_2$ (5 mL), the phases separated and the organic extract dried (MgSO$_4$), filtered, concentrated and purified by radial chromatography on silica gel (MeOH/NH$_4$OH/CH$_2$Cl$_2$; 1:1: 98) to give AMD9872 (48 mg, 40%) as a pale yellow solid. $^1$H NMR (CDCl$_3$) δ 1.71 (br, 1H), 2.09 (m, 2H), 2.29 (br, 1H), 2.73 (m, 1H), 2.85 (m, 1H), 3.81 (d, 1H, J=12.9 Hz), 3.90 (d, 1H, J=12.6 Hz), 4.06 (d, 2H, J=6.9 Hz), 4.09 (m, 1H), 4.77 (s, 2H), 6.50 (d, 1H, J=8.1 Hz), 6.62 (t, 1H, J=7.4 Hz), 6.94 (br, 1H), 7.04 (t, 1H, J=7.8 Hz), 7.05–7.25 (br m, 6H), 7.43 (d, 1H, J=7.8 Hz), 7.66 (br, 3H), 8.41 (d, 1H, J=3.9 Hz). $^{13}$C NMR (CDCl$_3$) δ 21.45, 21.80, 29.23, 42.32, 48.18, 54.10, 59.88, 110.27 (2C), 1 17.06 (2C), 121.71, 122.25 (5C), 122.48 (2C), 129.23 (2C), 130.91 (2C), 135.18, 137.70 (2C), 146.91 (2C), 147.16, 154.00, 154.19, 157.03. ES-MS m/z 514 (M+H). Anal. Calcd. for C$_{32}$H$_{31}$N$_7$.1.0CH$_2$Cl$_2$.0.3C$_6$H$_{14}$: C, 66.57; H, 5.98; N, 15.60. Found: C, 66.61; H, 5.78; N, 15.51.

EXAMPLE 49

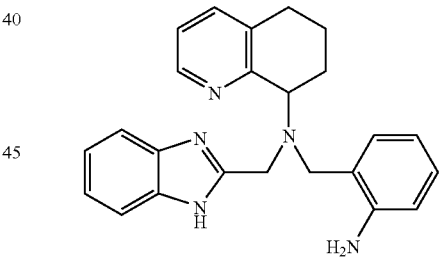

AMD9883: Preparation of (2-aminobenzyl)-(1H-benzimidazol-2-ylmethyl)-(5,6,7,8-tetrahydroquinolin-8-yl)-amine Using the general N-alkylation procedure: A solution of (5,6,7,8-tetrahydroquinolin-8-yl)-(2-aminobenzyl)-amine (0.20 g, 0.8 mmol), N,N-diisopropylethylamine (0.14 mL, 0.8 mmol) and potassium iodide (5 mg, 30 μmol) in CH$_3$CN (8 mL) was reacted with 1-(N-tert-butoxycarbonyl)-2-chloromethylbenzimidazole (0.145 g, 0.55 mmol) at 70° C. for 16 h to yield after purification by radial chromatography on silica gel (MeOH/NH$_4$OH/CH$_2$Cl$_2$; 1:1:98) the mono N-alkylated product (65 mg, 25%) as a pale yellow solid. $^1$H NMR (CDCl$_3$) δ 1.61 (s, 10H), 1.94 (m, 2H), 2.03 (br, 1H), 2.67 (m, 2H), 3.98 (d, 1H, J=12.3 Hz), 4.22 (m, 1H), 4.30 (d, 2H, J=9.9 Hz), 4.37 (d, 1H, J=11.1 Hz), 5.44 (br, 2H), 6.53

(m, 2H), 6.90 (m, 1H), 6.97 (t, 1H, J=6.7 Hz), 7.06 (d, 1H, J=7.5 Hz), 7.17 (d, 1H, J=7.5 Hz), 7.25 (d, 2H, J=7.2 Hz), 7.61 (m, 1H), 7.81 (m, 1H, J=3.6 Hz), 8.40 (d, 1H, J=4.5 Hz).

A solution of the material from above (65 mg, 0.13 mmol) in CH$_2$Cl$_2$/TFA (1:1, 1 mL) was stirred for 0.5 h and the solution concentrated under redcued pressure. The reaction was partitioned between 15% aqueous NaOH (3 mL) and CH$_2$Cl$_2$ (5 mL), the phases separated and the organic extract dried (MgSO$_4$), filtered, concentrated and purified by radial chromatography on silica gel (MeOH/NH$_4$OH/CH$_2$Cl$_2$; 1:1:150) to give AMD9883 (33 mg, 64%) as a pale yellow solid. $^1$H NMR (CDCl$_3$) δ 1.71 (br, 1H), 2.05 (m, 2H), 2.32 (br, 1H), 2.70 (m, 1H), 2.85 (m, 1H), 3.65 (d, 1H, J=12.6 Hz), 3.80 (d, 1H, J=12.6 Hz), 4.05 (m, 1H), 4.08 (d, 2H, J=4.8 Hz), 6.63 (t, 1H, J=8.7 Hz), 6.64 (t, 1H, J=6.6 Hz), 7.03 (t, 2H, J=7.2 Hz), 7.17 (m, 3H), 7.42 (d, 1H, J=7.2 Hz), 7.54 (br, 2H), 8.53 (d, 1H, J=4.2 Hz). $^{13}$C NMR (CDCl$_3$) δ 21.64, 21.91, 29.55, 48.22, 53.20, 60.93, 111.08, 116.59, 118.09, 119.14, 122.05 (4C), 122.52, 122.83, 129.19, 131.83, 135.22, 137.98, 147.09, 147.17, 156.04, 157.47. ES-MS m/z 384 (M+H). Anal. Calcd. for C$_{24}$H$_{25}$N$_5$.0.6CH$_2$Cl$_2$: C, 67.49; H, 6.04; N, 15.97. Found: C, 67.60; H, 6.21; N, 15.57.

EXAMPLE 50

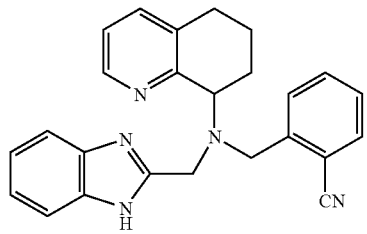

AMD9736: Preparation of (1H-Benzimidazol-2-ylmethyl)-(2-cyano-benzyl)-(5,6,7,8-tetrahydro-quinolin-8-yl)-amine (hydrobromide salt)

The intermediate [1-(tert-butoxycarbonyl)-(1H-benzimidazol-2-ylmethyl)]-(2-cyano-benzyl)-(5,6,7,8-tetrahydro-quinolin-8-yl)-amine (see AMD9720) (72 mg, 0.145 mmol) was refluxed in 6N HCl (5 mL) for 16 h. The solvent was removed under reduced pressure and the resultant salt dissolved in distilled water (0.8 mL) and ethanol (95%, 0.8 mL) and treated with NaOH (0.148 g, 3.69 mmol). The mixture was heated to 90° C. for 2 h and stirred at room temperature for 64 h. The biphasic system was diluted with water (4 mL) and extracted with ether (3×10 mL). The combined organic phases were dried (Na$_2$SO$_4$), filtered and concentrated under reduced pressure to give a white powder. Purification of the solid by radial chromatography (1 mm TLC plate, 60:1:1 CH$_2$Cl$_2$/CH$_3$OH/NH$_4$OH) gave the desired freebase (48 mg, 84%).

Following General Procedure D: Conversion of the material from above (48 mg) to the hydrobromide salt gave AMD9736 (45 mg, 64%). $^1$H NMR (D$_2$O) δ 1.85–2.01 (m, 1H), 2.17–2.52 (m, 3H), 2.98–3.14 (m, 2H), 3.95 (d, 1H, J=13.2 Hz), 4.15 (d, 1H, J=13.2 Hz), 4.46 (d, 1H, J=16.3 Hz), 4.63 (d, 1H, J=16.6 Hz), 6.96 (t, 1H, J=7.7 Hz), 7.27 (t, 1H, J=7.7 Hz), 7.35 (t, 1H, J=8.1 Hz), 7.49–7.60 (m, 4H), 7.92 (dd, 1H, J=7.9, 5.5 Hz), 8.40 (d, 1H, J=7.8 Hz), 8.71 (d, 1H, J=5.8 Hz). $^{13}$C NMR (D$_2$O) δ 18.14, 18.68, 25.56, 47.43, 53.07, 60.81, 109.76, 111.60 (2 carbons), 116.68, 123.81, 124.55 (2 carbons), 126.70, 128.29, 129.19, 131.29, 131.46, 137.66, 137.84, 138.58, 145.88, 147.73, 148.64. IR (CsI) ν 2224 (C≡N). ES-MS m/z 394 (M+H) Anal Calc. for C$_{25}$H$_{23}$N$_5$.2.0HBr.1.3H$_2$O: C, 51.88; H, 4.81; N, 12.10; Br, 27.61. Found: C, 51.86; H, 4.86; N, 11.78; Br, 27.78.

EXAMPLE 51

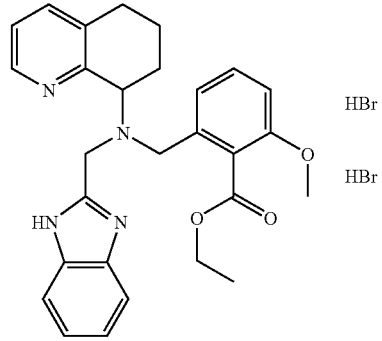

AMD11091: Preparation of 2-{[(1H-Benzimidazol-2-ylmethyl)-(5,6,7,8-tetrahydro-quinolin-8-yl)-amino]-methyl}-6-methoxy-benzoic acid ethyl ester (hydrobromide salt)

To a solution of ethyl 6-methylsalicylate (1.27 g, 6.97 mmol) in THF (35 mL) was added lithium hydroxide monohydrate (0.594 g, 14.2 mmol) followed by dimethyl sulfate (1.00 mL, 10.6 mmol). The resultant mixture was heated to reflux for 1 hour then cooled to room temperature. The mixture was diluted with diethyl ether (70 mL), washed with saturated aqueous NaHCO$_3$ (4×10 mL), dried (MgSO$_4$) and concentrated. Purification of the crude material by column chromatography on silica gel (9:1 hexanes-EtOAc) provided 1.23 g (91%) of ethyl 2-methoxy-6-methylbenzoate as a white solid. $^1$H NMR (CDCl$_3$) δ 1.38 (t, 3H, J=7.2 Hz), 2.30 (s, 3H), 3.82 (s, 3H), 4.40 (q, 2H, J=7.2 Hz), 6.76 (d, 1H, J=8.4 Hz), 6.79 (d, 1H, J=7.8 Hz), 7.23 (dd, 1H, J=7.8, 8.4 Hz).

To a solution of ethyl 2-methoxy-6-methylbenzoate (0.813 g, 4.19 mmol) in CCl$_4$ (8 mL) was added recrystallized N-bromosuccinimide (0.751 g, 4.22 mmol) followed by benzoyl peroxide (52 mg, 0.22 mmol). The resultant mixture was heated to reflux for 90 minutes then cooled to room temperature. The mixture was diluted with diethyl ether (50 mL), filtered through filter paper, and the filtrate was concentrated. Purification of the crude material by column chromatography (8:1 hexanes-EtOAc) provided 0.68 g (60%) of ethyl 6-(bromomethyl)-2-methoxybenzoate as a colorless oil. $^1$H NMR (CDCl$_3$) δ 1.42 (t, 3H, J=7.2 Hz), 3.84 (s, 3H), 4.45 (q, 2H, J=7.2 Hz), 4.50 (s, 2H), 6.89 (d, 1H, J=8.4 Hz), 7.01 (d, 1H, J=7.2 Hz), 7.34 (dd, 1H, J=7.2, 8.4 Hz).

To a solution of (1-tert-butoxycarbonyl-1H-Benzimidazol-2-ylmethyl)-(5,6,7,8-tetrahydro-quinolin-8-yl)-amine (0.409 g, 1.08 mmol) in CH$_3$CN (5 mL) was added N,N-diisopropylethylamine (0.38 mL, 2.18 mmol) followed by a solution of ethyl 6-(bromomethyl)-2-methoxybenzoate (0.454 g, 1.66 mmol) in CH$_3$CN (6 mL). The resultant mixture was heated to 60° C. for 22 hours then cooled to room temperature. The mixture was concentrated and the residue was partitioned between CH$_2$Cl$_2$ (50 mL) and brine (10 mL). The phases were separated and the aqueous phase was extracted with CH$_2$Cl$_2$ (3×10 mL). The combined organic extracts were dried (Na$_2$SO$_4$) and concentrated. Purification of the crude material by column chromatography on silica gel (25:1 CH$_2$Cl$_2$—CH$_3$OH) followed a further chromatographic purification by column chromatography on silica gel (2:1 hexanes-EtOAc) and radial chromatography on silica gel (2 mm plate, 100:1:1 CH$_2$Cl$_2$—CH$_3$OH—NH$_4$OH) provided 0.38 g (62%) of a white solid.

Using General Procedure D: Conversion of the solid from above (55 mg, 0.10 mmol) to the hydrobromide salt with simultaneous removal of the BOC-protecting group, followed by re-precipitation of the intermediate solid from methanol/ether gave AMD11091 (35 mg, 51%) as a gold solid. $^1$H NMR (D$_2$O) δ 1.23 (t, 3H, J=7.2 Hz), 1.82–1.90 (m, 1H), 2.17–2.28 (m, 2H), 2.34–2.40 (m, 1H), 3.00 (br s, 2H), 3.45 (s, 3H), 3.69 (d, 1H, J=12.6 Hz), 3.82 (d, 1H, J=12.6 Hz), 4.25–4.37 (m, 2H), 4.40 (d, 1H, J=15.9 Hz), 4.52 (d, 1H, J=15.9 Hz), 4.68 (dd, 1H, J=6.0, 9.3 Hz), 6.54 (d, 1H, J=8.4 Hz), 6.99 (d, 1H, J=7.5 Hz), 7.15 (dd, 1H, J=7.5, 8.4 Hz), 7.50–7.53 (m, 2H), 7.59–7.62 (m, 2H), 7.90 (dd, 1H, J=6.3, 7.5 Hz), 8.36 (d, 1H, J=7.8 Hz), 8.77 (d, 1H, J=5.7 Hz); $^{13}$C NMR (D$_2$O) δ 13.77, 20.42, 20.79, 27.77, 49.29, 53.67, 56.45, 62.55, 63.59, 112.11, 113.95, 123.03, 123.84, 126.07, 126.74, 130.62, 131.76, 134.36, 139.77, 140.89, 148.12, 150.49, 150.81, 156.10, 169.70. ES-MS m/z 471 (M+H). Anal. Calcd. for C$_{28}$H$_{30}$N$_4$O$_3$.2.2HBr.1.7H$_2$O: C, 49.52; H, 5.28; N, 8.25; Br, 25.88. Found: C, 49.89; H, 5.33; N, 8.19; Br, 25.53.

EXAMPLE 52

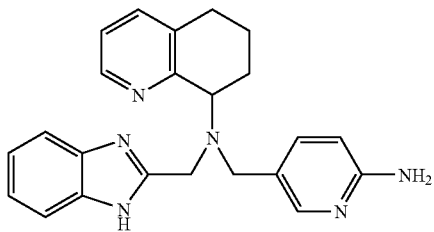

AMD9837: Preparation of (6-aminopyridin-3-ylmethyl)-(benzimidazol-2-ylmethyl)-(5,6,7,8-tetrahydroquinolin-8-yl)-amine (hydrobromide salt)

Preparation of 6-(N-tert-butoxycarbonylamino)-3-hydroxymethylpyridine

A solution of 6-aminonicotinic acid (2.0 g, 14.4 mmol) in anhydrous EtOH (70 mL) and concentrated sulfuric acid (14 mL) was heated to reflux for 16 h. The solution was concentrated under reduced pressure, neutralized with saturated aqueous Na$_2$CO$_3$ (50 mL) and extracted with CH$_2$Cl$_2$ (3×50 mL). The combined organic phases were dried (MgSO$_4$), filtered and concentrated to give 6-aminonicotinic acid ethyl ester (2.18 g, 92%) as a white powder. $^1$H NMR (CDCl$_3$) δ 1.37 (t, 3H, J=6.0 Hz), 4.34 (q, 2H, J=7.0 Hz), 4.89 (br s, 2H (NH$_2$)), 6.46 (d, 1H, J=7.5 Hz), 8.02 (d, 1H, J=7.5 Hz), 8.73 (s, 1H).

To a solution of 6-aminonicotinic acid ethyl ester (1.18 g, 7.1 mmol) in anhydrous THF (24 mL) was added a solution of lithium aluminum hydride (0.41 g, 10.6 mmol) in THF (12 mL) at 0° C. over 10 min and the mixture stirred for 1.5 h. To the reaction was added sequentially 0.5 mL H$_2$O, 0.5 mL 15% aqueous NaOH and 1.5 mL H$_2$O and the resultant slurry was filtered. The filtrate was dried (MgSO$_4$), filtered, concentrated and purified by column chromatography (10% MeOH/CH$_2$Cl$_2$) to give 6-amino-3-hydroxymethylpyridine (0.61 g, 69%) as colorless crystals. $^1$H NMR (MeOD) δ 3.31 (s, 1H (OH)), 4.43 (s, 2H), 6.58 (d, 1H, J=8.4 Hz), 7.48 (d, 1H, J=8.7 Hz), 7.85 (s, 1H).

To a solution of 6-amino-3-hydroxymethylpyridine (0.30 g, 2.4 mmol) in anhydrous tert-butanol (12.4 g, 16 mL) was added di-tert-butyldicarbonate (0.58 g, 2.7 mmol) and the mixture stirred 16 h at 40° C. The reaction was concentrated under reduced pressure and the crude residue purified by column chromatography on silica gel (7.5% MeOH/CH$_2$Cl$_2$) to afford the title alcohol (0.42 g, 77%) as a white solid. $^1$H NMR (CDCl$_3$) δ 1.54 (s, 9H), 1.74 (t, 1H (OH), J=6.0 Hz), 4.65 (d, 2H, J=6.0 Hz), 7.68 (d, 1H, J=9.0 Hz), 7.83 (br s, 1H (NH)), 7.95 (d, 1H, J=9.0 Hz), 8.24 (s, 1H).

Using General Procedure C: To a solution of 6-(N-tert-butoxycarbonylamino)-3-hydroxymethylpyridine (0.42 g, 1.9 mmol) and triethylamine (0.40 mL, 2.8 mmol) in CH$_2$Cl$_2$ (19 mL) was added methanesulfonyl chloride (0.20 mL, 2.4 mmol) and the mixture stirred at room temperature for 1 h. Purification of the crude product by column chromatography on silica gel (4% MeOH/CH$_2$Cl$_2$) afforded the desired mesylate (0.23 g, 42%). $^1$H NMR (CDCl$_3$) δ 1.54 (s, 9H), 3.37 (s, 3H), 4.40 (s, 2H), 7.68 (d, 1H, J=9.0 Hz), 7.95 (d, 1H, J=9.0 Hz), 8.11 (br s, 1H), 8.25 (s, 1H).

Using General Procedure for N-Alkylation: A solution of the mesylate from above (0.22 g, 0.8 mmol), N,N-diisopropylethylamine (0.20 mL, 1.2 mmol) and potassium chloride (10 mg, 0.04 mmol) in CH$_3$CN (8 mL) was reacted with (1-tert-butoxycarbonyl-1H-Benzimidazol-2-ylmethyl)-(5,6,7,8-tetrahydro-quinolin-8-yl)-amine (0.30 g, 0.8 mmol) at 70° C. for 16 h. Purification of the crude material by radial chromatography on silica gel (MeOH/NH$_4$OH/CH$_2$Cl$_2$; 1:1:98) gave the N-alkylated product (180 mg, 40%) as a flaky white solid. $^1$H NMR (CDCl$_3$) δ 1.49 (s, 9H), 1.70 (br s, 10H), 1.96 (m, 2H), 2.13 (m, 1H), 2.70 (m, 2H), 3.76 (d, 1H, J=15.0 Hz), 4.03 (d, 1H, J=15.0 Hz), 4.25 (m, 1H), 4.58 (s, 2H), 7.00 (m, 1H), 7.20 (m, 2H), 7.30 (s, 1H), 7.66 (m, 4H), 8.04 (s, 2H), 8.43 (dd, 1H, J=3.0 Hz).

Using General Procedure D: Conversion of the solid from above (30 mg) to the hydrobromide salt with simultaneous removal of the Boc group provided AMD9837 (0.034 g) as a white solid. $^1$H NMR (D$_2$O) δ 1.90 (br m, 1H), 2.20 (m, 2H), 2.40 (br m, 1H), 3.02 (br m, 2H), 3.70 (d, 1H, J=13.5 Hz), 3.83 (d, 1H, J=13.5 Hz), 4.37 (d, 1H, J=15.9 Hz), 4.58 (d, 1H, 16.2 Hz), 4.75 (m, 1H), 6.62 (d, 1H, J=9.3 Hz), 7.53 (d, 1H, J=1.5 Hz), 7.57 (dd, 2H, J=3.0, 6.0 Hz), 7.68 (d, 1H, J=2.1 Hz), 7.70 (m, 2H), 7.92 (dd, 1H, J=6.0, 7.8 Hz), 8.40 (d, 1H, J=7.2 Hz), 8.75 (d, 1H, J=4.8 Hz); $^{13}$C NMR (D$_2$O) δ 20.38, 20.92, 27.86, 49.32, 53.02, 62.53, 114.11 (4C), 121.78, 126.19, 127.24 (2C), 130.91, 134.41, 140.07 (2C), 141.11, 145.36, 148.33, 150.36, 151.72. ES-MS m/z 385 (M+H). Anal. Calcd. for C$_{23}$H$_{24}$N$_6$.2.9HBr.2.1H$_2$O: C, 42.21; H, 4.78; N, 12.84; Br, 35.10. Found: C, 42.29; H, 4.71; N, 12.58; Br, 35.09.

EXAMPLE 53

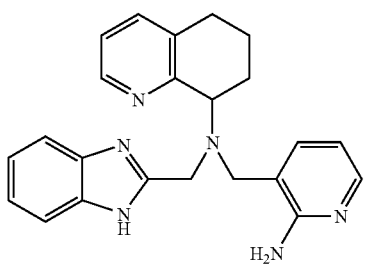

AMD9840: Preparation of (2-aminopyridin-3-ylmethyl)-(benzimidazol-2-ylmethyl)-(5,6,7,8-tetrahydro-8-quinolinyl)-amine (hydrobromide salt)

Preparation of 2-aminonicotinic aldehyde

A solution of 2-aminonicotinic acid (2.0 g, 14.4 mmol) in anhydrous EtOH (70 mL) and concentrated sulfuric acid (14 mL) was heated to reflux for 16 h. The solution was concentrated under reduced pressure, neutralized with saturated aqueous $Na_2CO_3$ (50 mL) and extracted with $CH_2Cl_2$ (3×50 mL). The combined organic phases were dried ($MgSO_4$), filtered and concentrated to give 2-aminonicotinic acid ethyl ester as a yellow solid (1.74 g, 74%). $^1$H NMR ($CDCl_3$) δ 1.40 (t, 3H, J=6.0 Hz), 4.34 (q, 2H, J=7.0 Hz), 6.41 (br s, 2H ($NH_2$)), 6.63 (m, 1H), 8.14 (d, 1H, J=7.8 Hz), 8.22 (s, 1H).

To a solution of 2-aminonicotinic acid ethyl ester (1.74 g, 10.5 mmol) in anhydrous THF (35 mL) was added a solution of lithium aluminum hydride (0.60 g, 15.7 mmol) in THF (17 mL) at 0° C. over 15 min and the mixture stirred for 1.5 h. To the reaction was added sequentially 0.6 mL $H_2O$, 0.6 mL 15% aqueous NaOH and 1.8 mL $H_2O$ and the resultant slurry was filtered. The filtrate was dried ($MgSO_4$), filtered, concentrated and purified by column chromatography (10% MeOH/$CH_2Cl_2$) to give 2-amino-3-hydroxymethylpyridine (1.03 g, 79%) as a yellow crystalline solid. $^1$H NMR ($CDCl_3$) δ 3.14 (br s, 1H (OH)), 4.60 (s, 2H), 5.00 (br s, 1H (NH)), 6.59 (t, 1H, J=6.0 Hz), 7.28 (d, 1H, J=7.5 Hz), 7.94 (d, 1H, J=7.5 Hz).

The alcohol (0.10 g, 0.8 mmol) from above was dissolved in $CH_2Cl_2$ (8 mL), treated with activated $MnO_2$ (0.70 g, 8 mmol) and stirred at room temperature for 1.5 h. The mixture was filtered through celite® and the cake was washed with $CH_2Cl_2$. The solvent was removed from the filtrate under reduced pressure and provided 2-aminonicotinic aldehyde (0.10 g, 99%) as a pale yellow crystalline solid. $^1$H NMR ($CDCl_3$) δ 6.75 (t, 1H, J=6.0 Hz), 7.81 (d, 1H, J=7.5 Hz), 8.27 (d, 1H, J=4.5 Hz), 9.86 (s, 1H, (CHO)).

Using General Procedure B: To a solution of 2-aminonicotinic aldehyde (47 mg, 0.4 mmol) and (1-tert-butoxycarbonyl-1H-Benzimidazol-2-ylmethyl)-(5,6,7,8-tetrahydroquinolin-8-yl)-amine (132 mg, 0.35 mmol) in $CH_2Cl_2$ (4 mL) was added sodium triacetoxyborohydride (126 mg, 0.59 mmol) and the mixture stirred at room temperature for 16 h. Purification of the crude product by column chromatography on silica gel (2% MeOH/$CH_2Cl_2$) gave the desired N-alkylated product (68 mg, 40%) as a white solid. $^1$H NMR ($CDCl_3$) δ 1.58 (s, 9H), 1.62 (m, 1H), 1.91 (m, 2H), 2.17 (m, 1H), 2.64 (m, 2H), 3.93 (d, 1H, J=12.0 Hz), 4.15 (m, 1H), 4.26 (d, 2H, J=3.0 Hz), 4.38 (d, 1H, J=12.0 Hz), 6.40 (t, 1H, J=4.5 Hz), 6.47 (br s, 2H), 6.97 (m, 1H), 7.27 (m, 4H), 7.61 (m, 1H), 7.84 (m, 2H), 8.40 (d, 1H, J=3.0 Hz).

Using General Procedure D: Conversion of the material from above (25 mg) to the hydrobromide salt with simultaneous removal of the Boc group provided AMD9840 (0.025 g) as a white solid. $^1$H NMR ($D_2O$) δ 1.87 (br m, 1H), 2.18 (m, 2H), 2.46 (br m, 1H), 2.98 (br m, 2H), 3.95 (d, 1H, J=14.1 Hz), 4.07 (d, 1H, J=14.1 Hz), 4.33 (d, 1H, J=16.2 Hz), 4.49 (d, 1H, J=15.9 Hz), 4.74 (m, 1H), 6.64 (t, 1H, J=6.9 Hz), 7.25 (dd, 1H, J=1.5, 6.3 Hz), 7.55 (m, 2H), 7.66 (m, 2H), 7.83 (t, 1H, J=6.9 Hz), 7.93 (dd, 1H, J=1.5, 7.4 Hz), 8.28 (d, 1H, J=7.2 Hz), 8.70 (,d, 1H, J=5.1 Hz); $^{13}$C NMR ($D_2O$) δ 20.45, 20.68, 27.95, 48.36, 52.51, 62.20, 113.24, 114.03 (2C), 120.49, 120.73, 126.09, 127.17 (2C), 130.89, 135.44, 140.70, 140.81, 146.12 (2C), 147.61, 150.32, 150.71. ES-MS m/z 385 (M+H). Anal. Calcd. for $C_{23}H_{24}N.6.3.0HBr.2.2H_2O$: C, 41.49; H, 4.74; N, 12.62; Br, 35.95. Found: C, 41.56; H, 4.61; N, 12.38; Br, 35.94.

EXAMPLE 54

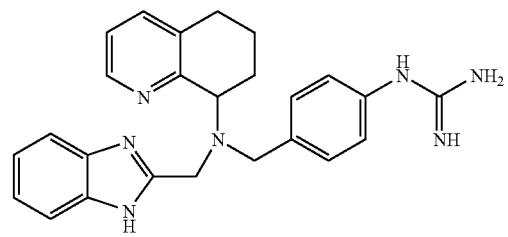

AMD9681: Preparation of N-(4-{[(1H-Benzimidazol-2-ylmethyl)-(5,6,7,8-tetrahydro-quinolin-8-yl)-amino]-methyl}-phenyl)-guanidine (hydrobromide salt)

To a solution of 4-aminobenzyl alcohol (0.127 g, 1.03 mmol) in dry THF (1 mL) was added N. N'-bis-(tert-butoxycarbonyl)-1H-pyrazole-1-carboxamidine (Tetrahedron Lett. 1993, 34, 3389) and the resultant mixture was stirred at room temperature for 26 h. The mixture was diluted with hexanes (1 mL) and filtered through a short silica gel column (100% hexanes followed by 1:1 hexanes/ethyl acetate). The appropriate fractions were concentrated to provide N, N'-bis-(tert-butoxycarbonyl)-N"-(4-hydroxymethyl-phenyl)-guanidine (0.309 g, 85%) as a white solid.

The alcohol (0.282 g, 0.771 mmol) from above was dissolved in $CH_2Cl_2$ (7 mL), treated with activated $MnO_2$ (0.696 g, 8.01 mmol) and stirred at room temperature overnight. The mixture was filtered through celite® and the cake was washed with $CH_2Cl_2$. The solvent was removed from the filtrate under reduced pressure and provided N, N'-bis-(tert-butoxycarbonyl)-N"-(4-formyl-phenyl)-guanidine (0.260 g, 93%) as a white solid. $^1$H NMR ($CDCl_3$) δ 1.53 (s, 9H), 1.55 (s, 9H), 7.85 (s, 4H), 9.93 (s, 1H), 10.34 (br s, 1H).

Using General Procedure B: Reaction of N, N'-bis-(tert-butoxycarbonyl)-N"-(4-formyl-phenyl)-guanidine (0.167 g, 0.49 mmol) and (1-tert-butoxycarbonyl-1H-Benzimidazol-2-ylmethyl)-(5,6,7,8-tetrahydro-quinolin-8-yl)-amine (0.151 g, 0.42 mmol) with NaBH(OAc)$_3$ (0.184 g, 0.87 mmol) in $CH_2Cl_2$ (4 mL) for 4.5 hours followed by purification of the crude material by radial chromatography on silica gel (2 mm plate, 20:1:1 CH$_2$Cl$_2$/CH$_3$OH/NH$_4$OH) provided the desired tertiary amine (0.101 g, 33%) as a white solid.

Using General Procedure D: Conversion of the white solid (101 mg) to the hydrobromide salt with simultaneous removal of the BOC-protecting group, followed by re-precipitation of the intermediate solid from methanol/ether, gave AMD9681 (66 mg) as a white solid. $^1$H NMR (D$_2$O) δ 1.81–1.92 (m, 1H), 2.19–2.30 (m, 2H), 2.41–2.46 (m, 1H), 3.01 (br s, 2H), 3.78 (d, 1H, J=12.9 Hz), 3.84 (d, 1H, J=12.9 Hz), 4.43 (d, 1H, J=16.5 Hz), 4.62 (d, 1H, J=16.5 Hz), 4.72–4.79 (m, 1H, overlaps with HOD), 6.84 (d, 2H, J=8.1 Hz), 7.21 (d, 2H, J=8.1 Hz), 7.49–7.53 (m, 2H), 7.56–7.60 (m, 2H), 7.91 (dd, 1H, J=6.0, 7.8 Hz), 8.38 (d, 1H, J=7.8 Hz), 8.73 (d, 1H, J=5.7 Hz); $^3$C NMR (D$_2$O) δ 20.43, 20.86, 27.83, 50.03, 56.40, 62.98, 113.84, 124.65, 126.08, 126.76, 130.47, 131.50, 134.21, 135.70, 139.65, 141.00, 148.26, 148.28, 150.83, 151.77; ES-MS m/z 426 (M+H). Anal. Calcd. for C$_{25}$H$_{27}$N$_7$·3.0 HBr·3.4 H$_2$O: C, 41.16; H, 5.08; N, 13.44; Br, 32.86. Found: C, 41.12; H, 4.86; N, 13.32; Br, 32.81.

EXAMPLE 55

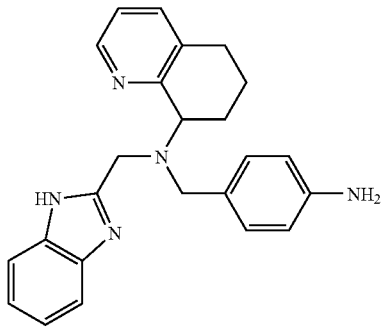

AMD9730: Preparation of (4-Amino-benzyl)-(1H-benzoimidazol-2-ylmethyl)-(5,6,7,8-tetrahydro-quinolin-8-yl)-amine (hydrobromide salt)

Preparation of (4-formyl-phenyl)-carbamic acid tert-butyl ester

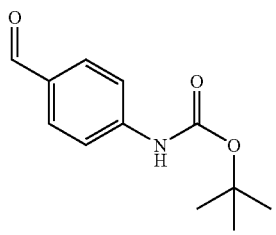

A solution of 4-aminobenzyl alcohol (607 mg, 4.93 mmol) and di-t-butyl dicarbonate (1.3 g, 6.0 mmol) in THF (16 mL) was stirred at room temperature for 24 h then concentrated. Purification of the crude material on silica gel (30% EtOAc/hexanes) gave a colourless oil (906 mg, 82%). $^1$H NMR (CDCl$_3$) δ 1.52 (s, 9H), 4.63 (d, 2H, J=5.7 Hz), 6.48 (br s, 1H), 7.32 (m, 4H).

To a solution of the alcohol from above (200 mg, 0.896 mmol) in CH$_2$Cl$_2$ (9 mL) was added activated MnO$_2$ (916 mg, 8.96 mmol) and the mixture stirred at room temperature overnight. The reaction mixture was filtered through Celite and the cake was washed with CH$_2$Cl$_2$. The solvent was removed from the filtrate under reduced pressure to give the title compound as colourless crystals (170 mg, 86%). $^1$H NMR (CDCl$_3$) δ 1.54 (s, 9H), 6.73 (br s, 1H), 7.54 (d, 2H, J=9 Hz), 7.83 (d, 2H, J=9 Hz), 9.90 (s, 1H).

Using General Procedure B: To a solution of [1-(tert-butoxycarbonyl)-(1H-benzimidazol-2-ylmethyl)]-(5,6,7,8-tetrahydro-quinolin-8-yl)-amine (83 mg, 0.22 mmol) and (4-formyl-phenyl)-carbamic acid tert-butyl ester (66 mg, 0.30 mmol) in THF (3 mL) was added acetic acid (0.017 mL, 0.30 mmol) and NaBH(OAc)$_3$ (190 mg, 0.896 mmol) and the mixture stirred at room temperature for 4 h. Purification of the crude yellow oil by chromatography on silica gel (300:5:1 CH$_2$Cl$_2$/MeOH/NH$_4$OH) gave a colourless foam (128 mg).

A solution of the foam from above in 1:1 trifluoroacetic acid/CH$_2$Cl$_2$ (4 mL) was stirred at room temperature for 45 min then concentrated. The residue was partitioned between CH$_2$Cl$_2$ (10 mL) and saturated aqueous NaHCO$_3$ (10 mL) and the aqueous phase was extracted with CH$_2$Cl$_2$. The combined organic phases were dried (MgSO$_4$), filtered and concentrated under reduced pressure. Purification of the crude material by chromatography on silica gel (600:5:1 EtOAc/MeOH/NH$_4$OH) gave a colourless foam (49 mg, 53%).

Using General Procedure D: Conversion of the colourless foam from above (49 mg, 0.13 mmol) to the hydrobromide salt gave AMD9730 (56 mg, 67%) as a yellow solid. $^1$H NMR (D$_2$O) δ 1.88 (m, 1H), 2.26 (m, 2H), 2.44 (m, 1H), 3.02 (m, 2H), 3.83 (d, 1H, J=13 Hz), 3.89 (d, 1H, J=13 Hz), 4.46 (d, 1H, J=16 Hz), 4.64 (d, 1H, J=16 Hz), 4.79 (m, 1H), 6.95 (d, 2H, J=8.1 Hz), 7.29 (d, 2H, J=8.4 Hz), 7.51–7.63 (m, 4H), 7.91 (m, 1H), 8.38 (d, 1H, J=7.8 Hz), 8.74 (d, 1H, J=5.7 Hz); $^{13}$C NMR (D$_2$O) δ 20.45, 20.86, 27.85, 50.06, 56.31, 62.82, 113.94, 122.85, 126.12, 126.85, 130.03, 130.50, 131.58, 137.51, 139.70, 140.98, 148.28, 150.75, 151.51. ES-MS m/z 384 (M+H). Anal Calcd for (C$_{24}$H$_{25}$N$_5$) 3.0(HBr) 1.6(H$_2$O): C, 44.01; H, 4.80; N, 10.69; Br, 36.59. Found: C, 43.84; H, 4.86; N, 10.40; Br, 36.85.

EXAMPLE 56

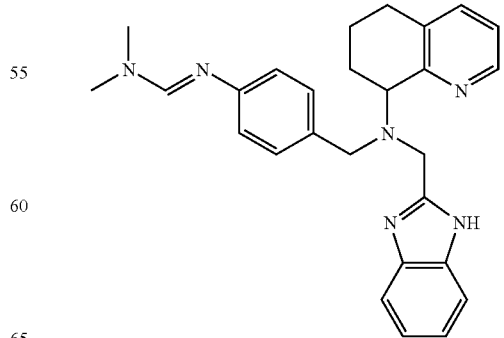

AMD9774: Preparation of N'-({[(1H-Benzimidazol-2-ylmethyl)-(5,6,7,8-tetrahydroquinolin-8-yl)-amino]-methyl}-phenyl)-N,N-dimethylformamidine Preparation of O-methanesulfonyl-4-(t-butoxycarbonyl)-aminobenzyl alcohol Using General Procedure C: To a solution of 4-(t-butoxycarbonyl)-aminobenzyl alcohol (446 mg, 2 mmol) in $CH_2Cl_2$ (10 mL) was added methanesulfonyl chloride (0.23 mL, 3 mmol) and triethylamine (0.56 mL, 4 mmol). The solution was stirred for 60 min at room temperature. Purification of the crude product by chromatography on silica gel (2% MeOH/$CH_2Cl_2$) gave the title compound (320 mg, 56%) as an oil. $^1$H NMR (CDCl$_3$) δ 3.14 (s, 3H), 4.39 (s, 2H), 6.53 (br s, 1H (NH)), 7.31 (m, 4H).

Using the general N-alkylation procedure: To a solution of the mesylate from above (213 mg, 0.75 mmol) and N,N-diisopropylethylamine (0.178 mL, 1.0 mmol) in $CH_3CN$ (10 mL) was added (1-tert-butoxycarbonyl-1H-benzimidazol-2-ylmethyl)-(5,6,7,8-tetrahydro-quinolin-8-yl)-amine (210 mg, 0.55 mmol) and the mixture stirred at 60 °C. for 4 h. Purification of the crude product by chromatography on silica gel (20:1 $CH_2Cl_2$/MeOH) gave (1H-N-t-butoxycarbonyl-benzimidazol-2-ylmethyl)-[4-(t-butoxycarbonylamino)-benzyl]-(5,6,7,8-tetrahydroquinolin-8-yl)-amine (126 mg, 39%). $^1$H NMR (CDCl$_3$) δ 1.41 (s, 9H), 1.68 (s, 9H), 2.03 (m, 3H), 2.20 (m, 1H), 2.75 (m, 2H), 3.83 (m, 1H), 3.99 (m, 1H), 4.30 (dd, 1H, J=8.4, 6.5 Hz), 4.61 (m, 2H), 6.26 (br s, 1H (NH)), 7.04 (m, 2H), 7.26 (m, 5H), 7.31 (m, 2H), 7.63 (m, 2H), 8.44 (m, 1H).

To a solution of (1H-N-t-butoxycarbonyl-benzimidazol-2-ylmethyl)-[4-(t-butoxycarbonylamino)-benzyl]-(5,6,7,8-tetrahydroquinolin-8-yl)-amine (62 mg, 0.106 mmol) in $CH_2Cl_2$ (2 mL) was added trifluoroacetic acid (1 mL). The mixture was stirred at room temperature for 2 h, then concentrated. The residue was taken up in $CH_2Cl_2$, washed with 15% NaOH (3 mL) and extracted repeatedly with $CH_2Cl_2$. The combined organic fractions were dried over anhydrous sodium sulfate, filtered and concentrated. The crude (1H-benzimidazol-2-ylmethyl)-[4-aminobenzyl]-(5,6,7,8-tetrahydroquinolin-8-yl)-amine was then added to a solution of 2-pyridinesulfonyl chloride (27 mg, 0.15 mmol) in DMF (1 mL). The resulting solution was stirred at room temperature for 30 min. The mixture was then concentrated, taken up in $CH_2Cl_2$ and washed with aqueous potassium carbonate. The organic fraction was then dried over anhydrous sodium sulfate, filtered, concentrated and purified by chromatography on silica gel (10:1:0.1 $CH_2Cl_2$:MeOH:NH$_4$OH) to afford N'-({[(1H-Benzimidazol-2-ylmethyl)-(5,6,7,8-tetrahydroquinolin-8-yl)-amino]-methyl}-phenyl)-N,N-dimethylformamnidine (21 mg, 47%). $^1$H NMR (CDCl$_3$) δ 1.69 (m, 1H), 2.01 (m, 3H), 2.25 (m, 1H), 2.73 (m, 2H), 2.93 (s, 3H), 3.60 (s, 3H), 3.62 (d, 1H, J=13.2 Hz), 3.68 (d, 1H, J=13.2 Hz), 3.98 (d, 1H, J=16.2 Hz), 4.01 (m, 1H), 4.12 (d, 1H, J=16.2 Hz), 6.80 (d, 2H, J=8.1 Hz), 7.16 (m, 4H), 7.26 (d, 1H, J=8.1 Hz), 7.38 (m, 2H), 7.40 (br s, 1H), 8.55 (d, 1H, J=4.8 Hz).

Using General Procedure D: Conversion of the N'-({[(1H-Benzimidazol-2-ylmethyl)-(5,6,7,8-tetrahydroquinolin-8-yl)-amino]-methyl}-phenyl)-N,N-dimethylformamidine (21 mg, 0.047 mmol) to the hydrobromide salt gave AMD9774 (14 mg) as a white solid. $^1$H NMR (D$_2$O). δ 1.91 (m, 1H), 2.29 (m, 2H), 2.43 (m, 1H), 3.05 (m, 2H), 3.13 (s, 3H), 3.37 (s, 3H), 3.79 (d, 1H, J=12.3 Hz), 3.86 (d, 1H, J=12.3 Hz), 4.44 (d, 1H, J=16.5 Hz), 4.63 (d, 1H, J=16.5 Hz), 4.82 (m, 1H), 6.82 (d, 2H, J=8.1 Hz), 7.22 (d, 2H, J=8.1 Hz), 7.50–7.63 (m, 4H), 7.95 (dd, 1H, J=7.8, 5.7 Hz), 8.41 (d, 1H, J=7.8 Hz), 8.78 (d, 1H, J=5.7 Hz). 13C NMR (D$_2$O) δ 20.45, 21.01, 27.86, 37.17, 44.08, 50.20, 54.46, 63.43, 114.05, 119.10, 126.14, 126.49, 130.54, 131.70, 134.46, 136.98, 139.73, 142.33, 148.32, 152.16, 152.94. ES-MS m/z 439 (M+H); Anal. Calcd. for (C$_{27}$H$_{30}$N$_6$×3.2 HBr×0.6 H$_2$O×0.6 HOAc): C, 45.51; H, 4.98; N, 11.29; Br, 34.35. Found: C, 45.28; H, 5.13; N, 11.14; Br, 34.32.

EXAMPLE 57

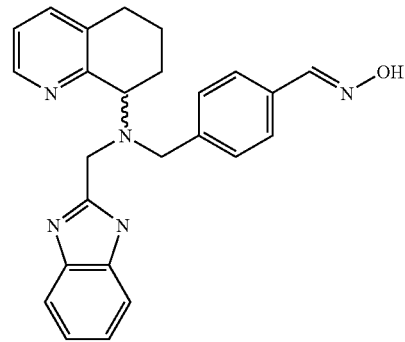

AMD9685: Preparation of 4-{[(1H-Benzimidazol-2-ylmethyl)-(5,6,7,8-tetrahydro-quinolin-8-yl)-amino]-methyl}-benzaldehyde oxime To a stirred solution of N'-(1H-benzimidazol-2-ylmethyl)-N'-(5,6,7,8-tetrahydro-8-quinolinyl)-1,4-benzenedimethanamine (200 mg, 0.50 mmol) in MeOH (5 mL) was added solid sodium tungstate dihydrate (332 mg, 1.0 mmol) followed by a 35 wt % aqueous solution of hydrogen peroxide (2.9 mL, 30 mmol). The resulting suspension was stirred 3 h, then saturated aqueous sodium bicarbonate (5 mL) was added. The phases were separated and the aqueous layer was extracted with $CH_2Cl_2$ (3×10 mL), then the combined organic extracts were washed once with brine (10 mL), dried (MgSO$_4$), and concentrated in vacuo. Purification of the crude material by flash chromatography (silica gel, 75:1:1 $CH_2Cl_2$MeOH/NH$_4$OH) afforded the title compound (130 mg, 63%) as a white solid. $^1$H NMR (CDCl$_3$) δ 1.63–1.66 (m, 1H), 1.97–2.07 (m, 2H), 2.25–2.27 (m, 1H), 2.66–2.72 (m, 1H), 2.80–2.85 (m, 1H), 3.65 (d, 1H, J=14 Hz), 3.71 (d, 1H, J=14 Hz), 5.03 (d, 1H, J=16 Hz), 4.14 (dd, 1H, J=9, 7 Hz), 4.21 (d, 1H, J=16 Hz), 7.11–7.19 (m, 3H), 7.41–7.48 (m, 6H), 7.65 (br d, 1H, J=5 Hz), 8.18 (s, 1H), 8.67 (dd, 1H, J=5, 1 Hz); $^{13}$C NMR (CDCl$_3$) δ 22.2, 23.9, 30.2, 49.5, 55.0, 61.2, 112.1, 119.4, 122.7, 123.3, 127.8, 130.1, 133.0, 136.2, 138.7, 141.4, 147.8, 150.0, 156.2, 157.7. ES-MS m/z 412 (M+H). Anal. Calcd. for C$_{25}$H$_{25}$N$_5$O.0.4H$_2$O.0.3CH$_2$Cl$_2$: C, 68.41; H, 5.99; N, 15.77. Found: C, 68.57; H, 5.86; N, 15.48.

EXAMPLE 58

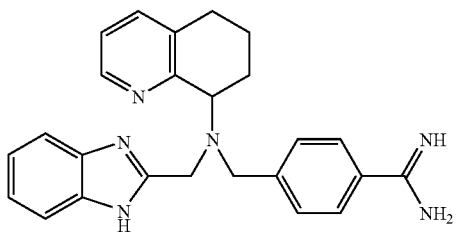

AMD9773: Preparation of [4-(1H-benzimidazol-2-ylmethyl)-(5,6,7,8-tetrahydroquinolin-8-yl)-aminomethyl]-benzamidine (hydrobromide salt)

Using General Procedure B: To a solution of 4-cyanobenzaldehyde (0.15 g, 1.1 mmol) and (1l-tert-butoxycarbonyl-1H-Benzimidazol-2-ylmethyl)-(5,6,7,8-tetrahydro-quinolin-8-yl)-amine (0.38 g, 1.0 mmol) in $CH_2Cl_2$ (10 mL) was added $NaBH(OAc)_3$ (0.36 g, 1.7 mmol) and the mixture stirred at room temperature for 6 h. Purification of the crude material by column chromatography on silica gel (2% MeOH/$CH_2Cl_2$) afforded the N-alkylated product (0.26 g, 72%) as a white solid. $^1$H NMR ($CDCl_3$) δ 1.74 (s, 10H), 1.95 (m, 1H), 2.02 (m, 1H), 2.30 (m, 1H), 2.75 (m, 2H), 3.80 (d, 1H, J=15.0 Hz), 3.97 (d, 1H, J=15.0 Hz), 4.31 (m, 1H), 4.65 (d, 1H, J=12.0 Hz), 4.75 (d, 1H, J=12.0 Hz), 7.04 (m, 1H), 7.16 (d, 1H, J=7.2 Hz), 7.22–7.30 (m, 5H), 7.51 (m, 1H), 7.61 (m, 1H), 8.45 (d, 1H, J=3.5 Hz).

To a solution of the material from above (0.26 g, 0.53 mmol) in anhydrous EtOH (3.5 mL) at 0° C. was bubbled HCl gas for 30 min and the mixture stirred at room temperature for an additional 4 h. The reaction was concentrated under reduced pressure and the resultant residue washed with diethyl ether (3×20 mL) and dried in vacuo to afford the desired ethoxyimine HCl salt which was used immmediately in the next reaction. $^1$H NMR ($D_2O$) δ 1.54 (t, 3H, J=6.9 Hz), 1.91 (m, 1H), 2.23 (m, 2H), 2.47 (m, 1H), 3.04 (m, 2H), 3.88 (d, 1H, J=12.9 Hz), 3.96 (d, 1H, J=13.2 Hz), 4;44 (d, 1H, J=15.6 Hz), 4.46 (q, 2H, J=6.9 Hz), 4.63 (d, 1H, J=16.5 Hz), 4.78 (m, 1H), 7.35 (d, 2H, J=8.4 Hz), 7.47–7.58 (m, 5H), 7.95 (t, 1H, J=6.2 Hz), 8.41 (d, 1H, J=6.2 Hz), 8.82 (d, 1H, J=3.5 Hz).

To a solution of (N-tert-butoxycarbonylbenzimidazol-2-ylmethyl)-(4-ethoxyiminebenzyl)-(5,6,7,8-tetrahydroquinolin-8-yl)-amine hydrochloride salt (from above) in anhydrous EtOH (3 mL) was added ammonium carbonate (0.24 g, 2.5 mmol) and the solution stirred at room temperature for 16 h. The reaction was concentrated under reduced pressure and purified by chromatography through a plug of silica gel (MeOH/$NH_4OH$/$CH_2Cl_2$, 15:10:75) to give the desired benzamidine (0.10 g, 48% yield over 2 steps) as a white powder. $^1$H NMR ($CDCl_3$) δ 1.68 (m, 1H), 2.03 (m, 2H), 2.27 (m, 1H), 2.78 (m, 2H), 3.78 (s, 2H), 3.92 (d, 1H, J=15.0 Hz), 4.09 (m, 1H), 4.20 (d, 1H, J=15.0 Hz), 5.68 (br, 1H), 6.12 (br, 1H), 7.18 (m, 3H), 7.46 (m, 3H), 7.57 (m, 2H), 7.65 (d, 2H, J=7.2 Hz), 8.71 (d, 1H, J=3.5 Hz).

Using General Procedure D: Conversion of the material from above (100 mg) to the hydrobromide salt provided AMD9773 (70 mg) as a white solid. $^1$H NMR ($D_2O$) δ 1.88 (br m, 1H), 2.25 (m, 2H), 2.45 (br m, 1H), 3.03 (br m, 2H), 3.88 (d, 1H, J=12.9 Hz), 3.95 (d, 1H, J=12.9 Hz), 4.45 (d, 1H, J=16.2 Hz), 4.63 (d, 1H, J=16.2 Hz), 4.79 (m, 1H), 7.36 (s, 4H), 7.47 (dd, 2H, J=3.0, 6.3 Hz), 7.58 (dd, 2H, J=3.0, 6.3 Hz), 7.93 (t, 1H, J=6.9 Hz), 8.40 (d, 1H, J=8.1 Hz), 8.77 (d, 1H, J=5.7 Hz); $^{13}$C NMR ($D_2O$) δ 20.43, 21.00, 27.87, 50.12, 56.72, 63.21, 113.97 (2C), 126.17, 126.67, 126.87 (2C), 127.56 (2C), 130.61, 130.85 (2C), 139.85, 141.09, 143.36 (2C), 148.27, 150.71, 151.44, 165.18. ES-MS m/z 411 (M+H). Anal. Calcd. for $C_{25}H_{26}N_6$·2.9HBr·2.0$H_2O$: C, 43.89; H, 4.85; N, 12.28; Br, 34.34. Found: C, 43.97; H, 4.90; N, 12.02; Br, 34.35.

EXAMPLE 59

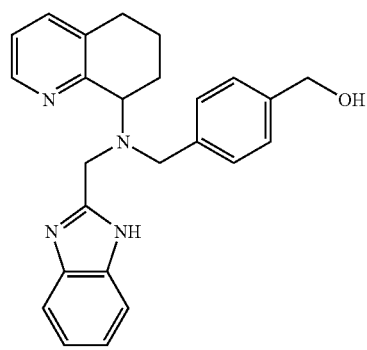

AMD9717: Preparation of 4-{[(1H-Benzimidazol-2-ylmethyl)-(5,6,7,8-tetrahydro-quinolin-8-yl)-amino]-methyl}-benzyl alcohol To a stirred solution of 8-amino-5,6,7,8-tetrahydroquinoline (5.56 g, 37.5 mmol) in dry MeOH (150 mL) was added 4-hydroxymethylbenzaldehyde (7.22 g, 52.5 mmol) under an argon atmosphere and the mixture was stirred overnight at room temperature. To the resultant solution was added sodium borohydride (2.85 g, 75 mmol) in three portions over 45 minutes and the reaction mixture stirred for 24 h to afford a pale yellow oil which was used in the next step without any further purification (see General Procedure B).

To a stirred solution of the oil from above (7.64 g) in dry $CH_3CN$ (100 mL) was added N,N-diisopropylethylamine (10 mL, 57 mmol), potassium iodide (0.24 g, 1.4 mmol) and 1-N-tert-butoxycarbonyl-2-chloromethylbenzimidazole (7.98 g, 29.9 mmol) as a solution in $CH_3CN$ (50 mL). The mixture was stirred under an argon atmosphere at 60° C. overnight. The reaction mixture was concentrated in vacuo, diluted with $CH_2Cl_2$ (100 mL) and washed with saturated aqueous ammonium chloride (150 mL). The aqueous layer was extracted with $CH_2Cl_2$ (2×50 mL) and the combined organic layers were dried ($Na_2SO_4$), filtered, and concentrated in vacuo.

A solution of the crude material from above in $CH_2Cl_2$/trifluoroacetic acid (2:1, 30 mL) was stirred for 3 h at room temperature. The reaction mixture was diluted with $CH_2Cl_2$ (30 mL) and concentrated in vacuo. The residue was diluted with $CH_2Cl_2$ (50 mL) and washed with 1N NaOH (50 mL). The aqueous layer was extracted with $CH_2Cl_2$ (2×30 mL) and the combined organic layers were dried ($Na_2SO_4$), filtered, and concentrated in vacuo to afford a brown foam. A small portion (111 mg) of the crude material was purified by radial chromatography on a 1 mm TLC grade silica gel plate ($CH_2Cl_2$/MeOH/$NH_4OH$, 100:1:1) to afford the free base, AMD9717, (31.4 mg, 28%) as a white foam. $^1$H NMR (CDCl₃) δ 1.68–1.77 (br m, 1H), 1.97–2.08 (m, 2H), 2.24–2.28 (m, 1H), 2.70–2.91 (m, 2H), 3.75 (s, 2H), 3.95 (d, 1H, J=16.8 Hz), 4.09 (m, 1H), 4.17 (d, 1H, J=16.8 Hz), 4.59 (s, 2H), 7.14–7.24 (m, 6H), 7.38–7.45 (m, 3H), 7.49–7.51 (m, 1H), 7.61–7.65 (m, 1H), 8.70 (d, 1H, J=4.8 Hz); ¹³C NMR (CDCl₃) δ 20.24, 21.78, 28.17, 47.73, 52.85, 59.21, 63.41, 120.42, 121.11, 125.75, 127.78, 133.84, 136.27, 137.16, 139.22, 145.76, 154.60, 156.10; ES-MS m/z 399 (M+H); Anal. Calcd. for C₂₅H₂₆N₄O.0.3CH₂Cl₂.0.25H₂O: C, 70.92; H, 6.37; N, 13.08. Found: C, 71.25; H, 6.53; N, 12.68.

EXAMPLE 60

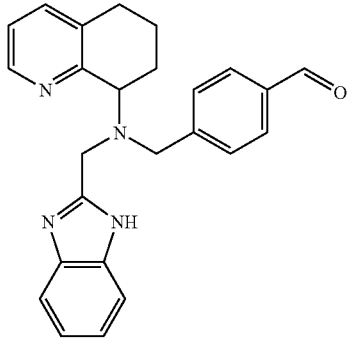

AMD9882: Preparation of 4-{[(1H-Benzimidazol-2-ylmethyl)-(5,6,7,8-tetrahydro-quinolin-8-yl)-amino]-methyl}-benzaldehyde To a stirred solution of the alcohol from above, 4-{[(1H-Benzimidazol-2-ylmethyl)-(5,6,7,8-tetrahydro-quinolin-8-yl)-amino]-methyl}-benzyl alcohol (AMD9717), (9.29 g) in dry CH₂Cl₂ (200 mL) was added MnO₂ (20.3 g, 233 mmol) and the mixture stirred for 4 h at room temperature. An additional portion of MnO₂ (8.5 g, 97.8 mmol) was then added and the mixture stirred overnight at room temperature. The reaction mixture was filtered through a celite pad, the cake washed with CHCl₃ and the resultant filtrate concentrated in vacuo. Purification of the crude product by column chromatography on silica gel (CH₂Cl₂/MeOH, 97:3 followed by 96:4) afforded the aldehyde (5.08 g, 34%, 5 steps) as a pale yellow solid. ¹H NMR (CDCl₃) δ 1.56–1.74 (br m, 2H), 1.92–2.09 (m, 2H), 2.28–2.32 (m, 1H), 2.70–2.94 (m, 2H), 3.84 (s, 2H), 3.94 (d, 1H, J=16.5 Hz), 4.08–4.14 (m, 1H), 4.23 (d, 1H, J=16.5 Hz), 7.18–7.26 (m, 4H), 7.45 (d, 1H, J=7.8 Hz), 7.56 (m, 4H), 7.76 (d, 2H, J=8.1 Hz), 8.72 (d, 1H, J=4.2 Hz), 9.92 (s, 1H). ¹³C NMR (CDCl₃) δ 21.29, 23.73, 29.11, 48.90, 53.90, 60.56, 121.85 (2 carbons), 122.53 (2 carbons), 129.04 (2 carbons), 129.86 (2 carbons), 134.89, 135.58, 137.57 (2 carbons), 146.69, 146.85, 155.58, 156.99, 191.85. ES-MS m/z 397 (M+H). Anal. Calcd. for C₂₅H₃₄N₄O.0.15CH₂Cl₂: C, 73.82; H, 5.98; N, 13.69. Found: C, 73.69; H, 6.16; N, 13.78.

EXAMPLE 61

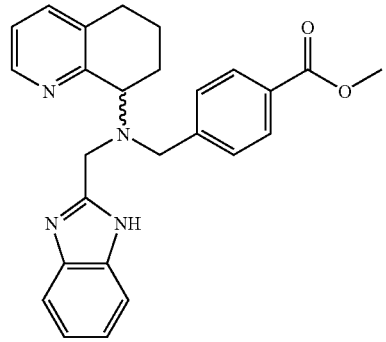

AMD9711: Preparation of 4-{[(1H-Benzimidazol-2-ylmethyl)-(5,6,7,8-tetrahydro-quinolin-8-yl)-amino]-methyl}-benzoic acid methyl ester Following General Procedure B: To a solution of (1-tert-butoxycarbonyl-1H-Benzimidazol-2-ylmethyl)-(5,6,7,8-tetrahydro-quinolin-8-yl)-amine (680 mg, 1.8 mmol) and methyl 4-formylbenzoate (295 mg, 1.8 mmol) in CH₂Cl₂ (10 mL) was added NaBH(OAc)₃ (763 mg, 3.6 mmol) and the mixture stirred for 18 h. The resulting crude material was taken up in neat TFA (2 mL) and stirred 3 h. Saturated aqueous sodium bicarbonate (10 mL) was cautiously added, and the resulting mixture was extracted with CH₂Cl₂ (3×20 mL), and the combined organic extracts were dried (MgSO₄), and concentrated in vacuo. Purification of the crude material by flash chromatography (silica gel, 50:2:1 CH₂Cl₂/MeOH/NH₄OH) afforded the title compound (565 mg, 74%) as a white solid. ¹H NMR (CDCl₃) δ 1.64–1.75 (m, 1H), 2.01–2.08 (m, 2H), 2.26–2.28 (m, 1H), 2.74–2.76 (m, 1H), 2.81–2.86 (m, 1H), 3.81 (s, 2H), 3.86 (s, 3H), 3.94 (d, 1H, J=17 Hz), 4.09 (dd, 1H, J=9, 7 Hz), 4.21 (d, 1H, J=17 Hz), 7.18–7.22 (m, 3H), 7.44 (br d, 1H, J=8 Hz), 7.49 (d, 2H, J=8 Hz), 7.50–7.53 (m, 1H), 7.64–7.66 (m, 1H), 7.91 (d, 2H, J=8 Hz), 8.70 (dd, 1H, J=5, 1 Hz); ¹³C NMR (CDCl₃) δ 21.2, 23.6, 29.0, 48.7, 51.9, 53.7, 111.0, 118.6, 121.5, 122.3, 129.3, 128.9, 129.5, 134.7, 137.2, 144.8, 146.8, 155.7, 157.1, 166.8. ES-MS m/z 427 (M+H). Anal. Calcd. for C₂₆H₂₆N₄O₂.0.6H₂O.0.3CH₂Cl₂: C, 68.26; H, 6.05; N, 12.11. Found: C, 68.57; H, 6.12; N, 11.75.

EXAMPLE 62

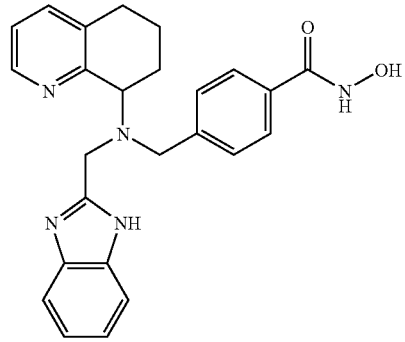

AMD9738: Preparation of (R,S)-4-{[(1H-Benzimidazol-2-ylmethyl)-(5,6,7,8-tetrahydro-quinolin-8-yl)-amino]-methyl}-N-hydroxy-benzamide To a stirred solution of 4-{[(1H-benzimidazol-2-ylmethyl)-(5,6,7,8-tetrahydro-quinolin-8-yl)-amino]-methyl}-benzoic acid methyl ester (AMD9711) (120 mg, 0.23 mmol) in dry MeOH (3 mL) was added hydroxylamine hydrochloride (32 mg, 0.46 mmol) followed by potassium hydroxide (39 mg, 0.69 mmol). The resulting solution was stirred for 18 h, at which point water (5 mL) and $CH_2Cl_2$ (5 mL) were added. The phases were separated and the aqueous layer was adjusted to pH 7 by the addition of saturated aqueous ammonium hydroxide, then extracted with $CH_2Cl_2$ (3×10 mL). The combined organic extracts were dried ($MgSO_4$), filtered and concentrated in vacuo. Purification of the crude material by radial chromatography (1 mm plate, 10:1:1 $CH_2Cl_2$/MeOH/$NH_4OH$) afforded the title compound (52 mg, 43%) as a white solid. $^1H$ NMR ($CDCl_3$) δ 1.58–1.61 (m, 1H), 1.87–1.91 (m, 2H), 2.12–2.14 (m, 1H), 2.61–2.66 (m, 1H), 2.73–2.77 (m, 1H), 3.55 (br s, 2H), 3.79 (br d, 1H, J=16 Hz), 3.98–4.00 (m, 1H), 4.09 (br d, 1H, J=16 Hz), 7.08–7.11 (m, 3H), 7.23–7.26 (m, 2H), 7.38 (br d, 1H, J=8 Hz), 7.48–7.51 (m, 4H), 8.60 (br d, 1H, J=4 Hz); $^{13}C$ NMR ($CDCl_3$) δ 21.2, 23.1, 29.1, 48.6, 53.9, 60.5, 121.9, 122.4, 127.0, 128.8, 130.7, 135.1, 137.7, 142.9, 146.7, 155.2, 156.7, 166.3. ES-MS m/z 428 (M+H). Anal. Calcd. for $C_{25}H_{25}N_5O\cdot 0.8CH_2Cl_2$: C, 64.63; H, 5.59; N, 14.61. Found: C, 64.94; H, 5.69; N, 14.23.

EXAMPLE 63

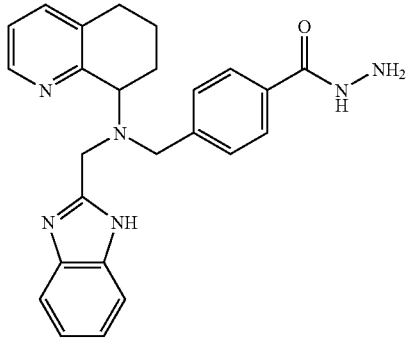

AMD9743: Preparation of 4-{[(1H-Benzimidazol-2-ylmethyl)-(5,6,7,8-tetrahydro-quinolin-8-yl)-amino]-methyl}-benzoic acid hydrazide To a stirred solution of 4-{[(1H-benzimidazol-2-ylmethyl)-(5,6,7,8-tetrahydro-quinolin-8-yl)-amino]-methyl}-benzoic acid methyl ester (AMD9711) (140 mg, 0.33 mmol) in dry ethanol (3 mL) was added hydrazine monohydrate (0.5 mL, 10.3 mmol) and the resulting mixture was heated at 80° C. for 24 h. Saturated aqueous sodium bicarbonate (5 mL) was added, the phases separated and the aqueous layer extracted with $CH_2Cl_2$ (3×10 mL). The combined organic extracts were dried ($MgSO_4$) and concentrated in vacuo. Purification of the crude material by radial chromatography (1 mm plate, 75:1:1 $CH_2Cl_2$—MeOH—$NH_4OH$) afforded the title compound (89 mg, 61%) as a white solid. $^1H$ NMR ($CDCl_3$) δ 1.64–1.68 (m, 1H), 1.94–2.04 (m, 2H), 2.20–2.24 (m, 1H), 2.66–2.72 (m, 1H), 2.78–2.83 (m, 1H), 3.73 (s, 2H), 3.93 (d, 1H, J=16 Hz), 4.00–4.12 (m, 3H), 4.15 (d, 1H, J=16 Hz), 7.14–7.18 (m, 3H), 7.40 (d, 2H, J=8 Hz), 7.50 (br d, 1H, J=7 Hz), 7.58 (d, 2H, J=8 Hz), 7.62 (br d, 1H, J=7 Hz), 8.06 (s, 1H), 8.66 (dd, 1H, J=5, 1Hz); $^{13}C$ NMR ($CDCl_3$) δ 21.2, 23.6, 29.0, 48.7, 53.7, 60.4, 111.4, 118.4, 121.5, 122.3, 126.9, 128.6, 131.5, 134.7, 137.3, 143.5, 146.8, 155.8, 157.1, 168.4. ES-MS m/z 427 (M+H). Anal. Calcd. for $C_{25}H_{26}N_6O\cdot 0.5CH_2Cl_2$: C, 65.31; H, 5.80; N, 17.92. Found: C, 65.22; H, 5.77; N, 17.97.

EXAMPLE 64

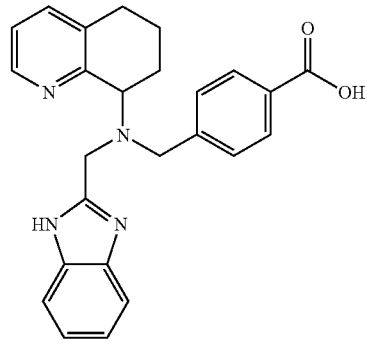

AMD9769: Preparation of 4-{[(1H-benzoimidazol-2-ylmethyl)-(5,6,7,8-tetrahydro-quinolin-8-yl)-amino]-methyl}-benzoic acid (hydrobromide salt)

To a solution of the 4-{[(1H-benzoimidazol-2-ylmethyl)-(5,6,7,8-tetrahydro-quinolin-8-yl)-amino]-methyl}-benzoic acid methyl ester (AMD9711) (90 mg, 0.21 mmol) in MeOH (2.5 mL) was added aqueous NaOH (3.5 m, 0.30 mL, 1.05 mmol). The reaction mixture was heated at 40° C. for 16 h after which the solution was concentrated, washed with saturated aqueous $NaHCO_3$ (10 mL) and extracted with $CH_2Cl_2$ (2×50 mL). The aqueous layer was acidified to pH 4 with 10% aqueous HCl, saturated with NaCl(s) and the product was extracted with $CH_2Cl_2$ (3×75 mL). The combined organic extracts were dried over $MgSO_4$ and concentrated to a light yellow foam. $^1H$ NMR (300 MHz, $CDCl_3$) δ 8.71 (d, 1H, J=5.8 Hz), 7.84 (d, 2H, J=8.1 Hz), 7.62 (br s, 2H), 7.52 (d, 1H, J=8.1 Hz), 7.35 (d, 2H, J=8.1 Hz), 7.23–7.17 (m, 3H), 4.29–4.21 (m, 2H), 3.95 (d, 1H, J=16.2 Hz), 3.74 (s, 2H), 2.95–2.86 (m, 1H), 2.79–2.74 (m, 1H), 2.37–2.25 (l m, 1H), 2.18–2.11 (m, 2H), 1.83–1.74 (m, 1H).

Following General Procedure D: Conversion of the foam from above to the hydrobromide salt gave AMD9769. $^1H$ NMR (300 MHz, $D_2O$) δ 8.77 (d, 1H, J=6.0 Hz), 8.41 (d, 1H, J=7.8 Hz), 7.94 (dd, 1H, J=7.5, 5.7 Hz), 7.53–7.42 (m, 6H), 7.22–7.19 (m, 2H), 4.78–4.73 (m, 1H), 4.62 (d, 1H, J=16.2 Hz), 4.43 (d, 1H, J=16.2 Hz), 3.87 (d, 1H, J=12.9 Hz), 3.78 (d, 1H, J=12.9 Hz), 3.05–3.03 (m, 2H), 2.47–2.43 (m, 1H), 2.32–2.21 (m, 2H), 1.93–1.87 (m, 1H); $^{13}C$ NMR (75.5 MHz, $D_2O$) δ 172.1, 153.5, 152.9, 150.4, 144.2, 143.2, 141.8, 132.6, 132.3, 131.7, 131.2, 128.9, 128.3, 115.9, 65.6, 58.9, 52.4, 30.0, 23.1, 22.5. ES-MS m/z 413.2 (M+H). Anal Calcd for $(C_{25}H_{24}N_4O_2)\cdot 2(HBr)\cdot 1.3(H_2O)$: C, 50.24; H, 4.82; N, 9.37; Br, 26.74. Found: C, 50.58; H, 4.96; N, 9.00; Br, 26.35.

EXAMPLE 65

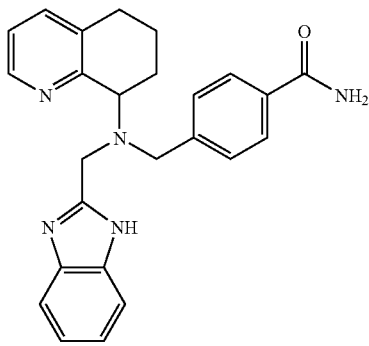

AMD9770: Preparation of 4-{[(1H-Benzimidazol-2-ylmethyl)-(5,6,7,8-tetrahydro-quinolin-8-yl)-amino]-methyl}-benzamide Preparation of 4-Formylbenzamide

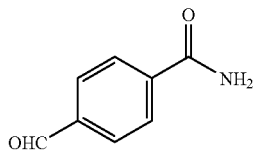

Neat thionyl chloride (1.94 mL, 27 mmol) was added dropwise to a stirred suspension of 4-formylbenzoic acid (2.0 g, 13 mmol) in dry $CH_2Cl_2$ (50 mL). The resulting slurry was stirred 18 h, at which time the solvent and excess thionyl chloride was removed in vacuo. The residual solid was redissolved in dry THF (50 mL) and ammonia gas was bubbled through the solution for 15 min, which resulted in the formation of a white precipitate. The mixture was poured into saturated aqueous sodium bicarbonate (30 mL) and chloroform (100 mL) was added. The phases were separated and the aqueous layer was extracted with $CHCl_3$ (3×30 mL). The combined organic extracts were dried ($MgSO_4$), filtered and concentrated in vacuo. Purification of the crude material by flash chromatography on silica gel (20:1:1 $CH_2Cl_2$—MeOH—$NH_4OH$) afforded the title compound (85 mg, 4%) as a white solid. $^1H$ NMR ($CDCl_3$) δ 5.96 (br s, 1H), 6.19 (br 2, 1H), 7.97 (s, 4H), 10.09 (s, 1H).

Following the General Procedure B: To a solution of (1-tert-butoxycarbonyl-1H-benzimidazol-2-ylmethyl)-(5,6,7,8-tetrahydro-quinolin-8-yl)-amine (216 mg, 0.57 mmol) and 4-formylbenzamide (85 mg, 0.57 mmol) in $CH_2Cl_2$ (5 mL) was added sodium triacetoxyborohydride (242 mg, 1.14 mmol) and the reaction stirred for 18 h. The resultant crude material was taken up in neat TFA (2 mL) and stirred 3 h. Saturated aqueous sodium bicarbonate (10 mL) was cautiously added, and the resulting mixture was extracted with $CH_2Cl_2$ (3×20 mL) then the combined organic extracts were dried ($MgSO_4$), filtered and concentrated in vacuo. Purification of the crude material by radial chromatography on silica gel (1 mm plate, 50:1:1 $CH_2Cl_2$—MeOH—$NH_4OH$) afforded the title compound (66 mg, 28%) as a white solid. $^1H$ NMR ($CDCl_3$) δ 1.67–1.73 (m, 1H), 2.00–2.08 (m, 2H), 2.26–2.30 (m, 1H), 2.71–2.76 (m, 1H), 2.82–2.87 (m, 1H), 3.80 (s, 2H), 3.92 (d, 1H, J=16 Hz), 4.09 (dd, 1H, J=9, 7 Hz), 4.20 (d, 1H, J=16 Hz), 5.56 (br s, 1H), 6.01 (br s, 1H), 7.17–7.22 (m, 3H), 7.43–7.53 (m, 4H), 7.65–7.67 (m, 3H), 8.70 (dd, 1H, J=5, 1 Hz); $^{13}C$ NMR ($CDCl_3$) δ 21.3, 23.7, 29.1, 48.7, 53.7, 60.5, 121.7, 122.4, 127.4, 128.7, 132.3, 134.8, 137.4, 143.8, 146.9, 155.8, 157.1, 169.1. ES-MS m/z 412 (M+H). Anal. Calcd. for $C_{25}H_{25}N_5O \cdot 1.45H_2O \cdot 0.6CH_2Cl_2$: C, 63.84; H, 6.34; N, 13.76. Found: C, 64.03; H, 5.95; N, 13.37.

EXAMPLE 66

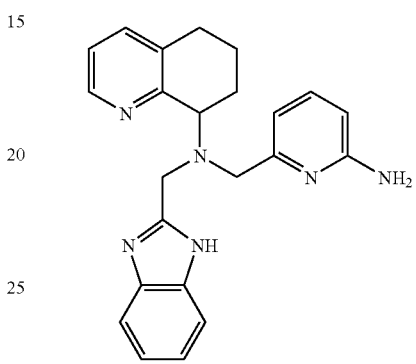

AMD11130: Preparation of (6-Amino-pyridin-2-ylmethyl)-(1H-benzimidazol-2-ylmethyl-(5,6,7,8-tetrahydro-quinolin-8-yl)-amine (hydrobromide salt)

Using the general N-alkylation procedure: To a stirred solution of N-[6-(bromomethyl)-2-pyridyl]pivalamide (prepared as described by Harata, M.; Hasegawa, K.; Jitsukawa, K.; Masuda, H.; Einaga, H. *Bull. Chem. Soc. Jpn* 1998, 71, 1031–1038) (0.129 g, 0.45 mmol) in dry $CH_3CN$ (10 mL) was added (1-tert-butoxycarbonyl-1H-benzimidazol-2-ylmethyl)-(5,6,7,8-tetrahydro-quinolin-8-yl)-amine (0.176 g, 0.47 mmol), N,N-diisopropylethylamine (0.20 mL, 1.15 mmol) and potassium iodide (12 mg, 0.048 mmol). The mixture was stirred under an argon atmosphere at 60° C. for 3.75 h. Purification of the crude material by column chromatography on silica gel ($CH_2Cl_2$/MeOH, 98:2 followed by 96:4) gave the alkylated product (0.148 g, 54%) as a brown oil.

Using General Procedure D: Conversion of the amine from above (43 mg, 0.074 mmol) to the hydrobromide salt with simultaneous removal of the Boc groups gave AMD11130 (41 mg, 84%) as a yellow solid. $^1H$ NMR ($D_2O$) δ 1.86–1.92 (m, 1H), 2.15–2.26 (m, 2H), 2.40–2.45 (m, 1H), 3.00–3.01 (m, 2H), 3.99 (d, 1H, J=14.4 Hz), 4.15 (d, 1H, J=14.7 Hz), 4.36 (d, 1H, J=15.9 Hz), 4.52 (d, 1H, J=15.9 Hz), 4.76–4.79 (m, 1H, overlap with HOD), 6.45 (d, 1H, J=9 Hz), 6.70 (d, 1H, J=6.9 Hz), 7.43 (dd, 1H, J=9, 7.5 Hz), 7.57 (dd, 2H, J=6.3, 3 Hz), 7.67 (dd, 2H, J=6.3, 3 Hz), 7.89 (dd, 1H, J=7.8, 6 Hz), 8.37 (d, 1H, J=7.5 Hz), 8.74 (d, 1H, J=5.7 Hz); $^{13}C$ NMR ($D_2O$) δ 20.30, 20.86, 27.81, 48.12, 54.65, 62.49, 113.24, 113.78, 114.19, 126.26, 127.22, 127.36, 130.88, 140.30, 141.10, 143.85, 144.14, 148.38, 149.38, 149.63; ES-MS m/z 385 (M+H); Anal. Calcd. for $C_{23}H_{24}N_6 \cdot 3.0HBr \cdot 1.8H_2O$: C, 41.88; H, 4.68; N, 12.74; Br, 36.34. Found: C, 41.85; H, 4.61; N, 12.45; Br, 36.44.

EXAMPLE 67

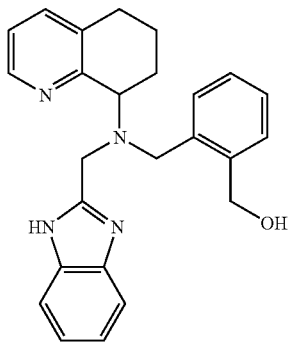

AMD 11157: Preparation of (2-{[(1H-Benzimidazol-2-ylmethyl)-(5,6,7,8-tetrahydro-quinolin-8-yl)-amino]-methyl}-phenyl)-methanol (free base)

Using general procedure B {direct reductive amination using NaBH(OAc)$_3$}: Reaction of phthalic dicarboxaldehyde (0.139 g, 1.04 mmol) and (1-tert-butoxycarbonyl-1H-Benzimidazol-2-ylmethyl)-(5,6,7,8-tetrahydro-quinolin-8-yl)-amine (0.183 g, 0.48 mmol) with NaBH(OAc)$_3$ (0.504 g, 2.38 mmol) in CH$_2$Cl$_2$ (5 mL) for 20 hours followed by purification of the crude material by radial chromatography on silica gel (2 mm plate, 100:1 CH$_2$Cl$_2$—CH$_3$OH) provided 0.108 g (45%) of a white foam. The foam (0.108 g, 0.22 mmol) was dissolved in CH$_2$Cl$_2$ (2 mL) and treated with trifluoroacetic acid (1 mL). The resultant solution was stirred at room temperature for 90 minutes then concentrated under reduced pressure. The residue was dissolved in CH$_2$Cl$_2$ (10 mL) and NaOH (1.0 M, ~10 mL) so that the aqueous phase was basic (pH 14). The phases were separated and the aqueous phase was extracted with CH$_2$Cl$_2$ (3×10 mL). The combined organic extracts were dried (Na$_2$SO$_4$) and concentrated. Purification of the crude material by radial chromatography on silica gel (1 mm plate, 100:1:1 CH$_2$Cl$_2$—CH$_3$OH—NH$_4$OH) provided 0.079 g (91%) of AMD 11157 as a white solid.

$^1$H NMR (CDCl$_3$) δ 1.61–1.76 (m, 2H), 1.89–2.02 (m, 1H), 2.07–2.13 (m, 1H), 2.33–2.40 (m, 1H), 2.69–2.90 (m, 2H), 3.81 (d, 1H, J=15.0 Hz), 3.82 (d, 1H, J=12.6 Hz), 3.95 (d, 1H, J=15.0 Hz), 3.98 (t, 1H, J=8.1 Hz), 4.06 (d, 1H, J=12.6 Hz), 4.50 (d, 1H, J=11.7 Hz), 4.63 (d, 1H), J=11.7 Hz), 7.06–7.21 (m, 6H), 7.38–7.46 (m, 3H), 7.62 (br s, 1H), 8.09 (br s, 1H), 8.44 (br d, 1H, J=4.2 Hz); $^{13}$C NMR (CDCl$_3$) δ 20.90, 21.40, 29.04, 49.28, 55.26, 60.09, 62.90, 111.04, 118.81, 121.48, 122.23, 127.93, 128.50, 130.95, 131.83, 134.83, 137.27, 137.63, 140.38, 146.78, 153.60, 156.28. ES-MS m/z 399 (M+H). Anal. Calcd. for C$_{25}$H$_{26}$N$_4$O.1.0H$_2$O: C, 72.09; H, 6.78; N, 13.45. Found: C, 72.15; H, 6.43; N, 13.29.

EXAMPLE 68

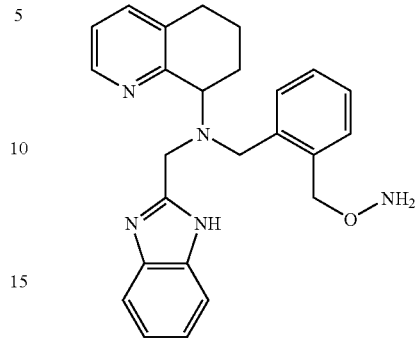

AMD11156: Preparation of O-(2-{[(1H-Benzimidazol-2-ylmethyl)-(5,6,7,8-tetrahydro-quinolin-8-yl)-amino]-methyl}-benzyl)-hydroxylamine (hydrobromide salt)

Preparation of 2-(2-Bromomethyl-benzyloxy)-isoindole-1,3-dione

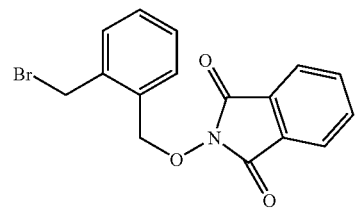

To a stirred solution of N-hydroxyphthalimide (0.60 g, 3.68 mmol) and Et$_3$N (0.60 mL, 4.30 mmol) in DMF (6 mL) was added α,α'-dibromo-o-xylene (3.30 g, 0.0125 mol) and the mixture stirred at room temperature for 4 h. The resultant brown precipitate was filtered and washed with CH$_2$Cl$_2$. The filtrate was diluted with EtOAc (40 mL) and water (30 mL) and the organic phase washed with brine (1×30 mL), dried (Na$_2$SO$_4$) and concentrated under reduced pressure. The resultant yellow oil was purified by column chromatography on silica gel (4:1 Hexanes/EtOAc) to give the title compound (581 mg, 46%) as a white solid. $^1$H NMR (CDCl$_3$) δ 4.99 (s, 2H), 5.37 (s, 2H), 7.27–7.40 (m, 2H), 7.41–7.45 (m, 2H), 7.73–7.76 (m, 2H), 7.81–7.84 (m, 2H).

Using the general alkylation procedure: To a stirred solution of 2-(2-bromomethyl-benzyloxy)-isoindole-1,3-dione (0.308 g, 0.89 mmol) in dry CH$_3$CN (10 mL) was added (1-tert-butoxycarbonyl-1H-benzimidazol-2-ylmethyl)-(5,6,7,8-tetrahydro-quinolin-8-yl)-amine (0.274 g, 0.725 mmol), N,N-diisopropylethylamine (0.21 mL, 1.21 mmol) and potassium iodide (12 mg, 0.048 mmol). The mixture was stirred under an argon atmosphere at 60° C. for 2.75 h. Purification of the crude material by column chromatography on silica gel (CH$_2$Cl$_2$/MeOH, 98:2 followed by 96:4) gave the alkylated product (0.32 g, 69%) as a white foam.

To a solution of the foam from above (219 mg, 0.34 mmol) in EtOH (96%, 5 mL) was added hydrazine monohydrate (0.10 mL, 2 mmol) and the solution stirred at room temperature for 3 days. The mixture was filtered (to remove the resultant white solid) and washed with CH$_2$Cl$_2$. The filtrate was concentrated under reduced pressure and purified by radial chromatography on silica gel (1 mm plate, $CH_2Cl_2$/ MeOH/$NH_4OH$, 100:1:1) to give the desired deprotected amine (44 mg, 31%) as a white foam.

Using General Procedure D: Conversion of the amine from above (39 mg, 0.094 mmol) to the hydrobromide salt gave AMD11156 (59 mg, 90%) as a white solid. $^1$H NMR ($D_2O$) δ 1.88–1.93 (m, 1H), 2.19–2.32 (m, 2H), 2.45–2.49 (m, 1H), 3.03–3.04 (m, 2H), 3.85 (d, 1H, J=13.5 Hz), 4.17 (d, 1H, J=13.5 Hz), 4.36 (d, 1H, J=16.2 Hz), 4.55 (d, 1H, J=16.2 Hz), 4.76–4.79 (m, 1H, overlap with HOD), 5.10 (d, 1H, J=10.8 Hz), 5.24 (d, 1H, J=10.8 Hz), 6.91 (t, 1H, J=7.5 Hz), 7.07 (d, 1H, J=6.9 Hz), 7.14 (t, 1H, J=7.5 Hz), 7.42 (d, 1H, J=7.5 Hz), 7.51 (dd, 2H, J=6.3, 3 Hz), 7.58 (dd, 2H, J=6.3, 3 Hz), 7.90 (dd, 1H, J=7.8, 6 Hz), 8.38 (d, 1H, J=7.5 Hz), 8.73 (d, 1H, J=5.7 Hz); $^{13}$C NMR ($D_2O$) δ 20.42, 20.80, 27.88, 48.98, 52.84, 62.08, 74.83, 113.93, 126.16, 126.81, 128.85, 130.56, 131.21, 131.52, 131.87, 136.51, 139.88, 141.13, 148.36, 150.49, 150.80; ES-MS m/z 414 (M+H); Anal. Calcd. for $C_{25}H_{27}N_5O.3.0HBr.2.2H_2O$: C, 43.15; H, 4.98; N, 10.06; Br, 34.45. Found: C, 43.37; H, 5.05; N, 9.87; Br, 34.33.

EXAMPLE 69

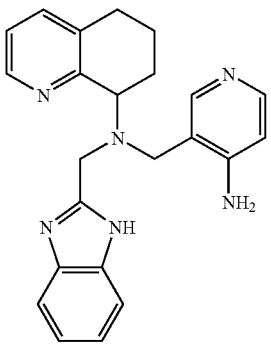

AMD11191: Preparation of (4-Amino-pyridin-3-ylmethyl)-(1H-benzimidazol-2-ylmethyl)-(5,6,7,8-tetrahydro-quinolin-8-yl)-amine (hydrobromide salt)

Using General Procedure B: To a stirred solution of (1H-Benzimidazol-2-ylmethyl)-(5,6,7,8-tetrahydro-quinolin-8-yl)-amine (252 mg, 0.91 mmol) and (3-Formyl-pyridin-4-yl)-carbamic acid tert-butyl ester (prepared as described by Venuti, M. C.; Stephenson, R. A. et al. *J. Med. Chem.* 1988, 31, 2136–2145) (206 mg, 0.93 mmol) in $CH_2Cl_2$ (9 mL) was added $NaBH(OAc)_3$ (243 mg, 1.15 mmol) and the resultant mixture was stirred at room temperature for 16 hours. A solution of the resultant crude yellow foam (0.30 g) in 5 N HCl/THF (1:1, 6 mL) was stirred for 3 days. The mixture was diluted with water (10 mL) and $CH_2Cl_2$ (25 mL) and made alkaline (pH >10) with 10 N NaOH (10 mL). The layers were separated and the aqueous phase was washed with $CH_2Cl_2$ (3×10 mL). The combined organic extracts were dried ($Na_2SO_4$), concentrated under reduced pressure and purified by radial chromatography on silica gel (2 mm plate, $CH_2Cl_2$/MeOH/ $NH_4OH$, 100:1:1 then 50:1:1 then 20:1:1) to give the free amine (100 mg, 29% over 2 steps) as a clear oil.

Using General Procedure D: Conversion of the amine from above (73 mg, 0.19 mmol) to the hydrobromide salt gave AMD11191 (120 mg, 90%) as a white solid. $^1$H NMR ($D_2O$) δ 1.87–1.91 (m, 1H), 2.15–2.26 (m, 2H), 2.45–2.50 (m, 1H), 3.00–3.02 (m, 2H), 4.02 (d, 1H, J=14.1 Hz), 4.13 (d, 1H, J=14.1 Hz), 4.34 (d, 1H, J=16.2 Hz), 4.45 (d, 1H, J=16.2 Hz), 4.76–4.79 (m, 1H, overlap with HOD), 6.40 (d, 1H, J=6.9 Hz), 7.38 (d, 1H, J=6.9 Hz), 7.56 (dd, 2H, J=6.3, 3 Hz), 7.66 (dd, 2H, J=6.3, 3 Hz), 7.89 (dd, 1H, J=7.8, 6 Hz), 8.08 (s, 1H), 8.35 (d, 1H, J=7.8 Hz), 8.74 (d, 1H, J=5.7 Hz); $^{13}$C NMR ($D_2O$) δ 20.41 (2 carbons), 27.92, 48.03, 51.51, 61.78, 109.58, 114.04, 115.89, 126.30, 127.34, 130.58, 138.61, 140.26, 140.69, 141.07, 148.25, 149.82, 150.33, 158.82; ES-MS m/z 385 (M+H); Anal. Calcd. for $C_{23}H_{24}N_6.3.1HBr.1.8H_2O.0.5C_4H_{10}O$: C, 42.60; H, 5.11; N, 11.92; Br, 35.15. Found: C, 42.91; H, 5.01; N, 11.88; Br, 34.76.

EXAMPLE 70

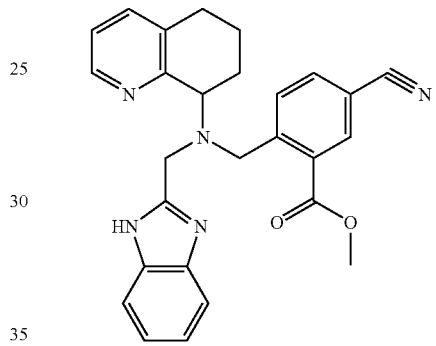

AMD11065: Preparation of 2-{[(1H-Benzimidazol-2-ylmethyl)-(5,6,7,8-tetrahydro-quinolin-8-yl)-amino]-methyl}-5-cyano-benzoic acid methyl ester Preparation of 2-methyl-5-nitro-benzoic acid methyl ester

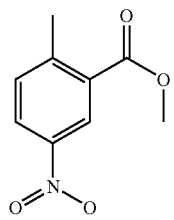

A solution of 2-methyl-5-nitrobenzoic acid (1.91 g, 10.6 mmol) and $H_2SO_4$ (catalytic) in MeOH (25 mL) was heated at reflux for 16 h, then concentrated in vacuo. The residue was dissolved in $CH_2Cl_2$ (50 mL), washed with saturated $NaHCO_3$(aq) (2×40 mL), then dried ($MgSO_4$), filtered, and concentrated in vacuo to give yellow crystals (1.50 g, 73%). $^1$H NMR ($CDCl_3$) δ 2.72 (s, 3H), 3.96 (s, 3H), 7.44 (d, 1H, J=9.0 Hz), 8.24 (dd, 1H, J=9.0, 3.0 Hz), 8.78 (d, 1H, J=3.0 Hz).

Preparation of 5-Amino-2-methyl-benzoic acid methyl ester

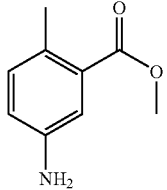

A solution of 2-methyl-5-nitro-benzoic acid methyl ester (1.50 g, 7.8 mmol) in 4:1 MeOH/EtOAc (20 mL) was shaken at room temperature with a suspension of 10% Pd/C (175 mg, 0.17 mmol) under hydrogen atmosphere (35 psi) for 17 h. The catalyst was removed by filtration over celite, and the filtrate was concentrated in vacuo to give a pale yellow oil (1.29 g, 99%). $^1$H NMR (CDCl$_3$) δ 2.46 (s, 3H), 3.63 (br s, 2H), 3.87 (s, 3H), 6.74 (dd, 1H, J=9.0, 3.0 Hz), 7.02 (d, 1H, J=6.0 Hz), 7.25 (d, 1H, J=3.0 Hz).

Preparation of 5-Cyano-2-methyl-benzoic acid methyl ester

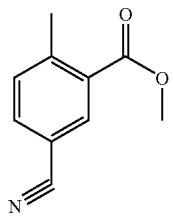

To a stirred suspension of 5-amino-2-methyl-benzoic acid methyl ester (1.29 g, 7.80 mmol) in H$_2$O (2.0 mL) was slowly added conc. HCl (2.0 mL) at room temperature. More H$_2$O (15 mL) was added, and the mixture was stirred at 0° C. while a solution of NaNO$_2$ (592 mg, 8.58 mmol) in H$_2$O (2.2 mL) was added dropwise. After the amine had completely dissolved, K$_2$CO$_3$(s) was added slowly at 0° C. until the solution was neutralized.

Copper(I) cyanide (838 mg, 9.36 mmol) was dissolved in a solution of NaCN (918 mg, 18.7 mmol) in H$_2$O (2.9 mL), and the solution was heated to 60° C. The cold neutralized diazonium salt solution was added dropwise to the vigorously stirred cyanide solution at 60° C. The mixture was heated to 110° C. for 1 h then allowed to cool to room temperature. The mixture was diluted with saturated NaHCO$_3$(aq) (15 mL) and extracted with CH$_2$Cl$_2$ (3×20 mL). The combined organic extracts were dried (MgSO$_4$), filtered, and concentrated in vacuo. The crude material was filtered through silica gel (20% EtOAc/hexanes) to give yellow crystals (990 mg, 72%). $^1$H NMR (CDCl$_3$) δ 2.68 (s, 3H), 3.93 (s, 3H), 7.38 (d, 1H, J=9.0 Hz), 7.66 (dd, 1H, J=9.0, 3.0 Hz), 8.22 (d, 1H, J=1.5Hz).

Preparation of 2-Bromomethyl-5-cyano-benzoic acid methyl ester

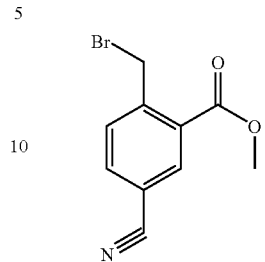

A mixture of 5-cyano-2-methyl-benzoic acid methyl ester (913 mg, 5.21 mmol), NBS (1.02 g, 5.73 mmol), and AIBN (128 mg, 0.780 mmol) in CCl$_4$ (20 mL) was heated at reflux for 24 h then allowed to cool to room temperature. The mixture was filtered, and the filtrate was concentrated in vacuo. Purification of the crude material by column chromatography on silica gel (10% EtOAc/hexanes) afforded yellow crystals (720 mg, 55%). $^1$H NMR (CDCl$_3$) δ 3.99 (s, 3H), 4.96 (s, 2H), 7.62 (d, 1H, J=9.0 Hz), 7.77 (dd, 1H, J=9.0, 3.0 Hz), 8.27 (d, 1H, J=3.0 Hz).

A mixture of 2-[(5,6,7,8-tetrahydro-quinolin-8-ylamino)-methyl]-benzoimidazole-1-carboxylic acid tert-butyl ester (762 mg, 2.01 mmol), 2-bromomethyl-5-cyano-benzoic acid methyl ester (511 mg, 2.01 mmol), potassium iodide (19 mg, 0.10 mmol), and N,N-diisopropylethylamine (0.53 mL, 3.02 mmol) in acetonitrile (16 mL) was heated at 60° C. for 16 h. The reaction mixture was concentrated in vacuo and the residue diluted with CH$_2$Cl$_2$ (25 mL) and saturated NaHCO$_3$ (aq) (30 mL). The layers were separated and the aqueous layer was extracted with CH$_2$Cl$_2$ (2×20 mL). The combined organic extracts were dried (MgSO$_4$), filtered, and concentrated in vacuo. Purification of the crude material on silica gel (500:10:1 CH$_2$Cl$_2$/MeOH/NH$_4$OH) gave a white foam (935 mg, 84%).

The purified material from above (50 mg, 0.11 mmol) was dissolved in dry CH$_2$Cl$_2$ (1.5 mL) and trifluoroacetic acid (2.0 mL) was added dropwise. The resultant mixture was stirred for 2.5 h at room temperature. The reaction mixture was diluted with CH$_2$Cl$_2$ (15 mL) and then concentrated in vacuo to remove any excess trifluoroacetic acid. The concentrate was diluted with CH$_2$Cl$_2$ (20 mL) and 1N NaOH (20 mL). The layers were separated and the aqueous layer was extracted with CH$_2$Cl$_2$ (2×15 mL) and then the combined organic layers were dried (Na$_2$SO$_4$), filtered, and concentrated in vacuo to afford AMD11165 as a yellow foam. $^1$H NMR (CDCl$_3$) δ 1.62–1.79 (m, 1H), 1.92–2.10 (m, 2H), 2.26–2.34 (m, 1H), 2.69–2.93 (m, 2H), 3.89 (s, 3H), 3.89 (d, 1H, J=16.5 Hz), 3.95 (d, 1H, J=16.2 Hz), 4.13 (m, 1H), 4.16 (d, 1H, J=16.5 Hz), 4.57 (d, 1H, J=15.9 Hz), 7.12–7.23 (m, 3H), 7.43 (d, 1H, J=7.8 Hz), 7.48 (br m, 1H), 7.58 (dd, 2H, J=7.8, 1.5 Hz), 7.94 (d, 1H, J=1.8 Hz), 8.00 (d, 1H, J=8.1 Hz), 8.62 (d, 1H, J=5.1 Hz). $^{13}$C NMR (CDCl$_3$) δ 21.72, 24.40, 29.46, 50.21, 53.01, 53.07, 111.08, 118.26, 122.28, 122.88, 130.88, 131.50, 134.05, 135.12, 135.20, 137.97, 147.17, 147.26, 155.56, 157.27, 166.75. ES-MS m/z 452 (M+H). Anal. Calcd. for C$_{27}$H$_{25}$N$_5$O$_2$.0.05CH$_2$Cl$_2$.0.8H$_2$O: C, 69.10; H, 5.72; N, 14.89. Found: C, 69.44; H, 5.87; N, 14.61.

EXAMPLE 71

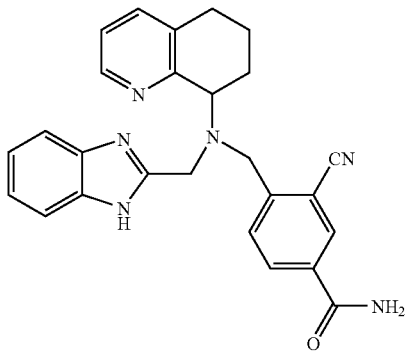

AMD11179: Preparation of 4-{[(1H-benzimidazol-2-ylmethyl)-(5,6,7,8-tetrahydroquinolin-8-yl)-amino]-methyl}-3-cyano-benzamide To 0.5 mL of Raney Nickel in water was added a solution of 2-{[(2-cyano-4-methoxycarbonyl-benzyl)-(5,6,7,8-tetrahydroquinolin-8-yl)-amino]-methyl}-benzimidazole-1-carboxylic acid tert-butyl ester (0.55 g, 1 mmol) in methanol (25 mL). The solution was then saturated with ammonia gas for 10 minutes. The reaction vessel was then shaken vigorously under an atmosphere of hydrogen (40 psi) for 16 hours. The mixture was filtered through a celite pad and the filtrate concentrated under reduced pressure. The crude residue was purified by column chromatography (88:12 $CH_2Cl_2$:MeOH) to afford to give the amide (0.20 g, 36%). $^1$H NMR (CDCl$_3$) δ 1.73 (m, 1H), 2.01 (m, 2H), 2.35 (m, 1H), 2.85 (m, 2H), 3.88 (t, 2H, J=15.9 Hz), 4.16 (m, 1H), 4.21 (d, 1H, J=9.6 Hz), 4.26 (d, 1H, J=7.8 Hz), 5.71 (br, 1H, NH), 6.12 (br, 1H, NH), 7.19 (m, 3H), 7.46 (d, 1H, J=7.8 Hz), 7.55 (br, 2H), 7.80 (d, 1H, J=8.1 Hz), 7.87 (d, 1H, J=8.1 Hz), 7.96 (s, 1H), 8.64 (dd, 1H, J=4.5 Hz). $^{13}$C NMR (CDCl$_3$) δ 21.71, 24.65, 29.44, 49.92, 53.09, 61.84, 112.81, 117.49, 122.30 (4C), 122.97, 130.44 (2C), 131.98, 132.32, 133.56, 135.37, 138.05 (2C), 147.13, 147.29, 155.27, 156.87, 167.82. ES-MS m/z 437 (M+H). Anal. Calcd. for $C_{26}H_{24}N_6O\cdot0.6CH_2Cl_2$: C, 65.54; H, 5.21; N, 17.24. Found: C, 65.93; H, 5.51; N, 17.44.

EXAMPLE 72

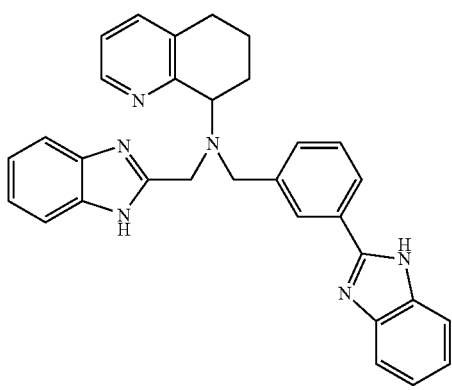

AMD9643: Preparation of [3-(1H-benzimidazol-2-yl)-benzyl]-(1H-benzimidazol-2-ylmethyl)-(5,6,7,8-tetrahydroquinolin-8-yl)-amine (hydrobromide salt)

Preparation of 3-(benzimidazol-2-yl)-benzyl alcohol

A solution of isoterephthalic acid monomethyl ester (1.00 g, 5.6 mmol) in thionyl chloride (12 mL) was stirred at 80° C. for 3.5 h. The solvent was removed under reduced pressure to afford isoterephthalic acid monomethyl ester chloride (1.06 g, 97%). $^1$H NMR (CDCl$_3$) δ 3.98 (s, 3H), 7.63 (t, 1H, J=7.8 Hz), 8.30 (d, 1H, J=7.8 Hz), 8.35 (d, 1H, J=7.8 Hz), 8.78 (s, 1H).

A solution of 2-nitroaniline (0.62 g, 4.5 mmol) and isoterephthalic acid monomethyl ester chloride (1.06 g, 5.3 mmol) in THF (5.6 mL) and pyridine (1.1 mL) was stirred for 2 h at room temperature. To this mixture was added saturated NaHCO$_3$ (20 mL) and the mixture extracted with ethyl acetate (3×20 mL). The combined organic extracts were dried (MgSO$_4$), filtered, concentrated and purified by column chromatography on silica gel (5% MeOH/CH$_2$Cl$_2$) to afford (2-nitrophenyl)-isoterephthalamic acid methyl ester (0.70 g, 52%) as a yellow solid. $^1$H NMR (CDCl$_3$) δ 3.99 (s, 3H), 7.27 (t, 1H, J=7.8 Hz), 7.65 (t, 1H, J=7.8 Hz), 7.75 (t, 1H, J=7.8 Hz), 8.17 (d, 1H, J=7.8 Hz), 8.30 (t, 2H, J=7.8 Hz), 8.67 (s, 1H), 8.99 (d, 2H, J=7.8 Hz), To a solution of (2-nitrophenyl)-isoterephthalamic acid methyl ester (0.70 g, 2.3 mmol) in glacial acetic acid (8 mL) was added iron powder (<5 μm mesh, 0.35 g, 6.3 mmol) and the mixture stirred at reflux for 1.5 h. The mixture was cooled, stirred at room temperature for 1 h and concentrated under reduced pressure. The residue was partitioned between saturated sodium bicarbonate (20 mL) and ethyl acetate (20 mL), the phases separated and the organic layer washed with saturated NaHCO$_3$ (20 mL). The organic extract was dried (MgSO$_4$), filtered and concentrated to give the cyclized methyl 3-(benzimidazol-2-yl)-benzoate ester (0.59 g, 100%). $^1$H NMR (CDCl$_3$) δ 3.93 (s, 3H), 7.30 (m, 2H), 7.57 (t, 2H, J=7.8 Hz), 7.88 (br, 1H), 8.12 (d, 1H, J=7.8 Hz), 8.35 (d, 1H, J=7.8 Hz), 8.64 (s, 1H), 10.10 (br, 1H (NH)).

To a solution of 3-(benzimidazol-2-yl)-benzoate ester (0.20 g, 0.8 mmol) in THF (8 mL) at −78° C. was added a solution of DIBAL-H (4.0 mL, 1.0 M in THF, 4.0 mmol). The reaction was allowed to warm to room temperature, stirred for 0.5 h and quenched with a saturated potassium sodium tartrate solution (15 mL). The biphasic mixture was stirred vigorously for 1 h, the phases separated and the organic layer dried (MgSO$_4$), filtered and concentrated to give 3-(benzimidazol-2-yl)-benzyl alcohol (0.12 g, 67%). $^1$H NMR (CD$_4$OD$_3$) δ 4.73 (s, 2H), 7.26 (m, 2H), 7.52 (m, 2H), 7.57 (m, 2H), 7.99 (m, 1H), 8.10 (s, 1H).

Using General Procedure C: To a solution of 3-(benzimidazol-2-yl)-benzyl alcohol (0.12 g, 0.5 mmol) and triethylamine (0.11 mL, 0.8 mmol) in THF (5 mL) was added methanesulfonyl chloride (55 μL, 0.7 mmol) and the mixture stirred at room temperature for 1 h. The resultant mesylate (0.15 g, 91%) was used without further purification in the next reaction. $^1$H NMR (CDCl$_3$) δ 3.14 (s, 3H), 5.38 (s, 2H), 7.27 (m, 2H), 7.62 (m, 4H), 8.12 (m, 1H), 8.19 (s, 1H).

Using the general alkylation procedure: A solution of the mesylate from above (0.15 g, 0.5 mmol), N,N-diisopropylethylamine (0.12 mL, 0.7 mmol) and potassium iodide (6 mg, 30 μmol) in CH$_3$CN (5 mL) was reacted (1-tert-butoxycarbonyl-1H-Benzimidazol-2-ylmethyl)-(5,6,7,8-tetrahydro-quinolin-8-yl)-amine (0.18 g, 0.5 mmol) at 60° C. for 3 h. Purification of the crude by column chromatography on silica gel (2% MeOH/CH$_2$Cl$_2$) gave the desired N-alkylated product (0.17 g, 60%) as a flaky white solid. $^1$H NMR (CDCl$_3$) δ 1.68 (s, 10H), 2.05 (m, 2H), 2.30 (m, 1H), 2.80 (m, 2H), 3.69 (d, 1H, J=12.0 Hz), 3.87 (d, 1H, J=15.0 Hz), 4.30 (d, 1H, J=15.0 Hz), 4.45 (m, 1H), 4.61 (d, 1H, J=15.0 Hz), 7.08 (m, 1H), 7.15–7.30 (m, 7H), 7.35 (d, 1H, J=7.8 Hz), 7.67 (d, 2H, J=7.8 Hz), 7.70 (m, 3H), 8.09 (d, 1H, J=7.8 Hz), 8.49 (d, 1H, J=3.5 Hz), 9.06 (s, 1H).

Using General Procedure D: Conversion of the material from above (50 mg) to the hydrobromide salt gave AMD9575 (0.062 g) as a beige solid. $^1$H NMR (D$_2$O) δ 1.91 (br m, 1H), 2.25 (m, 2H), 2.45 (br m, 1H), 3.04 (br m, 2H), 3.79 (d, 1H, J=12.9 Hz), 3.94 (d, 1H, J=13.2 Hz), 4.42 (d, 1H, J=16.2 Hz), 4.62 (d, 1H, J=16.2 Hz), 4.78 (m, 1H), 7.14 (d, 2H, J=5.4 Hz), 7.14 (m, 2H), 7.41 (m, 2H), 7.48 (d, 2H, J=6.9 Hz), 7.59 (dd, 2H, J=3.0, 6.3 Hz), 7.73 (dd, 2H, J=3.0, 6.0 Hz), 7.95 (t, 1H, J=6.9 Hz), 8.41 (d, 1H, J=8.1 Hz), 8.79 (d, 1H, J=5.7 Hz); $^{13}$C NMR (D$_2$O) δ 20.43, 21.15, 27.88, 50.15, 56.67, 63.59, 113.41 (2C), 114.16 (2C), 122.13, 126.26, 126.54 (2C), 126.69, 127.03 (2C), 127.46, 130.33, 130.83, 131.71, 135.08, 138.72, 139.91 (2C), 141.14, 147.47, 148.41 (2C), 150.54, 151.56. ES-MS m/z 485 (M+H). Anal. Calcd. for C$_{31}$H$_{28}$N$_6$·3.0HBr·2.9H$_2$O: C, 48.35; H, 5.09; N, 10.37; Br, 29.60. Found: C, 48.35; H, 4.96; N, 10.31; Br, 29.59.

EXAMPLE 73

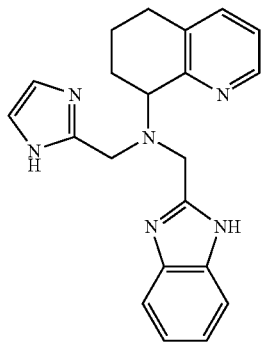

AMD9902: Preparation of (1H-Benzimidazol-2-ylmethyl)-(5,6,7,8-tetrahydroquinolin-8-yl)-(imidazol-2-yl)-methylamine (hydrobromide salt)

Using standard reductive amination conditions A, 1H-(benzimidazol-2-ylmethyl)-(5,6,7,8-tetrahydroquinolin-8-yl)-amine (207 mg, 0.75 mmol) was stirred with imidazole-2-carboxaldehyde (96 mg, 1.0 mmol) and sodium cyanoborohydride (95 mg, 1.5 mmol) in methanol (5 mL) for 48 hours. The solution was then concentrated. The residue was taken up in dichloromethane and washed with 1N sodium hydroxide (3 mL), then dried over anhydrous sodium sulfate, concentrated and purified by chromatography on silica gel (20:1 dichloromethane:methanol) to afford (1H-benzimidazol-2-ylmethyl)-(5,6,7,8-tetrahydroquinolin-8-yl)-(imidazol-2-yl)-methylamine (69 mg, 56%). $^1$H NMR (CDCl$_3$) δ 1.64 (m, 1H), 1.86 (m, 1H), 2.00 (m, 1H), 2.68 (m, 1H), 2.86 (m, 1H), 3.64 (d, 1H, J=14.6 Hz), 3.79 (d, 1H, J=15.4 Hz), 3.90 (m, 1H), 3.91 (d, 1H, J=15.4 Hz), 3.94 (d, 1H, J=14.6 Hz), 6.97 (s, 1H), 7.18 (m, 3H), 7.55 (d, 1H, J=9.0 Hz), 7.60 (m, 2H), 8.47 (d, 1H, J=4.9 Hz).

(1H-benzimidazol-2-ylmethyl)-(5,6,7,8-tetrahydroquinolin-8-yl)-(imidazol-2-yl)-methylamine (56 mg, 0.156 mmol) was taken up in acetic acid (1 mL), to which a saturated solution of HBr in acetic acid (1 mL) was added. The mixture was then stirred, precipitated and isolated as per procedure D to yield AMD9902 as a white crystalline solid (39 mg). $^1$H NMR (D$_2$O). δ 1.88 (m, 1H), 2.09 (m, 1H), 2.39 (m, 1H), 3.02 (m, 2H), 4.31 (d, 1H, J=15.6 Hz), 4.42 (d, 1H, J=12.6 Hz), 4.48 (d, 1H, J=12.6 Hz), 4.53 (d, 1H, J=15.6 Hz), 4.63 (m, 1H), 7.19 (s, 1H), 7.58 (m, 2H), 7.73 (m, 2H), 7.87 (dd, 1H, J=7.8, 4.9 Hz), 8.67 (d, 1H, J=4.9 Hz). $^{13}$C NMR (D$_2$O) δ 19.83, 20.26, 20.94, 27.30, 27.71, 47.37, 48.09, 61.93, 114.33, 120.20, 126.27, 126.64, 127.36, 131.08, 140.35, 140.98, 142.76, 148.42, 149.03, 151.26, 154.87. ES-MS m/z 359 (M+H); Anal. Calcd. for (C$_{21}$H$_{22}$N$_6$×2.7 HBr×1.9 H$_2$O×0.3 HOAc): C, 40.86; H, 4.87; N, 12.88; Br, 36.73. Found: C, 41.11; H, 4.73; N, 12.87; Br, 36.39.

EXAMPLE 74

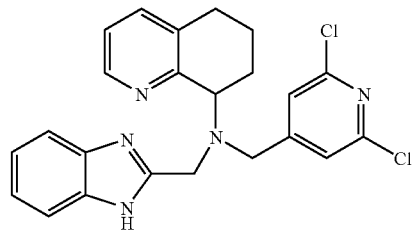

AMD9592: Preparation of 4-{[(1H-Benzimidazol-2-ylmethyl)-(5,6,7,8-tetrahydro-quinolin-8-yl)-amino]-methyl}-2,6-dichloropyridine (hydrobromide salt)

Preparation of methanesulfonic acid 2,6-dichloro-pyridin-4-ylmethyl ester

To a stirred solution of 2,6-dichloroisonicotinic acid (280 mg, 1.5 mmol) in THF (7.5 mL) was added dropwise a solution of BH$_3$-THF (1M in THF, 5.8 mL, 5.8 mmol) and the mixture stirred at reflux 65 h. The reaction was cooled, quenched with MeOH (10 mL) and concentrated under reduced pressure. To the resultant residue was added MeOH (10 mL) and the solution re-concentrated. This procedure was repeated five times and the resultant white solid (230 mg, 89%) was used without further purification in the next step.

Using General Procedure C: To an stirred, ice-cooled solution of the material from above (230 mg, 1.3 mmol) and triethylamine (0.50 mL, 3.9 mmol) in CH$_2$Cl$_2$ (13 mL) was added methanesulfonylchloride (0.10 mL, 0.3 mmol) and the mixture stirred for 30 minutes at 0° C. The desired crude mesylate (340 mg) wsa obtained as a pale yellow solid and used without further purification in the next step.

Using General Procedure for N-Alkylation: A solution of the material from above (330 mg, 1.3 mmol) and N,N-diisopropylethylamine (0.45 mL, 2.6 mmol) in CH$_3$CN (13 mL) was reacted with (1-tert-butoxycarbonyl-1H-Benzimidazol-2-ylmethyl)-(5,6,7,8-tetrahydro-quinolin-8-yl)-amine (470 mg, 1.2 mmol) overnight. Purification of the crude material by flash chromatography on silica gel (3:1 EtOAc/hexanes) provided the desired amine (400 mg, 58%) as a pale yellow solid.

Using General Procedure D: Conversion of the material from above (264 mg, 0.49 mmol) to the hydrobromide salt with simultaneous removal of the N-tert-butoxycarbonyl protecting group gave AMD9592 (280 mg, 92%) as a white powder. $^1$H NMR (D$_2$O) δ 1.80–1.97 (m, 1H), 2.12–2.21 (m, 2H), 2.33–2.45 (m, 1H), 2.97–3.01 (m, 2H), 3.83 (q, 2H, J=15 Hz), 3.78 (dd, 2H, J=66, 15 Hz), 4.73 (m, 1H), 7.18(s, 2H), 7.47–7.51 (m, 2H), 7.59–7.62 (m, 2H), 7.86 (t, 1H, J=6 Hz), 8.32 (d, 1H, J=7.5 Hz), 8.72 (d, 1H, J=6 Hz). $^{13}$C NMR (CDCl$_3$) δ 25.12, 25.90, 32.66, 54.46, 60.32, 67.92, 118.95 (2), 128.83(2), 131.11, 132.05(2), 135.43, 144.95, 146.02, 153.17, 154.63, 154.87, 155.07, 157.53. ES-MS m/z 439 (M+H). Anal. Calcd. for C$_{23}$H$_{21}$N$_5$Cl$_2$.1.0H$_2$O.2.0HBr: C, 44.69; H, 4.08; N, 11.33; Br, 25.85; Cl, 11.47. Found: C, 44.56; H, 4.22; N, 11.41; Br, 25.83; Cl, 11.46.

EXAMPLE 75

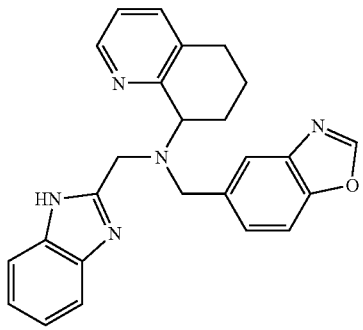

AMD9782: Preparation of (1H-benzoimidazol-2-ylmethyl)-benzooxazol-5-ylmethyl-(5,6,7,8-tetrahydro-quinolin-8-yl)-amine Preparation of 5-bromomethyl-benzoxazole

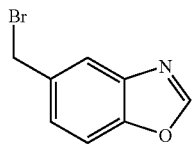

A mixture of 5-methylbenzoxazole (200 mg, 1.50 mmol), N-bromosuccinimide (321 mg, 1.80 mmol), and 2,2'-azobisisobutyronitrile (37 mg, 0.23 mmol) in CCl$_4$ (3 mL) was heated at reflux for 22 h. The mixture was filtered and the filtrate was concentrated under reduced pressure. Purification of the crude material on silica gel (5% EtOAc/hexanes) gave the title compound as a colourless crystals (126 mg, 39%). $^1$H NMR (CDCl$_3$) δ 4.64 (s, 2H), 7.46 (dd, 1H, J=8.6, 1.7 Hz), 7.57 (d, 1H, J=8.4 Hz), 7.83 (d, 1H, J=1.2 Hz), 8.12 (s, 1H).

Using General Procedure for N-Alkylation: A solution of 5-bromomethyl-benzoxazole (94 mg, 0.44 mmol), potassium iodide (3 mg, 0.02 mmol), and N,N-diisopropylethylamine (0.10 mL, 0.57 mmol) in CH$_3$CN (4 mL) was reacted with (1-tert-butoxycarbonyl-1H-Benzimidazol-2-ylmethyl)-(5,6,7,8-tetrahydro-quinolin-8-yl)-amine (152 mg, 0.402 mmol) at 60° C. for 22 h. Purification of the crude material by flash chromatography on silica gel (400:5:1 EtOAc/MeOH/NH$_4$OH) gave a yellow foam (124 mg, 60%).

A solution of the yellow foam (40 mg, 0.078 mmol) in 3:1 trifluoroacetic acid/CH$_2$Cl$_2$ (4 mL) was stirred at room temperature for 1 hour then concentrated. The residue was partitioned between CH$_2$Cl$_2$ and saturated NaHCO$_3$(aq), and the aqueous phase was extracted with CH$_2$Cl$_2$. The combined organic phases were dried (MgSO$_4$), filtered and concentrated to give the title compound as a yellow foam (32 mg, 89%). $^1$H NMR (CDCl$_3$) δ 1.68 (m, 1H), 2.04 (m, 2H), 2.28 (m, 1H), 2.71 (m, 1H), 2.86 (m, 1H), 3.86 (s, 2H), 3.98 (d, 1H, J=17 Hz), 4.09 (m, 1H), 4.22 (d, 1H, J=17 Hz), 7.19 (m, 3H), 7.44 (m, 3H), 7.58 (m, 2H), 7.87 (s, 1H), 8.02 (s, 1H), 8.73 (d, 1H, J=4.2 Hz); $^{13}$C NMR (CDCl$_3$) δ 21.77, 23.76, 29.58, 48.77, 54.24, 60.59, 110.95, 120.86, 122.08, 122.75, 126.73, 135.19, 136.57, 137.77, 140.56, 147.38, 149.70, 153.13, 156.32, 157.63. ES-MS m/z 410 (M+H). Anal Calcd for (C$_{25}$H$_{23}$N$_5$O) 0.23(H$_2$O) 0.53(CH$_2$Cl$_2$): C, 66.86; H, 5.39; N, 15.27. Found: C, 66.99; H, 5.55; N, 14.90.

EXAMPLE 76

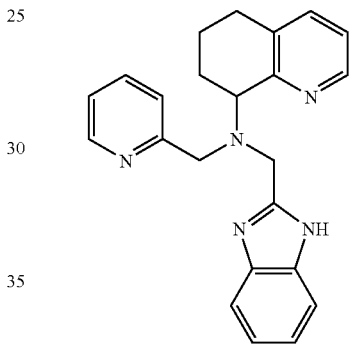

AMD9786: Preparation of pyridin-2-ylmethyl-(1H-benzimidazol-2-ylmethyl)-(5,6,7,8-tetrahydroquinolin-8-yl)-amine Using General Procedure for N-Alkylation: 2-Bromomethyl pyridine hydrochloride (104 mg, 0.413 mmol) was stirred with N,N-diisopopylethylamine (0.092 mL, 0.516 mmol) in CH$_3$CN (5 mL) for 10 min. Potassium carbonate (71 mg, 0.516 mmol) and (1-tert-butoxycarbonyl-benzimidazol-2-ylmethyl)-(5,6,7,8-tetrahydroquinolin-8-yl)-amine (130 mg, 0.344 mmol) were then added and the mixture was heated to 60° C. for 2 h. The dark solution was cooled, concentrated and the resultant the residue was taken up in CH$_2$Cl$_2$ and washed with aqueous ammonium carbonate. Purification of the residue by chromatography on silica gel (10% MeOH/CH$_2$Cl$_2$) yielded the product pyridin-2-ylmethyl-(1H-N-t-butoxycarbonyl-benzimidazol-2-ylmethyl)-(5,6,7,8-tetrahydroquinolin-8-yl)-amine (32 mg, 20%) as a white foam. $^1$H NMR (CDCl$_3$) δ 1.62 (s, 9H), 1.88–2.20 (m, 4H), 2.69–2.78 (m, 2H), 3.95 (d, 1H, J=16.1 Hz), 4.13 (d, 1H, J=16.1 Hz), 4.36 (t, 1H, J=6.8 Hz), 4.63 (d, 1H, J=12.8 Hz), 4.77 (d, 1H, J=12.8 Hz), 6.86 (m, 1H), 6.96 (m, 1H), 7.22–7.29 (m, 3H), 7.38 (t, 1H, J=7.8 Hz), 7.62 (m, 2H), 7.74 (m, 1H), 8.30 (d, 1H, J=6.0 Hz), 8.43 (d, 1H, J=5.2 Hz).

Using General Procedure D: Conversion of the foam from above (32 mg, 0.068 mmol) to the hydrobromide salt gave AMD9786 (28 mg) as a white solid. $^1$H NMR (D$_2$O). δ 1.81

(m, 1H), 2.19 (m, 2H), 2.45 (m, 1H), 3.00 (m, 2H), 4.23 (d, 1H, J=9.0 Hz), 4.38 (s, 1H), 4.43 (s, 1H), 4.59 (d, 1H, J=9.0 Hz), 4.77 (m, 1H), 7.46 (dd, 1H, J=5.3, 6.8 Hz), 7.53 (m, 2H), 7.63 (m, 2H), 7.72 (d, 1H, J=8.1 Hz), 7.86 (dd, 1H, J=7.8, 5.7 Hz), 8.04 (dt, 1H, J=7.8, 1.5 Hz), 8.34 (d, 1H, J=7.8 Hz), 8.49 (d, 1H, J=5.1 Hz), 8.70 (d, 1H, J=6.0 Hz). $^{13}$C NMR (D$_2$O) δ 20.32, 21.06, 27.74, 48.17, 55.59, 62.28, 114.23 (2C), 126.86, 126.16, 126.87, 127.16 (2C), 131.05, 140.23, 140.95, 144.03, 144.78, 148.10, 149.33, 149.68, 152.40. ES-MS m/z 440 (M+H); Anal. Calcd. for (C$_{23}$H$_{23}$N$_5$×2.9 HBr×1.7 H$_2$O): C, 43.52; H, 4.65; N, 11.03; Br, 36.51. Found: C, 43.50; H, 4.68; N, 10.96; Br, 36.58.

EXAMPLE 77

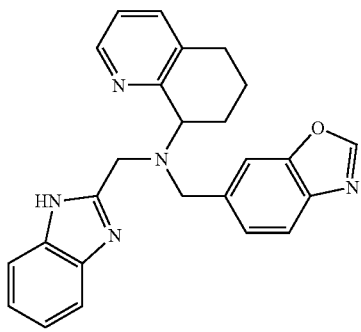

AMD9787: Preparation of (1H-benzimidazol-2-ylmethyl)-benzoxazol-6-ylmethyl-(5,6,7,8-tetrahydro-quinolin-8-yl)-amine Preparation of 6-bromomethyl-benzoxazole

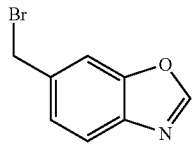

A mixture of 6-methylbenzoxazole (422 mg, 3.17 mmol), N-bromosuccinimide (677 mg, 3.80 mmol), and 2,2'-azobisisobutyronitrile (78 mg, 0.48 mmol) in CCl$_4$ (6.3 mL) was heated at reflux for 22 h. The mixture was filtered and the filtrate was concentrated under reduced pressure. Purification of the crude material on silica gel (4% EtOAc/hexanes) gave the title compound as colourless crystals (257 mg, 38%). $^1$H NMR (CDCl$_3$) δ 4.64 (s, 2H), 7.42 (dd, 1H, J=8.1, 1.5 Hz), 7.64 (d, 1H, J=1.2 Hz), 7.76 (d, 1H, J=8.4 Hz), 8.12 (s, 1H).

Using General Procedure for N-Alkylation: A solution of 6-bromomethyl-benzoxazole (113 mg, 0.533 mmol), potassium iodide (4 mg, 0.02 mmol), and N,N-diisopropylethylamine (0.12 mL, 0.69 mmol) in CH$_3$CN (4.4 mL) was reacted with (1-tert-butoxycarbonyl-1H-Benzimidazol-2-ylmethyl)-(5,6,7,8-tetrahydro-quinolin-8-yl)-amine (168 mg, 0.444 mmol) at 60° C. for 16 h. Purification of the crude material by flash chromatography on silica gel. Purification of the crude material on silica gel (600:5:1 EtOAc/MeOH/NH$_4$OH) gave a yellow oil (179 mg, 79%).

A solution of the yellow oil (173 mg, 0.339 mmol) in 3:1 trifluoroacetic acid/CH$_2$Cl$_2$ (4 mL) was stirred at room temperature for 1 h then concentrated. The residue was partitioned between CH$_2$Cl$_2$ and saturated NaHCO$_3$(aq), and the aqueous phase was extracted with CH$_2$Cl$_2$. The combined organic phases were dried (MgSO$_4$), filtered and concentrated to give the title compound AMD9787 as a yellow foam (118 mg, 79%). $^1$H NMR (CDCl$_3$) δ 1.70 (m, 1H), 2.04 (m, 2H), 2.29 (m, 1H), 2.73 (m, 1H), 2.87 (m, 1H), 3.88 (s, 2H), 3.98 (d, 1H, J=17 Hz), 4.11 (m, 1H), 4.22 (d, 1H, J=17 Hz), 7.19 (m, 3H), 7.42 (m, 2H), 7.62 (m, 3H), 7.71 (s, 1H), 8.01 (s, 1H), 8.73 (d, 1H, J=4.2 Hz); $^{13}$C NMR (CDCl$_3$) δ 21.23, 23.36, 29.06, 48.47, 53.88, 60.16, 110.74, 119.94, 121.52, 122.26, 125.07, 134.68, 137.25, 137.65, 139.20, 146.86, 150.08, 152.34, 155.73, 157.13. ES-MS m/z 410 (M+H). Anal Calcd for (C$_{25}$H$_{23}$N$_5$O) 0.6(H$_2$O) 0.2 (EtOAc): C, 70.76; H, 5.94; N, 15.99. Found: C, 70.88; H, 5.83; N, 16.07.

EXAMPLE 78

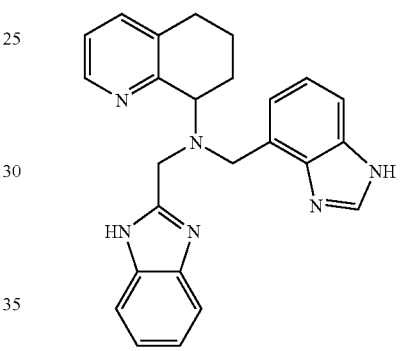

AMD9829: Preparation of (1H-benzimidazol-4-ylmethyl)-(1H-benzimidazol-2-ylmethyl -(5,6,7,8-tetrahydro-quinolin-8-yl)-amine (hydrobromide salt)

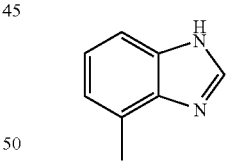

Preparation of 4-methyl-1H-benzimidazole

To a stirred solution of 2,3-diaminotoluene (1.00 g, 8.2 mmol) in CH$_2$Cl$_2$ (82 mL) was added trimethylorthoformate (4.5 mL, 41 mmol) and trifluoroacetic acid (0.32 mL, 4.1 mmol) and the mixture stirred at room temperature for 24 h after which the reaction mixture was diluted with CH$_2$Cl$_2$ (200 mL), and washed consecutively with saturated aqueous NaHCO$_3$ (40 mL) and H$_2$O (40 mL). The aqueous layers were reextracted with CH$_2$Cl$_2$ (2×100 mL). The combined organic extracts were dried over MgSO$_4$ and concentrated to a rusty brown solid (1.07 g, 97%). $^1$H NMR (300 MHz, CDCl$_3$) δ 8.08 (s, 1H), 7.49 (d, 1H, J=8.1 Hz), 7.23–7.18 (m, 1H), 7.10 (d, 1H, J=7.5 Hz), 2.64 (s, 3H).

Preparation of 4-bromomethyl-benzimidazole-1-carboxylic acid tert-butyl ester To a stirred solution of 4-methyl-1H-benzimidazole (1.05 g, 7.9 mmol) in THF (10 mL) was added di-tert-butyl dicarbonate (4.4 g, 20 mmol) in THF (6 mL). After 18 h the reaction mixture was concentrated to a brown syrup. Purification by column chromatography on silica gel (20:3—Hexanes:EtOAc) gave the desired product as a yellow syrup (1.66 g, 91%). $^1$H NMR (300 MHz, CDCl$_3$) δ 8.41 (s, 1H), 7.81 (d, 1H, J=8.1 Hz), 7.31–7.26 (m, 1H), 7.16 (d, 1H, J=7.5 Hz), 2.67 (s, 3H), 1.70 (s, 9H).

To a stirred solution of 4-methyl-benzimidazole-1-carboxylic acid tert-butyl ester (800 mg, 3.4 mmol) in CCl$_4$ (7 mL) was added N-bromosuccinimide (730 mg, 4.1 mmol) and 2,2'-azobis(2-methylpropionitrile) (84 mg, 0.51 mmol). The resultant mixture was heated at reflux for 18 h after which it was filtered and concentrated to a yellow/orange syrup and crystals (1.4 g). Purification by column chromatography on silica gel (200:15—Hexanes:EtOAc) gave the desired title compound as a yellow syrup (635 mg, 60%). $^1$H NMR (300 MHz, CDCl$_3$) δ 8.48 (s, 1H), 7.95 (dd, 1H, J=7.8, 1.5 Hz), 7.42–7.34 (m, 2H), 4.96 (s, 2H), 1.71 (s, 9H).

Using General Procedure for Alkylation: To a stirred solution of (1-t-butoxycarbonyl-benzimidazol-2-ylmethyl)-(5,6,7,8-tetrahydroquinolin-8-yl)-amine (1 53 mg, 0.40 mmol) and 4-bromomethyl-benzimidazole-1-carboxylic acid tert-butyl ester (167 mg, 0.48 mmol) in CH$_3$CN (5 mL) was added KI (3 mg, 0.02 mmol) and N,N-diisopropylethylamine (0.1 mL, 0.6 mmol) and the reaction mixture heated to 60° C. for 3 d. The resultant foam was dissolved in a mixture of CH$_2$Cl$_2$ (2 mL) and TFA (2 mL). After 3 h the solution was concentrated, redissolved in H$_2$O (~1 mL) and basified with 1N NaOH. The aqueous phase was extracted with CH$_2$Cl$_2$ (3×50 mL). The combined organic extracts were dried over MgSO$_4$ and concentrated to a light brown foam. Purification by column chromatography on silica gel (200:3:2—CH$_2$Cl$_2$:MeOH:NH$_4$OH) followed by radial chromatography on silica gel (1 mm plate, 100:1:1—CH$_2$Cl$_2$:MeOH:NH$_4$OH) afforded the desired product as a light yellow foam (38 mg, 23%). $^1$H NMR (300 MHz, CDCl$_3$) δ 8.59 (d, 1H, J=3.6 Hz), 8.00 (s, 1H), 7.72 (d, 1H, J=7.0 Hz), 7.58–7.35 (m, 3H), 7.20–7.13 (m, 5H), 4.19–4.08 (m, 3H), 3.97 (d, 1H, J=15 Hz), 3.84 (d, 1H, J=13.5 Hz), 2.90–2.75 (m, 2H), 2.54–2.50 (m, 1H), 2.15–2.11 (m, 1H), 2.04–1.92 (m, 1H), 1.79–65 (m, 1H).

Following General Procedure D: Conversion of the foam from above (38 mg) to the hydrobromide salt gave AMD9829. $^1$H NMR (300 MHz, D$_2$O) δ 9.15 (s, 1H), 8.78 (dd, 1H, J=5.7, 1.2 Hz), 8.39 (d, 1H, J=8.1 Hz), 7.92 (dd, 1H, J=7.8, 6.0 Hz), 7.49–7.42 (m, 3H), 7.41–7.36 (m, 2H), 7.28 (t, 1H, J=8.1 Hz), 7.15 (d, 1H, J=8.1 Hz), 4.89–4.83 (m, 1H), 4.54 (d, 1H, J=16.5 Hz), 4.40 (d, 1H, J=13.5 Hz), 4.34 (d, 1H, J=16.2 Hz), 4.16 (d, 1H, J=13.5 Hz), 3.06–3.03 (m, 2H), 2.56–2.52 (m, 1H), 2.31–2.22 (m, 2H), 1.97–1.94 (m, 1H); $^{13}$C NMR (75.5 MHz, D$_2$O) δ 150.4, 148.2, 141.0, 140.1, 140.0, 130.5, 130.0, 128.4, 126.9, 126.1, 123.7, 114.1, 113.6, 66.5, 63.1, 52.8, 49.1, 27.9, 21.0, 20.5. ES-MS m/z 409.3 (M+H). Anal Calcd for (C$_{25}$H$_{24}$N$_6$).2.9(HBr).2.2(H2O): C, 43.98; H, 4.62; N, 12.31; Br, 33.94. Found: C, 44.22; H, 4.75; N, 12.11; Br, 33.75.

EXAMPLE 79

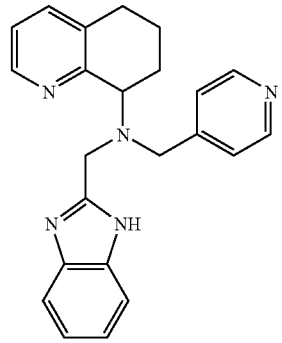

AMD9780: Preparation of (1H-Benzimidazol-2-ylmethyl)-pyridin-4-ylmethyl-(5,6,7,8-tetrahydro-quinolin-8-yl)-amine Following General Procedure B: To a solution of (1-tert-butoxycarbonyl-benzimidazol-2-ylmethyl)-(5,6,7,8-tetrahydroquinolin-8-yl)-amine (120 mg, 0.32 mmol) and 4-pyridinecarboxaldehyde (30 μL, 0.32 mmol) in CH$_2$Cl$_2$ (5 mL) was added sodium triacetoxyborohydride (136 mg, 0.64 mmol) and the reaction stirred for 18 h. The resulting crude material was taken up in neat TFA (1 mL) and stirred 3 h. Saturated aqueous sodium bicarbonate (5 mL) was added, and the resulting mixture was extracted with CH$_2$Cl$_2$ (3×10 mL) then the combined organic extracts were dried (MgSO$_4$), and concentrated in vacuo. Purification of the crude material by radial chromatography (1 mm plate, 50:1:1 CH$_2$Cl$_2$—MeOH—NH$_4$OH) afforded the title compound (83 mg, 70%) as a white solid. $^1$H NMR (CDCl$_3$) δ 1.68–1.72 (m, 1H), 1.97–2.06 (m, 2H), 2.26–2.30 (m, 1H), 2.74–2.77 (m, 1H), 2.80–2.86 (m, 1H), 3.77 (s, 2H), 3.92 (d, 1H, J=16 Hz), 4.09 (dd, 1H, J=9, 7 Hz), 4.17 (d, 1H, J=16 Hz), 7.18–7.22 (m, 3H), 7.36 (d, 2H, J=6 Hz), 7.44 (dd, 1H, J=7, 1 Hz), 7.52 (br d, 1H, J=7 Hz), 7.66 (br d, 1H, J=7 Hz), 8.46 (dd, 2H, J=5, 2 Hz), 8.70 (dd, 1H, J=5, 1 Hz); $^{13}$C NMR (CDCl$_3$) δ 21.2, 23.8, 29.0, 49.1, 53.0, 60.5, 110.9, 118.8, 121.4, 121.9, 122.5, 123.3, 133.7, 134.7, 137.4, 144.2, 146.9, 148.7, 149.8, 155.4, 156.9. ES-MS m/z 370 (M+H). Anal. Calcd. for C$_{23}$H$_{23}$N$_5$.0.2H$_2$O.0.2CH$_2$Cl$_2$: C, 71.44; H, 6.15; N, 17.95. Found: C, 71.63; H, 6.30; N, 17.77.

EXAMPLE 80

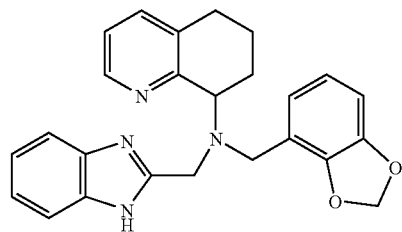

AMD9781: Preparation of (1H-Benzimidazol-2-ylmethyl)-(benzo[1.3]dioxol-4-ylmethyl)-(5,6,7,8-tetrahydro-quinolin-8-yl)-amine Following General Procedure B: To a solution of 2,3-(methylenedioxy)-benzaldehyde (57 mg, 0.379 mmol) and [1-(tert-butoxycarbonyl)-(1H-benzimidazol-2-ylmethyl)]-(5,6,7,8-tetrahydro-quinolin-8-yl)-amine (140 mg, 0.371 mmol) in $CH_2Cl_2$ (5 mL) was added $NaBH(OAc)_3$ (107 mg, 0.505 mmol) and the reaction stirred overnight. Purification of the resultant oil by radial chromatography on silica gel (2 mm TLC, 100:1:1 $CH_2Cl_2$: $CH_3OH$: $NH_4OH$) gave the N-alkylated amine (105 mg). A solution of this amine in TFA (2 mL) was stirred for 1 h then concentrated under reduced pressure and the resultant crude material partitioned between $CH_2Cl_2$ (15 mL) and saturated aqueous $NaHCO_3$ (15 mL). The phases were separated and the organic layer was dried ($Na_2SO_4$), filtered, concentrated and purified by radial chromatography (1 mm TLC plate, 125:1:1 $CH_2Cl_2$: $CH_3OH$: $NH_4OH$) to afford AMD9781 (45% over two steps). $^1H$ NMR ($CDCl_3$) δ 1.61–1.76 (m, 1H), 1.93–2.09 (m, 2H), 2.21–2.31 (m, 1H), 2.64–2.90 (m, 2H), 3.67 (d, 1H, J=14.0 Hz), 3.92 (d, 1H, J=13.8 Hz), 4.03 (d, 1H, J=16.5 Hz), 4.11 (dd, 1H, J=9.2, 6.8 Hz), 4.21 (d, 1H, J=16.7 Hz), 5.89 (s, 2H), 6.64 (d, 1H, J=7.0 Hz), 6.71 (t, 1H, J=7.7 Hz), 6.98 (d, 1H, J=8.1 Hz), 7.11–7.23 (m, 3H), 7.40 (d, 1H, J=7.6 Hz), 7.55–7.63 (m, 2H), 8.64 (d, 1H, J=3.6 Hz). $^{13}C$ NMR ($CDCl_3$) δ 21.54, 24.21, 29.31, 29.84, 47.82, 49.15, 60.63, 100.74, 107.42 (2 carbons), 120.85, 121.70, 121.74 (2 carbons), 122.34 (2 carbons), 122.76 (2 carbons), 134.80, 137.34 (2 carbons), 145.98, 146.95 (2 carbons), 147.07, 156.34, 157.45. ES-MS m/z 413 (M+H) Anal Calc. for $C_{25}H_{24}N_4O_2.0.8H_2O$: C, 70.34; H, 6.04; N, 13.12. Found: C, 70.44; H, 5.98; N, 12.88.

EXAMPLE 81

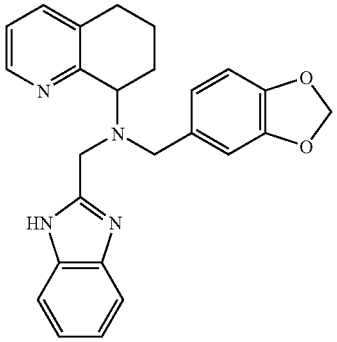

AMD9789: Preparation of benzo[1,3]dioxol-5-ylmethyl-(1H-benzoimidazol-2-ylmethyl)-(5,6,7,8-tetrahydro-quinolin-8-yl)-amine Using General Procedure B: To a solution of [1-(tert-butoxycarbonyl)-(1H-benzimidazol-2-ylmethyl)]-(5,6,7,8-tetrahydro-quinolin-8-yl)-amine (125 mg, 0.33 mmol), piperonal (50 mg, 0.33 mmol) and AcOH (0.02 mL, 0.33 mmol) in THF (3.3 mL) was added $NaBH(OAc)_3$ (210 mg, 0.99 mmol) and the resultant suspension stirred at room temperature for 16 h. The crude product was dissolved in a mixture of $CH_2Cl_2$ (~2 mL) and trifluoroacetic acid (~2 mL). After 1.5 h, the reaction mixture was concentrated, redissolved in $H_2O$ (~2 mL), and basified with 1N NaOH. The aqueous solution was extracted with $CH_2Cl_2$ (3×50 mL) and the combined organic extracts were dried over $MgSO_4$ and concentrated to a yellow syrup. The product was purified by column chromatography on silica gel (100:1:1—EtOAc: MeOH:$NH_4OH$) to give the titled compound as a white foam (45 mg, 33%). $^1H$ NMR (300 MHz, $CDCl_3$) δ 8.69 (d, 1H, J=3.3 Hz), 7.58 (br s, 2H), 7.43 (d, 1H, J=7.2 Hz), 7.21–7.16 (m, 3H), 6.99 (d, 1H, J=1.57 Hz), 6.79 (dd, 1H, J=8.1, 1.5 Hz), 6.65 (d, 1H, J=7.8 Hz), 5.86–5.85 (m, 2H), 4.15 (d, 1H, J=16.5 Hz), 4.09–4.06 (m, 1H), 3.98 (d, 1H, J=16.8 Hz), 3.64 (s, 2H), 2.91–2.80 (m, 1H), 2.74–2.67 (m, 1H), 2.27–2.17 (m, 1H), 2.06–1.64 (m, 2H), 1.75–1.64 (m, 1H); $^{13}C$ NMR (75.5 MHz, $CDCl_3$) δ 159.2, 158.0, 149.4, 148.7, 148.5, 139.0, 136.5, 135.0, 124.0, 123.5, 123.3, 110.7, 109.5, 102.5, 61.8, 55.5, 49.9, 31.0, 25.0, 23.1. ES-MS m/z 413.3 (M+H). Anal Calcd for ($C_{25}H_{24}N_4O_2$).0.8(H2O): C, 70.34; H, 6.04; N, 13.12. Found: C, 70.29; H, 5.99; N, 12.75.

EXAMPLE 82

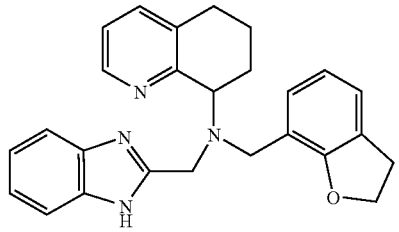

AMD9817: Preparation of (1H-Benzimidazol-2-ylmethyl)-(2,3-dihydro-benzofuran-7-ylmethyl)-(5,6,7,8-tetrahydro-quinolin-8-yl)-amine (hydrobromide salt)

Following General Procedure B: To a solution of 2,3-dihydrobenzofuran-7-carboxaldehyde (53.6 mg, 0.362 mmol) and [1-(tert-butoxycarbonyl)-(1H-benzimidazol-2-ylmethyl)]-(5,6,7,8-tetrahydro-quinolin-8-yl)-amine (136 mg, 0.361 mmol) $CH_2Cl_2$ (5 mL) was added $NaBH(OAc)_3$ (112 mg, 0.528 mmol) and the mixture stirred overnight. Purification of the crude product by radial chromatography on silica gel (1 mm TLC plate, 125:1:1 $CH_2Cl_2$:$CH_3OH$: $NH_4OH$) to gave the desired freebase (48 mg, 33%).

Following General Procedure D: Conversion of the amine from above (28 mg, 38%) gave AMD9817. $^1H$ NMR ($D_2O$) δ 1.84–2.01 (m, 1H), 2.08–2.29 (m, 2H), 2.34–2.54 (m, 2H), 2.70–2.83 (m, 1H), 2.95–3.12 (m, 2H), 3.39 (d, 1H, J=12.7 Hz), 3.57 (d, 1H, J=12.6 Hz), 4.37 (d, 1H, J=16.2 Hz), 4.48–4.73 (m, 3H) [4.60 (d, 1H, J=15.5 Hz)], 6.52–6.56 (m, 2H), 6.91 (dd, 1H, J=6.1, 2.7 Hz), 7.50 (dd, 2H, J=6.3, 2.8 Hz), 7.58 (dd, 2H, J=6.6, 3.0 Hz), 7.93 (dd, 1H, J=7.0, 5.9 Hz), 8.39 (d, 1H, J=7.0 Hz), 8.73 (d, 1H, J=5.0 Hz). $^{13}C$ NMR ($D_2O$) δ 20.48, 20.8, 27.43, 28.73, 50.35, 51.50, 63.64, 72.17, 113.74 (2 carbons), 117.76, 121.22, 125.49, 126.17, 126.64, 127.73 (2 carbons), 129.77, 130.53, 138.83 (2 carbons), 140.34, 147.85, 150.58, 151.78, 157.51. ES-MS m/z 411 (M+H) Anal Calc. for $C_{26}H_{26}N_4O.2.2HBr.2.1H_2O$: C, 49.86; H, 5.21; N, 8.94; Br, 28.07. Found: C, 50.16; H, 5.02; N, 9.03; Br, 27.68.

EXAMPLE 83

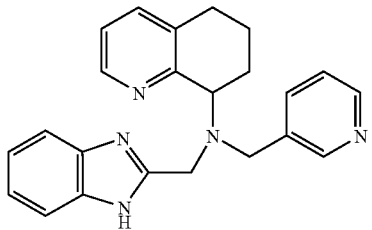

AMD9818: Preparation of (1H-Benzimidazol-2-ylmethyl)-pyridin-3-ylmethyl-(5,6,7,8-tetrahydro-guinolin-8-yl)-amine (hydrobromide salt)

Following General Procedure B: To a solution of 3-pyridine-carboxaldehyde (29 mg, 0.271 mmol) and [1-(tert-butoxycarbonyl)-(1H-benzoimidazol-2-ylmethyl)]-(5,6,7,8-tetrahydro-quinolin-8-yl)-amine (103 mg, 0.273 mmol) in $CH_2Cl_2$ (5 mL) was added NaBH(OAc)$_3$ (98 mg, 0.462 mmol) and the reaction stirred overnight. Purification of the crude product by radial chromatography (1 mm TLC plate, 80:1:1 $CH_2Cl_2$: $CH_3OH$: $NH_4OH$) gave the desired freebase (64 mg, 50%).

Following General Procedure D: Conversion of the amine from above (64 mg) to the hydrobromide salt gave AMD9818 (69 mg, 78%). $^1$H NMR (D$_2$O) δ 1.80–1.96 (m, 1H), 2.16–2.31 (m, 2H), 2.43–2.54 (m, 1H), 3.01–3.08 (m, 2H), 4.10 (d, 1H, J=14.1 Hz), 4.24 (d, 1H, J=13.9 Hz), 4.43 (d, 1H, J=16.4 Hz), 4.61 (d, 1H, J=15.6 Hz), 4.72–4.75 (m, 1H), 7.58 (dd, 2H, J=6.5, 3.3 Hz), 7.69 (dd, 2H, J=6.4, 3.4 Hz), 7.81 (dd, 1H, J=8.2, 6.0 Hz), 7.91 (dd, 1H, J=8.1, 6.0 Hz), 8.36–8.41 (m, 2H), 8.54 (d, 1H, J=8.0 Hz), 8.74–8.79 (m, 2H). $^{13}$C NMR (D$_2$O) δ 14.54, 20.29, 20.76, 27.83, 48.39, 53.46, 61.54, 66.47, 114.23 (2 carbons), 126.30, 127.29 (2 carbons), 127.42, 130.76, 137.43, 140.23, 141.21, 141.25, 141.63, 147.43, 148.44, 149.92, 150.13. ES-MS m/z 370 (M+H) Anal Calc. for $C_{23}H_{23}N_5$·3.0HBr·1.8H$_2$O: C, 42.85; H, 4.63; N, 10.86; Br, 37.19. Found: C, 43.22; H, 4.66; N, 10.69; Br, 36.85.

EXAMPLE 84

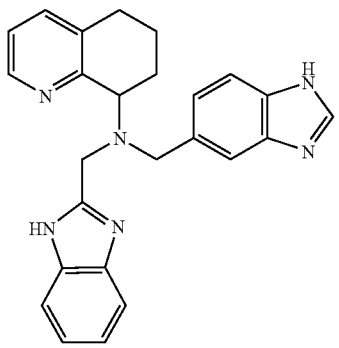

AMD9828: Preparation of (1H-benzoimidazol-5-ylmethyl)-(1H-benzoimidazol-2-ylmethyl)-(5,6,7,8-tetrahydro-quinolin-8-yl)-amine (hydrobromide salt)

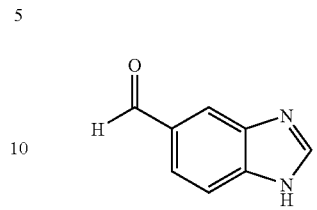

Preparation of 1H-benzoimidazole-5-carbaldehyde

LiAlH$_4$ (1.0 m in THF, 10 mL, 10 mmol) was added dropwise to a suspension of 5-benzimidazolecarboxylic acid (500 mg, 3.08 mmol) in THF (20 mL) at 0° C. The reaction mixture was warmed to room temperature and stirred for 24 h followed by heating at 50° C. for an addition 24 h. MeOH (4×5 mL) was added and the solution was concentrated between each addition. The resulting brown syrup was dried in vacuo for 3 h. The syrup was dissolved in 100:1—$CH_2Cl_2$:MeOH, filtered through celite and concentrated to a light brown foam (300 mg, 66%). To a stirred solution of the crude alcohol (300 mg, 2.0 mmol) in $CH_2Cl_2$ (10 mL) and MeOH (0.8 mL) was added manganese (IV) oxide (85%, 2.05 g, 20 mmol). The suspension was heated to 40° C. for 18 h, cooled to room temperature and filtered through celite. The filtrant was concentrated to a light yellow foam (260 mg). Purification of the crude material by column chromatography on silica gel (200:1:1—EtOAc:MeOH:NH$_4$OH) gave the title compound as a white powder (139 mg, 60%). $^1$H NMR (300 MHz, CD$_3$OD) δ 10.0 (s, 1H), 8.38 (s, 1H), 8.20 (s, 1H), 7.87 (d, 1H, J=9.0 Hz), 7.75 (d, 1H, J=9.0 Hz).

Using General Procedure BA: To a solution of [1-(tert-butoxycarbonyl)-(1H-benzoimidazol-2-ylmethyl)]-(5,6,7,8-tetrahydro-quinolin-8-yl)-amine (215 mg, 0.57 mmol), 1H-benzoimidazole-5-carbaldehyde (81 mg, 0.57 mmol) and AcOH (0.03 mL, 0.55 mmol) in THF (5.5 mL) was added NaBH(OAc)$_3$ (353 mg, 1.65 mmol) and the suspension stirred at room temperature for 24 h. The crude product was dissolved in a mixture of $CH_2Cl_2$ (~2 mL) and trifluoroacetic acid (~2 mL). After 3 h, the reaction mixture was concentrated, redissolved in H$_2$O (~2 mL), and basified with 1N NaOH. The aqueous solution was extracted with $CH_2Cl_2$ (3×50 mL) and the combined organic extracts were dried over MgSO$_4$ and concentrated to a yellow foam. The product was purified by column chromatography on silica gel (100:2:1—EtOAc:MeOH:NH$_4$OH) to give the titled compound as a light yellow foam (52 mg, 24%). $^1$H NMR (300 MHz, CDCl$_3$) δ 8.68 (d, 1H, J=3.3 Hz), 7.95 (s, 1H), 7.56 (br s, 4H), 7.41 (d, 1H, J=6.6 Hz), 7.27 (d, 1H, J=7.5 Hz), 7.18–7.14 (m, 3H), 4.15 (d, 1H, J=16.8 Hz), 4.10–4.06 (m, 1H), 4.00 (d, 1H, J=16.8 Hz), 3.85 (d, 1H, J=13.2 Hz), 3.77 (d, 1H, J=13.5 Hz), 2.90–2.73 (m, 1H), 2.73–2.68 (m, 1H), 2.26–2.21 (m, 1H, 2.08–2.00 (m, 2H), 1.79–1.64 (m, 1H).

Following General Procedure D: Conversion of the foam from above (52 mg) to the hydrobromide salt gave AMD9828. $^1$H NMR (300 MHz, D$_2$O) δ 8.81–8.78 (m, 2H), 8.43 (d, 1H, J=6.9 Hz), 7.95 (dd, 1H, J=8.1, 6 Hz), 7.54–7.51 (m, 2H), 7.44–7.35 (m, 5H), 4.85–4.79 (m, 1H), 4.64 (d, 1H, J=16.2 Hz), 4.46 (d, 1H, J=16.2 Hz), 4.07 (d, 1H, J=12.9 Hz), 4.00 (d, 1H, J=12.9 Hz), 3.08–3.05 (m, 2H), 2.51–2.48 (m, 1H), 2.35–2.22 (m, 2H), 1.98–1.93 (m, 1H); $^{13}$C NMR (75.5 MHz, D₂O) δ 151.7, 150.6, 148.4, 141.1, 139.9, 136.8, 135.8, 130.1, 129.8, 129.5, 128.9, 126.8, 126.2, 115.2, 114.7, 113.4, 63.5, 57.3, 50.0, 27.9, 21.1, 20.5. ES-MS m/z 409.3 (M+H). Anal Calcd for (C$_{25}$H$_{24}$N$_6$).2.9(HBr).3.0 (H$_2$O): C, 43.07; H, 4.76; N, 12.05; Br, 33.24. Found: C, 43.12; H, 4.65; N, 11.71; Br, 33.39.

EXAMPLE 85

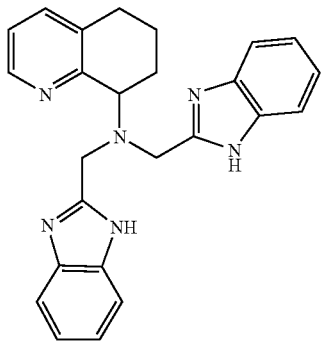

AMD9844: Preparation of Bis-(1H-benzimidazol-2-ylmethyl)-(5,6,7,8-tetrahydro-quinolin-8-yl)-amine (hydrobromide salt)

Following General Procedure for N-Alkylation: To a stirred solution of (1-tert-butoxycarbonyl-1H-Benzimidazol-2-ylmethyl)-(5,6,7,8-tetrahydro-quinolin-8-yl)-amine (7.64 g, 28.5 mmol) in dry CH$_3$CN (3 mL) was added 1-N-tert-butoxycarbonyl-2-chloromethylbenzimidazole (115 mg, 0.41 mmol), N,N-diisopropylethylamine (0.13 mL, 0.74 mmol), and potassium iodide (3 mg, 0.02 mmol) and the mixture was stirred under an argon atmosphere at 60° C. for 4 h. The crude yellow oil was dissolved in dry CH$_2$Cl$_2$ (2 mL) and trifluoroacetic acid (1 mL) was added dropwise. The resultant mixture was stirred overnight at room temperature. The reaction mixture was diluted with CH$_2$Cl$_2$ (10 mL) and then concentrated in vacuo to remove any excess trifluoroacetic acid. The concentrate was diluted with CH$_2$Cl$_2$ (20 mL) and extracted with 1N NaOH (30 mL). The aqueous layer was washed with CH$_2$Cl$_2$ (2×15 mL) and then the combined organic layers were dried (Na$_2$SO$_4$), filtered, and concentrated in vacuo. Purification by radial chromatography on a 2 mm TLC grade silica gel plate (CH$_2$Cl$_2$/MeOH/NH$_4$OH, 100:1:1 followed by 50:1:1) afforded the dibenzimidazole adduct (134 mg, 49%, 2 steps) as a colourless oil.

Using General Procedure D: Cnversion of the free base (134 mg, 0.33 mmol) to the hydrobromide salt gave AMD9844 as a beige solid (192 mg). ¹H NMR (D$_2$O) δ 1.87–2.04 (br m, 1H), 2.15–2.37 (m, 2H), 2.41–2.55 (br m, 1H), 2.99–3.12 (m, 2H), 4.46 (d, 2H, J=15.6 Hz), 4.65 (d, 2H, J=15.6 Hz), 4.92 (dd, 1H, J=10.2, 6.3 Hz), 7.34–7.44(m, 8H), 7.90 (dd, 1H, J=8.1, 6.0 Hz), 8.38 (d, 1H, J=7.8 Hz), 8.76 (d, 1H, J=5.7 Hz); ³C NMR (D$_2$O) δ 20.29, 21.27, 27.77, 48.75, 63.05, 113.81, 126.33, 127.28, 130.82, 140.52, 141.10, 148.45, 148.80, 148.92; ES-MS m/z 409 (M+H). Anal. Calcd. for C$_{25}$H$_{24}$N$_6$.3.0HBr.1.8H$_2$O.0.3C$_4$H$_{10}$O: C, 44.58; H, 4.80; N, 11.91; Br, 33.96. Found: C, 44.52; H, 4.68; N, 11.91; Br, 33.94.

EXAMPLE 86

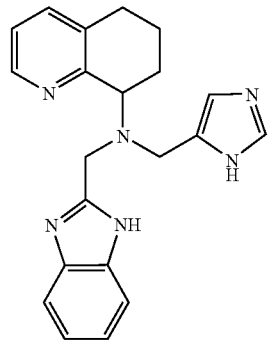

AMD9875: Preparation of (1H-Benzimidazol-2-ylmethyl)-(3H-imidazol-4-ylmethyl)-(5,6,7,8-tetrahydro-quinolin-8-yl)-amine (hydrobromide salt)

Using General Procedure B: Reaction of 4(5)-imidazolecarboxaldehyde (0.055 g, 0.57 mmol) and (1-tert-butoxycarbonyl-1H-Benzimidazol-2-ylmethyl)-(5,6,7,8-tetrahydro-quinolin-8-yl)-amine (0.164 g, 0.43 mmol) with NaBH(OAc)$_3$ (0.154 g, 0.73 mmol) in CH$_2$Cl$_2$ (4 mL) for 24 hours followed by purification of the crude material by radial chromatography on silica gel (2 mm plate, 20:1:1 CH$_2$Cl$_2$—CH$_3$OH—NH$_4$OH) provided 0.099 g (50%) of the desired tertiary amine as a white solid.

Using General Procedure D: Conversion of the white solid (99 mg) to the hydrobromide salt with simultaneous removal of the BOC-protecting group, followed by re-precipitation of the intermediate solid from methanol/ether, gave AMD9875 (97 mg) as a white solid. ¹H NMR (D$_2$O) δ 1.83–1.97 (m, 1H), 2.15–2.26 (m, 2H), 2.39–2.46 (m, 1H), 3.03–3.05 (m, 2H), 4.05 (d, 1H, J=15.0 Hz), 4.21 (d, 1H, J=15.0 Hz), 4.44 (d, 1H, J=16.2 Hz), 4.59 (d, 1H, J=16.2 Hz), 4.75 (dd, 1H, J=6.0, 10.2 Hz), 7.35 (s, 1H), 7.59–7.65 (m, 2H), 7.73–7.78 (m, 2H), 7.90 (dd, 1H), J=6.6, 7.2 Hz), 8.38 (d, 1H, J=8.1 Hz), 8.48 (s, 1H), 8.72 (d, 1H, J=5.7 Hz); ¹³C NMR (D$_2$O) δ 2.32, 20.66, 27.72, 46.28, 48.05, 61.54, 114.16, 118.98, 126.13, 127.27, 129.11, 130.73, 134.90, 140.07, 140.87, 148.31, 149.87, 150.31; ES-MS m/z 359 (M+H). Anal. Calcd. for C$_{21}$H$_{22}$N$_6$.3.0 HBr.2.6 H$_2$O: C, 38.92; H, 4.70; N, 12.97; Br, 36.99. Found: C, 39.02; H, 4.59; N, 12.72; Br, 37.02.

EXAMPLE 87

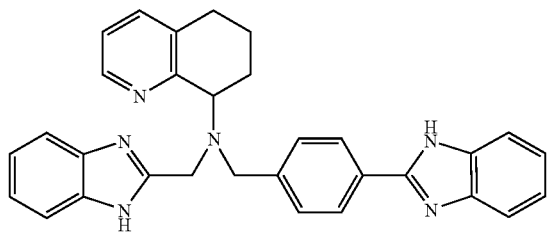

AMD9575: Preparation of [4-(1H-benzimidazol-2-yl)-benzyl]-(1H-benzimidazol-2-ylmethyl)-(5,6,7,8-tetrahydroquinolin-8-yl)-amine (hydrobromide salt)

Preparation of 4-(benzimidazol-2-yl)-benzaldehyde

A solution of 2-nitroaniline (0.41 g, 3.0 mmol) and methyl 4-chlorocarbonyl benzoate (0.65 g, 3.3 mmol) in THF (3.7 mL) and pyridine (0.8 mL) was stirred for 2 h at room temperature. The reaction was diluted with saturated sodium bicarbonate (10 mL) and EtOAc (15 mL), the phases separated and the aqueous phase extracted with EtOAc (2×10 mL). The combined organic extracts were dried ($Na_2SO_4$), filtered and concentrated under reduced pressure to afford (2-nitrophenyl)-terephthalamic acid methyl ester as a yellow solid (0.70 g, 78%). $^1$H NMR ($CDCl_3$) δ 3.97 (s, 3H), 7.25 (t, 1H, J=7.8 Hz), 7.74 (t, 1H, J=7.8 Hz), 8.04 (d, 2H, J=7.8 Hz), 8.20 (s, 1H (NH)), 8.20 (d, 2H, J=7.8 Hz), 8.30 (d, 1H, J=7.8 Hz), 8.99 (d, 1H, J=7.8 Hz).

To a solution of (2-nitrophenyl)-terephthalamic acid methyl ester (0.23 g, 0.76 mmol) in glacial acetic acid (2.5 mL) was added iron powder (<5 μm mesh, 0.12 g, 2.1 mmol) and the mixture stirred at reflux for 1 h. The mixture was cooled, stirred at room temperature for 2 h and concentrated under reduced pressure. The residue was partitioned between saturated sodium bicarbonate (10 mL) and ethyl acetate (10 mL), the phases separated and the organic layer washed with saturated $NaHCO_3$ (10 mL). The organic extract was dried ($MgSO_4$), filtered and concentrated to give cyclized methyl 4-(benzimidazol-2-yl)-benzoate (0.163 g, 86%). $^1$H NMR ($CDCl_3$) δ 3.96 (s, 3H), 7.32 (m, 2H), 7.53 (br, 1H), 7.84 (br, 1H), 8.17 (m, 4H), 9.65 (br, 1H (NH)).

To a solution of methyl 4-(benzimidazol-2-yl)-benzoate (0.23 g, 0.9 mmol) in THF (10 mL) at 0° C. was added a solution of DIBAL-H (5.0 mL, 1.0 M in THF, 5.0 mmol). The reaction was allowed to warm to room temperature, stirred for 1 h and quenched with a saturated potassium sodium tartrate solution (20 mL). The biphasic mixture was stirred vigorously for 1 h, the phases separated and the organic layer dried ($MgSO_4$), filtered, concentrated and purified by column chromatography on silica gel (7% $MeOH/CH_2Cl_2$) to give 4-(benzimidazol-2-yl)-benzyl alcohol (0.175 g, 87%). $^1$H NMR ($CD_4OD$) δ 3.30 (s, 1H (OH)), 4.69 (s, 2H), 7.26 (m, 2H), 7.53 (d, 2H, J=8.4 Hz), 7.60 (m, 2H), 8.07 (d, 2H, J=8.1 Hz).

4-(Benzimidazol-2-yl)-benzyl alcohol from above (0.175 g, 0.78 mmol) was dissolved in $CH_2Cl_2$ (5 mL) and THF (8 mL), treated with activated $MnO_2$ (0.68 g, 7.8 mmol) and stirred at room temperature for 1.5 h. The mixture was filtered through celite, the cake washed with $CH_2Cl_2$ and the solvent from the eluent removed under reduced pressure to afford 4-(benzimidazol-2-yl)-benzaldehyde (92 mg, 42%). $^1$H NMR ($CD_4OD$) δ 7.28 (m, 2H), 7.60 (br, 1H (NH)), 7.65 (d, 2H, J=7.8 Hz), 8.09 (d, 2H, J=7.8 Hz), 8.30 (d, 2H, J=9.0 Hz), 10.08 (s, 1H (CHO)).

Using General Procedure B: To a solution 4-(benzimidazol-2-yl)-benzaldehyde (39 mg, 0.175 mmol) and (1-tert-butoxycarbonyl-1H-Benzimidazol-2-ylmethyl)-(5,6,7,8-tetrahydro-quinolin-8-yl)-amine (60 mg, 0.16 mmol) in THF (2 mL) was added acetic acid (90 μL) and sodium triacetoxyborohydride (68 mg, 0.32 mmol) and the mixture stirred at 60° C. for 3 h. Purification of the crude product by radial chromatography on silica gel (0.7% MeOH/0.5% $NH_4OH/CH_2Cl_2$) afforded the desired [4-(1H-benzimidazol-2-yl)-benzyl]-(N-tert-butoxycarbonylbenzimidazol-2-ylmethyl)-(5,6,7,8-tetrahydroquinolin-8-yl)-amine (30 mg, 39%) as a flaky white solid. $^1$H NMR ($CDCl_3$) δ 1.72 (s, 10H), 1.97 (m, 2H), 2.26 (m, 1H), 2.73 (m, 2H), 3.80 (d, 1H, J=15.0 Hz), 4.00 (d, 1H, J=15.0 Hz), 4.35 (m, 1H), 4.71 (s, 2H), 7.00 (m, 1H), 7.14 (m, 2H), 7.24 (m, 3H), 7.33 (d, 2H, J=7.2 Hz), 7.47 (d, 2H), 7.53 (d, 1H, J=7.2 Hz), 7.63 (d, 1H, J=7.8 Hz), 7.67 (d, 2H, J=7.8 Hz), 7.79 (br, 1H), 8.39 (d, 1H, J=3.5 Hz), 9.92 (br, 1H (NH)).

Using General Procedure D: Conversion of the material from above (30 mg) to the hydrobromide salt to provide AMD9575 (0.026 g) as a white solid. $^1$H NMR ($D_2O$) δ 1.92 (br m, 1H), 2.25 (m, 2H), 2.47 (br m, 1H), 3.06 (br m, 2H), 3.78 (d, 1H, J=12.9 Hz), 3.9 (d, 1H, J=12.6 Hz), 4.44 (d, 1H, J=16.5 Hz), 4.63 (d, 1H, J=15.9 Hz), 4.80 (m, 1H), 7.01 (dd, 2H, J=6.0, 3.2 Hz), 7.37 (d, 2H, J=8.1 Hz), 7.43 (dd, 2H, J=3.2, 6.0 Hz), 7.54 (d, 2H, J=8.1 Hz), 7.58 (dd, 2H, J=3.0, 6.3 Hz), 7.74 (dd, 2H, J=3.0, 6.3 Hz), 7.97 (t, 1H, J=6.9 Hz), 8.44 (d, 1H), J=7.8 Hz), 8.81 (d, 1H, J=5.4 Hz); 13C NMR ($D_2O$) δ 19.74, 20.48, 27.23, 49.56, 55.99, 62.95, 113.15 (2C), 113.40 (2C), 120.78 (2C), 125.49 (2C), 125.62, 126.33 (2C), 126.41 (2C), 129.83, 130.79 (2C), 139.23 (2C), 140.50, 141.69, 146.89, 147.76 (2C), 149.95, 150.89. ES-MS m/z 485 (M+H). Anal. Calcd. for $C_{31}H_{28}N_6$·3.0HBr·3.6$H_2O$: C, 46.90; H, 4.86; N, 10.59; Br, 30.35. Found: C, 46.93; H, 4.74; N, 10.41; Br, 30.34.

EXAMPLE 88

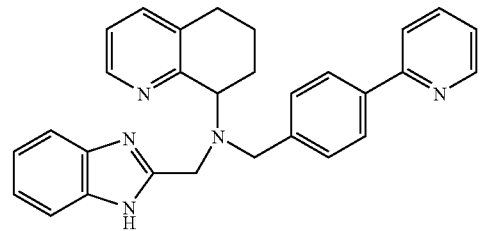

AMD9719: Preparation of (1H-Benzimidazol-2-ylmethyl)-(4-pyrid-2-yl-benzyl)-(5,6,7,8-tetrahydro-quinolin-8-yl)-amine (hydrobromide salt)

Following General Procedure B: To a solution of (1-tert-butoxycarbonyl-1H-Benzimidazol-2-ylmethyl)-(5,6,7,8-tetrahydro-quinolin-8-yl)-amine (174 mg, 0.462 mmol) and 4-pyrid-2-yl-benzenecarboxaldehyde (161 mg, 0.879 mmol) in $CH_2Cl_2$ (5 mL) was added $NaBH(OAc)_3$ (192 mg, 0.906 mmol) and the mixture stirred overnight. Purification of the crude material by radial chromatography (2 mm TLC plate, 100:1:1 $CH_2Cl_2/CH_3OH/NH_4OH$) provided the free base (0.135 g, 66%).

Following General Procedure D: Conversion of the material from above (135 mg) to the hydrobromide salt gave AMD9719 (0.154 g, 69%). $^1$H NMR ($D_2O$) δ 1.86–2.00 (m, 1H), 2.19–2.37 (m, 2H), 2.44–2.54 (m, 1H), 3.03–3.11 (m, 2H), 3.90 (d, 1H, J=12.7 Hz), 3.98 (d, 1H, J=13.2 Hz), 4.50 (d, 1H, J=16.4 Hz), 4.68 (d, 1H, J=16.6 Hz), 7.29 (dd, 2H, J=6.4, 3.3 Hz), 7.40–7.48 (m, 4H), 7.53 (dd, 2H, J=6.2, 3.1 Hz), 7.69 (d, 1H, J=8.5 Hz), 7.90–7.99 (m, 2H), 8.44 (d, 1H, J=7.9 Hz), 8.51 (t, 1H, J=8.0 Hz), 8.62 (d, 1H, J=5.6 Hz), 8.81 (d, 1H, J=5.3 Hz). $^{13}$C NMR ($D_2O$) δ 19.95, 20.58, 27.38, 49.79, 56.32, 63.04, 113.36 (2 carbons), 125.41, 125.71, 125.78, 126.21 (2 carbons), 127.29 (2 carbons), 129.66, 129.93, 130.91 (2 carbons), 139.31, 140.63, 140.95, 146.80 (2 carbons), 147.89 (2 carbons), 150.18, 150.59, 151.15. ES-MS m/z 446 (M+H) Anal. Calc. for $C_{29}H_{27}N_5 \cdot 3.1HBr \cdot 2.0H_2O$: C, 47.56; H, 4.69; N, 9.56; Br, 33.82. Found: C, 47.60; H, 4.76; N, 9.44; Br, 33.93.

EXAMPLE 89

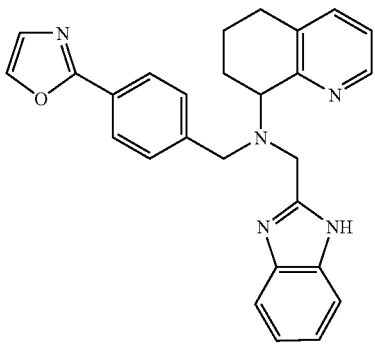

AMD9750: Preparation of (1H-Benzimidazol-2-ylmethyl)-[4-(oxazol-2-yl)-benzyl]-(5,6,7,8-tetrahydroquinolin-8-yl)-amine (hydrobromide salt)

Preparation of 4-(oxazol-2-yl)-benzyl alcohol (B. A. Anderson et al. *J. Org. Chem.* 1997, 62, 8634)

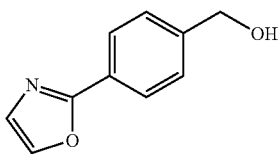

To a solution of oxazole (0.285 mL, 4 mmol) in THF (40 mL) at −78° C. was added n-butyllithium (1.83 mL of a 2.4M solution in hexanes, 4.4 mmol) and the reaction stirred for 30 min at −78° C. then zinc chloride (12 mL of 1M solution in THF, 12 mmol) was added. The mixture was then allowed to slowly warm to 0° C. and was stirred for 45 min. A solution of methyl-4-bromobenzoate (0.860 g, 4 mmol) in THF (10 mL) was added followed by a solution of bis-(triphenylphosphine)-palladium (II) chloride (140 mg, 0.2 mmol) and n-butyllithium (0.17 mL of a 2.4M solution in hexanes, 0.4 mmol) in THF (4 mL). The resultant dark brown mixture was warmed to reflux and stirred for 1 h. After cooling, the reaction mixture was diluted with ethyl acetate (30 mL), then washed with water (1×20 mL) and brine (1×20 mL). The organic layer was dried ($Na_2SO_4$), filtered, concentrated and purified by chromatography on silica gel (98:2 $CH_2C_2$/MeOH) to give the desired methyl-4-(oxazol-2-yl)-benzoate (340 mg, 42%) as a yellow oil. $^1$H NMR ($CDCl_3$) δ 3.94 (s, 3H), 7.28 (s, 1H), 7.76 (m, 1H), 8.09 (m, 4H).

To a solution of methyl-4-(oxazol-2-yl)-benzoate (0.203 g, 1 mmol) in $CH_2Cl_2$ (10 mL) 0° C. was added DIBAL-H (4 mL of a 1.0M solution in dichloromethane, 4 mmol) over 10 minutes. The resultant solution was stirred at 0° C. for 2 hours then quenched with an aqueous saturated solution of sodium potassium tartrate (20 mL) and the biphasic mixture stirred rapidly for 60 minutes. The phases were separated and the aqueous layer extracted with $CH_2Cl_2$ (3×10 mL). The combined organic fractions were dried ($Na_2SO_4$), filtered, concentrated and purified by chromatography on silica gel (10:1 $CH_2Cl_2$/MeOH) to afford the title alcohol (0.156 g, 89%). $^1$H NMR ($CDCl_3$) δ 3.42 (t, 1H, J=6.0 Hz (OH)), 4.77 (s, 2H, J=6.0 Hz), 7.24 (s, 1H), 7.47 (d, 2H, J=7.8 Hz), 7.71 (s, 1H), 8.05 (d, 2H, J=7.8 Hz).

Using General Procedure C: To a solution of 4-(oxazol-2-yl)-benzyl alcohol (156 mg, 0.89 mmol) in $CH_2Cl_2$ (10 mL) was added methanesulfonyl chloride (0.102 mL, 1.34 mmol) and triethylamine (0.250 mL, 1.79 mmol) and the mixture stirred for 30 min at room temperature. The resultant mesylate was obtained as a fine white powder and used directly in the next reaction without further purification. $^1$H NMR ($CDCl_3$) δ 3.00 (s, 3H), 3.67 (s, 2H), 7.26 (s, 1H), 7.51 (d, 2H, J=8.1 Hz), 7.74 (s, 1H), 8.07 (d, 2H, J=8.1 Hz).

Using the general alkylation procedure: To a solution of the mesylate from above (56 mg, 0.22 mmol), $K_2CO_3$ (60 mg, 0.44 mmol) and KI (2 mg, 0.01 mmol) in $CH_3CN$ (10 mL) was added (1-tert-butoxycarbonyl-1H-Benzimidazol-2-ylmethyl)-(5,6,7,8-tetrahydro-quinolin-8-yl)-amine (113 mg, 0.3 mmol) and the mixture stirred at 60° C. for 16 h. Purification of the crude material by chromatography on silica gel (10:1 $CH_2Cl_2$/MeOH) afforded the N-alkylated product (89 mg, 93%). $^1$H NMR ($CDCl_3$) δ 1.73 (s, 9H), 2.03 (m, 3H), 2.20 (m, 1H), 2.75 (m, 2H), 3.81 (d, 1H, J=16.1 Hz), 4.04 (d, 1H, J=16.1 Hz), 4.34 (dd, 1H, J=9.1, 6.2 Hz), 4.67 (s, 2H), 7.03 (m, 1H), 7.11–7.17 (m, 2H), 7.26 (m, 4H), 7.57–7.68 (m, 5H), 8.44 (d, 1H, J=5.1 Hz).

Using General Procedure D: Conversion of the amine from above (89 mg, 0.020 mmol) to the hydrobromide salt gave AMD9750 (14 mg) as a white solid. $^1$H NMR ($D_2O$). δ 2.07 (m, 1H), 2.26 (m, 2H), 2.44 (m, 1H), 3.05 (m, 2H), 3.81 (m, 3H), 4.42 (d, 1H, J=16.2 Hz), 4.63 (d, 1H, J=16.2 Hz), 7.18 (s, 1H), 7.24 (m, 2H), 7.43 (m, 2H), 7.83 (s, 1H), 7.83 (t, 1H, J=7.8 Hz), 8.43 (d, 1H, J=8.4 Hz), 8.82 (d, 1H, J=5.2 Hz). $^{13}$C NMR ($D_2O$) δ 20.42, 21.07, 27.83, 50.22, 56.69, 63.49, 113.67 (2C), 125.02, 126.14 (2C), 126.23 (2C), 126.69, 140.41, 130.81 (2C), 139.74, 140.35, 141.01, 148.33, 150.69, 151.41, 156.23, 161.09. ES-MS m/z 436 (M+H); Anal. Calcd. for ($C_{27}H_{25}N_5O \times 2.9$ HBr×2.0 $H_2O$): C, 45.92; H, 4.55; N, 9.92; Br, 32.81. Found: C, 46.01; 4.65; N, 9.55; Br, 32.75.

EXAMPLE 90

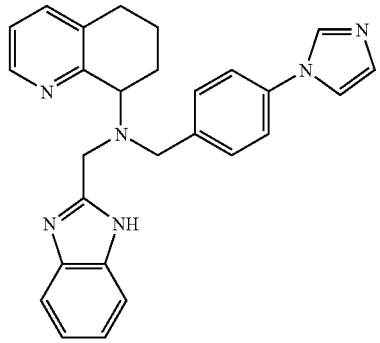

AMD9755: Preparation of (1H-Benzimidazol-2-ylmethyl)-(4-imidazol-1-yl-benzyl)-(5,6,7,8-tetrahydro-quinolin-8-yl)-amine (hydrobromide salt)

Using General Procedure B: Reaction of 4-(imidazol-1-yl)benzaldehyde (0.075 g, 0.44 mmol) and (1-tert-butoxycarbonyl-1H-Benzimidazol-2-ylmethyl)-(5,6,7,8-tetrahydro-quinolin-8-yl)-amine (0.107 g, 0.29 mmol) with NaBH(OAc)$_3$ (0.171 g, 0.81 mmol) in CH$_2$Cl$_2$ (3 mL) for 24 h followed by purification of the crude material by column chromatography on silica gel (25:1:1 CH$_2$Cl$_2$—CH$_3$OH—NH$_4$OH) provided 0.091 g (58%) of the desired tertiary amine as a white solid.

Using General Procedure D: Conversion of the white solid (91 mg) to the hydrobromide salt with simultaneous removal of the BOC-protecting group, followed by re-precipitation of the intermediate solid from methanol/ether, gave AMD9755 (89 mg) as a white solid. $^1$H NMR (D$_2$O) δ 1.86–2.02 (m, 1H), 2.22–2.36 (m, 2H), 2.48–2.52 (m, 1H), 3.06–3.08 (m, 2H), 3.90 (d, 1H, J=12.6 Hz), 3.98 (d, 1H, J=12.6 Hz), 4.90 (d, 1H, J=16.5 Hz), 4.69 (d, 1H, J=16.5 Hz), 4.79–4.87 (m, 1H, overlaps with HOD), 7.22 (d, 2H, J=8.7 Hz), 7.31 (dd, 1H, J=1.2, 1.5 Hz), 7.39–7.46 (m, 4H), 7.54–7.61 (m, 3H), 7.98 (dd, 1H, J=6.0, 7.8 Hz), 8.45 (d, 1H, J=7.5 Hz), 8.67 (s, 1H), 8.82 (d, 1H, J=5.4 Hz); $^{13}$C NMR (D$_2$O) δ 21.03, 21.67, 28.46, 50.80, 57.18, 64.09, 114.49, 121.28, 121.87, 122.61, 126.80, 127.32, 131.06, 132.52, 134.10, 134.84, 139.32, 140.40, 141.74, 148.99, 151.26, 152.38; ES-MS n/z 435 (M+H). Anal. Calcd. for C$_{27}$H$_{26}$N$_6$.3.2 HBr.3.4 H$_2$O: C, 42.97; H, 4.81; N, 11.14; Br, 33.88. Found: C, 43.00; H, 4.61; N, 10.89; Br, 33.93.

EXAMPLE 91

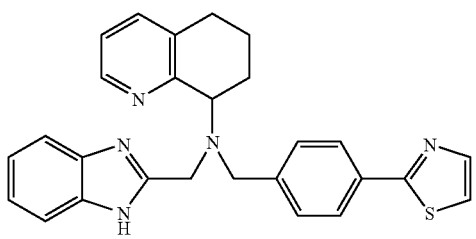

AMD9757: Preparation of [4-(thiazol-2-yl)-benzyl]-(1H-benzimidazol-2-ylmethyl)-(5,6,7,8-tetrahydro-quinolin-8-yl)-amine (hydrobromide salt)

Preparation of 4-(2-thiazolyl)-benzaldehyde

To a solution of 2-bromothiazole (0.26 g, 1.6 mmol) and 4-formylphenylboronic acid (0.48 g, 3.2 mmol) in toluene (16 mL) was added tetrakis(triphenylphosphine)palladium (0) (0.09 g, 0.08 mmol) and K$_2$CO$_3$ (0.33 g, 2.4 mmol) and the solution stirred at reflux for 16 h. The reaction was cooled to room temperature, diluted with water (50 mL) and ethyl acetate (50 mL). The organic layer was separated, washed with brine (30 mL), dried (MgSO$_4$), filtered, concentrated and purified by column chromatography on silica gel (2% MeOH/CH$_2$Cl$_2$) to give 4-(2-thiazolyl)-benzaldehyde (45 mg, 15%). $^1$H NMR (CDCl$_3$) δ 7.45 (d, 1H, J=3.0 Hz), 7.90 (d, 1H, J=3.0 Hz), 7.97 (d, 2H, J=7.8 Hz), 8.15 (d, 2H, J=7.2 Hz), 10.07 (s, 1H (CHO)).

Using General Procedure B: To a solution of 4-(2-thiazolyl)-benzaldehyde (45 mg, 0.24 mmol) and (1-tert-butoxycarbonyl-1H-Benzimidazol-2-ylmethyl)-(5,6,7,8-tetrahydro-quinolin-8-yl)-amine (81 mg, 0.21 mmol) in dichloromethane (2.5 mL) was added NaBH(OAc)$_3$ (77 mg, 0.36 mmol) and the mixture stirred at room temperature for 16 h. Purification of the crude by radial chromatography on silica gel (MeOH/NH$_4$OH/CH$_2$Cl$_2$, 1:1:98) gave the desired amine (34 mg, 28%) as a flaky white solid. $^1$H NMR (CDCl$_3$) δ 1.73 (m, 10H), 1.97 (m, 2H), 2.25 (m, 1H), 2.75 (m, 2H), 3.84 (d, 1H, J=15.0 Hz), 4.03 (d, 1H, J=15.0 Hz), 4.32 (m, 1H), 4.68 (s, 2H), 7.02 (m, 1H), 7.10 (t, 1H, J=7.2 Hz), 7.18 (t, 1H, J=7.2 Hz), 7.27 (m, 4H), 7.58 (d, 2H), J=7.8 Hz), 7.60 (m, 2H), 7.78 (d, 1H, J=3.0 Hz), 8.45 (d, 1H, J=3.5 Hz).

Using General Procedure D: Conversion of the solid from above (34 mg) to the hydrobromide salt provided AMD9757 (34 mg) as a white solid. $^1$H NMR (D$_2$O) δ 1.86 (br m, 1H), 2.23 (m, 2H), 2.43 (br m, 1H), 3.03 (br m, 2H), 3.70 (d, 1H, J=12.6 Hz), 3.84 (d, 1H, J=12.6 Hz), 4.42 (d, 1H, J=16.5 Hz), 4.62 (d, 1H, J=16.5 Hz), 4.77 (m, 1H), 7.21 (d, 2H, J=12.6 Hz), 7.22 (d, 2H, J=8.7 Hz), 7.40 (d, 2H, J=8.1 Hz), 7.45 (dd, 2H, J=3.0, 6.0 Hz), 7.66 (d, 1H, J=3.3 Hz), 7.83 (d, 1H, J=3.6 Hz), 7.94 (t, 1H, J=6.9 Hz), 8.40 (d, 1H, J=7.5 Hz), 8.78 (d, 1H, J=5.1 Hz); $^{13}$C NMR (D$_2$O) δ 20.43, 21.07, 27.85, 50.29, 56.73, 63.57, 113.70 (2C), 121.82, 126.19, 126.58 (4C), 130.42, 131.10 (2C), 139.75 (2C), 140.01, 140.13 (2C), 141.08, 148.36 (2C), 150.78, 151.54. ES-MS m/z 452 (M+H). Anal. Calcd. for C$_{27}$H$_{25}$N$_5$S.3.0HBr.2.0H$_2$O: C, 44.21; H, 4.41; N, 9.55; Br, 33.04. Found: C, 44.26; H, 4.37; N, 9.29; Br, 33.04.

EXAMPLE 92

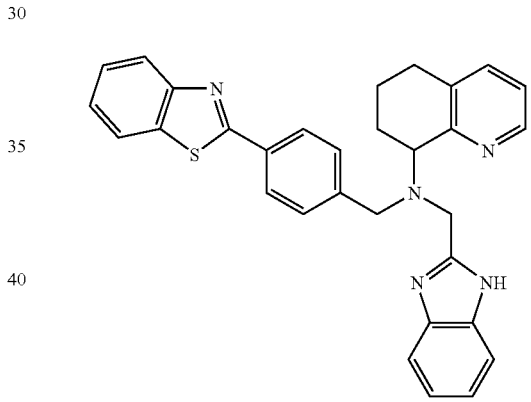

AMD9595: Preparation of (1H-Benzimidazol-2-ylmethyl)-[4-(benzothiazol-2-yl)-benzyl]-(5,6,7,8-tetrahydroquinolin-8-yl)-amine (hydrobromide salt)

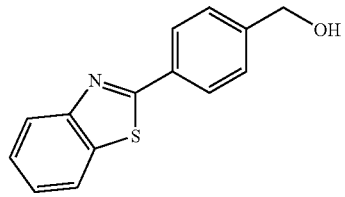

Preparation of 4-(benzothiazol-2-yl)-benzyl alcohol

To a 0° C. solution of methyl-4-(benzothiazol-2-yl)-benzoate (prepared as described by A. Brembilla, D. Roizard and P. Lochon *Synth. Commun.* 1990, 20, 3379) (1.08 g, 4 mmol) in THF (20 mL) was added DIBAL-H (20 mL of a 1.0M solution in THF, 20 mmol) over 10 minutes. The resulting solution was stirred at 0° C. for 2 hours, then an aqueous saturated solution of sodium potassium tartrate was added and the biphasic mixture stirred rapidly for 60 min. The phases were separated and the aqueous layer extracted with ether (3×20 mL). The combined organic fractions were dried ($Na_2SO_4$), concentrated and purified by column chromatography on silica gel (10:1 $CH_2Cl_2$/MeOH) to afford the title compound (0.69 g, 75%). $^1$H NMR ($CD_3OD$) δ 4.69 (s, 2H), 7.43 (t, 1H, J=7.8 Hz), 7.53 (m, 3H), 7.99 (m, 1H), 8.06 (m, 3H).

Using General Procedure C: To a solution of 4-(benzothiazol-2-yl)-benzyl alcohol (227 mg, 1.0 mmol) in $CH_2Cl_2$ (10 mL) was added methanesulfonyl chloride (0.092 mL, 1.2 mmol) and triethylamine (0.210 mL, 1.5 mmol) and the mixture stirred at room temperature for 30 min. The mesylate was collected as a fine white powder and used without further purification in the next reaction. $^1$H NMR ($CDCl_3$) δ 3.06 (s, 3H), 5.28 (s, 2H), 7.38 (t, 1H, J=6.2 Hz), 7.49 (t, 1H, J=6.2 Hz), 7.52 (d, 2H, J=7.1 Hz), 7.90 (d, 1H, J=6.2 Hz), 8.05 (d, 1H, J=6.2 Hz), 8.11 (d, 2H, J=7.1 Hz).

Using the general alkylation procedure: A solution of the mesylate from above (1 mmol), N,N-diisopropylethylamine (0.093 mL, 1.2 mmol), potassium iodide (13 mg, 0.10 mmol) and (1-tert-butoxycarbonyl-1H-Benzimidazol-2-yl-methyl)-(5,6,7,8-tetrahydro-quinolin-8-yl)-amine (400 mg, 1.1 mmol) in $CH_3CN$ (10 mL) was stirred at 70° C. for 3 h. Purification of the crude material by column chromatography on silica gel (10:1 $CH_2Cl_2$/MeOH) afforded the alkylated product (1H-N-t-butoxycarbonyl-benzimidazol-2-ylmethyl)-[4-(benzothiazol-2-yl)-benzyl]-(5,6,7,8-tetrahydro-quinolin-8-yl)-amine (354 mg, 71%). $^1$H NMR ($CDCl_3$) δ 1.63 (s, 9H), 2.06 (m, 3H), 2.25 (m, 1H), 2.75 (m, 2H), 3.81 (d, 1H, J=16.1 Hz), 4.02 (d, 1H, J=16.1 Hz), 4.34 (dd, 1H, J=8.3, 6.8 Hz), 4.65 (d, 1H, J=13.2 Hz), 4.69 (d, 1H, J=13.2 Hz), 7.03 (m, 1H), 7.09–7.11 (M, 2H), 7.30 (m, 4H), 7.46 (t, 1H, J=8.1 Hz), 7.62 (t, 2H, J=6.1 Hz), 7.69 (d, 1H, J=6.1 Hz), 7.85 (d, 1H, J=6.1 Hz), 8.00 (d, 1H, J=6.1 Hz), 8.44 (d, 1H, J=4.8 Hz).

Using General Procedure D: Conversion of the material from above (80 mg) to the hydrobromide salt with simultaneous removal of the N-tert-butoxycarbonyl protecting group gave AMD9595 (14 mg) as a white crystalline solid. $^1$H NMR ($D_2O$). δ 1.85 (m, 1H), 2.18 (m, 2H), 2.41 (m, 1H), 3.08 (m, 2H), 3.48 (m, 1H), 3.54 (dd, 1H, J=14.1, 7.2 Hz), 3.71 (d, 1H, J=11.7 Hz), 4.40 (d, 1H, J=15.9 Hz), 4.60 (d, 1H, J=15.9 Hz), 7.00 (dd, 1H, J=6.0, 3.0 Hz), 7.11 (d, 2H, J=7.8 Hz), 7.41 (m, 4H), 7.50 (d, J=7.8 Hz), 7.55 (t, 1H, J=7.2 Hz), 7.89 (d, 1H, J=8.1 Hz), 7.97 (m, 2H), 8.43 (d, 1H, J=8.1 Hz), 8.79 (d, 1H, J=5.1 Hz). $^{13}$C NMR ($D_2O$) δ 20.46, 21.08, 26.83, 51.44, 56.69, 62.35, 113.56 (2C), 121.81, 122.57, 126.26, 126.44, 126.94, 130.27, 130.61, 139.73, 140.02, 148.43, 151.69, 151.44, 158.83. ES-MS m/z 501 (M+H); Anal. Calcd. for ($C_{31}H_{27}N_5S$×3 HBr×3 $H_2O$): C, 46.63; H, 4.54; N, 8.77; Br, 30.02. Found: C, 46.88; H, 4.46; N, 8.66; Br, 29.84.

EXAMPLE 93

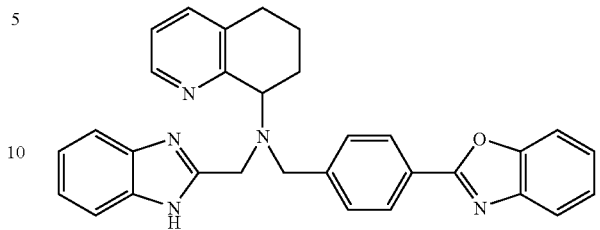

AMD9615: Preparation of [4-(benzoxazol-2-yl)-benzyl]-(1H-benzimidazol-2-ylmethyl)-(5,6,7,8-tetrahydroquinolin-8-yl)-amine (hydrobromide salt)

Preparation of 4-(benzoxazol-2-yl)-benzyl alcohol

A solution of 2-nitrophenol (0.50 g, 3.6 mmol) and methyl 4-chlorocarbonyl benzoate (0.79 g, 4.0 mmol) in THF (4.5 mL) and pyridine (0.9 mL) was stirred for 1 h at room temperature. The reaction was diluted with saturated sodium bicarbonate (10 mL) and EtOAc (15 mL), the phases separated and the aqueous phase extracted with EtOAc (2×10 mL). The combined organic extracts were dried ($Na_2SO_4$), filtered and concentrated under reduced pressure to afford (2-nitrophenyl)-terephthalic acid diester as a yellow solid (1.03 g, 96%). $^1$H NMR ($CDCl_3$) δ 3.98 (s, 3H), 7.40 (d, 1H, J=7.8 Hz), 7.47 (t, 1H, J=7.8 Hz), 7.74 (t, 1H, J=7.2 Hz), 8.18 (D, 1H, J=7.2 Hz), 8.19 (d, 2H, J=7.8 Hz), 8.27 (d, 2H, J=7.8 Hz).

To a solution of (2-nitrophenyl)-terephthalic acid diester (1.02 g, 3.3 mmol) in glacial acetic acid (11 mL) was added iron powder (<5 μm mesh, 0.51 g, 9.0 mmol) and the mixture stirred at reflux for 1.5 h. The mixture was cooled, stirred at room temperature for 2 h and concentrated under reduced pressure. The residue was partitioned between saturated sodium bicarbonate (25 mL) and ethyl acetate (25 mL), the phases separated and the organic layer washed with saturated $NaHCO_3$ (25 mL). The organic extract was dried ($MgSO_4$), filtered, concentrated and purified by column chromatography on silica gel (2% MeOH/$CH_2Cl_2$) to give (2-hydroxyphenyl)-terephthalamic acid methyl ester (0.37 g, 44%). $^1$H NMR ($CDCl_3$) δ 3.98 (s, 3H), 6.95 (t, 1H, J=7.8 Hz), 7.07 (d, 1H, J=7.8 Hz), 7.19 (t, 1H, J=7.8 Hz), 7.28 (d, 1H, J=7.8 Hz), 7.98 (d, 2H, J=8.4 Hz), 8.18 (d, 2H, J=7.8 Hz).

A solution of (2-hydroxyphenyl)-terephthalamic acid methyl ester (0.35 g, 1.3 mmol) in polyphosphoric acid (~5 mL) was heated to reflux for 3 h. The solution was cooled to 0° C., water added (100 mL) and solid $K_2CO_3$ introduced until pH 7–9 was attained. The residue was diluted with ethyl acetate (2×100 mL) and the organic extract dried ($MgSO_4$), filtered and concentrated to give cyclized methyl 4-(benzoxazol-2-yl)-benzoate (0.15 g, 45%) as a beige powder. $^1$H NMR ($CDCl_3$) δ 3.98 (s, 3H), 7.40 (m, 2H), 7.61 (m, 1H), 7.81 (m, 1H), 8.20 (d, 2H, J=7.8 Hz), 8.34 (d, 2H, J=7.8 Hz).

To a solution of methyl 4-(benzoxazol-2-yl)-benzoate (0.20 g, 0.8 mmol) in THF (8 mL) at −78° C. was added a solution of DIBAL-H (4.0 mL, 1.0 M in THF, 4.0 mmol). The reaction was allowed to warm to room temperature, stirred for 1 h and quenched with a saturated potassium sodium tartrate solution (15 mL). The biphasic mixture was stirred vigorously for 1 h, the phases separated and the organic layer dried (MgSO$_4$), filtered and concentrated to give the title alcohol (0.16 g, 89%). $^1$H NMR (CDCl$_3$) δ 1.80 (t, 1H (Oh)), 4.82 (d, 2H, J=6.0 Hz), 7.36 (m, 2H), 7.55 (d, 2H, J=8.4 Hz), 7.60 (m, 1H), 7.78 (m, 1H), 8.26 (d, 2H, J=8.4 Hz).

Using General Procedure C: To a solution of 4-(benzoxazol-2-yl)-benzyl alcohol (0.16 g, 0.7 mmol) and triethylamine (0.15 mL, 1.1 mmol) in THF (7 mL) was added methanesulfonyl chloride (75 μL, 1.0 mmol) and the mixture stirred at room temperature for 0.5 h. The reaction was quenched with a saturated solution of NaHCO$_3$ (10 mL) and the aqueous phase was extracted with CH$_2$Cl$_2$ (3×10 mL). The combined organic extracts were dried (MgSO$_4$), filtered and concentrated to give the mesylate (0.20 g, 93%) as a pale yellow crystalline solid. $^1$H NMR (CDCl$_3$) δ 3.00 (s, 3H), 5.33 (s, 2H), 7.38 (m, 2H), 7.60 (m, 3H), 7.78 (m, 1H), 8.32 (d, 2H, J=7.8 Hz).

Using the general alkylation procedure: A solution of the mesylate from above (0.20 g, 0.66 mmol), N,N-diisopropylethylamine (0.17 mL, 1.0 mmol) and potassium iodide (6 mg, 30 μmol) in CH$_3$CN (7 mL) was reacted (1-tert-butoxycarbonyl-1H-Benzimidazol-2-ylmethyl)-(5,6,7,8-tetrahydro-quinolin-8-yl)-amine (0.27 g, 0.72 mmol) at 60° C. for 4 h. Purification of the crude by column chromatography on silica gel (4% MeOH/CH$_2$Cl$_2$), gave the N-alkylated product (0.23 g, 59%) as a flaky white solid. $^1$H NMR (CDCl$_3$) δ 1.74 (s, 10H), 2.01 (m, 2H), 2.26 (m, 1H), 2.74 (m, 2H), 3.87 (d, 1H, J=15 Hz), 4.08 (d, 1H, J=15 Hz), 4.35 (m, 1H), 4.70 (s, 2H), 7.00–7.20 (m, 3H), 7.30–7.40 (m, 5H), 7.55–7.65 (m, 3H), 7.68 (m, 1H), 7.87 (d, 2H, J=7.8 Hz), 8.42 (d, 1H, J=3.5 Hz).

Using General Procedure D: Conversion of the material from above (90 mg) to the hydrobromide salt gave AMD9615 (0.10 g) as a pale brown solid. $^1$H NMR (D$_2$O) δ 1.86 (br m, 1H), 2.08 (m, 2H), 2.34 (br m, 1H), 3.00 (br m, 2H), 3.04 (d, 1H), 3.50 (d, 1H, J=12.3 Hz), 4.30 (d, 1H, J=16.2 Hz), 4.52 (d, 1H, J=16.2 Hz), 4.66 (m, 1H), 6.91 (br d, 2H, J=7.2 Hz), 6.95 (d, 2H, J=8.1 Hz), 7.30 (br s, 2H), 7.32 (s, 2H), 7.35 (d, 2H, J=8.7 Hz), 7.49 (br m, 2H), 7.98 (t, 1H, J=6.8 Hz), 8.44 (d, 1H, J=7.8 Hz), 8.76 (d, 1H, J=5.7 Hz); $^{13}$C NMR (D$_2$O) δ 20.32, 21.00, 27.87, 50.20, 55.90, 63.25, 111.25, 113.57 (2C), 119.04, 124.64, 125.47, 126.12 (2C), 126.26 (2C), 126.99 (2C), 130.29 (2C), 139.68 (2C), 139.87, 140.26, 141.00, 148.49 (2C), 149.88, 150.63, 151.29, 162.00. ES-MS m/z 486 (M+H). Anal. Calcd. for C$_{31}$H$_{27}$N$_5$O.2.1HBr.0.9H$_2$O: C, 55.18; H, 4.62; N, 10.38; Br, 25.28. Found: C, 55.18; H, 4.65; N, 10.39; Br, 25.28.

EXAMPLE 94

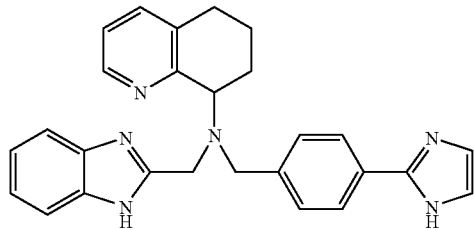

AMD9716: Preparation of [4-(1H-imidazol-2-yl)-benzyl]-(1H-benzimidazol-2-ylmethyl)-(5,6,7,8-tetrahydroquinolin-8-yl)-amine (hydrobromide salt)

Preparation of methyl [(N-sulfonic acid dimethylamide)-imidazol-2-yl]-benzyl alcohol To a solution of imidazole-1-sulfonic acid dimethylamide (1.03 g, 5.9 mmol) in THF (5.9 mL) at −78° C. was added n-butyllithium (3.2 mL, 2.42 M in THF) and the solution stirred at −78° C. for 15 min. To this mixture was added a solution of zinc chloride (0.80 g, 5.9 mmol) in THF (4.4 mL) at −78° C. and the reaction warmed to room temperature and stirred for 0.5 h. To the resultant mixture was added tetrakis (triphenylphosphine)palladium(0) (0.27 g, 0.2 mmol), a solution of methyl 4-bromobenzoate (0.85 g, 3.9 mmol) in THF (2.6 mL) and zinc chloride (1.6 g, 11.8 mmol) and the reaction heated to reflux for 6 h. The reaction was quenched with saturated NH$_4$Cl (50 mL), the layers separated and the organic layer washed with brine (1×30 mL), dried (MgSO$_4$), filtered, concentrated and purified by column chromatography on silica gel (2% MeOH/CH$_2$Cl$_2$) to give methyl [(N-sulfonic acid dimethylamide)-imidazol-2-yl]-benzoate (0.56 g, 47%) as a brown solid. $^1$H NMR (CDCl$_3$) δ 2.53 (s, 6H), 3.95 (s, 3H), 7.14 (s, 1H), 7.48 (s, 1H), 7.79 (d, 1H, J=7.8 Hz), 8.12 (d, 1H, J=7.8 Hz).

To a solution of methyl [(N-sulfonic acid dimethylamide)-imidazol-2-yl]-benzoate (0.56 g, 1.8 mmol) in THF (18 mL) at −78° C. was added a solution of DIBAL-H (9.1 mL, 1.0 M in THF). The reaction was allowed to warm to room temperature, stirred for 1 h and quenched with a saturated potassium sodium tartrate solution (25 mL). The biphasic mixture was stirred vigorously for 1 hour, the phases separated and the organic layer dried (MgSO$_4$), filtered and concentrated to give methyl [(N-sulfonic acid dimethylamide)-imidazol-2-yl]-benzyl alcohol (0.39 g, 76%). $^1$H NMR (CDCl$_3$) δ 2.49 (s, 6H), 4.72 (s, 2H), 7.10 (s, 1H), 7.36 (d, 2H, J=7.2 Hz), 7.75 (s, 1H), 7.61 (d, 2H, J=7.2 Hz).

Using General Procedure C: To a solution of the alcohol from above (0.39 g, 1.4 mmol) and triethylamine (0.30 mL, 2.1 mmol) in THF (14 mL) was added methanesulfonyl chloride (0.15 mL, 1.9 mmol) and the mixture stirred at room temperature for 1 hour. The resultant mesylate (0.50 g) was used used without further purification in the next reaction. $^1$H NMR (CDCl$_3$) δ 2.54 (s, 6H), 3.00 (s, 3H), 3.68 (s, 2H), 7.13 (s, 1H), 7.46 (s, 1H), 7.48 (d, 2H, J=7.8 Hz).

Using the general alkylation procedure: A solution of the mesylate from above (0.29 g, 0.8 mmol), N,N-diisopropylethylamine (0.21 mL, 1.2 mmol) and potassium iodide (10 mg, 40 μmol) in CH$_3$CN (9 mL) was reacted (1-tert-butoxycarbonyl-1H-Benzimidazol-2-ylmethyl)-(5,6,7,8-tetrahydro-quinolin-8-yl)-amine (0.31 g, 0.8 mmol) at 60° C. for 16 h. Purification of the crude by column chromatography on silica gel (6% MeOH/CH$_2$Cl$_2$) gave the desired amine (0.25 g, 48%) as a flaky white solid. $^1$H NMR (CDCl$_3$) δ 1.72 (s, 10H), 1.93 (m, 2H), 2.13 (m, 1H), 2.27 (s, 6H), 2.74 (m, 2H), 3.90 (d, 1H, J=15 Hz), 4.25 (d, 1H, J=15 Hz), 4.26 (m, 1H), 4.55 (d, 1H, J=15 Hz), 4.65 (d, 1H, J=15 Hz), 7.00 (m, 2H), 7.26 (m, 4H), 7.44 (m, 4H), 7.66 (m, 1H), 7.75 (m, 1H), 8.44 (d, 1H, J=3.5 Hz).

A solution of the protected imidazolyl-amine from above (0.25 g, 0.5 mmol) in 2 M HCl (4 mL) was heated to reflux for 16 h. The mixture was diluted with 15% aqueous NaOH (20 mL) and extracted with CH$_2$Cl$_2$ (2×20 mL). The organic layer was separated, dried (MgSO$_4$), filtered, concentrated and purified by column chromatography on silica gel (5% MeOH/CH$_2$Cl$_2$) to give the desired amine (0.10 g, 60%) as a white solid. $^1$H NMR (CDCl$_3$) δ 1.60 (m, 1H), 1.85 (m, 2H), 2.13 (m, 1H), 2.74 (m, 2H), 3.52 (d, 1H, J=13.5 Hz), 3.62 (d, 1H, J=13.5 Hz), 3.88 (d, 1H, J=16.5 Hz), 4.00 (m, 1H), 4.06 (d, 1H, J=16.5 Hz), 7.02 (s, 2H), 7.15–7.25 (m, 5H), 7.38 (d, 1H, J=7.8 Hz), 7.57 (m, 2H), 7.66 (d, 2H, J=8.1 Hz), 8.63 (d, 1H, J=4.2 Hz).

Using General Procedure D: Conversion of the solid from above (100 mg) to the hydrobromide salt gave AMD9716 (0.125 g) as a white solid. $^1$H NMR (D$_2$O) δ 1.87 (br m, 1H), 2.26 (m, 2H), 2.47 (br m, 1H), 3.05 (br m, 2H), 3.87 (d, 1H, J=12.6 Hz), 3.94 (d, 1H, J=12.9 Hz), 4.45 (d, 1H, J=16.2 Hz), 4.64 (d, 1H, J=16.2 Hz), 4.75 (m, 1H), 7.25 (dd, 2H, J=3.0, 6.0 Hz), 7.37 (s, 4H), 7.42 (s, 2H), 7.47 (dd, 2H, J=3.0, 6.0 Hz), 7.95 (t, 1H, J=8.4 Hz), 8.42 (d, 1H, J=8.1 Hz), 8.80 (d, 1H, J=5.7 Hz); $^{13}$C NMR (D$_2$O) δ 28.72, 29.38, 36.15, 58.51, 65.13, 71.86, 122.09 (2C), 128.20 (2C), 130.21, 134.22 (2C), 134.43 (3C), 138.98, 139.62 (2C), 148.16 (2C), 149.34 (2C), 156.51 (2C), 159.04, 159.98. ES-MS m/z 435 (M+H). Anal. Calcd. for C$_{27}$H$_{26}$N$_6$.3.2HBr.1.4H$_2$O: C, 45.61; H, 4.74; N, 11.34; Br, 34.64. Found: C, 45.61H, 4.81; N, 11.37; Br, 34.65.

Using General Procedure D: Conversion of the white foam (36 mg) to the hydrobromide salt, followed by re-precipitation of the intermediate solid from methanol/ether, gave AMD9841 (35 mg) as a white solid. $^1$H NMR (D$_2$O) δ 1.87–2.00 (m, 1H), 2.22–2.39 (m, 2H), 2.45–2.51 (m, 1H), 3.06–3.09 (m, 2H), 3.84–3.96 (m, 4H), 4.53 (d, 1H, J=16.5 Hz), 4.70 (d, 1H, J=16.5 Hz), 4.78–4.85 (m, 1H, overlaps with HOD), 6.26 (d, 1H, J=7.2 Hz), 6.96 (d, 2H, J=7.8 Hz), 7.31 (d, 2H, J=7.8 Hz), 7.34–7.43 (m, 3H), 7.51–7.55 (m, 2H), 7.60–7.64 (m, 2H), 7.96 (dd, 1H, J=6.0, 8.1 Hz), 8.44 (d, 1H, J=7.8 Hz), 8.79 (d, 1H, J=5.4 Hz); $^{13}$C NMR (D$_2$O) δ 20.50, 21.00, 27.90, 40.58, 50.45, 56.75, 63.43, 113.93, 126.12, 126.78, 128.91, 128.99, 129.14, 129.36, 130.05, 130.55, 130.57, 131.06, 135.97, 139.48, 139.71, 141.05, 141.20, 148.30, 150.94, 152.15; ES-MS m/z 474 (M+H). Anal. Calcd. for C$_{31}$H$_{31}$N$_5$.3.0 HBr.2.2 H$_2$O: C, 49.25; H, 5.12; N, 9.26; Br, 31.71. Found: C, 49.31; H, 5.21; N, 9.13; Br, 31.62.

EXAMPLE 95

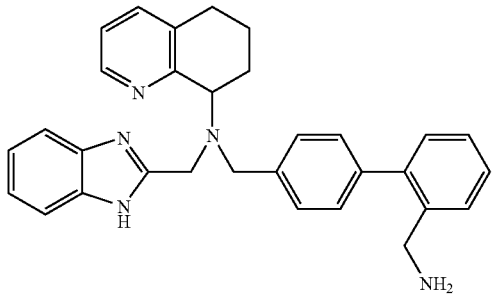

AMD 9841: Preparation of (2'-Aminomethyl-biphenyl-4-ylmethyl)-(1H-benzimidazol-2-ylmethyl)-(5,6,7,8-tetrahydro-quinolin-8-yl)-amine (hydrobromide salt)

Using the general alkylation procedure: To a solution of (1-tert-butoxycarbonyl-1H-Benzimidazol-2-ylmethyl)-(5,6,7,8-tetrahydro-quinolin-8-yl)-amine (0.194 g, 0.51 mmol) in CH$_3$CN (5 mL) was added N,N-diisopropylethylamine (0.30 mL, 1.72 mmol) followed by 4'-bromomethyl-2-cyanobiphenyl (0.303 g, 1.11 mmol) and the resultant mixture heated to 60° C. for 25 h. Purification of the crude material by column chromatography on silica gel (10:1:1 CH$_2$Cl$_2$—CH$_3$OH—NH$_4$OH) followed by radial chromatography on silica gel (2 mm plate, 100:1:1 CH$_2$Cl$_2$—CH$_3$OH—NH$_4$OH) provided a tan foam (79 mg).

The intermediate from above (79 mg, 0.14 mmol) was dissolved in NH$_3$ saturated methanol (3 mL) in a Parr hydrogenation bottle. Raney nickel (50 mg) was rinsed with MeOH (3×), transferred into the hydrogenation flask containing the nitrile and the mixture was hydrogenated at 50 psi for 24 h. The mixture was filtered through Celite® and the cake was washed with methanol. The eluant was concentrated under reduced pressure. Purification of the crude material by radial chromatography on silica gel (1 mm plate, 50:1:1 CH$_2$Cl$_2$—CH$_3$OH—NH$_4$OH) provided 36 mg (54%) of the free base of the title compound as a white foam.

EXAMPLE 96

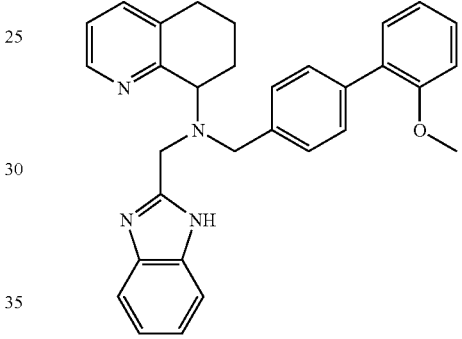

AMD9785: Preparation of (1H-Benzimidazol-2-ylmethyl)-(2'-methoxy-biphenyl-4-ylmethyl)-(5,6,7,8-tetrahydro-quinolin-8-yl)-amine (hydrobromide salt)

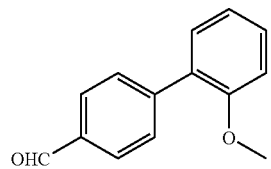

Preparation of 2'-methoxy-biphenyl-4-carboxaldehyde

To a stirred degassed solution of 4-bromobenzaldehyde (218 mg, 1.18 mmol) and 2-methoxybenzeneboronic acid (188 mg, 1.24 mmol) in DME/THF (5 mL, 4:1) were added a 2 M Na$_2$CO$_3$ solution (1.6 mL) and Pd(PPh$_3$)$_4$ (63 mg, 0.055 mmol). The reaction mixture was flushed with argon and maintained under argon while being heated at 85° C. overnight. The mixture was then cooled and diluted with EtOAc (25 mL) and water (25 mL). The aqueous layer was washed with EtOAc (2×10 mL) and the combined organic extracts dried (Na$_2$SO$_4$), filtered and concentrated. Purification of the resultant oil by column chromatography with silica gel (Hexanes/Et$_2$O, 80:20) afforded the title compound (230 mg, 92%) as a clear oil. $^1$H NMR (CDCl$_3$) δ 3.84 (s, 3H), 7.01–7.09 (m, 2H), 7.33–7.39 (m, 2H), 7.71 (d, 2H, J=6 Hz), 7.93 (d, 2H, J=6 Hz), 10.05 (s, 1H).

Using General Procedure B: To a stirred solution of (1-tert-butoxycarbonyl-1H-benzimidazol-2-ylmethyl)-(5,6,7,8-tetrahydro-quinolin-8-yl)-amine (95 mg, 0.25 mmol) and 2'-methoxy-biphenyl-4-carboxaldehyde (55 mg, 0.26 mmol) in CH$_2$Cl$_2$ (5 mL) was added NaBH(OAc)$_3$ (83 mg, 0.39 mmol) and the resultant mixture was stirred at room temperature overnight. Purification of the crude material by radial chromatography on silica gel gel (1 mm plate, 50:1:1 CH$_2$Cl$_2$/MeOH/NH$_4$OH) afforded the desired amine (75 mg, 52%) as a clear oil.

Using General Procedure D: Conversion of the oil from above (34 mg, 0.059 mmol) to the hydrobromide salt with simultaneous removal of the N-tert-butoxycarbonyl protecting group followed by re-precipitation of the intermediate solid from methanol/ether gave AMD9785 (25 mg, 63%) as a white solid. $^1$H NMR (D$_2$O) δ 1.89–1.94 (m, 1H), 2.20–2.27 (m, 2H), 2.31–2.44 (m, 1H), 3.03–3.05 (m, 2H), 3.68 (s, 3H), 3.76 (d, 1H, J=12.3 Hz), 3.84 (d, 1H, J=16.5 Hz), 4.63 (d, 1H, J=16.5 Hz), 4.74–4.89 (m, 1H, overlap with HOD), 6.36 (d, 1H), J=7.5 Hz), 6.96 (t, 1H, J=7.5 Hz), 7.02–7.05 (m, 3H), 7.19 (d, 2H, J=7.8 Hz), 7.33 (dd, 1H, J=8.1, 7.8 Hz), 7.44 (dd, 2H, J=6, 3 Hz), 7.56 (dd, 2H, J=6, 3 Hz), 7.93 (dd, 1H, J=7.2, 6.6 Hz), 8.40 (d, 1H, J=7.8 Hz), 8.76 (d, 1H, J=5.7 Hz); $^{13}$C NMR (D$_2$O) δ 19.71, 20.15, 27.08, 49.63, 55.13, 55.91, 62.54, 111.67, 113.02, 120.58, 125.29, 125.91; 128.68, 129.09, 129.32, 129.76, 130.34, 134.47, 137.26, 138.86, 140.17, 147.45, 150.22, 151.23, 155.17. ES-MS m/z 475 (M+H). Anal. Calcd. for C$_{31}$H$_{30}$N$_4$O2.1HBr.1.3H$_2$O: C, 55.74; H, 5.24; N, 8.39; Br, 25.12. Found: C, 55.67; H, 5.26; N, 8.27; Br, 25.30.

EXAMPLE 97

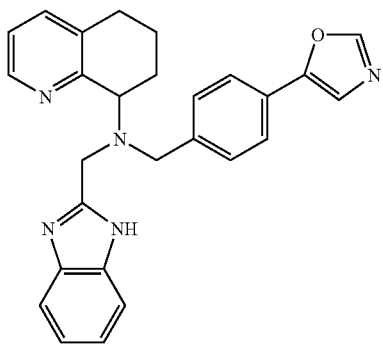

AMD9791: Preparation of (1H-Benzimidazol-2-ylmethyl)-(4-oxazol-5-yl-benzyl)-(5,6,7,8-tetrahydro-quinolin-8-yl)-amine (hydrobromide salt)

Preparation of 4-(oxazol-5-yl)benzaldehyde

To a stirred solution of the 4-(oxazol-5-yl)benzyl alcohol (prepared as described by Tanaka, A.; Terasawa, T.; Hagihara, H.; Sakuma, Y.; Ishibe, N.; Sawada, M.; Takasugi, H.; Tanaka, H. *J. Med. Chem.* 1998, 41, 2390–2410) (0.23 g, 1.31 mmol) in CH$_2$Cl$_2$/MeOH (20:1, 10.5 mL) was added activated MnO$_2$ (1.01 g, 11.6 mmol) and the mixture stirred at room temperature overnight. The reaction was then diluted with CH$_2$Cl$_2$ (10 mL) and filtered through Celite®, washing with CHCl$_3$. The filtrate was concentrated to give the crude aldehyde as a beige solid (0.164 g) which used without further purification in the next reaction. $^1$H NMR (CDCl$_3$) δ 7.52 (s, 1H), 7.82 (d, 2H, J=9 Hz), 7.95 (d, 2H, J=9 Hz), 7.99 (s, 1H), 10.02 (s, 1H).

Using General Procedure B: To a stirred solution of (1-tert-butoxycarbonyl-1H-benzimidazol-2-ylmethyl)-(5,6,7,8-tetrahydro-quinolin-8-yl)-amine (133 mg, 0.35 mmol) and 4-(oxazol-5-yl)benzaldehyde (80 mg, 0.45 mmol) in CH$_2$Cl$_2$ (10 mL) was added NaBH(OAc)$_3$ (107 mg, 0.50 mmol) and the resultant mixture was stirred at room temperature overnight. The resultant crude oil was dissolved in CH$_2$Cl$_2$/TFA (1:1, 2 mL) and the mixture stirred for 2 h. The reaction was then concentrated and diluted with CH$_2$Cl$_2$ (30 mL) and 1 N NaOH (30 mL). The aqueous layer was washed with CH$_2$Cl$_2$ (2×10 mL) and the combined organic extracts were dried (Na$_2$SO$_4$), filtered and concentrated. Purification of the crude foam by radial chromatography on silica gel gel (2 mm plate, 50:1:1 CH$_2$Cl$_2$/MeOH/NH$_4$OH) afforded the free amine (50 mg, 33% over 2 steps) as a yellow foam.

Using General Procedure D: Conversion of the foam from above (50 mg, 0.11 mmol) to the hydrobromide salt followed by re-precipitation of the intermediate solid from methanol/ether gave AMD9791 (70 mg, 87%) as a yellow solid. $^1$H NMR (D$_2$O) δ 1.86–1.90 (m, 1H), 2.16–2.27 (m, 2H), 2.38–2.43 (m, 1H), 2.99–3.02 (m, 2H), 3.60 (d, 1H, J=12.3 Hz), 3.76 (d, 1H, J=12.3 Hz), 4.38 (d, 1H, J=16.5 Hz), 4.57 (d, 1H, J=16.5 Hz), 4.72–4.79 (m, 1H, overlap with HOD), 7.12–7.19 (m, 5H), 7.23 (dd, 2H, J=6, 3 Hz), 7.43 (dd, 2H, J=6, 3 Hz), 7.92 (dd, 1H, 7.8, 5.7 Hz), 8.16 (s, 1H), 8.37 (d, 1H, J=7.2 Hz), 8.76 (d, 1H, J=5.7 Hz); $^{13}$C NMR (D$_2$O δ 20.43, 21.01, 27.83, 50.22, 56.66, 63.41, 113.62, 120.71, 124.26, 126.12, 126.36, 126.78, 130.44, 130.76, 137.01, 139.68, 140.96, 148.27, 150.79, 151.60, 152.13. ES-MS m/z 436 (M+H). Anal. Calcd. for C$_{27}$H$_{25}$N$_5$.2.8HBr.1.9H$_2$O: C, 46.57; H, 4.57; N, 10.06; Br, 32.13. Found: C, 46.56; H, 4.61; N, 9.73; Br, 32.14.

EXAMPLE 98

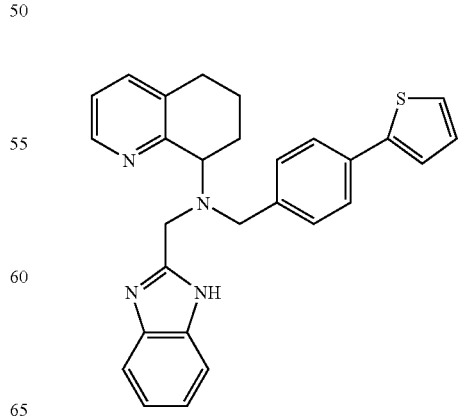

AMD9792: Preparation of (1H-Benzimidazol-2-ylmethyl)-(5,6,7,8-tetrahydro-guinolin-8-yl)-(4-thiophen-2-yl-benzyl)-amine (hydrobromide salt)

EXAMPLE 99

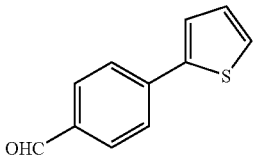

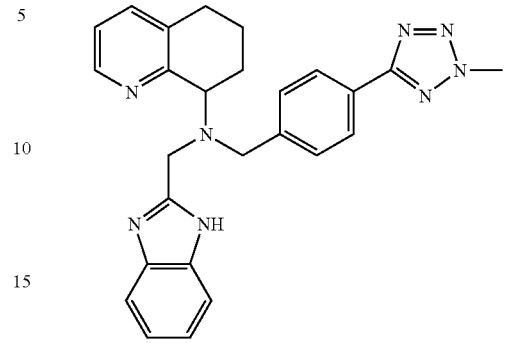

Preparation of 4-thiophen-2-yl-benzaldehyde

AMD9778: Preparation of (1H-Benzimidazol-2-ylmethyl)-[4-(2-methyl-2H-tetrazol-5-yl)-benzyl]-(5,6,7,8-tetrahydro-quinolin-8-yl)-amine (hydrobromide salt)

To a stirred degassed solution of 4-bromobenzaldehyde (371 mg, 2.00 mmol) and thiophene-2-boronic acid (287 mg, 2.24 mmol) in DME/THF (5 mL, 4:1) were added a 2 M $Na_2CO_3$ solution (3.0 mL) and $Pd(PPh_3)_4$ (110 mg, 0.095 mmol). The reaction mixture was flushed with argon and maintained under argon while being heated at 85° C. over 2 days. The mixture was then cooled and diluted with EtOAc (35 mL) and water (30 mL). The aqueous layer was washed with EtOAc (2×10 mL) and the combined organic extracts dried ($Na_2SO_4$), filtered and concentrated. Purification of the resultant oil by column chromatography on silica gel (Hexanes/EtOAc, 4:1) afforded the title compound (293 mg, 78%) as a yellow solid. $^1$H NMR ($CDCl_3$) δ 7.14 (dd, 1H, J=5.1, 3.6 Hz), 7.40 (dd, 1H, J=5.1, 0.9 Hz), 7.46 (dd, 1H, J=3.6, 0.9 Hz), 7.76 (d, 2H, J=8.4 Hz), 7.88 (d, 2H, J=8.4 Hz), 10.00 (s, 1H).

Using General Procedure B: To a stirred solution of (1H-benzimidazol-2-ylmethyl)-(5,6,7,8-tetrahydro-quinolin-8-yl)-amine (144 mg, 0.52 mmol) and 4-thiophen-2-yl-benzaldehyde (100 mg, 0.53 mmol) in $CH_2Cl_2$ (5 mL) was added $NaBH(OAc)_3$ (160 mg, 0.75 mmol) and the resultant mixture was stirred at room temperature overnight. Purification of the crude material by radial chromatography on silica gel gel (2 mm plate, 50:1:1 $CH_2Cl_2$/2MeOH/$NH_4OH$) afforded the desired amine (133 mg, 57%) as a yellow foam.

Using General Procedure D: Conversion of the foam from above (115 mg, 0.26 mmol) to the hydrobromide salt followed by re-precipitation of the intermediate solid from methanol/ether gave AMD9792 (134 mg, 82%) as a yellow solid. $^1$H NMR ($D_2O$) δ 1.73–1.77 (m, 1H), 2.00–2.11 (m, 2H), 2.24–2.28 (m, 1H), 2.84–2.88 (m, 2H), 3.12 (d, 1H, J=12.3 Hz), 3.45 (d, 1H, J=12.3 Hz), 4.20 (d, 1H, J=16.5 Hz), 4.37 (d, 1H, J=16.5 Hz), 4.46 (dd, 1H, J=10.2, 6 Hz), 6.85 (d, 2H, J=8.1 Hz), 6.90–6.97 (m, 4H), 7.17 (dd, 2H, J=6, 3 Hz), 7.26 (d, 1H, J=5.1 Hz), 7.37 (dd, 2H, J=6, 3 Hz), 7.84 (dd, 1H, J=7.8, 5.7 Hz), 8.25 (d, 1H, J=7.8 Hz), 8.66 (d, 1H, J=4.7 Hz); $^{13}$C NMR ($D_2O$) 620.39, 20.85, 27.77, 50.08, 56.18, 63.03, 113.58, 124.19, 125.34, 126.05, 126.12, 126.63, 128.72, 130.36, 130.67, 133.71, 135.22, 139.52, 140.76, 142.84, 148.28, 150.66, 151.42. ES-MS m/z 451 (M+H). Anal. Calcd. for $C_{28}H_{26}N_4Se2.0HBr.0.9H_2O$: C, 53.50; H, 4.78; N, 8.91; Br, 25.42. Found: C, 53.65; H, 4.98; N, 8.66; Br, 25.32.

To a stirred solution of 8-amino-5,6,7,8-tetrahydroquinoline (170 mg, 1.15 mmol) in dry MeOH (10 mL) was added 4-(2-methyl-2H-tetrazol-5-yl)benzaldehyde (prepared as described by Bold, G.; Fassler, A.; Capraro, H.-G.; Cozens, R.; Klimkait, T.; Lazdins, J.; Mestan, J.; Poncioni, B.; Rosel, J.; Stover, D.; Tintelnot-Blomley, M.; Acemoglu, F.; Beck, W.; Boss, E.; Eschbach, M.; Hurlimann, T.; Masso, E.; Roussel, S.; Ucci-Stoll, K.; Wyss, D.; Lang, M. *J. Med. Chem.* 1998, 41, 3387–3401) (220 mg, 1.17 mmol) and the mixture stirred for 1.5 h at room temperature. The initial yellow-orange suspension became a dark orange homogeneous solution after this time. The mixture was concentrated in vacuo, analyzed by $^1$H NMR and redissolved in MeOH (10 mL). To this solution was added $NaBH_4$ (85 mg, 2.25 mmol) and the mixture stirred for. 1 h. The reaction was concentrated in vacuo and diluted with $CH_2Cl_2$ (40 mL) and saturated aqueous sodium bicarbonate (40 mL). The aqueous phase was washed with $CH_2Cl_2$ (2×10 mL) and the combined organic extracts dried ($Na_2SO_4$), filtered and concentrated to afford an orange-brown oil (422 mg) which was used without purification in the next reaction.

Following the general alkylation procedure: To a stirred solution of the secondary amine from above (205 mg, 0.64 mmol) in $CH_3CN$ (5 mL) was added N,N-diisopropylethylamine (0.23 mL, 1.32 mmol), KI (24 mg, 0.14 mmol) and 1-(tert-butoxycarbonyl)-2-(chloromethyl)benzimidazole (165 mg, 0.62 mmol). The mixture was stirred at 60° C. for 3 h. Purification of the resultant brown oil by column chromatography on silica gel ($CH_2Cl_2$/MeOH, 98:2 then 96:4) followed by radial chromatography on silica gel gel (1 mm plate, $CH_2Cl_2$/MeOH, 98:2) afforded the desired alkylated amine (44 mg, 43% over 2 steps) as a brown foam.

Using General Procedure D: Conversion of the foam from above (44 mg, 0.08 mmol) to the hydrobromide salt with simultaneous removal of the N-tert-butoxycarbonyl protecting group followed by re-precipitation of the intermediate solid from methanol/ether gave AMD9778 (45 mg, 87%) as a pale brown solid. $^1$H NMR ($D_2O$) δ 1.89–1.94 (m, 1H), 2.19–2.27 (m, 2H), 2.43–2.47 (m, 1H), 3.03–3.05 (m, 2H), 3.72 (d, 1H, J=12.6 Hz), 3.84 (d, 1H, J=12.6 Hz), 4.35 (s, 2H), 4.43 (d, 1H, J=16.5 Hz), 4.61 (d, 1H, J=16.5 Hz), 4.79–4.89 (m, 1H, overlap with HOD), 7.15 (dd, 2H, J=6, 3 Hz), 7.24 (d, 2H, J=8.1 Hz), 7.41 (dd, 2H, J=6, 3 Hz), 7.46

(d, 2H, J=8.1 Hz), 7.95 (dd, 1H, J=7.5, 6.3 Hz), 8.41 (d, 1H, J=8.1 Hz), 8.79 (d, 1H, J=5.1 Hz); $^{13}$C NMR (D$_2$O δ 20.45, 21.07, 27.86, 40.01, 50.30, 56.78, 63.54, 113.67, 125.64, 126.18, 126.32, 126.42, 130.42, 130.91, 139.31, 139.75, 141.04, 148.33, 150.77, 151.62, 163.70. ES-MS m/z 451 (M+H). Anal. Calcd. for C$_{26}$H$_{26}$N$_8$·2.1HBr·1.5H$_2$O: C, 48.23; H, 4.84; N, 17.31; Br, 25.92. Found: C, 17.05; Br, 25.63.

EXAMPLE 100

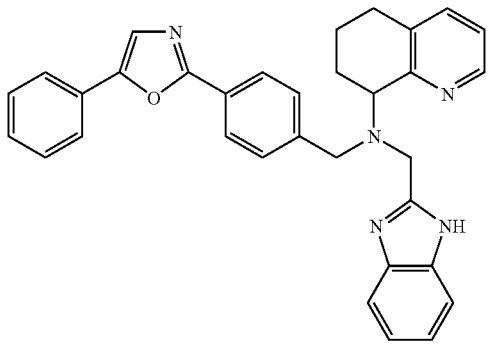

AMD9715: Preparation of (1H-Benzimidazol-2-ylmethyl)-[4-(5-phenyloxazol-2-yl)-benzyl]-(5,6,7,8-tetrahydroquinolin-8-yl)-amine Preparation of
Methyl-N-(2-oxo-2-phenylethyl)-terephthalamate To a solution of 2-aminoacetophenone (516 mg, 3.0 mmol) and triethylamine (0.84 mL, 6 mmol) in CH$_2$Cl$_2$ (20 mL) at 0° C. was added methyl-4-chlorocarbonyl-benzoate (594 mg, 3.0 mmol) dropwise over 10 min. The solution was then allowed to warm to room temperature and stirred for 90 min. The solution was washed with saturated aqueous NH$_4$Cl (20 mL) and the aqueous layer extracted with CH$_2$Cl$_2$ (2×10 mL). The combined organic extracts were dried (Na$_2$SO$_4$), filtered and concentrated in vacuo to afford the desired methyl-N-(2-oxo-2-phenylethyl)-terephalamate as pale yellow crystals (835 mg, 94%). $^1$H NMR (CDCl$_3$) δ 3.94 (s, 3H), 4.97 (d, 2H, J=5.4 Hz), 7.35 (br s, 1H), 7.50 (m, 2H), 7.53 (m, 1H), 7.92 (d, 2H, J=6.6 Hz), 8.04 (d, 2H, J=6.6 Hz), 8.11 (d, 2H, J=6.9 Hz).

Preparation of
methyl-4-(5-phenyloxazol-2-yl)-benzoate (as
Described by Wipf, P., Miller, C. P. *J. Org. Chem.*
1993, 58, 3604)

To a solution of triphenylphosphine (524 mg, 2.0 mmol) and triethylamine (0.56 mL, 4.0 mmol) in CH$_2$Cl$_2$ (10 mL) was added iodine (480 mg, 1.9 mmol) and the mixture stirred for 15 min. A solution of methyl-N-(2-oxo-2-phenylethyl)-terephalamate (297 mg, 1.0 mmol) in CH$_2$Cl$_2$ (5 mL) was added and the resultant mixture was stirred at room temperature overnight. The organic phase was washed with 5% aqueous sodium thiosulfate solution (1×15 mL) and saturated NaHCO$_3$ (1×15 mL) and then dried (Na$_2$SO$_4$), filtered and concentrated in vacuo. The resultant oily residue was purified by column chromatography on silica gel (1:1 Hexanes/EtOAc) to afford the desired product, methyl-4-(5-phenyloxazol-2-yl)-benzoate, as a yellow oil (69 mg, 24%). $^1$H NMR (CDCl$_3$) δ 3.86 (s, 3H), 7.20 (m, 1H), 7.23 (t, 1H, J=6.3 Hz), 7.41 (s, 1H), 7.64 (m, 2H), 8.04 (m, 4H). ES-MS m/z 280 (M+H).

To a solution of methyl-4-(5-phenyloxazol-2-yl)-benzoate (56 mg, 0.19 mmol) in CH$_2$Cl$_2$ (8 mL) at −78° C. was added DIBAL-H (1 mL of a 1.0 M solution in CH$_2$Cl$_2$, 1.0 mmol) and the solution stirred at −78° C. for 90 min. A saturated aqueous solution of sodium potassium tartrate (5 mL) was added to the reaction and the mixture allowed to warm to room temperature. The bi-phasic mixture was stirred rapidly for 60 min, the layers separated and the aqueous layer was extracted with CH$_2$Cl$_2$ (2×10 mL). The combined organic fractions were dried (Na$_2$SO$_4$), filtered and concentrated in vacuo to afford the desired alcohol, 2-(4-hydroxymethylphenyl)-5-phenyloxazole, as a pale yellow oil (46 mg, 96%). $^1$H NMR (CDCl$_3$) δ 3.41 (t, 1H (OH), J=7.0 Hz), 4.77 (d, 2H, J=7.0 Hz), 7.33 (m, 1H), 7.45 (m, 5H), 7.72 (d, 2H, J=6.4 Hz), 8.08 (d, 2H, J=8.1 Hz).

Following General Procedure C: To a solution of the alcohol from above (123 mg, 0.5 mmol) and triethylamine (0.105 mL, 0.75 mmol) in CH$_2$Cl$_2$ (8 mL) was added methanesulfonyl chloride (0.05 mL, 0.65 mmol) and the mixture stirred at room temperature for 10 min. The desired crude 2-(4-(methanesulfonatomethylphenyl))-5-phenyloxazole was obtained as a pale yellow oil and used directly without further purification in the next reaction.

Following the general alkylation procedure: To a solution of the mesylate from above (0.5 mmol) and (1-tert-butoxycarbonyl-1H-Benzimidazol-2-ylmethyl)-(5,6,7,8-tetrahydro-quinolin-8-yl)-amine (264 mg, 0.7 mmol) in CH$_3$CN (8 mL) was added N,N-diisopropylethylamine (0.145 mL, 0.8 mmol) and potassium iodide (8 mg, 0.05 mmol) and the resultant mixture heated to 60° C. overnight. The crude residue was purified by column chromatography on silica gel (CH$_2$Cl$_2$/MeOH, 95:5) to afford the desired tertiary amine, (1H-1-tert-butoxycarbonyl-benzimidazol-2-ylmethyl)-[4-(5-phenyloxazol-2-yl)-benzyl]-(5,6,7,8-tetrahydroquinolin-8-yl)-amine, as a pale yellow foam (209 mg, 68%). $^1$H NMR (CDCl$_3$) δ 1.63 (s, 9H), 2.01 (m, 2H), 2.26 (m, 1H), 2.69–2.82 (m, 3H), 3.83 (d, 1H, J=16.1 Hz), 4.05 (d, 1H, J=16.1 Hz), 4.32 (m, 1H), 4.69 (s, 2H), 7.12 (m, 1H), 7.15–7.20 (m, 3H), 7.33–7.46 (m, 6H), 7.58–7.73 (m, 6H), 8.44 (d, 1H, J=4.9 Hz). ES-MS m/z 612 (M+H).

Using General Procedure D: Conversion of the foam from above (31 mg, 0.05 mmol) to the hydrobromide salt followed by re-precipitation of the intermediate solid from methanol/ether gave AMD9715 (28 mg) as a white solid. $^1$H NMR (D$_2$O) δ 1.93 (m, 1H), 2.07 (m, 2H), 2.40 (m, 1H), 3.05 (m, 2H), 3.37 (m, 1H), 3.56 (m, 1H), 4.35 (d, 1H, J=16.5 Hz), 4.58 (d, 1H, J=16.5 Hz), 4.77 (m, 1H), 7.04 (m, 4H), 7.30–7.37 (m, 6H), 7.49 (t, 2H, J=7.2 Hz), 7.64 (m, 2H), 7.92 (dd, 1H, J=7.8, 5.4 Hz), 8.44 (d, 1H, J=7.8 Hz), 8.77 (d, 1H, J=5.4 Hz); $^{13}$C NMR (D$_2$O) δ 21.93, 22.13, 29.24, 50.89, 57.87, 63.37, 115.13 (2C), 124.32, 125.65 (2C), 127.33, 127.43 (2C), 127.83 (2C), 128.11, 130.40, 130.60 (2C), 132.33 (2C), 133.04, 140.22, 141.84, 144.99, 147.24, 149.33, 153.14, 154.87. ES-MS m/z 512 (M+H). Anal. Calcd. for C$_{33}$H$_{29}$N$_5$O·2.8HBr·2H$_2$O: C, 51.20; H, 4.66; N, 9.05; Br, 28.90. Found: C, 51.16; H, 4.59; N, 8.87; Br, 28.76.

EXAMPLE 101

Inhibition of Chemokine Induced Ca Flux Measured on a FLIPR (Molecular Devices) Reagents:

Loading dye: Fluo-3, AM (Molecular Probes F-1241) is dissolved in anhydrous DMSO and stored frozen in aliquots. To increase the solubility of the dye in the loading medium, 10% (w/v) pluronic acid (Molecular Probes F-127) is added to the Fluo-3 stock solution immediately before use.

Flux Buffer:

HBSS+20 mM Hepes buffer+0.2% BSA, pH 7.4. HBSS 10× [(w/o phenol red and sodium bicarbonate (Gibco 14 065-049)]; Hepes buffer 1M (Gibco 15 630-056), BSA (Sigma A3675). The flux buffer is vacuum-filtered and stored refrigerated for a maximum of 5 days. Before use in the experiment, the buffer is warmed at 37° C. in a waterbath.

Antagonists:

The test compounds were diluted in flux buffer and added to 4 wells of a black microplate (4 parallel measurements per compound). The following control wells were used: 100% response control (no inhibition), flux buffer was added; 100% inhibition control: chemokine was added at 5-times the concentration required to induce a Ca flux.

Preparation of the Agonist (Chemokine) Plate

The chemokines are diluted in flux buffer to concentrations that are 4-fold higher than the desired concentrations required for stimulation of the cells (i.e. 2.5 nM for SDF-1α). The chemokines were added to untreated 96-well Sero well compound plates (International Medical, Sterilin code 611F96). In the negative control well's (baseline monitoring), flux buffer is added instead of chemokine. As a positive control to check for dye loading efficiency, 20 μM digitonin (final concentration) was also included. The agonist plate was incubated in the FLIPR (37° C.) for 15–30 min.

Cell Loading Protocol for Measuring Inhibition of SDF-1α Induced Ca Flux in SUP-T1 Cells.

SUP-T1 cells were centrifuged at room temperature (RT) and re-suspended in loading medium (RPMI-1640 containing 2% FBS and 4 μM Fluo-3, AM). The cells were incubate at room temperature for 45 min. then washed twice in flux buffer then incubated in flux buffer at room temperature for 10 min. The cells were centrifuged and re-suspended in flux buffer at a density of $3\times10^6$ cells per mL. A 100 μL aliquot of the cell suspension ($3\times10^5$ cells) was added to each well of a black microplate (Costar 3603), which already contains 50 μL of a solution of the test compound (at concentrations that are 3-fold higher than the desired final compound concentrations). The microplate is then gently centrifuged at room temperature. Homogeneous spreading of the cells on the bottom of the microplate wells was then confirmed with a microscope and the microplate was incubated in the FLIPR (37° C.) for 10 min. prior to testing.

Fluorescence Measurements as a Function of Time on the FLIPR

The FLIPR settings (camera exposure time and laser power) are adjusted to obtain initial fluorescence values between 8,000 and 10,000 units. After monitoring a 20 second-baseline, the agonist (chemokine) (50 μL) is added by automatic pipettor with black pipette tips. Fluorescence is measured simultaneously in all wells of the microplate every 2 seconds (first 2 min) and thereafter every 6 seconds (additional 2 min). The average ca-flux measured in each set of 4 identical wells (one test compound) was calculated by the FLIPR software.

Using the above method, the compounds of the current invention were found to inhibit SDF-1α induced Ca flux in SUP-T1 cells between 0–100% at a fixed concentration of 5 μg/mL.

EXAMPLE 102

Assay for Inhibition of HIV-1 (NL4.3) Replication in MT-4 Cells

Inhibition of HIV-1 NL4.3 (or III$_B$) replication assays were performed as previously described (Bridger et al. J. Med. Chem. 1999, 42, 3971–3981; De Clercq et al. Proc. Natl. Acad. Sci, 1992, 89, 5286–5290; De Clercq et al. Antimicrob. Agents Chemother. 1994, 38, 668–674; Bridger et al. J. Med. Chem. 1995, 38, 366–378). Anti-HIV activity and cytotoxicity measurements were carried out in parallel. They were based on the viability of MT-4 cells that had been infected with HIV in the presence of various concentrations of the test compounds. After the MT-4 cells were allowed to proliferate for 5 days, the number of viable cells was quantified by a tetrazolium-based colorimetric 3-(4,5-dimethylthiazol-2-yl)-2,5-diphenyltetrazolium bromide (MTT) procedure in 96-well microtrays. In all of these assays, viral input (viral multiplicity of infection, MOI) was 0.01, or 100 times the 50% cell culture infective dose (CCID$_{50}$). The EC$_{50}$ was defined as the concentration required to protect 50% of the virus-infected cells against viral cytopathicity.

When compounds of the current invention were tested for inhibition of HIV-1 NL4.3 or III$_B$ replication in MT-4 cells, they were found to exhibit EC$_{50}$'s of 0.002–20.0 μg/mL.

The following compounds of Formula 1 are also prepared in a similar manner to those set forth above:

(4-Aminomethyl-pyridin-3-ylmethyl)-(1H-benzoimidazol-2-ylmethyl)-(5,6,7,8-tetrahydro-quinolin-8-yl)-amine (3-Aminomethyl-pyridin-4-ylmethyl)-(1H-benzoimidazol-2-ylmethyl)-(5,6,7,8-tetrahydro-quinolin-8-yl)-amine 1-(3-Aminomethyl-4-{[(1H-benzoimidazol-2-ylmethyl)-(5,6,7,8-tetrahydro-quinolin-8-yl)-amino]-methyl}-phenyl)-ethanone 1-(5-Aminomethyl-2-{[(1H-benzoimidazol-2-ylmethyl)-(5,6,7,8-tetrahydro-quinolin-8-yl)-amino]-methyl}-phenyl)-ethanone 3-Aminomethyl-4-{[(1H-benzoimidazol-2-ylmethyl)-(5,6,7,8-tetrahydro-quinolin-8-yl)-amino]-methyl}-benzenesulfonamide 5-Aminomethyl-2-{[(1H-benzoimidazol-2-ylmethyl)-(5,6,7,8-tetrahydro-quinolin-8-yl)-amino]-methyl}-benzenesulfonamide N-(3-Aminomethyl-4-{[(1H-benzoimidazol-2-ylmethyl)-(5,6,7,8-tetrahydro-quinolin-8-yl)-amino]-methyl}-benzyl)-hydroxylamine N-(5-Aminomethyl-2-{[(1H-benzoimidazol-2-ylmethyl)-(5,6,7,8-tetrahydro-quinolin-8-yl)-amino]-methyl}-benzyl)-hydroxylamine N-(3-Aminomethyl-4-{[(1H-benzoimidazol-2-ylmethyl)-(5,6,7,8-tetrahydro-quinolin-8-yl)-amino]-methyl}-benzyl)-O-methyl-hydroxylamine N-(5-Aminomethyl-2-{[(1H-benzoimidazol-2-ylmethyl)-(5,6,7,8-tetrahydro-quinolin-8-yl)-amino]-methyl}-benzyl)-O-methyl-hydroxylaamine (4-Aminomethyl-2-methoxymethyl-benzyl)-(1H-benzoimidazol-2-ylmethyl)-(5,6,7,8-tetrahydro-quinolin-8-yl)-amine (2-Aminomethyl-4-methoxymethyl-benzyl)-(1H-benzoimidazol-2-ylmethyl)-(5,6,7,8-tetrahydro-quinolin-8-yl)-amine N-(2-{[(1H-Benzoimidazol-2-ylmethyl)-(5,6,7,8-tetrahydro-quinolin-8-yl)-amino]-methyl}-benzyl)-formamide N-(4-{[(1H-Benzoimidazol-2-ylmethyl)-(5,6,7,8-tetrahydro-quinolin-8-yl)-amino]-methyl}-benzyl)-formamide N-(2-{[(1H-Benzoimidazol-2-ylmethyl)-(5,6,7,8-tetrahydro-quinolin-8-yl)-amino]-methyl}-benzyl)-hydroxylamine (1H-Benzoimidazol-2-ylmethyl)-(2,6-bis-aminomethyl-benzyl)-(5,6,7,8-tetrahydro-quinolin-8-yl)-amine (3-Aminomethyl-2-{[(1H-benzoimidazol-2-ylmethyl)-(5,6,7,8-tetrahydro-quinolin-8-yl)-amino]-methyl}-phenyl)-methanol (2-Aminomethyl-6-methoxymethyl-benzyl)-(1H-benzoimidazol-2-ylmethyl)-(5,6,7,8-tetrahydro-quinolin-8-yl)-amine N-(3-Aminomethyl-2-{[(1H-benzoimidazol-2-ylmethyl)-(5,6,7,8-tetrahydro-quinolin-8-yl)-amino]-methyl}-benzyl)-hydroxyl amine N-(3-Aminomethyl-2-{[(1H-benzoimidazol-2-ylmethyl)-(5,6,7,8-tetrahydro-quinolin-8-yl)-amino]-methyl}-benzyl)-O-methyl-hydroxylamine

[2-Aminomethyl-4-(1H-imidazol-2-yl)-benzyl]-(1H-benzoimidazol-2-ylmethyl)-(5,6,7,8-tetrahydro-quinolin-8-yl)-amine

[2-Aminomethyl-4-(1-methyl-1H-imidazol-2-yl)-benzyl]-(1H-benzoimidazol-2-ylmethyl)-(5,6,7,8-tetrahydro-quinolin-8-yl)-amine

[2-Aminomethyl-4-(2H-pyrazol-3-yl)-benzyl]-(1H-benzoimidazol-2-ylmethyl)-(5,6,7,8-tetrahydro-quinolin-8-yl)-amine

[2-Aminomethyl-4-(1-methyl-1H-pyrazol-3-yl)-benzyl]-(1H-benzoimidazol-2-ylmethyl)-(5,6,7,8-tetrahydro-quinolin-8-yl)-amine

[2-Aminomethyl-4-(1H-[1,2,4]triazol-3-yl)-benzyl]-(1H-benzoimidazol-2-ylmethyl)-(5,6,7,8-tetrahydro-quinolin-8-yl)-amine

[2-Aminomethyl-4-(1-methyl-1H-[1,2,4]triazol-3-yl)-benzyl]-(1H-benzoimidazol-2-ylmethyl)-(5,6,7,8-tetrahydro-quinolin-8-yl)-amine (2-Aminomethyl-4-oxazol-2-yl-benzyl)-(1H-benzoimidazol-2-ylmethyl)-(5,6,7,8-tetrahydro-quinolin-8-yl)-amine (2-Aminomethyl-4-furan-2-yl-benzyl)-(1H-benzoimidazol-2-ylmethyl)-(5,6,7,8-tetrahydro-quinolin-8-yl)-amine

[2-Aminomethyl-4-(tetrahydro-furan-2-yl)-benzyl]-(1H-benzoimidazol-2-ylmethyl)-(5,6,7,8-tetrahydro-quinolin-8-yl)-amine (2-Aminomethyl-4-thiazol-2-yl-benzyl)-(1H-benzoimidazol-2-ylmethyl)-(5,6,7,8-tetrahydro-quinolin-8-yl)-amine

[2-Aminomethyl-4-(1H-tetrazol-5-yl)-benzyl]-(1H-benzoimidazol-2-ylmethyl)-(5,6,7,8-tetrahydro-quinolin-8-yl)-amine

[2-Aminomethyl-4-(2-methyl-2H-tetrazol-5-yl)-benzyl]-(1H-benzoimidazol-2-ylmethyl)-(5,6,7,8-tetrahydro-quinolin-8-yl)-amine (2-Aminomethyl-4-pyridin-2-yl-benzyl)-(1H-benzoimidazol-2-ylmethyl)-(5,6,7,8-tetrahydro-quinolin-8-yl)-amine (2-Aminomethyl-4-piperidin-2-yl-benzyl)-(1H-benzoimidazol-2-ylmethyl)-(5,6,7,8-tetrahydro-quinolin-8-yl)-amine (4-Aminomethyl-3-{[(1H-benzoimidazol-2-ylmethyl)-(5,6,7,8-tetrahydro-quinolin-8-yl)-amino]-methyl}-phenyl)-methanol (2-Aminomethyl-5-methoxymethyl-benzyl)-(1H-benzoimidazol-2-ylmethyl)-(5,6,7,8-tetrahydro-quinolin-8-yl)-amine (4-Aminomethyl-5-{[(1H-benzoimidazol-2-ylmethyl)-(5,6,7,8-tetrahydro-quinolin-8-yl)-amino]-methyl}-pyridin-2-yl)-methanol (4-Aminomethyl-6-methoxymethyl-pyridin-3-ylmethyl)-(1H-benzoimidazol-2-ylmethyl)-(5,6,7,8-tetrahydro-quinolin-8-yl)-amine (1H-Benzoimidazol-2-ylmethyl)-(4,6-bis-aminomethyl-pyridin-3-ylmethyl)-(5,6,7,8-tetrahydro-quinolin-8-yl)-amine (4-Allylaminomethyl-2-aminomethyl-benzyl)-(1H-benzoimidazol-2-ylmethyl)-(5,6,7,8-tetrahydro-quinolin-8-yl)-amine (2-Allylaminomethyl-4-aminomethyl-benzyl)-(1H-benzoimidazol-2-ylmethyl)-(5,6,7,8-tetrahydro-quinolin-8-yl)-amine (2-Aminomethyl-4-cyclopropylaminomethyl-benzyl)-(1H-benzoimidazol-2-ylmethyl)-(5,6,7,8-tetrahydro-quinolin-8-yl)-amine (4-Aminomethyl-2-cyclopropylaminomethyl-benzyl)-(1H-benzoimidazol-2-ylmethyl)-(5,6,7,8-tetrahydro-quinolin-8-yl)-amine (2-Aminomethyl-5-chloro-benzyl)-(1H-benzoimidazol-2-ylmethyl)-(5,6,7,8-tetrahydro-quinolin-8-yl)-amine (2-Aminomethyl-5-bromo-benzyl)-(1H-benzoimidazol-2-ylmethyl)-(5,6,7,8-tetrahydro-quinolin-8-yl)-amine (2-Aminomethyl-5-nitro-benzyl)-(1H-benzoimidazol-2-ylmethyl)-(5,6,7,8-tetrahydro-quinolin-8-yl)-amine 4-Aminomethyl-3-{[(1H-benzoimidazol-2-ylmethyl)-(5,6,7,8-tetrahydro-quinolin-8-yl)-amino]-methyl}-benzonitrile (5-Amino-2-aminomethyl-benzyl)-(1H-benzoimidazol-2-ylmethyl)-(5,6,7,8-tetrahydro-quinolin-8-yl)-amine (2-Aminomethyl-5-trifluoromethyl-benzyl)-(1H-benzoimidazol-2-ylmethyl)-(5,6,7,8-tetrahydro-quinolin-8-yl)-amine (2-Aminomethyl-4-fluoro-benzyl)-(1H-benzoimidazol-2-ylmethyl)-(5,6,7,8-tetrahydro-quinolin-8-yl)-amine (2-Aminomethyl-4-chloro-benzyl)-(1H-benzoimidazol-2-ylmethyl)-(5,6,7,8-tetrahydro-quinolin-8-yl)-amine (2-Aminomethyl-4-bromo-benzyl)-(1H-benzoimidazol-2-ylmethyl)-(5,6,7,8-tetrahydro-quinolin-8-yl)-amine (2-Aminomethyl-4-nitro-benzyl)-(1H-benzoimidazol-2-ylmethyl)-(5,6,7,8-tetrahydro-quinolin-8-yl)-amine 3-Aminomethyl-4-{[(1H-benzoimidazol-2-ylmethyl)-(5,6,7,8-tetrahydro-quinolin-8-yl)-amino]-methyl}-benzonitrile (4-Amino-2-aminomethyl-benzyl)-(1H-benzoimidazol-2-ylmethyl)-(5,6,7,8-tetrahydro-quinolin-8-yl)-amine (2-Aminomethyl-4-trifluoromethyl-benzyl)-(1H-benzoimidazol-2-ylmethyl)-(5,6,7,8-tetrahydro-quinolin-8-yl)-amine (4-Aminomethyl-2-fluoro-benzyl)-(1H-benzoimidazol-2-ylmethyl)-(5,6,7,8-tetrahydro-quinolin-8-yl)-amine (4-Aminomethyl-2-chloro-benzyl)-(1H-benzoimidazol-2-ylmethyl)-(5,6,7,8-tetrahydro-quinolin-8-yl)-amine (4-Aminomethyl-2-bromo-benzyl)-(1H-benzoimidazol-2-ylmethyl)-(5,6,7,8-tetrahydro-quinolin-8-yl)-amine (4-Aminomethyl-2-nitro-benzyl)-(1H-benzoimidazol-2-ylmethyl)-(5,6,7,8-tetrahydro-quinolin-8-yl)-amine
5-Aminomethyl-2-{[(1H-benzoimidazol-2-ylmethyl)-(5,6,7,8-tetrahydro-quinolin-8-yl)-amino]-methyl}-benzonitrile
(2-Amino-4-aminomethyl-benzyl)-(1H-benzoimidazol-2-ylmethyl)-(5,6,7,8-tetrahydro-quinolin-8-yl)-amine
(4-Aminomethyl-2-trifluoromethyl-benzyl)-(1H-benzoimidazol-2-ylmethyl)-(5,6,7,8-tetrahydro-quinolin-8-yl)-amine
(5-Aminomethyl-thiophen-2-ylmethyl)-(1H-benzoimidazol-2-ylmethyl)-(5,6,7,8-tetrahydro-quinolin-8-yl)-amine
(4-Aminomethyl-thiophen-3-ylmethyl)-(1H-benzoimidazol-2-ylmethyl)-(5,6,7,8-tetrahydro-quinolin-8-yl)-amine
(4-Aminomethyl-furan-3-ylmethyl)-(1H-benzoimidazol-2-ylmethyl)-(5,6,7,8-tetrahydro-quinolin-8-yl)-amine
(4-Aminomethyl-1H-pyrrol-3-ylmethyl)-(1H-benzoimidazol-2-ylmethyl)-(5,6,7,8-tetrahydro-quinolin-8-yl)-amine
(4-Aminomethyl-1-methyl-1H-pyrrol-3-ylmethyl)-(1H-benzoimidazol-2-ylmethyl)-(5,6,7,8-tetrahydro-quinolin-8-yl)-amine
(4-Aminomethyl-1H-pyrazol-3-ylmethyl)-(1H-benzoimidazol-2-ylmethyl)-(5,6,7,8-tetrahydro-quinolin-8-yl)-amine
(4-Aminomethyl-1-methyl-1H-pyrazol-3-ylmethyl)-(1H-benzoimidazol-2-ylmethyl)-(5,6,7,8-tetrahydro-quinolin-8-yl)-amine
(3-Aminomethyl-1H-pyrazol-4-ylmethyl)-(1H-benzoimidazol-2-ylmethyl)-(5,6,7,8-tetrahydro-quinolin-8-yl)-amine
(3-Aminomethyl-1-methyl-1H-pyrazol-4-ylmethyl)-(1H-benzoimidazol-2-ylmethyl)-(5,6,7,8-tetrahydro-quinolin-8-yl)-amine
(5-Aminomethyl-3H-imidazol-4-ylmethyl)-(1H-benzoimidazol-2-ylmethyl)-(5,6,7,8-tetrahydro-quinolin-8-yl)-amine
(5-Aminomethyl-1-methyl-1H-imidazol-4-ylmethyl)-(1H-benzoimidazol-2-ylmethyl)-(5,6,7,8-tetrahydro-quinolin-8-yl)-amine
(5-Aminomethyl-thiazol-4-ylmethyl)-(1H-benzoimidazol-2-ylmethyl)-(5,6,7,8-tetrahydro-quinolin-8-yl)-amine
(5-Aminomethyl-pyrimidin-4-ylmethyl)-(1H-benzoimidazol-2-ylmethyl)-(5,6,7,8-tetrahydro-quinolin-8-yl)-amine
(5-Aminomethyl-pyridazin-4-ylmethyl)-(1H-benzoimidazol-2-ylmethyl)-(5,6,7,8-tetrahydro-quinolin-8-yl)-amine
(5-Allylaminomethyl-2-{[(1H-benzoimidazol-2-ylmethyl)-(5,6,7,8-tetrahydro-quinolin-8-yl)-amino]-methyl}-phenyl)-methanol
(3-Allylaminomethyl-4-{[(1H-benzoimidazol-2-ylmethyl)-(5,6,7,8-tetrahydro-quinolin-8-yl)-amino]-methyl}-phenyl)-methanol
(4-Allylaminomethyl-2-methoxymethyl-benzyl)-(1H-benzoimidazol-2-ylmethyl)-(5,6,7,8-tetrahydro-quinolin-8-yl)-amine
(3-Allylaminomethyl-4-methoxymethyl-benzyl)-(1H-benzoimidazol-2-ylmethyl)-(5,6,7,8-tetrahydro-quinolin-8-yl)-amine
(2-{[(1H-Benzoimidazol-2-ylmethyl)-(5,6,7,8-tetrahydro-quinolin-8-yl)-amino]-methyl}-5-cyclopropylaminomethyl-phenyl)-methanol
(4-{[(1H-Benzoimidazol-2-ylmethyl)-(5,6,7,8-tetrahydro-quinolin-8-yl)-amino]-methyl}-3-cyclopropylaminomethyl-phenyl)-methanol
(1H-Benzoimidazol-2-ylmethyl)-(4-cyclopropylaminomethyl-2-methoxymethyl-benzyl)-(5,6,7,8-tetrahydro-quinolin-8-yl)-amine
(1H-Benzoimidazol-2-ylmethyl)-(2-cyclopropylaminomethyl-4-methoxymethyl-benzyl)-(5,6,7,8-tetrahydro-quinolin-8-yl)-amine
5-Aminomethyl-2-{[(1H-benzoimidazol-2-ylmethyl)-(5,6,7,8-tetrahydro-quinolin-8-yl)-amino]-methyl}-benzamide
5-Aminomethyl-2-{[(1H-benzoimidazol-2-ylmethyl)-(5,6,7,8-tetrahydro-quinolin-8-yl)-amino]-methyl}-N-hydroxy-benzamide
5-Aminomethyl-2-{[(1H-benzoimidazol-2-ylmethyl)-(5,6,7,8-tetrahydro-quinolin-8-yl)-amino]-methyl}-benzoic acid hydrazide
5-Aminomethyl-2-{[(1H-benzoimidazol-2-ylmethyl)-(5,6,7,8-tetrahydro-quinolin-8-yl)-amino]-methyl}-benzoic acid
(1H-Benzoimidazol-2-ylmethyl)-(2,4-bis-allylaminomethyl-benzyl)-(5,6,7,8-tetrahydro-quinolin-8-yl)-amine
(4-Allylaminomethyl-2-cyclopropylaminomethyl-benzyl)-(1H-benzoimidazol-2-ylmethyl)-(5,6,7,8-tetrahydro-quinolin-8-yl)-amine
(2-Allylaminomethyl-4-cyclopropylaminomethyl-benzyl)-(1H-benzoimidazol-2-ylmethyl)-(5,6,7,8-tetrahydro-quinolin-8-yl)-amine
(1H-Benzoimidazol-2-ylmethyl)-(2,4-bis-cyclopropylaminomethyl-benzyl)-(5,6,7,8-tetrahydro-quinolin-8-yl)-amine
(2-Aminomethyl-4-propyl-benzyl)-(1H-benzoimidazol-2-ylmethyl)-(5,6,7,8-tetrahydro-quinolin-8-yl)-amine
(4-Allyl-2-aminomethyl-benzyl)-(1H-benzoimidazol-2-ylmethyl)-(5,6,7,8-tetrahydro-quinolin-8-yl)-amine
Acetic acid 3-aminomethyl-4-{[(1H-benzoimidazol-2-ylmethyl)-(5,6,7,8-tetrahydro-quinolin-8-yl)-amino]-methyl}-benzyl ester
Acetic acid 5-aminomethyl-2-{[(1H-benzoimidazol-2-ylmethyl)-(5,6,7,8-tetrahydro-quinolin-8-yl)-amino]-methyl}-benzyl ester
Acetic acid 4-{[(1H-benzoimidazol-2-ylmethyl)-(5,6,7,8-tetrahydro-quinolin-8-yl)-amino]-methyl}-3-cyclopropylaminomethyl-benzyl ester
Acetic acid 2-{[(1H-benzoimidazol-2-ylmethyl)-(5,6,7,8-tetrahydro-quinolin-8-yl)-amino]-methyl}-5-cyclopropylaminomethyl-benzyl ester
Acetic acid 3-allylaminomethyl-4-{[(1H-benzoimidazol-2-ylmethyl)-(5,6,7,8-tetrahydro-quinolin-8-yl)-amino]-methyl}-benzyl ester
Acetic acid 5-allylaminomethyl-2-{[(1H-benzoimidazol-2-ylmethyl)-(5,6,7,8-tetrahydro-quinolin-8-yl)-amino]-methyl}-benzyl ester
5-Aminomethyl-2-{[(1H-benzoimidazol-2-ylmethyl)-(5,6,7,8-tetrahydro-quinolin-8-yl)-amino]-methyl}-benzaldehyde oxime
3-Aminomethyl-4-{[(1H-benzoimidazol-2-ylmethyl)-(5,6,7,8-tetrahydro-quinolin-8-yl)-amino]-methyl}-benzaldehyde oxime
N-(5-Aminomethyl-2-{[(1H-benzoimidazol-2-ylmethyl)-(5,6,7,8-tetrahydro-quinolin-8-yl)-amino]-methyl}-benzyl)-acetamide
N-(3-Aminomethyl-4-{[(1H-benzoimidazol-2-ylmethyl)-(5,6,7,8-tetrahydro-quinolin-8-yl)-amino]-methyl}-benzyl)-acetamide N-(3-(Acetylamino-methyl)-4-{[(1H-benzoimidazol-2-ylmethyl)-(5,6,7,8-tetrahydro-quinolin-8-yl)-amino]-methyl}-benzyl)-acetamide N-(2-{[(1H-Benzoimidazol-2-ylmethyl)-(5,6,7,8-tetrahydro-quinolin-8-yl)-amino]-methyl}-benzyl)-acetamide (6-Aminomethyl-1,3-dihydro-isobenzofuran-5-ylmethyl)-(1H-benzoimidazol-2-ylmethyl)-(5,6,7,8-tetrahydro-quinolin-8-yl)-amine (4-Aminomethyl-1,3-dihydro-isobenzofuran-5-ylmethyl)-(1H-benzoimidazol-2-ylmethyl)-(5,6,7,8-tetrahydro-quinolin-8-yl)-amine (7-Aminomethyl-1,3-dihydro-isobenzofuran-4-ylmethyl)-(1H-benzoimidazol-2-ylmethyl)-(5,6,7,8-tetrahydro-quinolin-8-yl)-amine

The invention claimed is:

1. A compound of the formula (1)

and the salts thereof
wherein
$R^1$ is selected from halo, substituted or unsubstituted alkyl, substituted or unsubstituted hydroxyl, substituted or unsubstituted amino, substituted or unsubstituted thiol, and substituted or unsubstituted acyl;
k is 0–3;
each n is independently 0 or 1;
each R is independently H or alkyl (1–6C);
W is pyridyl, oxazolyl, or imidazolyl; wherein W is optionally substituted with $Y_j$;
j is 0–3;
each Y is benzyl, halo, or
–$(CR_2)_m NR^5{}_2$;
wherein R is H or alkyl (1–6C), m is independently 0–4, and each $R^5$ is independently H, alkyl (1–6C), alkenyl (2–6C), alkynyl (2–6C), or acyl (1–6C), each optionally substituted by one or more nonaromatic, nonheterocyclic substituent(s) and a indicates the linker between Ring A and N and b indicates the linker between ring E and the N.

2. The compound of claim 1, wherein E comprises a pi bond coupled to one N.

3. The compound of claim 1, wherein k is 0–1.

4. The compound of claim 1, wherein one of $(CR_2)^a{}_n$ and $(CR_2)^b{}_n$ is $CH_2$ and the other is a bond.

5. The compound of claim 4, wherein $(CR_2)^a{}_n$ is a bond and $(CR_2)^b{}_n$ is $CH_2$.

6. The compound of claim 1, wherein W is optionally substituted with benzyl, halo, or $(CR_2)_m$—$NH_2$ where m=0–1.

7. The compound of claim 1, wherein said compound is selected from the group consisting of (1H-benzimidazol-2-ylmethyl)-(5,6,7,8-tetrahydroquinolin-8-yl)-[(1-benzyl-2-aminomethyl)-imidazol-5-ylmethyl)]-amine;
6-aminomethylpyridin-3-ylmethyl-(1H-benzimidazol-2-ylmethyl)-(5,6,7,8-tetrahydroquinolin-8-yl)-amine;
(6-aminopyridin-3-ylmethyl)-(benzimidazol-2-ylmethyl)-(5,6,7,8-tetrahydroquinolin-8-yl)-amine;
(2-aminopyridin-3-ylmethyl)-(benzimidazol-2-ylmethyl)-(5,6,7,8-tetrahydro-8-quinolinyl)-amine;
(6-amino-pyridin-2-ylmethyl)-(1H-benzimidazol-2-ylmethyl)-(5,6,7,8-tetrahydro-quinolin-8-yl)-amine;
(4-amino-pyridin-3-ylmethyl)-(1H-benzimidazol-2-ylmethyl)-(5,6,7,8-tetrahydro-quinolin-8-yl)-amine;
(1H-benzimidazol-2-ylmethyl)-(5,6,7,8-tetrahydroquinolin-8-yl)-(imidazol-2-yl)-methylamine;
4-{[(1H-benzimidazol-2-ylmethyl)-(5,6,7,8-tetrahydro-quinolin-8-yl)-amino]-methyl}-2,6-dichloropyridine;
pyridin-2-ylmethyl-(1H-benzimidazol-2-ylmethyl)-(5,6,7,8-tetrahydroquinolin-8-yl)-amine;
(1H-benzimidazol-2-ylmethyl)-pyridin-4-ylmethyl-(5,6,7,8-tetrahydro-quinolin-8-yl)-amine;
(1H-benzimidazol-2-ylmethyl)-pyridin-3-ylmethyl-(5,6,7,8-tetrahydro-quinolin-8-yl)-amine; and
(1H-Benzimidazol-2-ylmethyl)-(3H-imidazol-4-ylmethyl-(5,6,7,8-tetrahydro-quinolin-8-yl)-amine;

or a salt thereof.

8. A pharmaceutical composition comprising a therapeutically effective amount of the compound of claim 1 and a pharmaceutically acceptable carrier.

9. The pharmaceutical composition of claim 8, wherein $(CR_2)^a{}_n$ is a bond and $(CR_2)^b{}_n$ is $CH_2$.

10. The pharmaceutical composition of claim 8, wherein ring E comprises a pi bond coupled to one N.

11. A pharmaceutical composition for modulating chemokine receptor activity comprising a therapeutically effective amount of the compound of claim 7 and a pharmaceutically acceptable carrier.

12. The pharmaceutical composition of claim 8, wherein k is 0–1.

* * * * *

UNITED STATES PATENT AND TRADEMARK OFFICE
CERTIFICATE OF CORRECTION

| | | |
|---|---|---|
| PATENT NO. | : 7,091,217 B2 | Page 1 of 1 |
| APPLICATION NO. | : 10/799386 | |
| DATED | : August 15, 2006 | |
| INVENTOR(S) | : Gary Bridger et al. | |

It is certified that error appears in the above-identified patent and that said Letters Patent is hereby corrected as shown below:

Title Page, Delete "(22) PCT Filed: Mar. 11, 2004" and Insert:

--(22)  PCT Filed:       Sep. 17, 2001

(86)  PCT No.:         PCT/US01/29590

§ 371 (c)(1), (2), (4) Date:   Mar. 28, 2002

(87)  PCT Pub. No.:    WO02/34745
         PCT Pub. Date:   May 2, 2002--

Signed and Sealed this

Fifteenth Day of April, 2008

JON W. DUDAS
*Director of the United States Patent and Trademark Office*